United States Patent
Kaiser et al.

(10) Patent No.: US 9,765,052 B2
(45) Date of Patent: Sep. 19, 2017

(54) ANTHRANILAMIDE COMPOUNDS, THEIR MIXTURES AND THE USE THEREOF AS PESTICIDES

(71) Applicant: BASF SE, Ludwigshafen (DE)

(72) Inventors: Florian Kaiser, Mannheim (DE);
Karsten Koerber, Eppelheim (DE);
Prashant Deshmukh, Mannheim (DE);
Matthias Pohlman, Freinsheim (DE);
Jean-Yves Wach, Mannheim (DE);
Juergen Langewald, Mannheim (DE);
Egon Haden, Speyer (DE); Deborah L. Culbertson, Fuquay Varina, NC (US);
W. David Rogers, Durham, NC (US);
Koshi Gunjima, Toyohashi (JP);
Michael David, Raleigh, NC (US);
Franz Josef Braun, Durham, NC (US)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 14/767,677

(22) PCT Filed: Feb. 20, 2014

(86) PCT No.: PCT/EP2014/053272
§ 371 (c)(1),
(2) Date: Aug. 13, 2015

(87) PCT Pub. No.: WO2014/128188
PCT Pub. Date: Aug. 28, 2014

(65) Prior Publication Data
US 2015/0376163 A1 Dec. 31, 2015

Related U.S. Application Data

(60) Provisional application No. 61/766,737, filed on Feb. 20, 2013.

(51) Int. Cl.
| | |
|---|---|
| *A01P 7/00* | (2006.01) |
| *C07D 401/04* | (2006.01) |
| *A61P 33/00* | (2006.01) |
| *A01N 43/56* | (2006.01) |
| *A61K 31/4439* | (2006.01) |
| *A01N 25/00* | (2006.01) |

(52) U.S. Cl.
CPC ........... *C07D 401/04* (2013.01); *A01N 25/00* (2013.01); *A01N 43/56* (2013.01)

(58) Field of Classification Search
CPC ....... A01N 25/00; A01N 43/56; C07D 401/04
USPC ...................................................... 546/268.1
See application file for complete search history.

(56) References Cited

U.S. PATENT DOCUMENTS

| | | | |
|---|---|---|---|
| 2,333,106 A | 11/1943 | Kendall et al. | |
| 5,998,424 A | 12/1999 | Galemmo, Jr. et al. | |
| 2003/0229050 A1* | 12/2003 | Lahm | A01N 37/22 514/63 |
| 2004/0110777 A1 | 6/2004 | Annis et al. | |
| 2007/0129407 A1* | 6/2007 | Koyanagi | C07D 401/04 514/341 |
| 2007/0232598 A1 | 10/2007 | Funke et al. | |
| 2008/0293798 A1* | 11/2008 | Dietz | A01N 43/56 514/407 |
| 2009/0275471 A1 | 11/2009 | Funke et al. | |
| 2010/0028304 A1* | 2/2010 | Koyanagi | A01N 43/56 424/93.5 |

(Continued)

FOREIGN PATENT DOCUMENTS

| | | |
|---|---|---|
| DE | 102006042437 | 10/2007 |
| EP | 1717237 | 11/2006 |

(Continued)

OTHER PUBLICATIONS

Fassler; Phytopathology 2011, 101, S51.*
Anonymous, "Pesticide Resistance," [online] (2012), pp. 1-7.
Denholm et al., "Tactics for Managing Pesticide Resistance in Arthropods: Theory and Practice Quick Links to Online Content," Annu. Rev. Enlomol., (1992), pp. 91-101.
International Preliminary Report on Patentability, issued in PCT/EP2014/053272, dated Aug. 25, 2015.
International Search Report, issued in PCT/EP2014/053272, dated Jun. 2, 2014.
Isaacs et al., "Insect Ryanodine Receptor: Distinct by Coupled Insecticide Binding Sites for [N—C 3 H 3]Chlorantraniliprole, Flubendiamide, and [3 H]Ryanodine," Chemical Research in Toxicology, vol. 25, No. 8, (2012), pp. 1571-1573.

(Continued)

*Primary Examiner* — Noble Jarrell
*Assistant Examiner* — Daniel Carcanague
(74) *Attorney, Agent, or Firm* — Brinks Gilson & Lione

(57) ABSTRACT

Compounds of formula (I)

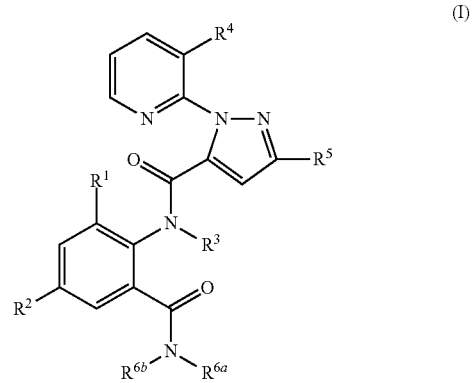

wherein
$R^1$, $R^2$, $R^3$, $R^4$, $R^5$, $R^{6a}$ and $R^{6b}$ are as defined in the description;
or a stereoisomer, salt, tautomer or N-oxide, or a polymorphic crystalline form, a co-crystal
or a solvate of a compound or a stereoisomer, salt, tautomer or N-oxide thereof,
and to mixtures, methods and uses thereof.

18 Claims, No Drawings

(56) References Cited

U.S. PATENT DOCUMENTS

| | | | | |
|---|---|---|---|---|
| 2011/0311503 A1* | 12/2011 | Funke | ............... | A61K 31/661 424/93.46 |
| 2012/0083463 A1* | 4/2012 | Maue | ............... | A01N 43/40 514/30 |
| 2015/0250175 A1* | 9/2015 | Koerber | ............... | A01N 43/56 504/100 |
| 2015/0296801 A1* | 10/2015 | Brahm | ............... | A01N 63/04 504/117 |
| 2015/0305331 A1* | 10/2015 | Gewehr | ............... | A01N 37/42 504/100 |
| 2015/0313241 A1* | 11/2015 | Brahm | ............... | A01N 47/24 504/100 |
| 2015/0327556 A1* | 11/2015 | Brahm | ............... | A01N 63/00 504/117 |
| 2016/0100585 A1* | 4/2016 | Brahm | ............... | A01N 63/00 504/100 |

FOREIGN PATENT DOCUMENTS

| | | |
|---|---|---|
| EP | 1900730 | 3/2008 |
| EP | 2255625 | 12/2010 |
| FR | 2 301 250 | 9/1976 |
| WO | WO 96/38442 | 12/1996 |
| WO | WO 03015518 | 2/2003 |
| WO | WO 03015519 | 2/2003 |
| WO | WO 2004067528 | 8/2004 |
| WO | WO 2005077934 | 8/2005 |
| WO | WO 2006068669 | 6/2006 |
| WO | WO 2007017433 | 2/2007 |
| WO | WO 2008010897 | 1/2008 |
| WO | WO 2008034785 | 3/2008 |
| WO | WO 2008072783 | 6/2008 |
| WO | WO 2011062291 | 5/2011 |
| WO | WO 2011134876 | 11/2011 |
| WO | WO2011147952 | * 12/2011 |
| WO | WO2012004293 | * 1/2012 |
| WO | WO 2014053395 | 4/2014 |
| WO | WO 2014053396 | 4/2014 |
| WO | WO 2014053401 | 4/2014 |
| WO | WO 2014053402 | 4/2014 |
| WO | WO 2014053403 | 4/2014 |
| WO | WO 2014053404 | 4/2014 |
| WO | WO 2014053405 | 4/2014 |
| WO | WO 2014053406 | 4/2014 |
| WO | WO 2014053407 | 4/2014 |
| WO | WO 2014079820 | 5/2014 |

OTHER PUBLICATIONS

Perring et al., "Management of Plant Viral Diseases through Chemical Control of Insect Vectors," Annual Review of Entomology, vol. 44, No. 1, (1999), pp. 457-481.

Selby et al., "Discovery of Cyantraniliprole, a Potent and Selective Anthranilic Diamide Ryanodine Receptor Activator with Cross-Spectrum Insecticidal Activity," Bioorganic & Medicinal Chemistry Letters, vol. 23, (2013), pp. 6341-6345.

Zhou et al., "Synthesis and Insecticidal Activities of 2,3-Dihydroquinazolin-4(1H)-one Derivatives Targeting Calcium Channel," Bioorganic a& Medicinal Chemistry, vol. 21, (2013), pp. 4968-4975.

Murray, W. M., et al., "Synthesis of 3-(1,5-Diphenyl-3-pyrazolyl)aryl Propanoates," J. Heterocyclic Chem., 27:1933-40 (1990).

Penning, Thomas D., et al. "Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib)", J. Med Chem. 1997, p. 1347-1365, vol. 40.

Shao et al., "Cycloxaprid Insecticide: Nicotinic Acetylcholine Receptor Binding Site and Metabolism," Journal of Agricultural and Food Chemistry, vol. 61, (2013), pp. 7883-7888.

Office Action, issued in corresponding CN Application No. 201480022464.0, dated Apr. 19, 2017.

* cited by examiner

ANTHRANILAMIDE COMPOUNDS, THEIR MIXTURES AND THE USE THEREOF AS PESTICIDES

This application is a National Stage application of International Application No. PCT/EP2014/053272, filed Feb. 20, 2014, which claims the benefit of U.S. Provisional Application No. 61/766,737, filed Feb. 20, 2013.

DESCRIPTION

The present invention relates to anthranilamide compounds of formula (I),

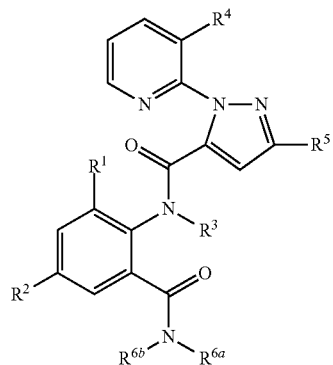

wherein
- $R^1$ is selected from the group consisting of halogen, methyl and halomethyl;
- $R^2$ is selected from the group consisting of hydrogen, halogen, halomethyl and cyano;
- $R^3$ is selected from hydrogen, $C_1$-$C_4$ alkyl;
- $R^4$ is hydrogen or halogen;
- $R^5$ is selected from fluoro, bromo, chloro, difluoromethyl, trifluoromethyl, nitro, cyano, $OCH_3$, $OCF_3$, $OCHF_2$, $OCH_2F$, $OCH_2CF_3$;
- $R^{6a}$ is selected from hydrogen, $C_1$-$C_4$-alkyl, $C_3$-$C_8$-cycloalkyl, $C_3$-$C_8$-cycloalkyl-methyl, $C_3$-$C_8$-cycloalkyl-ethyl;
- $R^{6b}$ is selected from hydrogen, $C_1$-$C_4$-alkyl;

or a stereoisomer, salt, tautomer or N-oxide, or a polymorphic crystalline form, a co-crystal or a solvate of a compound or a stereoisomer, salt, tautomer or N-oxide thereof, (=hereinafter defined as "compounds according to the invention")
and to mixtures, methods and uses thereof.

The term "compound of formula (I) or a stereoisomer, salt, tautomer or N-oxide thereof" is understood to include a polymorphic crystalline form, a co-crystal or a solvate of a compound or a stereoisomer, salt, tautomer or N-oxide, even if not mentioned explicitly.

These compounds are referred to as "compounds I" herein or as "compounds according to the invention", in particular the compounds of embodiment A, B and C.

The compounds according to the invention are particularly useful for controlling invertebrate pests, in particular for controlling arthropods and nematodes and especially insects.

Especially, the invention relates to mixtures and uses of said anthranilamide compounds according to the invention, and to compositions comprising the compounds according to the invention. The invention especially also relates to certain uses of the compounds according to the invention:

In one Embodiment, of the invention, the invention relates to the compounds of formula (I) itself and their stereoisomers, salts, tautomers or N-oxides.

In another embodiment of the invention, the invention relates to mixtures of the compounds of formula (I) itself and their stereoisomers, salts, tautomers or N-oxides, especially their salts, with insecticides, and optionally further active ingredients.

In another embodiment of the invention, the invention relates to mixtures of the compounds of formula (I) itself and their stereoisomers, salts, tautomers or N-oxides, especially their salts, with fungicides, and optionally further active ingredients.

In another embodiment of the invention, the invention relates to mixtures of the compounds of formula (I) itself and their stereoisomers, salts, tautomers or N-oxides, especially their salts, with other pesticides, and optionally further active ingredients.

In another embodiment of the invention, the invention relates to the use of the compounds of formula (I) itself and their stereoisomers, salts, tautomers or N-oxides, especially their salts, and their mixtures, in soil and seed treatment application methods, especially for controlling and/or combating animal pests in soil application methods and seed treatment methods, wherein the active compound of formula (I) is applied directly and/or indirectly to the plant and/or to plant propagation material by drenching the soil, by drip application onto the soil, by soil injection, by dipping or by treatment of seeds.

In another embodiment of the invention, the invention relates to the use of the compounds of formula (I) itself and their stereoisomers, salts, tautomers or N-oxides, especially their salts, and their mixtures, on genetically modified plants, or the use in a method for controlling pests and/or increasing the plant health of a cultivated plant with at least one modification as compared to the respective non-modified control, comprising the application of at least one pesticide to a plant with at least one modification, parts of such plant, plant propagation material, or at its locus of growth, wherein the pesticide is a pesticide compound of formula (I).

In another embodiment of the invention, the invention relates to the use of the compounds of formula (I) itself and their stereoisomers, salts, tautomers or N-oxides, especially their salts, and their mixtures, in non-agronomic applications, especially in nettings, e.g. mosquito nets, and the use against ants, flies, termites and other pests, especially household pests.

In another embodiment of the invention, the invention relates to the use of the compounds of formula (I) itself and their stereoisomers, salts, tautomers or N-oxides, especially their salts, and their mixtures, for increasing the health of plants, for increasing the yield, the resistance against fungi or animal pests or external factors like heat, cold or drought, and for increasing the quality of the crops and other parameters.

In another embodiment of the invention, the invention relates to uses and methods of the compounds according to the invention and their mixtures, of reducing insect-vectored viral infection and transmission in plants, methods of reducing damage to plants caused by viral infection, methods of crop enhancement including methods for improving plant growth, vigour and yield, by application of anthranilamide compounds, and their mixtures with selected other pesticides.

In another embodiment of the invention, the invention relates to a method, in which the compounds of formula (I) itself and their stereoisomers, salts, tautomers or N-oxides, especially their salts, and their mixtures, are used for controlling Lepidoptera or Coleoptera that are resistant to other insecticides and are surprisingly useful in this context.

In another embodiment of the invention, the invention relates to a method, in which the compounds of formula (I) itself and their stereoisomers, salts, tautomers or N-oxides, especially their salts, and their mixtures, are used for controlling Lepidoptera or Coleoptera that are resistant to other ryanodin modulator insecticides and are surprisingly useful in this context.

However, although some of the anthranilamide compounds of formula (I) themselves and their combined application with other insecticides are known to have shown activity against certain crop damaging insect pests, the compounds of formula I and some of their selected mixtures with pesticidally active compounds (II) have not yet been described for solving discussed problems as mentioned above.

The compounds of formula I as well as the terms "compounds for methods according to the (present) invention", "compounds according to the (present) invention" or "compounds of formula (I)" or "compound(s) I", where all compound(s) are applied in methods and uses according to the present invention, comprise the compound(s) as defined herein as well as a known stereoisomer, salt, tautomer or N-oxide thereof.

The term "composition(s) according to the invention" or "composition(s) of the present invention" encompasses composition(s) comprising at least one compound of formula I or mixtures of the compounds of formula I with other pesticidally active compound(s) II for being used and/or applied in methods according to the invention as defined above.

Depending on the substitution pattern, the compounds of the formula (I) may have one or more centers of chirality, in which case they are present as mixtures of enantiomers or diastereomers. The invention provides both the pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond, nitrogen-sulfur double bond or amide group. The term "stereoisomer(s)" encompasses both optical isomers, such as enantiomers or diastereomers, the latter existing due to more than one center of chirality in the molecule, as well as geometrical isomers (cis/trans isomers).

Salts of the compounds of the present invention are preferably agriculturally and veterinarily acceptable salts. They can be formed in a customary method, e.g. by reacting the compound with an acid if the compound of the present invention has a basic functionality or by reacting the compound with a suitable base if the compound of the present invention has an acidic functionality.

In general, suitable "agriculturally useful salts" or "agriculturally acceptable salts" are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

Veterinarily acceptable salts of the compounds of the present invention encompass the salts of those cations or the acid addition salts which are known and accepted in the art for the formation of salts for veterinary use. Suitable acid addition salts, e.g. formed by compounds of the present invention containing a basic nitrogen atom, e.g. an amino group, include salts with inorganic acids, for example hydrochlorides, sulfates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The compounds of the formula (I) may be present in the form of their N-oxides. The term "N-oxide" includes any compound of the present invention which has at least one tertiary nitrogen atom that is oxidized to an N-oxide moiety. N-oxides of compounds (I) can in particular be prepared by oxidizing the ring nitrogen atom(s) of the pyridine ring and/or the pyrazole ring with a suitable oxidizing agent, such as peroxo carboxylic acids or other peroxides. The person skilled in the art knows if and in which positions compounds of the formula (I) of the present invention may form N-oxides.

The compounds of the present invention may be amorphous or may exist in one ore more different crystalline states (polymorphs) which may have different macroscopic properties such as stability or show different biological properties such as activities. The present invention includes both amorphous and crystalline compounds of formula (I), their enantiomers or diastereomers, mixtures of different crystalline states of the respective compound of formula (I), its enantiomers or diastereomers, as well as amorphous or crystalline salts thereof.

The term "co-crystal" denotes a complex of the compounds according to the invention or a stereoisomer, salt, tautomer or N-oxide thereof, with one or more other molecules (preferably one molecule type), preferably a molecule which is a compound solid at room temperature, wherein usually the ratio of the compound according to the invention and the other molecule is a stoichiometric ratio.

The term "solvate" denotes a co-complex of the compounds according to the invention, or a stereoisomer, salt, tautomer or N-oxide thereof, with solvent molecules. The solvent is usually liquid. Examples of solvents are methanol, ethanol, toluol, xylol. A preferred solvent which forms solvates is water, which solvates are referred to as "hydrates". A solvate or hydrate is usually characterized by the presence of a fixed number of n molecules solvent per m molecules compound according to the invention (stoichiometric ratio ratio).

Co-crystals and solvates only differ by the nature of the partner molecule, i.e. in the case of co-crystals, the partner molecule is solid at room temperature, and in the case of solvates, the partner molecule is liquid at room temperature.

In one embodiment of the invention, the invention relates to co-crystals and solvates of the compounds according to the invention, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine. A partially or fully halogenated radical is termed below also "halo-radical". For example, partially or fully halogenated alkyl is also termed haloalkyl.

The term "alkyl" as used herein denotes in each case a straight-chain or branched alkyl group having usually from 1 to 12 or 1 to 10 carbon atoms, frequently from 1 to 6 carbon atoms, preferably 1 to 4 carbon atoms and in particular from 1 to 3 carbon atoms. Examples of $C_1$-$C_4$-alkyl are methyl, ethyl, n-propyl, isopropyl, n-butyl, 2-butyl (sec-butyl), isobutyl and tert-butyl. Examples for $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl, 2-propylpentyl, nonyl, decyl, 2-propylheptyl and 3-propylheptyl.

The term "haloalkyl" as used herein denotes in each case a straight-chain or branched alkyl group having usually from 1 to 10 carbon atoms ("$C_1$-$C_{10}$-haloalkyl"), frequently from 1 to 6 carbon atoms ("$C_1$-$C_6$-haloalkyl"), more frequently 1 to 4 carbon atoms ("$C_1$-$C_{10}$-haloalkyl"), wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl. Halomethyl is methyl in which 1, 2 or 3 of the hydrogen atoms are replaced by halogen atoms. Examples are bromomethyl, chloromethyl, dichloromethyl, trichloromethyl, fluoromethyl, difluoromethyl, trifluoromethyl, chlorofluoromethyl, dichlorofluoromethyl, chlorodifluoromethyl and the like. Examples for $C_1$-$C_2$-fluoroalkyl are fluoromethyl, difluoromethyl, trifluoromethyl, 1-fluoroethyl, 2-fluoroethyl, 2,2-difluoroethyl, 2,2,2-trifluoroethyl, pentafluoroethyl, and the like. Examples for $C_1$-$C_2$-haloalkyl are, apart those mentioned for $C_1$-$C_2$-fluoroalkyl, chloromethyl, dichloromethyl, trichloromethyl, bromomethyl, chlorofluoromethyl, dichlorofluoromethyl, chlorodifluoromethyl, 1-chloroethyl, 2-chloroethyl, 2,2,-dichloroethyl, 2,2,2-trichloroethyl, 2-chloro-2-fluoroethyl, 2-chloro-2,2-difluoroethyl, 2,2-dichloro-2-fluoroethyl, 1-bromoethyl, and the like. Examples for $C_1$-$C_4$-haloalkyl are, apart those mentioned for $C_1$-$C_2$-haloalkyl, 1-fluoropropyl, 2-fluoropropyl, 3-fluoropropyl, 3,3-difluoropropyl, 3,3,3-trifluoropropyl, heptafluoropropyl, 1,1,1-trifluoroprop-2-yl, 3-chloropropyl, 4-chlorobutyl and the like.

The term "cycloalkyl" as used herein (and in the cycloalkyl moieties of other groups comprising a cycloalkyl group, e.g. cycloalkylalkyl) denotes in each case a mono- or bicyclic cycloaliphatic radical having usually from 3 to 10 carbon atoms ("$C_3$-$C_{10}$-cycloalkyl"), preferably 3 to 8 carbon atoms ("$C_3$-$C_8$-cycloalkyl") or in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl.

The term "halocycloalkyl" as used herein denotes in each case a mono- or bicyclic cycloaliphatic radical having usually from 3 to 10 carbon atoms, preferably 3 to 8 carbon atoms or in particular 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "cycloalkyl-alkyl" used herein denotes a cycloalkyl group, as defined above, which is bound to the remainder of the molecule via an alkylene group. The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, 1-cyclopropylethyl, 2-cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "alkoxy" as used herein denotes in each case a straight-chain or branched alkyl group usually having from 1 to 10 carbon atoms ("$C_1$-$C_{10}$-alkoxy"), frequently from 1 to 6 carbon atoms ("$C_1$-$C_6$-alkoxy"), preferably 1 to 4 carbon atoms ("$C_1$-$C_4$-alkoxy"), which is bound to the remainder of the molecule via an oxygen atom. $C_1$-$C_2$-Alkoxy is methoxy or ethoxy. $C_1$-$C_4$-Alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof. The term "haloalkoxy" as used herein denotes in each case a straight-chain or branched alkoxy group, as defined above, having from 1 to 10 carbon atoms ("$C_1$-$C_{10}$-haloalkoxy"), frequently from 1 to 6 carbon atoms ("$C_1$-$C_6$-haloalkoxy"), preferably 1 to 4 carbon atoms ("$C_1$-$C_4$-haloalkoxy"), more preferably 1 to 3 carbon atoms ("$C_1$-$C_3$-haloalkoxy"), wherein the hydrogen atoms of this group are partially or totally replaced with halogen atoms, in particular fluorine atoms. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

Compounds of Formula (I) and Preferences

Anthranilamide compounds of formula (I) can be prepared according to the methods described in WO2001/070671, WO2003/015519, WO2003/015518, WO2003/016282, WO2003/016283, and also in WO2013/024009 and WO2013/024010, without being limited to the routes given therein. If the variables are slightly different, a person skilled in the art will know how to perform the method described for specific examples to another similar compound by analogous methods.

Compounds of formula (I) as described below in embodiment A may also be prepared as described in WO2005/077934, and in WO2008/072743, WO2008/072745 and WO2008/155990.

The preparation of the compounds of formula I above may lead to them being obtained as isomer mixtures. If desired, these can be resolved by the methods customary for this purpose, such as crystallization or chromatography, also on optically active adsorbate, to give the pure isomers.

Agronomically acceptable salts of the compounds I can be formed in a customary manner, e.g. by reaction with an acid of the anion in question.

The remarks made below as to preferred embodiments of the variables (substituents) of the compounds of formulae (I) are valid on their own as well as preferably in combination with each other, as well as in combination with the stereoisomers, tautomers, N-oxides or salts thereof, and, where applicable, as well as concerning the uses and methods according to the invention and the compositions according to the invention.

In a preferred embodiment, the invention relates to mixtures, methods and uses of compounds of formula (I-0), which are compounds of formula (I) in which R3 is hydrogen, and R6b is hydrogen:

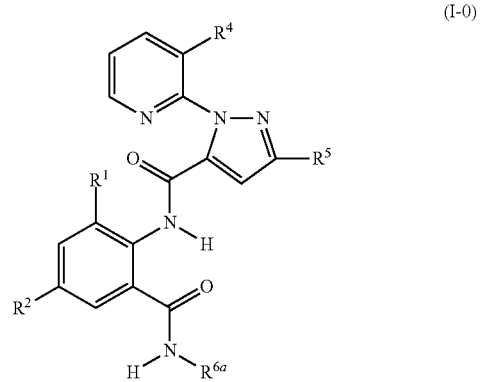

(I-0)

Embodiment A

In embodiment A, the invention relates to mixtures, methods and uses of compounds of formula (I)

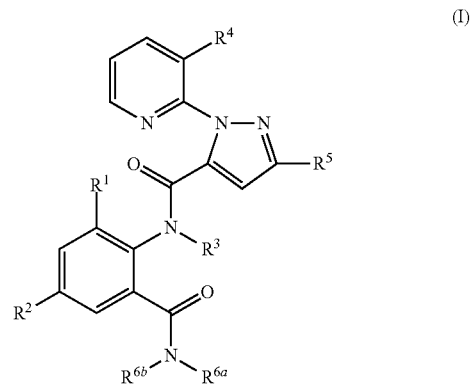

(I)

wherein
R$^1$ is selected from the group consisting of halogen, methyl and halomethyl;
R$^2$ is selected from the group consisting of hydrogen, halogen, halomethyl and cyano;
R$^3$ is selected from hydrogen, $C_1$-$C_6$ alkyl;
R$^4$ is hydrogen or halogen;
R$^5$ is selected from fluoro, bromo, chloro, difluoromethyl, trifluoromethyl, nitro, cyano, $OCH_3$, $OCF_3$, $OCHF_2$, $OCH_2F$, $OCH_2CF_3$;

$R^{6a}$ is selected from $C_3$-$C_8$-cycloalkyl-methyl, $C_3$-$C_8$-cycloalkyl-ethyl;

$R^{6b}$ is selected from hydrogen, $C_1$-$C_4$-alkyl;

or a stereoisomer, salt, tautomer or N-oxide, or a solvate of a stereoisomer, salt, tautomer or N-oxide, thereof.

The remarks made below as to preferred embodiments of the variables (substituents) of the compounds of formulae (I) are valid on their own as well as preferably in combination with each other, as well as in combination with the stereoisomers, tautomers, N-oxides or salts thereof, and, where applicable, as well as concerning the uses and methods according to the invention and the compositions according to the invention.

Preferred compounds according to the invention are compounds of formulae (I) or a stereoisomer, N-oxide or salt thereof, wherein the salt is an agriculturally or veterinarily acceptable salt.

The compounds I of formula (I) and their examples include their tautomers, racemic mixtures, individual pure enantiomers and diasteroemers and their optically active mixtures.

The term compounds, stereoisomers, tautomers, N-oxides or salts thereof may also include a polymorphic crystalline form, a co-crystal or a solvate of a compound or a stereoisomer, salt, tautomer or N-oxide.

Preferred are compounds of formula (I-0),

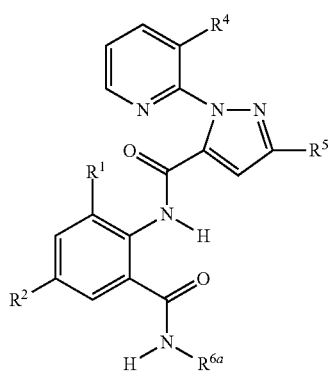

(I-0)

wherein
$R^1$ is selected from the group consisting of halogen, methyl and halomethyl;
$R^2$ is selected from the group consisting of hydrogen, halogen, halomethyl and cyano;
$R^4$ is hydrogen or halogen;
$R^5$ is selected from fluoro, bromo, chloro, difluoromethyl, trifluoromethyl, nitro, cyano, $OCH_3$, $OCF_3$, $OCHF_2$, $OCH_2F$, $OCH_2CF_3$;
$R^{6a}$ is selected from $C_3$-$C_8$-cycloalkyl-methyl, $C_3$-$C_8$-cycloalkyl-ethyl.

Preferred are compounds of formula (I-0), wherein
$R^1$ is selected from the group consisting of bromo, chloro, methyl;
$R^2$ is selected from the group consisting of chloro, cyano, methyl;
$R^4$ is chloro;
$R^5$ is selected from bromo, chloro, difluoromethyl, trifluoromethyl,
$R^{6a}$ is selected from cyclopropyl-methyl, $C_3$-$C_8$-cyclopropyl-ethyl.

Especially preferred compounds are compounds of formula (I-0) as listed in table A.

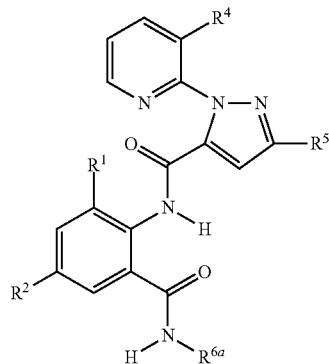

(I-0)

TABLE A

| Compound No. | $R^1$ | $R^2$ | $R^4$ | $R^5$ | $R^{6a}$ |
|---|---|---|---|---|---|
| I-A-1 | Br | Cl | Cl | Br | CPE |
| I-A-2 | Br | Cl | Cl | Cl | CPE |
| I-A-3 | Br | Cl | Cl | $CF_3$ | CPE |
| I-A-4 | Br | CN | Cl | Br | CPE |
| I-A-5 | Br | CN | Cl | Cl | CPE |
| I-A-6 | Br | CN | Cl | $CF_3$ | CPE |
| I-A-7 | Br | $CH_3$ | Cl | Br | CPE |
| I-A-8 | Br | $CH_3$ | Cl | Cl | CPE |
| I-A-9 | Br | $CH_3$ | Cl | $CF_3$ | CPE |
| I-A-10 | Cl | Cl | Cl | Br | CPE |
| I-A-11 | Cl | Cl | Cl | Cl | CPE |
| I-A-12 | Cl | Cl | Cl | $CF_3$ | CPE |
| I-A-13 | Cl | CN | Cl | Br | CPE |
| I-A-14 | Cl | CN | Cl | Cl | CPE |
| I-A-15 | Cl | CN | Cl | $CF_3$ | CPE |
| I-A-16 | Cl | $CH_3$ | Cl | Br | CPE |
| I-A-17 | Cl | $CH_3$ | Cl | Cl | CPE |
| I-A-18 | Cl | $CH_3$ | Cl | $CF_3$ | CPE |
| I-A-19 | $CH_3$ | Cl | Cl | Br | CPE |
| I-A-20 | $CH_3$ | Cl | Cl | Cl | CPE |
| I-A-21 | $CH_3$ | Cl | Cl | $CF_3$ | CPE |
| I-A-22 | $CH_3$ | CN | Cl | Br | CPE |
| I-A-23 | $CH_3$ | CN | Cl | Cl | CPE |
| I-A-24 | $CH_3$ | CN | Cl | $CF_3$ | CPE |
| I-A-25 | $CH_3$ | $CH_3$ | Cl | Br | CPE |
| I-A-26 | $CH_3$ | $CH_3$ | Cl | Cl | CPE |
| I-A-27 | $CH_3$ | $CH_3$ | Cl | $CF_3$ | CPE |
| I-A-28 | Br | Cl | Cl | Br | CPM |
| I-A-29 | Br | Cl | Cl | Cl | CPM |
| I-A-30 | Br | Cl | Cl | $CF_3$ | CPM |
| I-A-31 | Br | CN | Cl | Br | CPM |
| I-A-32 | Br | CN | Cl | Cl | CPM |
| I-A-33 | Br | CN | Cl | $CF_3$ | CPM |
| I-A-34 | Br | $CH_3$ | Cl | Br | CPM |
| I-A-35 | Br | $CH_3$ | Cl | Cl | CPM |
| I-A-36 | Br | $CH_3$ | Cl | $CF_3$ | CPM |
| I-A-37 | Cl | Cl | Cl | Br | CPM |
| I-A-38 | Cl | Cl | Cl | Cl | CPM |
| I-A-39 | Cl | Cl | Cl | $CF_3$ | CPM |
| I-A-40 | Cl | CN | Cl | Br | CPM |
| I-A-41 | Cl | CN | Cl | Cl | CPM |
| I-A-42 | Cl | CN | Cl | $CF_3$ | CPM |
| I-A-43 | Cl | $CH_3$ | Cl | Br | CPM |
| I-A-44 | Cl | $CH_3$ | Cl | Cl | CPM |
| I-A-45 | Cl | $CH_3$ | Cl | $CF_3$ | CPM |
| I-A-46 | $CH_3$ | Cl | Cl | Br | CPM |
| I-A-47 | $CH_3$ | Cl | Cl | Cl | CPM |
| I-A-48 | $CH_3$ | Cl | Cl | $CF_3$ | CPM |
| I-A-49 | $CH_3$ | CN | Cl | Br | CPM |
| I-A-50 | $CH_3$ | CN | Cl | Cl | CPM |
| I-A-51 | $CH_3$ | CN | Cl | $CF_3$ | CPM |
| I-A-52 | $CH_3$ | $CH_3$ | Cl | Br | CPM |

TABLE A-continued

| Compound No. | $R^1$ | $R^2$ | $R^4$ | $R^5$ | $R^{6a}$ |
|---|---|---|---|---|---|
| I-A-53 | $CH_3$ | $CH_3$ | Cl | Cl | CPM |
| I-A-54 | $CH_3$ | $CH_3$ | Cl | $CF_3$ | CPM |

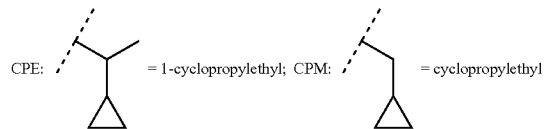

In one embodiment of the invention, the invention relates to the mixtures and methods/uses of compounds I-A-1 to I-A-54.

Special preference is given to compound I-A-1:

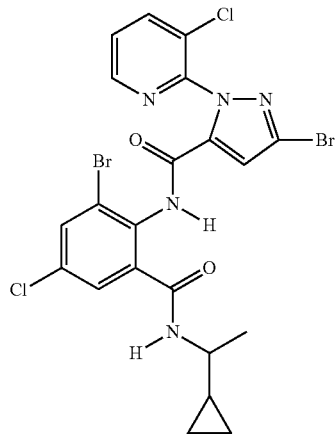

(I-A-1)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In one embodiment of the invention, the invention relates to the mixtures and methods/uses of compound I-A-1.

Special preference is given to compound I-A-28:

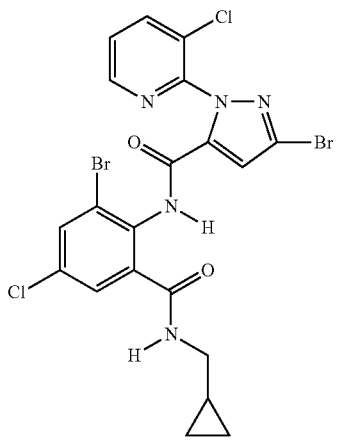

(I-A-28)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In one embodiment of the invention, the invention relates to the mixtures and methods/uses of compound I-A-28.

Embodiment B

In embodiment B, the invention relates to compounds, mixtures, methods and uses of compounds of formula (IB)

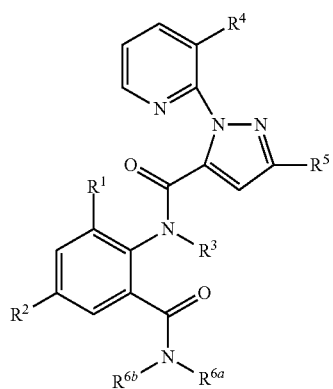

(I)

wherein
$R^1$ is selected from the group consisting of halogen, methyl and halomethyl;
$R^2$ is selected from the group consisting of hydrogen, halogen, halomethyl and cyano;
$R^3$ is selected from hydrogen, $C_1$-$C_6$ alkyl;
$R^4$ is hydrogen or halogen;
$R^5$ is selected from fluoro, bromo, chloro, difluoromethyl, trifluoromethyl, nitro, cyano, $OCH_3$, $OCF_3$, $OCHF_2$, $OCH_2F$, $OCH_2CF_3$;
$R^{6a}$ is selected from hydrogen, $C_1$-$C_4$-alkyl, $C_3$-$C_8$-cycloalkyl;
$R^{6b}$ is selected from hydrogen, $C_1$-$C_4$-alkyl;
or a stereoisomer, salt, tautomer or N-oxide thereof.

Preferred are compounds of formula (I-0)

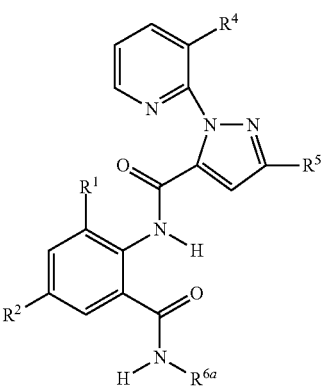

(I-0)

wherein
$R^1$ is selected from the group consisting of halogen, methyl and halomethyl;
$R^2$ is selected from the group consisting of hydrogen, halogen, halomethyl and cyano;
$R^4$ is hydrogen or halogen;

$R^5$ is selected from fluoro, bromo, chloro, difluoromethyl, trifluoromethyl, nitro, cyano, $OCH_3$, $OCF_3$, $OCHF_2$, $OCH_2F$, $OCH_2CF_3$;

$R^{6a}$ is selected from hydrogen, $C_1$-$C_4$-alkyl.

Preferred are compounds of formula (I-0), wherein $R^1$ is selected from the group consisting of bromo, chloro, methyl;

$R^2$ is selected from the group consisting of chloro, cyano, methyl;

$R^4$ is chloro;

$R^5$ is selected from bromo, chloro, difluoromethyl, trifluoromethyl, $R^{6a}$ is selected from hydrogen, methyl, ethyl.

Especially preferred compounds are compounds of formula (I-0) as listed in table B.

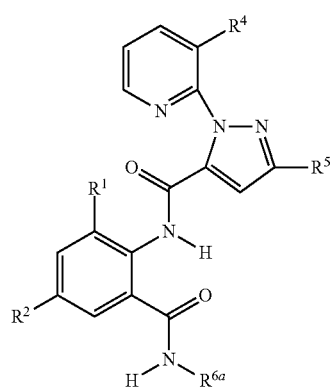

(I-0)

TABLE B

| Compound No. | $R^1$ | $R^2$ | $R^4$ | $R^5$ | $R^{6a}$ |
|---|---|---|---|---|---|
| I-B-1 | Br | Cl | Cl | Br | $CH_3$ |
| I-B-2 | Br | Cl | Cl | Cl | $CH_3$ |
| I-B-3 | Br | Cl | Cl | $CF_3$ | $CH_3$ |
| I-B-4 | Br | Cl | Cl | $CHF_2$ | $CH_3$ |
| I-B-5 | Br | CN | Cl | Br | $CH_3$ |
| I-B-6 | Br | CN | Cl | Cl | $CH_3$ |
| I-B-7 | Br | CN | Cl | $CF_3$ | $CH_3$ |
| I-B-8 | Br | CN | Cl | $CHF_2$ | $CH_3$ |
| I-B-9 | Br | $CH_3$ | Cl | Br | $CH_3$ |
| I-B-10 | Br | $CH_3$ | Cl | Cl | $CH_3$ |
| I-B-11 | Br | $CH_3$ | Cl | $CF_3$ | $CH_3$ |
| I-B-12 | Br | $CH_3$ | Cl | $CHF_2$ | $CH_3$ |
| I-B-13 | Br | Br | Cl | Br | $CH_3$ |
| I-B-14 | Br | Br | Cl | Cl | $CH_3$ |
| I-B-15 | Br | Br | Cl | $CF_3$ | $CH_3$ |
| I-B-16 | Br | Br | Cl | $CHF_2$ | $CH_3$ |
| I-B-17 | Cl | Cl | Cl | Br | $CH_3$ |
| I-B-18 | Cl | Cl | Cl | Cl | $CH_3$ |
| I-B-19 | Cl | Cl | Cl | $CF_3$ | $CH_3$ |
| I-B-20 | Cl | Cl | Cl | $CHF_2$ | $CH_3$ |
| I-B-21 | Cl | CN | Cl | Br | $CH_3$ |
| I-B-22 | Cl | CN | Cl | Cl | $CH_3$ |
| I-B-23 | Cl | CN | Cl | $CF_3$ | $CH_3$ |
| I-B-24 | Cl | CN | Cl | $CHF_2$ | $CH_3$ |
| I-B-25 | Cl | $CH_3$ | Cl | Br | $CH_3$ |
| I-B-26 | Cl | $CH_3$ | Cl | Cl | $CH_3$ |
| I-B-27 | Cl | $CH_3$ | Cl | $CF_3$ | $CH_3$ |
| I-B-28 | Cl | $CH_3$ | Cl | $CHF_2$ | $CH_3$ |
| I-B-29 | Cl | Br | Cl | Br | $CH_3$ |
| I-B-30 | Cl | Br | Cl | Cl | $CH_3$ |
| I-B-31 | Cl | Br | Cl | $CF_3$ | $CH_3$ |
| I-B-32 | Cl | Br | Cl | $CHF_2$ | $CH_3$ |
| I-B-33 | $CH_3$ | Cl | Cl | Br | $CH_3$ |
| I-B-34 | $CH_3$ | Cl | Cl | Cl | $CH_3$ |
| I-B-35 | $CH_3$ | Cl | Cl | $CF_3$ | $CH_3$ |
| I-B-36 | $CH_3$ | Cl | Cl | $CHF_2$ | $CH_3$ |
| I-B-37 | $CH_3$ | CN | Cl | Br | $CH_3$ |
| I-B-38 | $CH_3$ | CN | Cl | Cl | $CH_3$ |
| I-B-39 | $CH_3$ | CN | Cl | $CF_3$ | $CH_3$ |
| I-B-40 | $CH_3$ | CN | Cl | $CHF_2$ | $CH_3$ |
| I-B-41 | $CH_3$ | $CH_3$ | Cl | Br | $CH_3$ |
| I-B-42 | $CH_3$ | $CH_3$ | Cl | Cl | $CH_3$ |
| I-B-43 | $CH_3$ | $CH_3$ | Cl | $CF_3$ | $CH_3$ |
| I-B-44 | $CH_3$ | $CH_3$ | Cl | $CHF_2$ | $CH_3$ |
| I-B-45 | $CH_3$ | Br | Cl | Br | $CH_3$ |
| I-B-46 | $CH_3$ | Br | Cl | Cl | $CH_3$ |
| I-B-47 | $CH_3$ | Br | Cl | $CF_3$ | $CH_3$ |
| I-B-48 | $CH_3$ | Br | Cl | $CHF_2$ | $CH_3$ |
| I-B-49 | Br | Cl | Cl | Br | $CH(CH_3)_2$ |
| I-B-50 | Br | Cl | Cl | Cl | $CH(CH_3)_2$ |
| I-B-51 | Br | Cl | Cl | $CF_3$ | $CH(CH_3)_2$ |
| I-B-52 | Br | Cl | Cl | $CHF_2$ | $CH(CH_3)_2$ |
| I-B-53 | Br | CN | Cl | Br | $CH(CH_3)_2$ |
| I-B-54 | Br | CN | Cl | Cl | $CH(CH_3)_2$ |
| I-B-55 | Br | CN | Cl | $CF_3$ | $CH(CH_3)_2$ |
| I-B-56 | Br | CN | Cl | $CHF_2$ | $CH(CH_3)_2$ |
| I-B-57 | Br | $CH_3$ | Cl | Br | $CH(CH_3)_2$ |
| I-B-58 | Br | $CH_3$ | Cl | Cl | $CH(CH_3)_2$ |
| I-B-59 | Br | $CH_3$ | Cl | $CF_3$ | $CH(CH_3)_2$ |
| I-B-60 | Br | $CH_3$ | Cl | $CHF_2$ | $CH(CH_3)_2$ |
| I-B-61 | Br | Br | Cl | Br | $CH(CH_3)_2$ |
| I-B-62 | Br | Br | Cl | Cl | $CH(CH_3)_2$ |
| I-B-63 | Br | Br | Cl | $CF_3$ | $CH(CH_3)_2$ |
| I-B-64 | Br | Br | Cl | $CHF_2$ | $CH(CH_3)_2$ |
| I-B-65 | Cl | Cl | Cl | Br | $CH(CH_3)_2$ |
| I-B-66 | Cl | Cl | Cl | Cl | $CH(CH_3)_2$ |
| I-B-67 | Cl | Cl | Cl | $CF_3$ | $CH(CH_3)_2$ |
| I-B-68 | Cl | Cl | Cl | $CHF_2$ | $CH(CH_3)_2$ |
| I-B-69 | Cl | CN | Cl | Br | $CH(CH_3)_2$ |
| I-B-70 | Cl | CN | Cl | Cl | $CH(CH_3)_2$ |
| I-B-71 | Cl | CN | Cl | $CF_3$ | $CH(CH_3)_2$ |
| I-B-72 | Cl | CN | Cl | $CHF_2$ | $CH(CH_3)_2$ |
| I-B-73 | Cl | $CH_3$ | Cl | Br | $CH(CH_3)_2$ |
| I-B-74 | Cl | $CH_3$ | Cl | Cl | $CH(CH_3)_2$ |
| I-B-75 | Cl | $CH_3$ | Cl | $CF_3$ | $CH(CH_3)_2$ |
| I-B-76 | Cl | $CH_3$ | Cl | $CHF_2$ | $CH(CH_3)_2$ |
| I-B-77 | Cl | Br | Cl | Br | $CH(CH_3)_2$ |
| I-B-78 | Cl | Br | Cl | Cl | $CH(CH_3)_2$ |
| I-B-79 | Cl | Br | Cl | $CF_3$ | $CH(CH_3)_2$ |
| I-B-80 | Cl | Br | Cl | $CHF_2$ | $CH(CH_3)_2$ |
| I-B-81 | $CH_3$ | Cl | Cl | Br | $CH(CH_3)_2$ |
| I-B-82 | $CH_3$ | Cl | Cl | Cl | $CH(CH_3)_2$ |
| I-B-83 | $CH_3$ | Cl | Cl | $CF_3$ | $CH(CH_3)_2$ |
| I-B-84 | $CH_3$ | Cl | Cl | $CHF_2$ | $CH(CH_3)_2$ |
| I-B-85 | $CH_3$ | CN | Cl | Br | $CH(CH_3)_2$ |
| I-B-86 | $CH_3$ | CN | Cl | Cl | $CH(CH_3)_2$ |
| I-B-87 | $CH_3$ | CN | Cl | $CF_3$ | $CH(CH_3)_2$ |
| I-B-88 | $CH_3$ | CN | Cl | $CHF_2$ | $CH(CH_3)_2$ |
| I-B-89 | $CH_3$ | $CH_3$ | Cl | Br | $CH(CH_3)_2$ |
| I-B-90 | $CH_3$ | $CH_3$ | Cl | Cl | $CH(CH_3)_2$ |
| I-B-91 | $CH_3$ | $CH_3$ | Cl | $CF_3$ | $CH(CH_3)_2$ |
| I-B-92 | $CH_3$ | $CH_3$ | Cl | $CHF_2$ | $CH(CH_3)_2$ |
| I-B-93 | $CH_3$ | Br | Cl | Br | $CH(CH_3)_2$ |
| I-B-94 | $CH_3$ | Br | Cl | Cl | $CH(CH_3)_2$ |
| I-B-95 | $CH_3$ | Br | Cl | $CF_3$ | $CH(CH_3)_2$ |
| I-B-96 | $CH_3$ | Br | Cl | $CHF_2$ | $CH(CH_3)_2$ |
| I-B-97 | Br | Cl | Cl | Br | H |
| I-B-98 | Br | Cl | Cl | Cl | H |
| I-B-99 | Br | Cl | Cl | $CF_3$ | H |
| I-B-100 | Br | Cl | Cl | $CHF_2$ | H |
| I-B-101 | Br | CN | Cl | Br | H |
| I-B-102 | Br | CN | Cl | Cl | H |
| I-B-103 | Br | CN | Cl | $CF_3$ | H |
| I-B-104 | Br | CN | Cl | $CHF_2$ | H |
| I-B-105 | Br | $CH_3$ | Cl | Br | H |
| I-B-106 | Br | $CH_3$ | Cl | Cl | H |
| I-B-107 | Br | $CH_3$ | Cl | $CF_3$ | H |
| I-B-108 | Br | $CH_3$ | Cl | $CHF_2$ | H |
| I-B-109 | Br | Br | Cl | Br | H |
| I-B-110 | Br | Br | Cl | Cl | H |
| I-B-111 | Br | Br | Cl | $CF_3$ | H |
| I-B-112 | Br | Br | Cl | $CHF_2$ | H |
| I-B-113 | Cl | Cl | Cl | Br | H |

TABLE B-continued

| Compound No. | $R^1$ | $R^2$ | $R^4$ | $R^5$ | $R^{6a}$ |
|---|---|---|---|---|---|
| I-B-114 | Cl | Cl | Cl | Cl | H |
| I-B-115 | Cl | Cl | Cl | $CF_3$ | H |
| I-B-116 | Cl | Cl | Cl | $CHF_2$ | H |
| I-B-117 | Cl | CN | Cl | Br | H |
| I-B-118 | Cl | CN | Cl | Cl | H |
| I-B-119 | Cl | CN | Cl | $CF_3$ | H |
| I-B-120 | Cl | CN | Cl | $CHF_2$ | H |
| I-B-121 | Cl | $CH_3$ | Cl | Br | H |
| I-B-122 | Cl | $CH_3$ | Cl | Cl | H |
| I-B-123 | Cl | $CH_3$ | Cl | $CF_3$ | H |
| I-B-124 | Cl | $CH_3$ | Cl | $CHF_2$ | H |
| I-B-125 | Cl | Br | Cl | Br | H |
| I-B-126 | Cl | Br | Cl | Cl | H |
| I-B-127 | Cl | Br | Cl | $CF_3$ | H |
| I-B-128 | Cl | Br | Cl | $CHF_2$ | H |
| I-B-129 | $CH_3$ | Cl | Cl | Br | H |
| I-B-130 | $CH_3$ | Cl | Cl | Cl | H |
| I-B-131 | $CH_3$ | Cl | Cl | $CF_3$ | H |
| I-B-132 | $CH_3$ | Cl | Cl | $CHF_2$ | H |
| I-B-133 | $CH_3$ | CN | Cl | Br | H |
| I-B-134 | $CH_3$ | CN | Cl | Cl | H |
| I-B-135 | $CH_3$ | CN | Cl | $CF_3$ | H |
| I-B-136 | $CH_3$ | CN | Cl | $CHF_2$ | H |
| I-B-137 | $CH_3$ | $CH_3$ | Cl | Br | H |
| I-B-138 | $CH_3$ | $CH_3$ | Cl | Cl | H |
| I-B-139 | $CH_3$ | $CH_3$ | Cl | $CF_3$ | H |
| I-B-140 | $CH_3$ | $CH_3$ | Cl | $CHF_2$ | H |
| I-B-141 | $CH_3$ | Br | Cl | Br | H |
| I-B-142 | $CH_3$ | Br | Cl | Cl | H |
| I-B-143 | $CH_3$ | Br | Cl | $CF_3$ | H |
| I-B-144 | $CH_3$ | Br | Cl | $CHF_2$ | H |

Special preference is given to compound (I-B-33), which is known under the common name chlorantraniliprole (Rynaxypyr®)

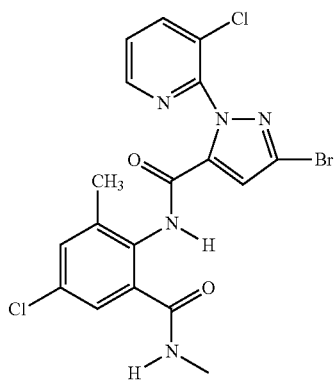

(I-B-33)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

Special preference is also given to compound (I-B-37), which is known under the common name cyantraniliprole (Cyazypyr©):

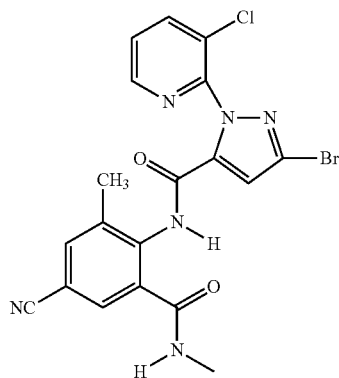

(I-B-37)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

Especially preferred compounds are compounds of formula (I-0-H):

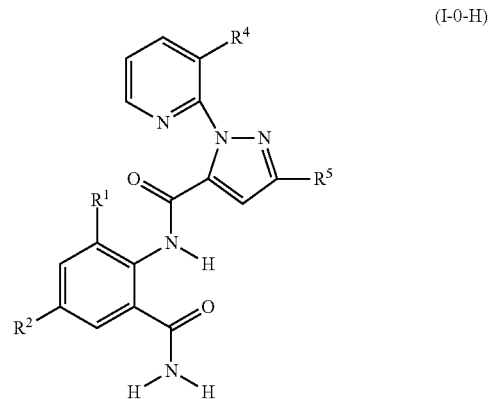

(I-0-H)

wherein $R^1$, $R^2$, $R^4$ and $R^5$ are as described herein.

Especially preferred are the compounds I-B-97 to I-144 as defined in Table B.

In a further aspect of the invention, the invention relates to compound (I-B-115):

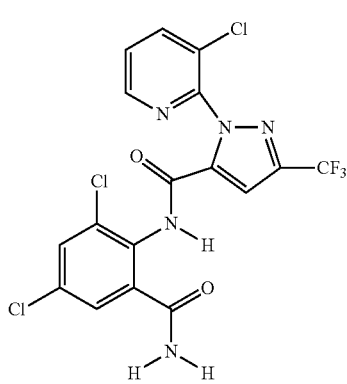

(I-B-115)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-B-131):

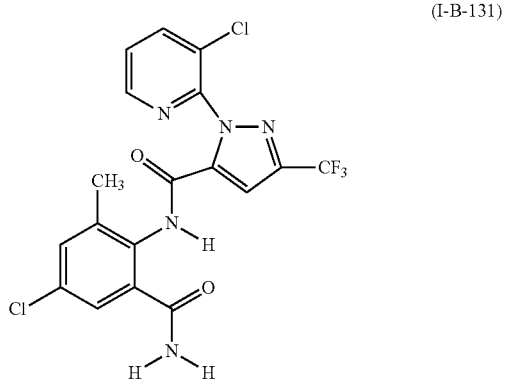 [SMILES: Cc1cc(Cl)cc(C(N)=O)c1NC(=O)c1cc(C(F)(F)F)nn1-c1ncccc1Cl]

(I-B-131)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-B-132):

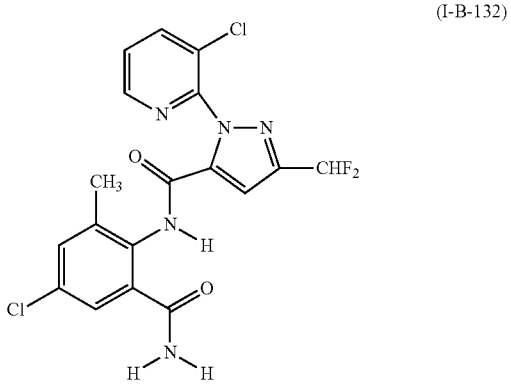 [SMILES: Cc1cc(Cl)cc(C(N)=O)c1NC(=O)c1cc(C(F)F)nn1-c1ncccc1Cl]

(I-B-132)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a preferred embodiment, the invention relates to compound (I-B-131), and its mixtures, uses and methods as described herein.

EXAMPLES

The compounds I of Embodiment B can be accomplished according to standard methods of organic chemistry, e.g. by the methods or working examples described in WO2001/070671, WO2003/015519, WO2003/015518, WO2003/016282, WO2003/016283, WO2005/077934, and in WO2008/072743, WO2008/072745 and WO2008/155990. and also in WO2013/024009 and WO2013/024010, or analogously thereto.

The characterization can be done by coupled High Performance Liquid Chromatography/mass spectrometry (HPLC/MS), by NMR or by their melting points.

Method A: Analytical HPLC column: RP-18 column Chromolith Speed ROD from Merck KgaA (Germany). Elution: acetonitrile+0.1% trifluoroacetic acid (TFA)/water+ 0.1% trifluoroacetic acid (TFA) in a ratio of from 5:95 to 95:5 in 5 minutes at 40° C.

Method B: Analytical UPLC column: Phenomenex Kinetex 1,7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0,8-1,0 mL/min in 1,50 minutes at 60° C. MS-method: ESI positive.

$^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

Preparation Examples

Example 1

N-(2-carbamoyl-4-chloro-6-methyl-phenyl)-2-(3-chloro-2-pyridyl)-5-(trifluoromethyl)pyrazole-3-carboxamide (I-B-131)

To a suspension of N-[4-chloro-2-[(diethyl-$\lambda^4$-sulfanylidene)carbamoyl]-6-methyl-phenyl]-2-(3-chloro-2-pyridyl)-5-(trifluoromethyl)pyrazole-3-carboxamide (prepared according to WO 2007/006670, 750 g) in glacial acetic acid (1.5 L) was added an aqueous solution of hydrochloric acid (272 g of a 37% solution) at 55° C. within 60 minutes. After 20 hours at this temperature, the clear solution formed a precipitate that was collected by filtration upon cooling. The solid was washed with acetic acid and ethyl acetate. Drying in vacuum at 55° C. yielded the title compound (570 g, 86%).

Characterization by $^1$H-NMR (400 MHz, DMSO-d$_6$) [delta]: 10.42 (s, 1H), 8.54 (d, 1H), 8.22 (d, 1H), 7.80 (s, 1H), 7.74 (s, 1H), 7.65 (m, 1H), 7.50 (m, 2H), 7.41 (s, 1H), 2.16 (s, 3H).

Using the method described above in Example 1, the following compounds I have been prepared:

Example 2

N-(2-carbamoyl-4-cyano-6-methyl-phenyl)-2-(3-chloro-2-pyridyl)-5-(2,2,2-trifluoroethoxyl)pyrazole-3-carboxamide Characterization by HPLC-MS: 1.036 min, m/z=479.3 (Method B)

Example 3

5-bromo-2-(3-chloro-2-pyridyl)-N-(2,4-dibromo-6-carbamoyl-phenyl)pyrazole-3-carboxamide Characterization by HPLC-MS: 1.038 min, m/z=579.9 (Method B)

Example 4

N-(2-carbamoyl-4,6-dichloro-phenyl)-2-(3-chloro-2-pyridyl)-5-(trifluoromethyl)pyrazole-3-carboxamide Characterization by HPLC-MS: 1.092 min, m/z=478.2 (Method B)

Example 5

N-(2-carbamoyl-4-chloro-6-methyl-phenyl)-2-(3-chloro-2-pyridyl)-5-(difluoromethyl)pyrazole-3-carboxamide Characterization by HPLC-MS: 2.791 min, m/z=440.0 (Method A)

Example 6

N-(2-carbamoyl-4-cyano-6-methyl-phenyl)-2-(3-chloro-2-pyridyl)-5-(difluoromethyl)pyrazole-3-carboxamide Characterization by HPLC-MS: 2.537 min, m/z=431.0 (Method A)

Example 7

N-(2-bromo-6-carbamoyl-4-chloro-phenyl)-2-(3-chloro-2-pyridyl)-5-(difluoromethyl)pyrazole-3-carboxamide Characterization by HPLC-MS: 2.888 min, m/z=505.9 (Method A)

Example 8

N-(2-carbamoyl-4-chloro-6-methyl-phenyl)-2-(3-chloro-2-pyridyl)-5-(difluoromethoxy)pyrazole-3-carboxamide Characterization by HPLC-MS: 2.984 min, m/z=456.0 (Method A)

Example 9

N-(2-carbamoyl-4,6-dichloro-phenyl)-2-(3-chloro-2-pyridyl)-5-(difluoromethoxy)pyrazole-3-carboxamide Characterization by HPLC-MS: 1.009 min, m/z=476.1 (Method B)

Example 10

N-(2-carbamoyl-4-cyano-6-methyl-phenyl)-2-(3-chloro-2-pyridyl)-5-(difluoromethoxy)pyrazole-3-carboxamide Characterization by HPLC-MS: 0.956 min, m/z=447.2 (Method B)

Special preference is given to the compounds I-B-115 and I-B-131, in particular to compound I-B-131.

Compound I-B-131 shows surprisingly favourable properties regarding environmental fate, safety, consumer safety, toxicology, ecotoxicology and other parameters.

Biological Example

Degradation of the compound (I-B-131) and compound (I-B-33) in soil was compared. The two compounds were incubated in neutral sandy loam soil (LUFA 5M) at 27° C. and 40% of the max. water-holding capacity over a period of 90 days. Soil extraction was carried out with acetonitrile followed by acetonitrile/water (1/1) and the extracted test compounds were quantified by HPLC-MS. The following $DT_{50}$ values (referring to 20° C.) were obtained assuming single first order (SFO) or double first order in parallel (DFOP) kinetics:

With a $DT_{50}$ of 41 days, compound (I-B-131) was significantly faster degraded in the neutral sandy loam soil LUFA 5M than compound (I-B-33) which degraded with a $DT_{50}$ of 89 days.

From an environmental perspective, this is an advantage of compound (I-B-131) over compound (I-B-33).

The closest state of the art is the EPA Pesticide Fact Sheet of chlorantraniliprole, found on www.epa.gov/opp00001/chem_search/reg_actions/registration/fs_PC-090100_01-Apr-08.pdf, in which the compound (I-B-33) is disclosed (IN-F9N04, page 13).

The difference between compound (I-B-131) and (I-B-33) is only the substituent at the pyrazole ring, which is trifluoromethyl in the case of (I-B-131) instead of bromo in the case of (I-B-33).

The technical difference resulting therefrom is that the halflife value $DT_{50}$ is significantly lower, i.e. that it is degraded faster in the soil.

The aim of the present invention was therefore to find substances with a faster degradability in the soil.

There was no hint in the mentioned closest state of the art that the substitution of the bromo atom by a trifluoromethyl group would lead to the desired effect.

A person skilled in the art would not have expected that the structurally related compounds (I-B-131) and (I-B-33) show such a difference in behaviour.

Embodiment C

In embodiment C, the invention relates to compounds, mixtures, methods and uses of compounds of formula (I-C)

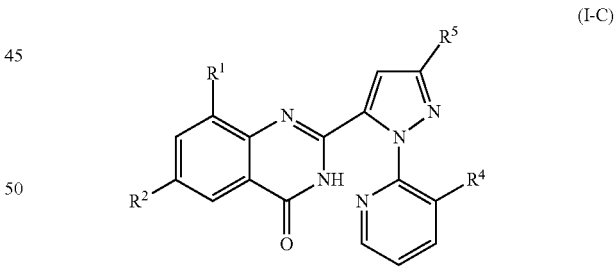

(I-C)

wherein
$R^1$ is selected from the group consisting of halogen, methyl and halomethyl;
$R^2$ is selected from the group consisting of hydrogen, halogen, halomethyl and cyano;
$R^4$ is hydrogen or halogen;
$R^5$ is selected from fluoro, bromo, chloro, difluoromethyl, trifluoromethyl, nitro, cyano, $OCH_3$, $OCF_3$, $OCHF_2$, $OCH_2F$, $OCH_2CF_3$;
or a stereoisomer, salt, tautomer or N-oxide thereof, or a polymorphic crystalline form, a co-crystal or a solvate of a compound or a stereoisomer, salt, tautomer or N-oxide thereof.

The compounds of Embodiment C are quinazolinone compounds.

The compounds described in Embodiment C, i.e. compounds of formula I-C, and also in individualized form, may be useful in the mixtures, methods, uses, processes as described in embodiments E1 to E10. They may also be useful in itself, e.g. as marker for the presence of precursor compounds. Precursor compounds of compounds of formula (I-C) are compounds, which degrade under certain conditions to compounds of formula (I-C).

Preferred are compounds of formula (I-C), wherein $R^1$ is selected from the group consisting of bromo, chloro, methyl;

$R^2$ is selected from the group consisting of chloro, cyano, methyl;

$R^4$ is chloro;

$R^5$ is selected from bromo, chloro, difluoromethyl, trifluoromethyl.

Especially preferred compounds are compounds of formula (I-C) as listed in table C.

TABLE C

| Compound No. | $R^1$ | $R^2$ | $R^4$ | $R^5$ |
|---|---|---|---|---|
| I-C-1 | Br | Cl | Cl | Br |
| I-C-2 | Br | Cl | Cl | Cl |
| I-C-3 | Br | Cl | Cl | $CF_3$ |
| I-C-4 | Br | Cl | Cl | $CHF_2$ |
| I-C-5 | Br | CN | Cl | Br |
| I-C-6 | Br | CN | Cl | Cl |
| I-C-7 | Br | CN | Cl | $CF_3$ |
| I-C-8 | Br | CN | Cl | $CHF_2$ |
| I-C-9 | Br | $CH_3$ | Cl | Br |
| I-C-10 | Br | $CH_3$ | Cl | Cl |
| I-C-11 | Br | $CH_3$ | Cl | $CF_3$ |
| I-C-12 | Br | $CH_3$ | Cl | $CHF_2$ |
| I-C-13 | Br | Br | Cl | Br |
| I-C-14 | Br | Br | Cl | Cl |
| I-C-15 | Br | Br | Cl | $CF_3$ |
| I-C-16 | Br | Br | Cl | $CHF_2$ |
| I-C-17 | Cl | Cl | Cl | Br |
| I-C-18 | Cl | Cl | Cl | Cl |
| I-C-19 | Cl | Cl | Cl | $CF_3$ |
| I-C-20 | Cl | Cl | Cl | $CHF_2$ |
| I-C-21 | Cl | CN | Cl | Br |
| I-C-22 | Cl | CN | Cl | Cl |
| I-C-23 | Cl | CN | Cl | $CF_3$ |
| I-C-24 | Cl | CN | Cl | $CHF_2$ |
| I-C-25 | Cl | $CH_3$ | Cl | Br |
| I-C-26 | Cl | $CH_3$ | Cl | Cl |
| I-C-27 | Cl | $CH_3$ | Cl | $CF_3$ |
| I-C-28 | Cl | $CH_3$ | Cl | $CHF_2$ |
| I-C-29 | Cl | Br | Cl | Br |
| I-C-30 | Cl | Br | Cl | Cl |
| I-C-31 | Cl | Br | Cl | $CF_3$ |
| I-C-32 | Cl | Br | Cl | $CHF_2$ |
| I-C-33 | $CH_3$ | Cl | Cl | Br |
| I-C-34 | $CH_3$ | Cl | Cl | Cl |
| I-C-35 | $CH_3$ | Cl | Cl | $CF_3$ |
| I-C-36 | $CH_3$ | Cl | Cl | $CHF_2$ |
| I-C-37 | $CH_3$ | CN | Cl | Br |
| I-C-38 | $CH_3$ | CN | Cl | Cl |
| I-C-39 | $CH_3$ | CN | Cl | $CF_3$ |
| I-C-40 | $CH_3$ | CN | Cl | $CHF_2$ |
| I-C-41 | $CH_3$ | $CH_3$ | Cl | Br |
| I-C-42 | $CH_3$ | $CH_3$ | Cl | Cl |
| I-C-43 | $CH_3$ | $CH_3$ | Cl | $CF_3$ |
| I-C-44 | $CH_3$ | $CH_3$ | Cl | $CHF_2$ |
| I-C-45 | $CH_3$ | Br | Cl | Br |
| I-C-46 | $CH_3$ | Br | Cl | Cl |
| I-C-47 | $CH_3$ | Br | Cl | $CF_3$ |
| I-C-48 | $CH_3$ | Br | Cl | $CHF_2$ |

Special preference is given to compound (I-C-35):

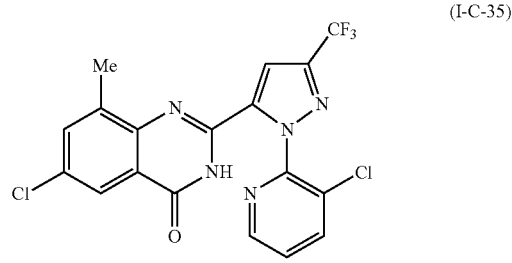 [SMILES: Cc1cc(Cl)cc2c(=O)[nH]c(-c3cc(C(F)(F)F)nn3-c3ncccc3Cl)nc12]

(I-C-35)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

Compound (I-B-131) is a precursor of compound (I-C-35), which is therefore useful as a marker for the presence of (I-B-131).

Special preference is also given to compound (I-C-36):

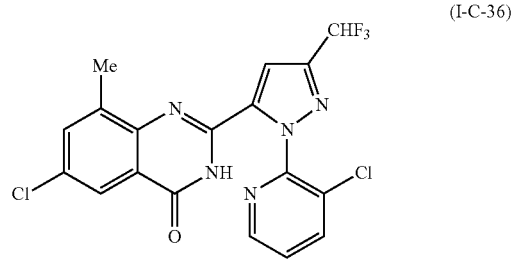

(I-C-36)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-C-19):

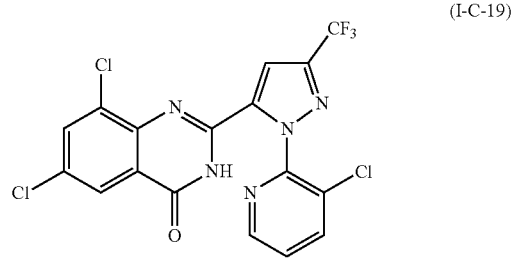 [SMILES: O=c1[nH]c(-c2cc(C(F)(F)F)nn2-c2ncccc2Cl)nc2c(Cl)cc(Cl)cc12]

(I-C-19)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-C-33):

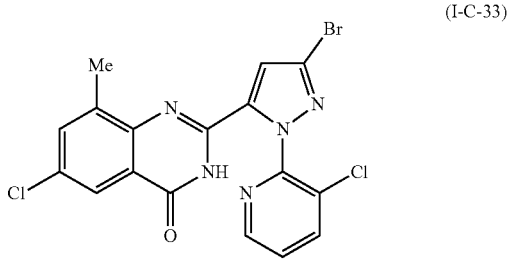

(I-C-33)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-C-37):

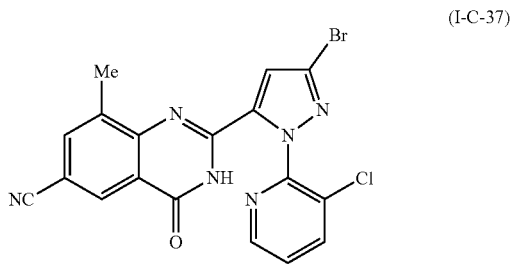 [SMILES: Cc1cc(C#N)cc2c(=O)[nH]c(-c3cc(Br)nn3-c3ncccc3Cl)nc12]

(I-C-37)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-C-39):

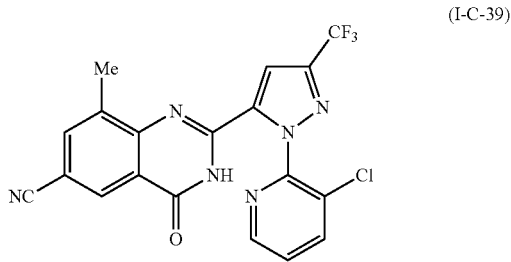 [SMILES: Cc1cc(C#N)cc2c(=O)[nH]c(-c3cc(C(F)(F)F)nn3-c3ncccc3Cl)nc12]

(I-C-39)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In a further aspect of the invention, the invention relates to compound (I-C-40):

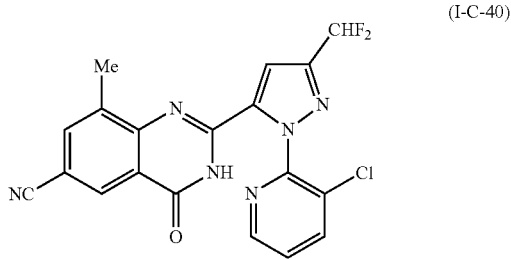 [SMILES: Cc1cc(C#N)cc2c(=O)[nH]c(-c3cc(C(F)F)nn3-c3ncccc3Cl)nc12]

(I-C-40)

and, in the context of this invention, as mentioned above, also to a stereoisomer, salt, tautomer or N-oxide, or a polymorphic crystalline form or a solvate of a stereoisomer, salt, tautomer or N-oxide thereof, and to mixtures, methods and uses thereof.

In accordance with the examples and analytical procedures as described under Embodiment B, the following example was prepared:

Example 11

6-chloro-2-[2-(3-chloro-2-pyridyl)-5-(trifluoromethyl)pyrazol-3-yl]-8-methyl-1H-quinazolin-4-one
(I-C-35)

To a suspension of N-(2-carbamoyl-4-chloro-6-methylphenyl)-2-(3-chloro-2-pyridyl)-5-(trifluoromethyl)pyrazole-3-carboxamide (from Example 1=Compound (I-B-131], 570 g) in methanol (1.5 L) was added NaOH (1.18 kg of a 5% aqueous solution). The mixture was stirred at 55-60° C. for 4 hours and cooled. Water (5 L) was added and the pH was adjusted to 1 by addition of aqueous hydrochloric acid. The resulting solids were collected by filtration, washed with water and dried in vacuum at 55° C. to obtain the title compound (550 g, with a 90% purity, 95% yield).

Characterization by $^1$H-NMR (400 MHz, DMSO-$d_6$) [delta]: 13.12 (s, 1H), 8.59 (d, 1H), 8.33 (d, 1H), 7.96 (s, 1H), 7.88 (d, 1H), 7.75 (m, 1H), 7.63 (m, 1H), 1.68 (s, 3H).

Special preference is given to the compounds I-C-35 and I-C-36, in particular to compound I-C-35.

The compounds of embodiment A, B, C are referred to as "compounds I" herein or as "compounds according to the invention".

Special preference is given to the compounds of Table ABC.

TABLE ABC

| Comp. I |
|---|
| I-A-1 |
| I-A-28 |
| I-B-115 |
| I-B-131 |
| I-B-132 |
| I-C-19 |
| I-C-35 |
| I-C-36 |

In one embodiment CL-2, the invention relates to the following sub-embodiments:

Embodiment CL-2-1: Anthranilamide Compounds of Formula (I-0-H)

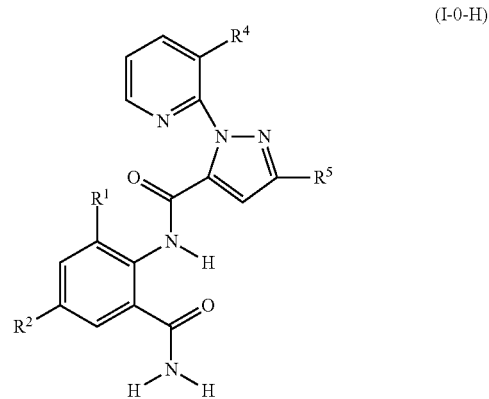

(I-0-H)

wherein
R¹ is selected from the group consisting of halogen, methyl and halomethyl;
R² is selected from the group consisting of hydrogen, halogen, halomethyl and cyano;
R⁴ is hydrogen or halogen;
R⁵ is selected from fluoro, bromo, chloro, difluoromethyl, trifluoromethyl, nitro, cyano, $OCH_3$, $OCF_3$, $OCHF_2$, $OCH_2F$, $OCH_2CF_3$;
or a stereoisomer, salt, tautomer or N-oxide, or a polymorphic crystalline form, a co-crystal or a solvate of a compound or a stereoisomer, salt, tautomer or N-oxide thereof.

Embodiment CL-2-2: Anthranilamide compound according to embodiment CL-2-1, which is the compound (I-B-131):

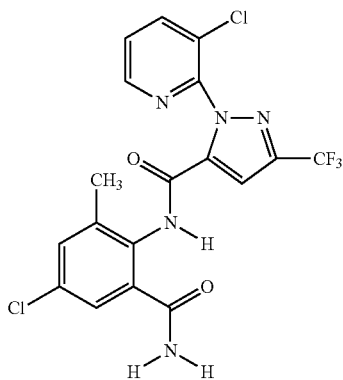

(I-B-131)

or a stereoisomer, salt, tautomer or N-oxide, or a polymorphic crystalline form, a co-crystal or a solvate of a compound or a stereoisomer, salt, tautomer or N-oxide thereof.

Embodiment CL-2-2a: Anthranilamide compound according to embodiment CL-2-1, which is the compound (I-B-115):

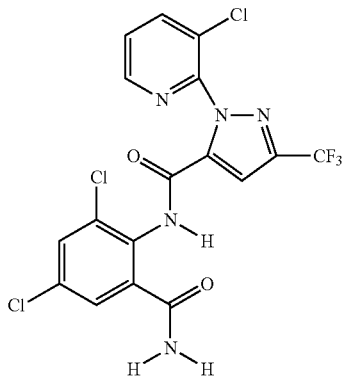

(I-B-115)

or a stereoisomer, salt, tautomer or N-oxide, or a polymorphic crystalline form, a co-crystal or a solvate of a compound or a stereoisomer, salt, tautomer or N-oxide thereof.

Embodiment CL-2-3: Anthranilamide compound according to embodiment CL-2-1, which is the compound (I-B-132):

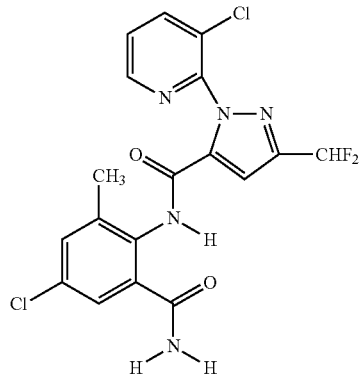

(I-B-132)

or a stereoisomer, salt, tautomer or N-oxide, or a polymorphic crystalline form, a co-crystal or a solvate of a compound or a stereoisomer, salt, tautomer or N-oxide thereof.

Embodiment CL-2-4: Compound (I-C-35):

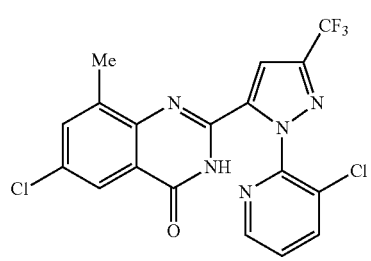

(I-C-35)

or a stereoisomer, salt, tautomer or N-oxide, or a polymorphic crystalline form, a co-crystal or a solvate of a compound or a stereoisomer, salt, tautomer or N-oxide thereof.

Embodiment CL-2-5: Compound (I-C-36):

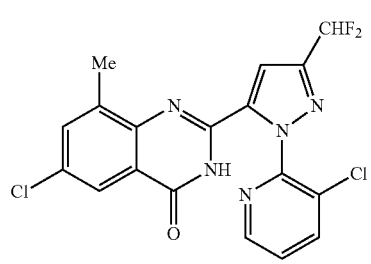

(I-C-36)

or a stereoisomer, salt, tautomer or N-oxide, or a polymorphic crystalline form, a co-crystal or a solvate of a compound or a stereoisomer, salt, tautomer or N-oxide thereof.

Embodiment CL-2-5a: Compound (I-C-19):

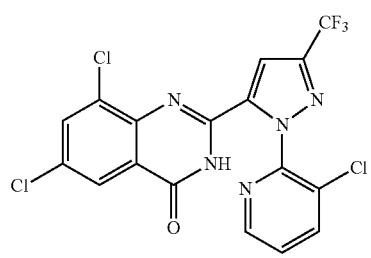

(I-C-19)

or a stereoisomer, salt, tautomer or N-oxide, or a polymorphic crystalline form, a co-crystal or a solvate of a compound or a stereoisomer, salt, tautomer or N-oxide thereof.

Embodiment CL-2-6: Mixture of a compound according to any of embodiments CL-2-1 to CL-2-5 (including the alternative embodiments CL-2-2a and CL-2-5a) with an insecticide.

Embodiment CL-2-7: Mixture of a compound according to any of embodiments CL-2-1 to CL-2-5 (including the alternative embodiments CL-2-2a and CL-2-5a) with a fungicide.

Embodiment CL-2-8: Use of at least one compound or mixture according to any of the preceding embodiments for controlling and/or combating animal pests in soil application methods and seed treatment methods, wherein the active compound is applied directly and/or indirectly to the plant and/or to plant propagation material by drenching the soil, by drip application onto the soil, by soil injection, by dipping or by treatment of seeds.

Embodiment CL-2-9: A method for controlling pests and/or increasing the plant health of a cultivated plant with at least one modification as compared to the respective non-modified control plant, comprising the application of at least one compound or mixture according to any of embodiments CL-2-1 to CL-2-5 (including the alternative embodiments CL-2-2a and CL-2-5a) a plant with at least one modification, parts of such plant, plant propagation material, or at its locus of growth.

Embodiment CL-2-10: A method for controlling non-crop pests, comprising contacting the pests or their food supply, habitat, breeding grounds or their locus with at least one compound according to any of embodiments CL-2-1 to CL-2-5 (including the alternative embodiments CL-2-2a and CL-2-5a).

Embodiment CL-2-11: Netting or textile material, impregnated with a compound according to any of embodiments CL-2-1 to CL-2-5 (including the alternative embodiments CL-2-2a and CL-2-5a), or a mixture thereof.

Embodiment CL-2-12: A method for controlling a population of social insects, comprising contacting the pests or their food supply, habitat, breeding grounds or their locus with at least one compound according to any of embodiments CL-2-1 to CL-2-5 (including the alternative embodiments CL-2-2a and CL-2-5a), or a mixture thereof.

Embodiment CL-2-13: Use of a compound according to any of embodiments CL-2-1 to CL-2-5 (including the alternative embodiments CL-2-2a and CL-2-5a), or a mixture thereof, or a composition comprising said compound,
for controlling non-crop pests, and/or
for controlling flies, mosquitoes (Diptera), and/or
for protecting stored products, and/or
for protecting stored tobacco, nuts, cocoa, fruits, and/or
for controlling resistant mosquitoes and/or bed bugs, and/or
for controlling a population of social insects, and/or
for controlling termites (Isoptera), and/or
for controlling ants (Hymenoptera), and/or
for controlling crickets, grasshoppers, locusts (Orthoptera).

Embodiment CL-2-14: A method of improving plant health, which method comprises applying at least one compound according to any of embodiments CL-2-1 to CL-2-5 (including the alternative embodiments CL-2-2a and CL-2-5a), or a mixture thereof, or a composition comprising said compound.

Embodiment CL-2-15: A method for reducing nitrous oxide emission from soils comprising treating a plant growing on the respective soil and/or the locus where the plant is growing or is intended to grow and/or the seeds from which the plant grows with at least one compound according to any of embodiments CL-2-1 to CL-2-5 (including the alternative embodiments CL-2-2a and CL-2-5a), or a mixture thereof, or a composition comprising said compound.

Embodiment CL-2-16: Use of at least one compound according to any of embodiments CL-2-1 to CL-2-5 (including the alternative embodiments CL-2-2a and CL-2-5a), or a mixture thereof, or a composition comprising said compound, for reducing insect-vectored viral infection in a plant.

Embodiment CL-2-17: A method of controlling insects, which are resistant to an insecticide, which method comprises applying to said insecticide resistant insects at least one compound according to any of embodiments CL-2-1 to CL-2-5 (including the alternative embodiments CL-2-2a and CL-2-5a), or a mixture thereof, or a composition comprising said compound.

Embodiment CL-2-18: Method according to claim embodiment CL-2-17, wherein the insecticide to which the insect is resistant, is a ryanodin-modulator insecticide.

Embodiments of Methods and Uses

Embodiment E1-General

The details given in E1, including preferences and examples, are valid on their own and also in the embodiments E2 to E10.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new and more effective agents for combating invertebrate pests, in particular insects, arachnids and nematodes.

It is an object of the present invention to provide further compounds having a high pesticidal activity against invertebrate pests, in particular against insect, arachnid or nematode pest. The compounds should show a broad activity spectrum against a large number of different invertebrate pests, in particular against difficult to control insects, arachnids, acarids and nematodes. It can also be advantageous if the compounds allow to control specific pests which are difficult to control, or if they allow the application on a certain crop. The compounds should have properties which allow to prepare stable and active compositions therefrom.

Furthermore, there is a desire for pesticide compounds or combination of compounds, which when applied improve plants, which may result in "plant health", "vitality of plant propagation material" or "increased plant yield".

It is therefore an object of the present invention to provide agricultural combinations which solves one or more than one of the discussed problems as
reducing the dosage rate,
enhancing the spectrum of activity,
combining knock-down activity with prolonged control,
improving resistance management,
Improved plant health;
Improved vitality of plant propagation material, also termed seed vitality;
Increased plant yield.

It has been found that the above objectives can be achieved by certain anthranilamide compounds of the general formula (I), as defined herein, including their stereoisomers, salts (in particular their agriculturally or veterinarily acceptable salts), tautomers and N-oxides.

Moreover, the present invention also relates to and includes the following embodiments:

- an agricultural or veterinary composition comprising at least one compound of formula (I) or a stereoisomer, salt (in particular an agriculturally or veterinarily acceptable salts), tautomer, or N-oxide thereof (=compound according to the invention), and at least one liquid and/or solid carrier.
- a method for combating or controlling invertebrate pests, which method comprises contacting said pest or its food supply, habitat or breeding grounds with a pesticidally effective amount of at least one compound according to the invention, or a composition as defined herein.
- a method for protecting growing plants from attack or infestation by invertebrate pests, which method comprises contacting a plant, or soil or water in which the plant is growing, with a pesticidally effective amount of at least one compound according to the invention, or a composition as defined herein.
- a method for the protection of plant propagation material, especially seeds, from soil insects and of the seedlings' roots and shoots from soil and foliar insects comprising contacting the plant propagation material respectively seeds before sowing and/or after pregermination with at least one compound according to the invention, or a composition as defined herein.
- seed comprising a compound according to the invention, in an amount of from 0.1 g to 10 kg per 100 kg of the plant propagation material.
- use of a compound according to the invention, or a composition as defined herein for combating or controlling invertebrate pests of the group of insects, arachnids or nematodes.
- use of a compound according to the invention, or a composition as defined herein for protecting growing plants from attack or infestation by invertebrate pests.
- use of a compound according to the invention or a composition as defined herein for combating or controlling invertebrate parasites in and on animals.
- a method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasiticidally effective amount of a compound according to the invention, or a composition as defined in claim herein.
- a compound according to the invention for use as a medicament.
- a compound according to the invention for use in the treatment, control, prevention or protection of animals against infestation or infection by parasites.

Pests

The details like the pests given in E1, including preferences and examples, are valid on their own and also in the embodiments E2 to E10.

The compounds and mixtures according to the invention are in particular suitable for efficiently controlling arthropodal pests such as arachnids, myriapedes and insects as well as nematodes.

The compounds and mixtures according to the invention are especially suitable for efficiently combating the following pests:

insects from the order of the lepidopterans (Lepidoptera), for example *Acronicta major, Adoxophyes orana, Aedia leucomelas, Agrotis* spp. such as *Agrotis fucosa, Agrotis segetum, Agrotis ypsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea; Heliothis* spp. such as *Heliothis armigera, Heliothis virescens, Heliothis zea; Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua; Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha; Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis; Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae; Plathypena scabra, Plutella maculipennis, Plutella xyostella, Prodenia* spp., *Pseudaletia* spp., *Pseudoplusia includens, Pyrausta nubilalis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera litura, Thaumatopoea pityocampa, Thermesia gemmatalis, Tinea pellionella, Tineola bisselliella, Tortrix viridana, Trichoplusia* spp. such as *Trichoplusia ni; Tuta absoluta*, and *Zeiraphera canadensis*, beetles (Coleoptera), for example *Acanthoscehdes obtectus, Adoretus* spp., *Agelastica aln, Agrilus sinuatus, Agriotes* spp. such as *Agriotes fuscicollis, Agriotes lineatus, Agriotes obscurus; Amphimallus solstitialis, Anisandrus dispar, Anobium punctatum, Anomala rufocuprea, Anoplophora* spp. such as *Anoplophora glabripennis; Anthonomus* spp. such as *Anthonomus grandis, Anthonomus pomorum; Anthrenus* spp., *Aphthona euphoridae, Apogonia* spp., *Athous haemorrhoidalis, Atomaria* spp. such as *Atomaria linearis; Attagenus* spp., *Aulacophora femoralis, Blastophagus piniperda, Blitophaga undata, Bruchidius obtectus, Bruchus* spp. such as *Bruchus lentis, Bruchus pisorum, Bruchus rufimanus; Byctiscus betulae, Callosobruchus chinensis, Cassida nebulosa, Cerotoma trifurcata, Cetonia aurata, Ceuthorhynchus* spp. such as *Ceuthorrhynchus assimilis, Ceuthorrhynchus napi; Chaetocnema tibialis, Cleonus mendicus, Conoderus* spp.

such as *Conoderus vespertinus*; *Cosmopolites* spp., *Costelytra zealandica*, *Crioceris asparagi*, *Cryptorhynchus lapath*, *Ctenicera* ssp. such as *Ctenicera destructor*; *Curculio* spp., *Dectes texanus*, *Dermestes* spp., *Diabrotica* spp. such as *Diabrotica 12-punctata Diabrotica speciosa*, *Diabrotica longicornis*, *Diabrotica semipunctata*, *Diabrotica virgifera*; *Epilachna* spp. such as *Epilachna varivestis*, *Epilachna vigintioctomaculata*; *Epitrix* spp. such as *Epitrix hirtipennis*; *Eutinobothrus brasiliensis*, *Faustinus cubae*, *Gibbium psylloides*, *Heteronychus arator*, *Hylamorpha elegans*, *Hylobius abietis*, *Hylotrupes bajulus*, *Hypera brunneipennis*, *Hypera postica*, *Hypothenemus* spp., *Ips typographus*, *Lachnosterna consanguinea*, *Lema bilineata*, *Lema melanopus*, *Leptinotarsa* spp. such as *Leptinotarsa decemlineata*, *Limonius californicus*, *Lissorhoptrus oryzophilus*, *Lissorhoptrus oryzophilus*, *Lixus* spp., *Lyctus* spp. such as *Lyctus bruneus*; *Melanotus communis*, *Meligethes* spp. such as *Meligethes aeneus*; *Melolontha hippocastani*, *Melolontha melolontha*, *Migdolus* spp., *Monochamus* spp. such as *Monochamus alternatus*; *Naupactus xanthographus*, *Niptus hololeucus*, *Oryctes rhinoceros*, *Oryzaephilus surinamensis*, *Otiorrhynchus sulcatus*, *Otiorrhynchus ovatus*, *Otiorrhynchus sulcatus*, *Oulema oryzae*, *Oxycetoniajucunda*, *Phaedon cochleariae*, *Phyllobius pyri*, *Phyllopertha horticola*, *Phyllophaga* spp., *Phyllotreta* spp. such as *Phyllotreta chrysocephala*, *Phyllotreta nemorum*, *Phyllotreta striolata*; *Phyllophaga* spp., *Phyllopertha horticola*, *Popillia japonica*, *Premnotrypes* spp., *Psylliodes chrysocephala*, *Ptinus* spp., *Rhizobius ventralis*, *Rhizopertha dominica*, *Sitona lineatus*, *Sitophilus* spp. such as *Sitophilus granaria*, *Sitophilus zeamais*; *Sphenophorus* spp. such as *Sphenophorus levis*; *Sternechus* spp. such as *Sternechus subsignatus*; *Symphyletes* spp., *Tenebrio molitor*, *Tribolium* spp. such as *Tribolium castaneum*; *Trogoderma* spp., *Tychius* spp., *Xylotrechus* spp., and *Zabrus* spp. such as *Zabrus tenebrioides*, flies, mosquitoes (Diptera), e.g. *Aedes* spp. such as *Aedes aegypti*, *Aedes albopictus*, *Aedes vexans*; *Anastrepha ludens*, *Anopheles* spp. such as *Anopheles albimanus*, *Anopheles crucians*, *Anopheles freeborni*, *Anopheles gambiae*, *Anopheles leucosphyrus*, *Anopheles maculipennis*, *Anopheles minimus*, *Anopheles quadrimaculatus*, *Anopheles sinensis*; *Bibio hortulanus*, *Calliphora erythrocephala*, *Calliphora vicina*, *Cerafitis capitata*, *Ceratitis capitata*, *Chrysomyia* spp. such as *Chrysomya bezziana*, *Chrysomya hominivorax*, *Chrysomya macellaria*; *Chrysops atlanticus*, *Chrysops discalis*, *Chrysops silacea*, *Cochliomyia* spp. such as *Cochliomyia hominivorax*; *Contarinia* spp. such as *Contarinia sorghicola*; *Cordylobia anthropophaga*, *Culex* spp. such as *Culex nigripalpus*, *Culex pipiens*, *Culex quinquefasciatus*, *Culex tarsalis*, *Culex tritaeniorhynchus*; *Culicoides furens*, *Culiseta inornata*, *Culiseta melanura*, *Cuterebra* spp., *Dacus cucurbitae*, *Dacus oleae*, *Dasineura brassicae*, *Delia* spp. such as *Delia antique*, *Delia coarctata*, *Delia platura*, *Delia radicum*; *Dermatobia hominis*, *Drosophila* spp., *Fannia* spp. such as *Fannia canicularis*; *Gastraphilus* spp. such as *Gasterophilus intestinalis*; *Geomyza Tripunctata*, *Glossina fuscipes*, *Glossina morsitans*, *Glossina palpalis*, *Glossina tachinoides*, *Haematobia irritans*, *Haplodiplosis equestris*, *Hippelates* spp., *Hylemyia* spp. such as *Hylemyia platura*; *Hypoderma* spp. such as *Hypoderma lineata*; *Hyppobosca* spp., *Leptoconops torrens*, *Liriomyza* spp. such as *Liriomyza sativae*, *Liriomyza trifolii*; *Lucilia* spp. such as *Lucilia caprina*, *Lucilia cuprina*, *Lucilia sericata*; *Lycoria pectoralis*, *Mansonia titillanus*, *Mayetiola* spp. such as *Mayetiola destructor*; *Musca* spp. such as *Musca autumnalis*, *Musca domestica*; *Muscina stabulans*, *Oestrus* spp. such as *Oestrus ovis*; *Opomyza florum*, *Oscinella* spp. such as *Oscinella frit*; *Pegomya hysocyami*, *Phlebotomus argentipes*, *Phorbia* spp. such as *Phorbia antiqua*, *Phorbia brassicae*, *Phorbia coarctata*; *Prosimulium mixtum*, *Psila rosae*, *Psorophora columbiae*, *Psorophora discolor*, *Rhagoletis cerasi*, *Rhagoletis pomonella*, *Sarcophaga* spp. such as *Sarcophaga haemorrhoidalis*; *Simulium vittatum*, *Stomoxys* spp. such as *Stomoxys calcitrans*; *Tabanus* spp. such as *Tabanus atratus*, *Tabanus bovinus*, *Tabanus lineola*, *Tabanus similis*; *Tannia* spp., *Tipula oleracea*, *Tipula paludosa*, and *Wohlfahrtia* spp., thrips (Thysanoptera), e.g. *Baliothrips biformis*, *Dichromothrips corbetti*, *Dichromothrips* ssp., *Enneothrips flavens*, *Frankliniella* spp. such as *Frankliniella fusca*, *Frankliniella occidentalis*, *Frankliniella tritici*; *Heliothrips* spp., *Hercinothrips femoralis*, *Kakothrips* spp., *Rhipiphorothrips cruentatus*, *Scirtothrips* spp. such as *Scirtothrips citri*; *Taeniothrips cardamoni*, *Thrips* spp. such as *Thrips oryzae*, *Thrips palmi*, *Thrips tabaci*;

termites (Isoptera), e.g. *Calotermes flavicollis*, *Coptotermes formosanus*, *Heterotermes aureus*, *Heterotermes longiceps*, *Heterotermes tenuis*, *Leucotermes flavipes*, *Odontotermes* spp., *Reticulitermes* spp. such as *Reticulitermes speratus*, *Reticulitermes flavipes*, *Reticulitermes grassei*, *Reticulitermes lucifugus*, *Reticulitermes santonensis*, *Reticulitermes virginicus*; *Termes natalensis*, cockroaches (Blattaria—Blattodea), e.g. *Acheta domesticus*, *Blatta orientalis*, *Blattella asahinae*, *Blattella germanica*, *Gryllotalpa* spp., *Leucophaea maderae*, *Locusta* spp., *Melanoplus* spp., *Periplaneta americana*, *Periplaneta australasiae*, *Periplaneta brunnea*, *Periplaneta fuligginosa*, *Periplaneta japonica*, bugs, aphids, leafhoppers, whiteflies, scale insects, cicadas (Hemiptera), e.g. *Acrosternum* spp. such as *Acrosternum hilare*; *Acyrthosipon* spp. such as *Acyrthosiphon onobrychis*, *Acyrthosiphon pisum*; *Adelges laricis*, *Aeneolamia* spp., *Agonoscena* spp., *Aleurodes* spp., *Aleurolobus barodensis*, *Aleurothrixus* spp., *Amrasca* spp., *Anasa tristis*, *Antestiopsis* spp., *Anuraphis cardui*, *Aonidiella* spp., *Aphanostigma piri*, *Aphidula nasturtii*, *Aphis* spp. such as *Aphis fabae*, *Aphis forbesi*, *Aphis gossypii*, *Aphis grossulariae*, *Aphis pomi*, *Aphis sambuci*, *Aphis schneider*, *Aphis spiraecola*, *Arboridia apicalis*, *Arilus critatus*, *Aspidiella* spp., *Aspidiotus* spp., *Atanus* spp., *Aulacorthum solani*, *Bemisia* spp. such as *Bemisia argentifolii*, *Bemisia tabaci*; *Blissus* spp. such as *Blissus leucopterus*; *Brachycaudus cardui*, *Brachycaudus helichrysi*, *Brachycaudus persicae*, *Brachycaudus prunicola*, *Brachycolus* spp., *Brevicoryne brassicae*, *Calligypona marginata*, *Calocoris* spp., *Campylomma livida*, *Capitophorus horni*, *Carneocephala fulgida*, *Cavelerius* spp., *Ceraplastes* spp., *Ceratovacuna lanigera*, *Cercopidae*, *Cerosipha gossypii*, *Chaetosiphon fragaefolii*, *Chionaspis tegalensis*, *Chlorita onukii*, *Chromaphis juglandicola*, *Chrysomphalus ficus*, *Cicadulina mbila*, *Cimex* spp. such as *Cimex hemipterus*, *Cimex lectularius*; *Coccomytilus halli*, *Coccus* spp., *Creontiades dilutus*, *Cryptomyzus ribis*, *Cryptomyzus ribis*, *Cyrtopeltis notatus*, *Dalbulus* spp., *Dasynus piperis*, *Dialeurades* spp., *Diaphorina* spp., *Diaspis* spp., *Dichelops furcatus*, *Diconocoris hewetti*, *Doralis* spp., *Dreyfusia nordmannianae*, *Dreyfusia piceae*, *Drosicha* spp., *Dysaphis* spp. such as *Dysaphis plantaginea*, *Dysaphis pyri*, *Dysaphis radicola*, *Dysaulacorthum pseudosolani*, *Dysdercus* spp. such as *Dysdercus cingulatus*, *Dysdercus* intermedius; Dysmicoccus spp., Empoasca spp. such as Empoasca fabae, Empoasca solana, Eriosoma spp., Erythroneura spp., Eurygaster spp. such as Eurygaster integriceps; Euscelis bilobatus, Euschistus spp. such as Euschistuos heros, Euschistus impictiventris, Euschistus servus; Geococcus coffeae, Halyomorpha spp. such as Halyomorpha halys; Heliopeltis spp., Homalodisca coagulata, Horcias nobilellus, Hyalopterus pruni, Hyperomyzus lactucae, Icerya spp., Idiocerus spp., Idioscopus spp., Laodelphax striatellus, Lecanium spp., Lepidosaphes spp., Leptocorisa spp., Leptoglossus phyllopus, Lipaphis erysimi, Lygus spp. such as Lygus hesperus, Lygus lineolaris, Lygus pratensis; Macropes excavatus, Macrosiphum spp. such as Macrosiphum rosae, Macrosiphum avenae, Macrosiphum euphorbiae; Mahanarva fimbriolata, Megacopta cribraria, Megoura viciae, Melanaphis pyrarius, Melanaphis sacchari, Metcafiella spp., Metopolophium dirhodum, Miridae spp., Monellia costalis, Monelliopsis pecanis, Myzus spp. such as Myzus ascalonicus, Myzus cerasi, Myzus persicae, Myzus varians; Nasonovia ribis-nigri, Nephotettix spp. such as Nephotettix malayanus, Nephotettix nigropictus, Nephotettix parvus, Nephotettix virescens; Nezara spp. such as Nezara viridula; Nilaparvata lugens, Oebalus spp., Oncometopia spp., Orthezia praelonga, Parabemisia myricae, Paratrioza spp., Parlatoria spp., Pemphigus spp. such as Pemphigus bursarius; Pentomidae, Peregrinus maidis, Perkinsiella saccharicida, Phenacoccus spp., Phloeomyzus passerinii, Phorodon humul, Phylloxera spp., Piesma quadrata, Piezodorus spp. such as Piezodorus guildinii, Pinnaspis aspidistrae, Planococcus spp., Protopulvinaria pyriformis, Psallus seriatus, Pseudacysta persea, Pseudaulacaspis pentagona, Pseudococcus spp. such as Pseudococcus comstocki; Psylla spp. such as Psylla mali, Psylla piri; Pteromalus spp., Pyrilla spp., Quadraspidiotus spp., Quesada gigas, Rastrococcus spp., Reduvius senilis, Rhodnius spp., Rhopalomyzus ascalonicus, Rhopalosiphum spp. such as Rhopalosiphum pseudobrassicas, Rhopalosiphum insertum, Rhopalosiphum maidis, Rhopalosiphum padi; Sagatodes spp., Sahibergella singularis, Saissetia spp., Sappaphis mala, Sappaphis mali, Scaphoides titanus, Schizaphis graminum, Schizoneura lanuginosa, Scotinophora spp., Selenaspidus articulatus, Sitobion avenae, Sogata spp., Sogatella furcifera, Solubea insularis, Stephanitis nashi, Stictocephala festina, Tenalaphara malayensis, Thyanta spp. such as Thyanta perditor; Tibraca spp., Tinocallis caryaefoliae, Tomaspis spp., Toxoptera spp. such as Toxoptera aurantii; Trialeurodes spp. such as Trialeurodes vaporariorum; Triatoma spp., Trioza spp., Typhlocyba spp., Unaspis spp. such as Unaspis yanonensis; and Viteus vitifoli, ants, bees, wasps, sawflies (Hymenoptera), e.g. Athalia rosae, Atta capiguara, Atta cephalotes, Atta cephalotes, Atta laevigata, Atta robusta, Atta sexdens, Atta texana, Bombus spp., Camponotus floridanus, Crematogaster spp., Dasymutilla occidentalis, Diprion spp., Dolichovespula maculata, Hoplocampa spp. such as Hoplocampa minuta, Hoplocampa testudinea; Lasius spp. such as Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenopsis geminata, Solenopsis invicta, Solenopsis richter, Solenopsis xyloni, Vespa spp. such as Vespa crabro, and Vespula squamosa, crickets, grasshoppers, locusts (Orthoptera), e.g. Acheta domestica, Calliptamus italicus, Chortoicetes termi-nifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus, and Zonozerus variegatus, arachnids (Arachnida), such as acari, e.g. of the families Argasidae, Ixodidae and Sarcoptidae, such as Amblyomma spp. (e.g. Amblyomma americanum, Amblyomma variegatum, Amblyomma maculatum), Argas spp. (e.g. Argas persicus), Boophilus spp. (e.g. Boophilus annulatus, Boophilus decoloratus, Boophilus microplus), Dermacentor silvarum, Dermacentor andersoni, Dermacentor variabilis, Hyalomma spp. (e.g. Hyalomma truncatum), Ixodes spp. (e.g. Ixodes ricinus, Ixodes rubicundus, Ixodes scapularis, Ixodes holocyclus, Ixodes pacificus), Ornithodorus spp. (e.g. Ornithodorus moubata, Ornithodorus hermsi, Ornithodorus turicata), Ornithonyssus bacoti, Otobius megnini, Dermanyssus gallinae, Psoroptes spp. (e.g. Psoroptes ovis), Rhipicephalus spp. (e.g. Rhipicephalus sanguineus, Rhipicephalus appendiculatus, Rhipicephalus evertsi), Rhizoglyphus spp., Sarcoptes spp. (e.g. Sarcoptes scabiei), and Eriophyidae spp. such as Acaria sheldoni, Aculops spp. (e.g. Aculops pelekassi) Aculus spp. (e.g. Aculus schlechtendali), Epitrimerus pyri, Phyllocoptruta oleivora and Eriophyes spp. (e.g. Eriophyes sheldoni); Tarsonemidae spp. such as Hemitarsonemus spp., Phytonemus pallidus and Polyphagotarsonemus latus, Stenotarsonemus spp.; Tenuipalpidae spp. such as Brevipalpus spp. (e.g. Brevipalpus phoenicis); Tetranychidae spp. such as Eotetranychus spp., Eutetranychus spp., Oligonychus spp., Tetranychus cinnabarinus, Tetranychus kanzawai, Tetranychus pacificus, Tetranychus telarius and Tetranychus urticae; Bryobia praetiosa, Panonychus spp. (e.g. Panonychus ulmi, Panonychus citri), Metatetranychus spp. and Oligonychus spp. (e.g. Oligonychus pratensis), Vasates lycopersici; Araneida, e.g. Latrodectus mactans, and Loxosceles reclusa. And Acarus siro, Chorioptes spp., Scorpio maurus fleas (Siphonaptera), e.g. Ceratophyllus spp., Ctenocephalides felis, Ctenocephalides canis, Xenopsylla cheopis, Pulex irritans, Tunga penetrans, and Nosopsyllus fasciatus, silverfish, firebrat (Thysanura), e.g. Lepisma saccharina and Thermobia domestica, centipedes (Chilopoda), e.g. Geophilus spp., Scutigera spp. such as Scutigera coleoptrata;

millipedes (Diplopoda), e.g. Blaniulus guttulatus, Narceus spp.,

Earwigs (Demnnaptera), e.g. forficula auricularia, lice (Phthiraptera), e.g. Damalinia spp., Pediculus spp. such as Pediculus humanus capitis, Pediculus humanus corporis; Pthirus pubis, Haematopinus spp. such as Haematopinus eurysternus, Haematopinus suis; Linognathus spp. such as Linognathus vituli; Bovicola bovis, Menopon gallinae, Menacanthus stramineus and Solenopotes capillatus, Trichodectes spp., springtails (Collembola), e.g. Onychiurus ssp. such as Onychiurus armatus, They are also suitable for controlling nematodes: plant parasitic nematodes such as root knot nematodes, Meloidogyne hapla, Meloidogyne incognita, Meloidogyne javanica, and other Meloidogyne species; cyst-forming nematodes, *Globodera rostochiensis* and other *Globodera* species; *Heterodera avenae, Heterodera glycines, Heterodera schachtii, Heterodera trifoli* and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus* Mamiya et Kiyohara, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaciand* other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species such as *Tylenchulus semipenetrans*; Dagger nematodes, *Xiphinema* species; and other plant parasitic nematode species.

Examples of further pest species which may be controlled by compounds of formula (I) include: from the class of the Bivalva, for example, *Dreissena* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus, Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*; from the order of the Isopoda, for example, *Armadillidium vulgare, Oniscus asellus, Porcellio scaber*; from the order of the Symphyla, for example, *Scutigerella immaculata*.

Further examples of pest species which may be controlled by compounds I include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. such as *Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucllia* spp., *Lyogenys fuscus, Mahanarva* spp., *Maladera matrida, Marasmia* spp., *Mastotermes* spp., *Mealybugs, Megascelis* ssp, *Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseolia oryzae; Oxycaraenus hyalinipennis, Plusia* spp., *Pomacea canaliculata, Procornitermes* ssp, *Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata, Sesamia* spp. such as *Sesamia inferens, Sogaella frucifera, Solenapsis geminata, Spissistilus* spp., *Stalk borer, Stenchaetothrips biformis, Steneotarsonemus spinki, Sylepta derogata, Telehin licus, Trichostrongylus* spp.

The compounds and mixtures of the present invention are particularly useful for controlling insects, preferably sucking or piercing insects such as insects from the genera Thysanoptera, Diptera and Hemiptera, and chewing-biting pests such as insects from the genera of Lepidoptera and Coleoptera, in particular the following species: Thysanoptera: *Frankiniella fusca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola*, and *Tabanus similis, Tipula oleracea*, and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae,*

*Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humul, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii.*

Lepidoptera, in particular: *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus ignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Putella xyostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

The compounds and mixtures of the present invention are particularly useful for controlling insects from the order of Coleoptera, in particular *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastan, Melolontha melolontha, Oulema oryzae, Otiorrhynchus sulcatus, Otiorrhynchus ovatus, Phaedon cochleariae, Phyillobius pyri, Phyillotreta chrysocephala, Phyllophaga sp., Phyllopertha horticola, Phyllotreta nemorum, Phyllotreta striolata, Popilla japonica, Sitona lineatus* and *Sitophilus granaria.*

The compounds and mixtures of the present invention are particularly useful for controlling insects of the orders Lepidoptera, Coleoptera, Hemiptera and Thysanoptera. The compounds and mixtures of the present invention are especially suitable for efficiently combating pests like insects from the order of the lepidopterans (Lepidoptera), beetles (Coleoptera), flies and mosquitoes (Diptera), *thrips* (Thysanoptera), termites (Isoptera), bugs, aphids, leafhoppers, whiteflies, scale insects, cicadas (Hemiptera), ants, bees, wasps, sawflies (Hymenoptera), crickets, grasshoppers, locusts (Orthoptera), and also Arachnoidea, such as arachnids (Acarina).

The details like the application patterns given here in E1, including preferences and examples, are valid on their own and also in the embodiments E2 to E10.

In one embodiment, the invention relates to methods and uses, wherein a compound of embodiment A as defined herein, is applied in an application type which corresponds in each case to one row of Table AP-T or Table P-C.

In one embodiment, the invention relates to methods and uses, wherein a compound of embodiment B as defined herein, is applied in an application type which corresponds in each case to one row of Table AP-T or Table P-C.

In one embodiment, the invention relates to methods and uses, wherein a compound of embodiment C as defined herein, is applied in an application type which corresponds in each case to one row of Table AP-T or Table P-C.

In one embodiment, the invention relates to methods and uses, wherein a compound of of Table ABC as listed herein, is applied in an application type which corresponds in each case to one row of Table AP-T or Table P-C.

In one embodiment, the invention relates to methods and uses, wherein the compound I-A-1 is applied in an application type which corresponds in each case to one row of Table AP-T or Table P-C.

In one embodiment, the invention relates to methods and uses, wherein the compound I-A-28 is applied in an application type which corresponds in each case to one row of Table AP-T or Table P-C.

In one embodiment, the invention relates to methods and uses, wherein the compound I-B-115 is applied in an application type which corresponds in each case to one row of Table AP-T or Table P-C.

In one embodiment, the invention relates to methods and uses, wherein the compound I-B-131 is applied in an application type which corresponds in each case to one row of Table AP-T or Table P-C.

In one embodiment, the invention relates to methods and uses, wherein the compound I-B-132 is applied in an application type which corresponds in each case to one row of Table AP-T or Table P-C.

In one embodiment, the invention relates to methods and uses, wherein the compound I-C-19 is applied in an application type which corresponds in each case to one row of Table AP-T or Table P-C.

In one embodiment, the invention relates to methods and uses, wherein the compound, I-C-35 is applied in an application type which corresponds in each case to one row of Table AP-T or Table P-C.

In one embodiment, the invention relates to methods and uses, wherein the compound I-C-36 is applied in an application type which corresponds in each case to one row of Table AP-T or Table P-C.

In a preferred embodiment, the compounds and mixtures according to the invention, especially the mixtures as individualized herein, especially the mixtures according to table M and M-F as shown herein, have the following application types:

TABLE AP-T

| Appl. type | Crop | Pest |
|---|---|---|
| AP-T-1 | Soybeans | Spodoptera littoralis |
| AP-T-2 | Soybeans | Anticarsia gemmatalis |
| AP-T-3 | Soybeans | Spodoptera exigua |
| AP-T-4 | Soybeans | Stinkbug |
| AP-T-5 | Soybeans | Helicoverpa sp. |
| AP-T-6 | Soybeans | Spodoptera eridania |
| AP-T-7 | Corn | Spodoptera Frugiperta |
| AP-T-8 | Corn | Spodoptera exigua |
| AP-T-9 | Rice | Sesamia inferens |
| AP-T-10 | Rice | Cnaphalocerus medinalis |
| AP-T-11 | Rice | Chilo suppressalis |
| AP-T-12 | Rice | Leptocorisa oratorius |
| AP-T-13 | Rice | Brown plant hopper |
| AP-T-14 | Cotton | Spodoptera littoralis |
| AP-T-15 | Cotton | Thrips spp. |
| AP-T-16 | Cotton | Spodoptera eridania |
| AP-T-17 | Cotton | Helicoverpa sp. |
| AP-T-18 | Canola | Pollen beetle |
| AP-T-19 | SPC | Tuta Absoluta |
| AP-T-20 | SPC | Fruit Borer |
| AP-T-21 | SPC | Spodoptera littoralis |
| AP-T-22 | SPC | Plusia gamma |
| AP-T-23 | SPC | Plutella xylostella |
| AP-T-24 | SPC | Frankliniella occidentalis |
| AP-T-25 | SPC | Trichoplusia ni |
| AP-T-26 | SPC | Pieris rapae |
| AP-T-27 | SPC | Spodoptera sp. |
| AP-T-28 | SPC | Crocidolomia pavonana |
| AP-T-29 | SPC | Pyrausta furnacalis |
| AP-T-30 | SPC | Liromyza trifolii |
| AP-T-31 | SPC | Cydia pomonella |
| AP-T-32 | SPC | Epitrix sp. |
| AP-T-33 | SPC | Leptinotarsa decemlineata |
| AP-T-34 | SPC | Bemisia tabaci |
| AP-T-35 | SPC | Thrips tabaci |
| AP-T-36 | SPC | Spodoptera eridania |
| AP-T-37 | SPC | Lobesia botrana |
| AP-T-38 | SPC | Altica chapybea |
| AP-T-39 | SPC | Phyllocnistis citrella |
| AP-T-40 | SPC-FV | Tuta Absoluta |
| AP-T-41 | SPC-FV | Fruit Borer |
| AP-T-42 | SPC-FV | Spodoptera littoralis |
| AP-T-43 | SPC-FV | Plusia gamma |
| AP-T-44 | SPC-FV | Plutella xylostella |
| AP-T-45 | SPC-FV | Frankliniella occidentalis |
| AP-T-46 | SPC-FV | Trichoplusia ni |
| AP-T-47 | SPC-FV | Pieris rapae |
| AP-T-48 | SPC-FV | Spodoptera sp. |
| AP-T-49 | SPC-FV | Crocidolomia pavonana |
| AP-T-50 | SPC-FV | Pyrausta furnacalis |
| AP-T-51 | SPC-FV | Liromyza trifolii |
| AP-T-52 | SPC-FV | Cydia pomonella |
| AP-T-53 | SPC-FV | Epitrix sp. |
| AP-T-54 | SPC-FV | Leptinotarsa decemlineata |
| AP-T-55 | SPC-FV | Bemisia tabaci |
| AP-T-56 | SPC-FV | Thrips tabaci |
| AP-T-57 | SPC-FV | Spodoptera eridania |
| AP-T-58 | SPC-FV | Lobesia botrana |
| AP-T-59 | SPC-FV | Altica chapybea |
| AP-T-60 | SPC-FV | Phyllocnistis citrella |
| AP-T-61 | Tomato | Tuta Absoluta |
| AP-T-62 | Tomato | Fruit Borer |
| AP-T-63 | Tomato | Spodoptera littoralis |
| AP-T-64 | Tomato | Plusia gamma |
| AP-T-65 | Tomato | Plutella xylostella |
| AP-T-66 | Tomato | Frankliniella occidentalis |
| AP-T-67 | Tomato | Trichoplusia ni |
| AP-T-68 | Tomato | Pieris rapae |
| AP-T-69 | Tomato | Spodoptera sp. |
| AP-T-70 | Tomato | Crocidolomia pavonana |
| AP-T-71 | Tomato | Pyrausta furnacalis |
| AP-T-72 | Tomato | Liromyza trifolii |
| AP-T-73 | Tomato | Cydia pomonella |
| AP-T-74 | Tomato | Epitrix sp. |
| AP-T-75 | Tomato | Leptinotarsa decemlineata |
| AP-T-76 | Tomato | Bemisia tabaci |
| AP-T-77 | Tomato | Thrips tabaci |
| AP-T-78 | Tomato | Spodoptera eridania |
| AP-T-79 | Tomato | Lobesia botrana |
| AP-T-80 | Tomato | Altica chapybea |
| AP-T-81 | Tomato | Phyllocnistis citrella |
| AP-T-82 | Pepper | Tuta Absoluta |
| AP-T-83 | Pepper | Fruit Borer |
| AP-T-84 | Pepper | Spodoptera littoralis |
| AP-T-85 | Pepper | Plusia gamma |
| AP-T-86 | Pepper | Plutella xylostella |
| AP-T-87 | Pepper | Frankliniella occidentalis |
| AP-T-88 | Pepper | Trichoplusia ni |
| AP-T-89 | Pepper | Pieris rapae |
| AP-T-90 | Pepper | Spodoptera sp. |
| AP-T-91 | Pepper | Crocidolomia pavonana |
| AP-T-92 | Pepper | Pyrausta furnacalis |
| AP-T-93 | Pepper | Liromyza trifolii |
| AP-T-94 | Pepper | Cydia pomonella |
| AP-T-95 | Pepper | Epitrix sp. |
| AP-T-96 | Pepper | Leptinotarsa decemlineata |
| AP-T-97 | Pepper | Bemisia tabaci |
| AP-T-98 | Pepper | Thrips tabaci |
| AP-T-99 | Pepper | Spodoptera eridania |
| AP-T-100 | Pepper | Lobesia botrana |
| AP-T-101 | Pepper | Altica chapybea |
| AP-T-102 | Pepper | Phyllocnistis citrella |
| AP-T-103 | Eggplant | Tuta Absoluta |
| AP-T-104 | Eggplant | Fruit Borer |
| AP-T-105 | Eggplant | Spodoptera littoralis |
| AP-T-106 | Eggplant | Plusia gamma |
| AP-T-107 | Eggplant | Plutella xylostella |

TABLE AP-T-continued

| Appl. type | Crop | Pest |
|---|---|---|
| AP-T-108 | Eggplant | Frankliniella occidentalis |
| AP-T-109 | Eggplant | Trichoplusia ni |
| AP-T-110 | Eggplant | Pieris rapae |
| AP-T-111 | Eggplant | Spodoptera sp. |
| AP-T-112 | Eggplant | Crocidolomia pavonana |
| AP-T-113 | Eggplant | Pyrausta furnacalis |
| AP-T-114 | Eggplant | Liromyza trifolii |
| AP-T-115 | Eggplant | Cydia pomonella |
| AP-T-116 | Eggplant | Epitrix sp. |
| AP-T-117 | Eggplant | Leptinotarsa decemlineata |
| AP-T-118 | Eggplant | Bemisia tabaci |
| AP-T-119 | Eggplant | Thrips tabaci |
| AP-T-120 | Eggplant | Spodoptera eridania |
| AP-T-121 | Eggplant | Lobesia botrana |
| AP-T-122 | Eggplant | Altica chapybea |
| AP-T-123 | Eggplant | Phyllocnistis citrella |
| AP-T-124 | SPC-LV | Tuta Absoluta |
| AP-T-125 | SPC-LV | Fruit Borer |
| AP-T-126 | SPC-LV | Spodoptera littoralis |
| AP-T-127 | SPC-LV | Plusia gamma |
| AP-T-128 | SPC-LV | Plutella xylostella |
| AP-T-129 | SPC-LV | Frankliniella occidentalis |
| AP-T-130 | SPC-LV | Trichoplusia ni |
| AP-T-131 | SPC-LV | Pieris rapae |
| AP-T-132 | SPC-LV | Spodoptera sp. |
| AP-T-133 | SPC-LV | Crocidolomia pavonana |
| AP-T-134 | SPC-LV | Pyrausta furnacalis |
| AP-T-135 | SPC-LV | Liromyza trifolii |
| AP-T-136 | SPC-LV | Cydia pomonella |
| AP-T-137 | SPC-LV | Epitrix sp. |
| AP-T-138 | SPC-LV | Leptinotarsa decemlineata |
| AP-T-139 | SPC-LV | Bemisia tabaci |
| AP-T-140 | SPC-LV | Thrips tabaci |
| AP-T-141 | SPC-LV | Spodoptera eridania |
| AP-T-142 | SPC-LV | Lobesia botrana |
| AP-T-143 | SPC-LV | Altica chapybea |
| AP-T-144 | SPC-LV | Phyllocnistis citrella |
| AP-T-145 | Cabbage | Tuta Absoluta |
| AP-T-146 | Cabbage | Fruit Borer |
| AP-T-147 | Cabbage | Spodoptera littoralis |
| AP-T-148 | Cabbage | Plusia gamma |
| AP-T-149 | Cabbage | Plutella xylostella |
| AP-T-150 | Cabbage | Frankliniella occidentalis |
| AP-T-151 | Cabbage | Trichoplusia ni |
| AP-T-152 | Cabbage | Pieris rapae |
| AP-T-153 | Cabbage | Spodoptera sp. |
| AP-T-154 | Cabbage | Crocidolomia pavonana |
| AP-T-155 | Cabbage | Pyrausta furnacalis |
| AP-T-156 | Cabbage | Liromyza trifolii |
| AP-T-157 | Cabbage | Cydia pomonella |
| AP-T-158 | Cabbage | Epitrix sp. |
| AP-T-159 | Cabbage | Leptinotarsa decemlineata |
| AP-T-160 | Cabbage | Bemisia tabaci |
| AP-T-161 | Cabbage | Thrips tabaci |
| AP-T-162 | Cabbage | Spodoptera eridania |
| AP-T-163 | Cabbage | Lobesia botrana |
| AP-T-164 | Cabbage | Altica chapybea |
| AP-T-165 | Cabbage | Phyllocnistis citrella |
| AP-T-166 | Lettuce | Tuta Absoluta |
| AP-T-167 | Lettuce | Fruit Borer |
| AP-T-168 | Lettuce | Spodoptera littoralis |
| AP-T-169 | Lettuce | Plusia gamma |
| AP-T-170 | Lettuce | Plutella xylostella |
| AP-T-171 | Lettuce | Frankliniella occidentalis |
| AP-T-172 | Lettuce | Trichoplusia ni |
| AP-T-173 | Lettuce | Pieris rapae |
| AP-T-174 | Lettuce | Spodoptera sp. |
| AP-T-175 | Lettuce | Crocidolomia pavonana |
| AP-T-176 | Lettuce | Pyrausta furnacalis |
| AP-T-177 | Lettuce | Liromyza trifolii |
| AP-T-178 | Lettuce | Cydia pomonella |
| AP-T-179 | Lettuce | Epitrix sp. |
| AP-T-180 | Lettuce | Leptinotarsa decemlineata |
| AP-T-181 | Lettuce | Bemisia tabaci |
| AP-T-182 | Lettuce | Thrips tabaci |
| AP-T-183 | Lettuce | Spodoptera eridania |
| AP-T-184 | Lettuce | Lobesia botrana |
| AP-T-185 | Lettuce | Altica chapybea |
| AP-T-186 | Lettuce | Phyllocnistis citrella |
| AP-T-187 | SPC-T | Tuta Absoluta |
| AP-T-188 | SPC-T | Fruit Borer |
| AP-T-189 | SPC-T | Spodoptera littoralis |
| AP-T-190 | SPC-T | Plusia gamma |
| AP-T-191 | SPC-T | Plutella xylostella |
| AP-T-192 | SPC-T | Frankliniella occidentalis |
| AP-T-193 | SPC-T | Trichoplusia ni |
| AP-T-194 | SPC-T | Pieris rapae |
| AP-T-195 | SPC-T | Spodoptera sp. |
| AP-T-196 | SPC-T | Crocidolomia pavonana |
| AP-T-197 | SPC-T | Pyrausta furnacalis |
| AP-T-198 | SPC-T | Liromyza trifolii |
| AP-T-199 | SPC-T | Cydia pomonella |
| AP-T-200 | SPC-T | Epitrix sp. |
| AP-T-201 | SPC-T | Leptinotarsa decemlineata |
| AP-T-202 | SPC-T | Bemisia tabaci |
| AP-T-203 | SPC-T | Thrips tabaci |
| AP-T-204 | SPC-T | Spodoptera eridania |
| AP-T-205 | SPC-T | Lobesia botrana |
| AP-T-206 | SPC-T | Altica chapybea |
| AP-T-207 | SPC-T | Phyllocnistis citrella |
| AP-T-208 | Potatoes | Tuta Absoluta |
| AP-T-209 | Potatoes | Fruit Borer |
| AP-T-210 | Potatoes | Spodoptera littoralis |
| AP-T-211 | Potatoes | Plusia gamma |
| AP-T-212 | Potatoes | Plutella xylostella |
| AP-T-213 | Potatoes | Frankliniella occidentalis |
| AP-T-214 | Potatoes | Trichoplusia ni |
| AP-T-215 | Potatoes | Pieris rapae |
| AP-T-216 | Potatoes | Spodoptera sp. |
| AP-T-217 | Potatoes | Crocidolomia pavonana |
| AP-T-218 | Potatoes | Pyrausta furnacalis |
| AP-T-219 | Potatoes | Liromyza trifolii |
| AP-T-220 | Potatoes | Cydia pomonella |
| AP-T-221 | Potatoes | Epitrix sp. |

TABLE AP-T-continued

| Appl. type | Crop | Pest |
|---|---|---|
| AP-T-222 | Potatoes | Leptinotarsa decemlineata |
| AP-T-223 | Potatoes | Bemisia tabaci |
| AP-T-224 | Potatoes | Thrips tabaci |
| AP-T-225 | Potatoes | Spodoptera eridania |
| AP-T-226 | Potatoes | Lobesia botrana |
| AP-T-227 | Potatoes | Altica chapybea |
| AP-T-228 | Potatoes | Phyllocnistis citrella |
| AP-T-229 | Potatoes | wireworm |
| AP-T-230 | Onions | Tuta Absoluta |
| AP-T-231 | Onions | Fruit Borer |
| AP-T-232 | Onions | Spodoptera littoralis |
| AP-T-233 | Onions | Plusia gamma |
| AP-T-234 | Onions | Plutella xylostella |
| AP-T-235 | Onions | Frankliniella occidentalis |
| AP-T-236 | Onions | Trichoplusia ni |
| AP-T-237 | Onions | Pieris rapae |
| AP-T-238 | Onions | Spodoptera sp. |
| AP-T-239 | Onions | Crocidolomia pavonana |
| AP-T-240 | Onions | Pyrausta furnacalis |
| AP-T-241 | Onions | Liromyza trifolii |
| AP-T-242 | Onions | Cydia pomonella |
| AP-T-243 | Onions | Epitrix sp. |
| AP-T-244 | Onions | Leptinotarsa decemlineata |
| AP-T-245 | Onions | Bemisia tabaci |
| AP-T-246 | Onions | Thrips tabaci |
| AP-T-247 | Onions | Spodoptera eridania |
| AP-T-248 | Onions | Lobesia botrana |
| AP-T-249 | Onions | Altica chapybea |
| AP-T-250 | Onions | Phyllocnistis citrella |
| AP-T-251 | ST | Agrotis ipsilon |
| AP-T-252 | ST | Spodoptera frugiperta |
| AP-T-253 | ST | Phyllotreta sp. |
| AP-T-254 | ST | Stem Girdler |
| AP-T-255 | ST | Agriotes sp. |
| AP-T-256 | ST | Delia platura |

(Abbreviations: SPC = specialty crops; SPC-FV = fruiting vegetable; SPC-LV = leafy vegetable; SPC-T: tubers; ST = seed treatment)

Especially, the compounds and mixtures according to the invention and the compositions comprising them, especially the compounds shown in Table C, show excellent efficacy in control of the following pests in the following crops:

TABLE P-C

| | Pest | Crop |
|---|---|---|
| P-C-1 | Cnaphalocerus medinalis | Rice |
| P-C-2 | Chilo suppressalis | Rice |
| P-C-3 | Spodoptera frugiperda | Rice |
| P-C-4 | Spodoptera exigua | Rice |
| P-C-5 | Spodoptera sp. | Rice |
| P-C-6 | Plutella xylostella | Rice |
| P-C-7 | Tuta absoluta | Rice |
| P-C-8 | Lygus hesperus | Rice |
| P-C-9 | Spodoptera frugiperda | Corn |
| P-C-10 | Spodoptera exigua | Corn |
| P-C-11 | Spodoptera sp. | Corn |
| P-C-12 | Plutella xylostella | Corn |
| P-C-13 | Tuta absoluta | Corn |
| P-C-14 | Leptinotarsa decemlineata | Corn |
| P-C-15 | Lygus hesperus | Corn |
| P-C-16 | Spodoptera frugiperda | Chickpea |
| P-C-17 | Spodoptera exigua | Chickpea |
| P-C-18 | Spodoptera sp. | Chickpea |
| P-C-19 | Plutella xylostella | Chickpea |
| P-C-20 | Tuta absoluta | Chickpea |
| P-C-21 | Leptinotarsa decemlineata | Chickpea |
| P-C-22 | Lygus hesperus | Chickpea |
| P-C-23 | Spodoptera frugiperda | Cabbage |
| P-C-24 | Spodoptera exigua | Cabbage |
| P-C-25 | Spodoptera sp. | Cabbage |
| P-C-26 | Plutella xylostella | Cabbage |
| P-C-27 | Tuta absoluta | Cabbage |
| P-C-28 | Leptinotarsa decemlineata | Cabbage |
| P-C-29 | Lygus hesperus | Cabbage |
| P-C-30 | Spodoptera frugiperda | Broccoli |
| P-C-31 | Spodoptera exigua | Broccoli |
| P-C-32 | Spodoptera sp. | Broccoli |
| P-C-33 | Plutella xylostella | Broccoli |
| P-C-34 | Tuta absoluta | Broccoli |
| P-C-35 | Leptinotarsa decemlineata | Broccoli |
| P-C-36 | Lygus hesperus | Broccoli |
| P-C-37 | Spodoptera frugiperda | Tomato |
| P-C-38 | Spodoptera exigua | Tomato |
| P-C-39 | Spodoptera sp. | Tomato |
| P-C-40 | Plutella xylostella | Tomato |
| P-C-41 | Tuta absoluta | Tomato |
| P-C-42 | Leptinotarsa decemlineata | Tomato |
| P-C-43 | Lygus hesperus | Tomato |
| P-C-44 | Spodoptera frugiperda | Potato |
| P-C-45 | Spodoptera exigua | Potato |
| P-C-46 | Spodoptera sp. | Potato |
| P-C-47 | Plutella xylostella | Potato |
| P-C-48 | Tuta absoluta | Potato |
| P-C-49 | Leptinotarsa decemlineata | Potato |
| P-C-50 | Lygus hesperus | Potato |
| P-C-51 | Spodoptera frugiperda | Alfalfa |
| P-C-52 | Spodoptera exigua | Alfalfa |
| P-C-53 | Spodoptera sp. | Alfalfa |
| P-C-54 | Plutella xylostella | Alfalfa |
| P-C-55 | Tuta absoluta | Alfalfa |
| P-C-56 | Leptinotarsa decemlineata | Alfalfa |
| P-C-57 | Lygus hesperus | Alfalfa |
| P-C-58 | Spodoptera frugiperda | Soy |
| P-C-59 | Spodoptera exigua | Soy |
| P-C-60 | Spodoptera sp. | Soy |
| P-C-61 | Plutella xylostella | Soy |
| P-C-62 | Tuta absoluta | Soy |
| P-C-63 | Leptinotarsa decemlineata | Soy |
| P-C-64 | Lygus hesperus | Soy |
| P-C-65 | tortricides | tree fruits |
| P-C-66 | tortricides | grapes |
| P-C-67 | Tuta absoluta | fruiting vegetables |
| P-C-68 | Lepidoptera | field brassica |
| P-C-69 | coleoptera | potatoe |
| P-C-70 | Coleoptera | oil-seed rape |
| P-C-71 | Lepidoptera | corn |
| P-C-72 | Lepidoptera | cotton |
| P-C-73 | thrips | flowers |
| P-C-74 | Eupoecilia ambiguella | grape |
| P-C-75 | Lobesia botrana | grape |
| P-C-76 | Haltica ampelophaga | grape |
| P-C-77 | Cydia pomonella | apple |
| P-C-78 | Grapholita molesta | Peach |
| P-C-79 | Phyllocnistis citrella | Citrus |
| P-C-80 | Tuta absoluta | Tomato |
| P-C-81 | Tuta absoluta | Tomato (greenhouse) |
| P-C-82 | Scrobipalpula absoluta | Tomato |
| P-C-83 | Scrobipalpula absoluta | Tomato (greenhouse) |
| P-C-84 | Thrips sp. | flower |
| P-C-85 | Thrips sp | Tagetes |
| P-C-86 | Leptinotarsa decemlineata (Colorado potato beetle) | potatoe |
| P-C-87 | Pieris brassicae | Cabbage |
| P-C-88 | Anticarsia (Thermesia) gemmatalis | Soybean |
| P-C-89 | Spodoptera littoralis | Soybean |
| P-C-90 | Plutella xylostella | Collard |
| P-C-91 | Plutella xylostella | Cabbage |
| P-C-92 | Pieris rapae | Cabbage |
| P-C-93 | Sesamia nonagriodes | Corn |
| P-C-94 | Helicoverpa armigera | Corn |

TABLE P-C-continued

| | Pest | Crop |
|---|---|---|
| P-C-95 | Ostrinia nubilalis | Corn |
| P-C-96 | Spodoptera sp. | Soybean |
| P-C-97 | Earias sp. | Cotton |
| P-C-98 | Spodoptera sp. | Cabbage |
| P-C-99 | Pyrausta furnacalis | Corn |
| P-C-100 | Spodoptera sp. | Corn |
| P-C-101 | Spodoptera frugiperda | Corn |
| P-C-102 | Chilo suppressalis | Rice |
| P-C-103 | Cnaphalocrocis medinalis | Rice |
| P-C-104 | Sesamia inferens | Rice |
| P-C-105 | Phyllotreta sp | Cabbage |
| P-C-106 | Epitrix fuscula | Eggplant |
| P-C-107 | Diabrotica virgifera virgifera | Corn (Seed Treatment) |
| P-C-108 | Pollen beetle | oilseed rape |
| P-C-109 | Meligethes aeneus | Oilseed rape |
| P-C-110 | Pollen beetle | flowers |
| P-C-111 | Meligethes aeneus | flowers |
| P-C-112 | Pollen beetle | vegetables |
| P-C-113 | Meligethes aeneus | vegetables |
| P-C-114 | Pollen beetle | Brassica |
| P-C-115 | Meligethes aeneus | Brassica |

The application types are understood to include several applications per crop season, so as to control first and second and higher generations of pests.

Formulations

The details like the formulations given here in E1, including preferences and examples, are valid on their own and also in the embodiments E2 to E10.

The compounds and mixtures according to the present invention can be converted into the customary formulations, for example solutions, emulsions, suspensions, dusts, powders, pastes and granules. The use form depends on the particular intended purpose; in each case, it should ensure a fine and even distribution of the compounds and mixtures according to the invention.

Therefore the invention also relates to agrochemical compositions comprising an auxiliary and compound or a mixture according to the invention, i.e. a mixture of at least one compound I and of at least one compound II according to the present invention.

An agrochemical composition comprises a pesticidally effective amount of a pesticidal compound or mixture according to the invention. The term "effective amount" denotes an amount of the composition or of the mixture, which is sufficient for controlling harmful pests on cultivated plants or in the protection of materials and which does not result in a substantial damage to the treated plants. Such an amount can vary in a broad range and is dependent on various factors, such as the animal pests species to be controlled, the treated cultivated plant or material, the climatic conditions and the specific mixture used.

The compounds and mixtures according to the present invention can be converted into customary types of agrochemical compositions, e. g. solutions, emulsions, suspensions, dusts, powders, pastes, gran-ules, pressings, capsules, and mixtures thereof. Examples for composition types are suspen-sions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl¬ naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkyl-polyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or poly-ethyleneamines.

Suitable adjuvants are compounds, which have a neglectable or even no pesticidal activity themselves, and which improve the biological performance of the compound I or the mixture according to the invention on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)
10-60 wt % of a compound I or a mixture according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)
5-25 wt % of a compound I or a mixture according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)
15-70 wt % of a compound I or a mixture according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)
5-40 wt % of a compound I or a mixture according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)
In an agitated ball mill, 20-60 wt % of a compound I or a mixture according to the invention are comminuted with addition of 2-10 wt % dispersants and wetting agents (e.g. sodium lignosulfonate and alcohol ethoxylate), 0,1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)
50-80 wt % of a compound I or a mixture according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)
50-80 wt % of a compound I or a mixture according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)
In an agitated ball mill, 5-25 wt % of a compound I or a mixture according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)
5-20 wt % of a compound I or a mixture according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

x) Microcapsules (CS)
An oil phase comprising 5-50 wt % of a compound I or a mixture according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

xi) Dustable Powders (DP, DS)

1-10 wt % of a compound I or a mixture according to the invention are ground finely and mixed intimately with up to 100 wt % solid carrier, e.g. finely divided kaolin.

xii) Granules (GR, FG)

0.5-30 wt % of a compound I or a mixture according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I or a mixture according to the invention are dissolved in up to 100 wt % organic solvent, e.g. aromatic hydrocarbon.

The compositions types i) to xiii) may optionally comprise further auxiliaries, such as 0,1-1 wt % bactericides, 5-15 wt % anti-freezing agents, 0,1-1 wt % anti-foaming agents, and 0,1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

In one embodiment, a suspoconcentration (SC) is preferred for the application in crop protection. In one sub-embodiment thereof, the SC agrochemical composition comprises between 50 to 500 g/L (grams per Litre), or between 100 and 250 g/L, or 100 g/L or 150 g/L or 200 g/L or 250 g/L.

In a further embodiment, the granules according to formulation type xii are especially preferred for the application in rice.

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compound I or a mixture according to the invention and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.001 to 1 kg per ha, more preferably from 0.005 to 0.9 kg per ha, in particular from 0.005 to 0.5 kg per ha.

In treatment of plant propagation materials such as seeds, e. g. by dusting, coating or drenching seed, amounts of active substance of from 0.1 to 1000 g, preferably from 0.1 to 300 g, more preferably from 0.1 to 100 g and most preferably from 0.25 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes, and have received much practical attention as substitutes to synthetic chemical plant protection products (PPPs).

Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multi-cellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

Applications

The details like the application patterns given here in E1, including preferences and examples, are valid on their own and also in the embodiments E2 to E10.

Due to their excellent activity, the compounds and mixtures according to the invention may be used for controlling invertebrate pests.

The compounds I and their mixtures can be applied simultaneously, that is jointly or separately, or in succession, that is immediately one after another and thereby creating the mixture "in-situ" on the desired location, as e.g. the plant, the sequence, in the case of separate application, generally not having any effect on the result of the control measures.

The compounds I and their mixtures are usually applied in a weight ratio of from 5000:1 to 1:5000, preferably from 1000:1 to 1:1000, preferably from 625:1 to 1:625, preferably 500:1 to 1:100, preferably from 100:1 to 1:100 preferably from 20:1 to 1:50, preferably from 20:1 to 1:20, preferably from 10:1 to 1:10, in particular from 5:1 to 1:20, in particular from 5:1 to 1:10, in particular from 5:1 to 1:5.

Depending on the desired effect, the application rates of the compounds and mixtures according to the invention are from 5 g/ha to 2000 g/ha, preferably from 0.5 g/ha to 1000 g/ha, preferably from 1 to 750 g/ha, in particular from 5 to 500 g/ha.

The compounds and mixtures according to the invention are effective through both contact and ingestion.

The compounds and mixtures according to the invention can be applied to any and all developmental stages, such as egg, larva, pupa, and adult. The pests may be controlled by contacting the target pest, its food supply, habitat, breeding ground or its locus with a pesticidally effective amount of the inventive compounds and mixtures or of compositions comprising them.

According to a preferred embodiment, the compounds and mixtures according to the invention are used in crop protection, especially for the protection of living plants.

According to another specific embodiment of the invention, the mixtures according to the present invention are employed via soil application. Soil application is especially favorable for use against ants, termites, crickets, or cockroaches.

According to another embodiment of the invention, for use against non crop pests such as ants, termites, wasps, flies, mosquitoes, crickets, locusts, or cockroaches the mixtures according to the present invention are prepared into a bait preparation.

The bait can be a liquid, a solid or a semisolid preparation (e.g. a gel).

The animal pest (also referred to as "invertebrate pest"), i.e. the insects, arachnids and nematodes, the plant, soil or water in which the plant is growing can be contacted with the compounds and mixtures according to the invention or composition(s) comprising them by any application method known in the art. As such, "contacting" includes both direct contact (applying the compounds/mixtures/compositions directly on the animal pest or plant—typically to the foliage, stem or roots of the plant) and indirect contact (applying the compounds/mixtures/compositions to the locus of the animal pest or plant).

The compounds and mixtures according to the invention or the pesticidal compositions comprising them may be used to protect growing plants and crops from attack or infestation by animal pests, especially insects, acaridae or arachnids by contacting the plant/crop with a pesticidally effective amount of the compounds and mixtures according to the invention. The term "crop" refers both to growing and harvested crops.

The compounds and mixtures according to the invention and the compositions comprising them are particularly important in the control of a multitude of insects on various cultivated plants, such as cereal, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

Particularly preferred is the application of the compounds and mixtures according to the invention and the compositions comprising them on rice. Particularly preferred is the application of the compounds and mixtures according to the invention and the compositions comprising them on soybeans. Particularly preferred is the application of the compounds and mixtures according to the invention and the compositions comprising them on corn.

Also preferred is the application of the compounds and mixtures according to the invention, especially the mixtures as individualized herein, e.g. in Table AP-T, on specialty crops like fruits and vegetables. In one embodiment thereof, the application is on fruiting vegetables, and especially on tomato, on pepper or on eggplant.

In another embodiment thereof, the application is on leafy vegetables, and especially on cabbage or on lettuce.

In still another embodiment thereof, the application is on tubers (tuber vegetables), and especially on potato or on onion.

The compounds and mixtures according to the invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habitat, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I and at least one active compound II.

Moreover, animal pests may be controlled by contacting the target pest, its food supply, habitat, breeding ground or its locus with a pesticidally effective amount of a mixture according to the invention. As such, the application may be carried out before or after the infection of the locus, growing crops, or harvested crops by the pest.

The compounds and mixtures according to the invention can also be applied preventively to places at which occurrence of the pests is expected.

The compounds and mixtures according to the invention may be also used to protect growing plants from attack or infestation by pests by contacting the plant with a pesticidally effective amount of compounds and mixtures according to the invention. As such, "contacting" includes both direct contact (applying the compounds/compositions directly on the pest and/or plant—typically to the foliage, stem or roots of the plant) and indirect contact (applying the compounds and mixtures according to the invention/compositions to the locus of the pest and/or plant). "Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, the genetic material of which has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5): 1225-35., Curr Opin Chem Biol. 2006 October; 10(5):487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A-0242236, EP-A-242246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lyso-zym (e. g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

In general, "pesticidally effective amount" means the amount of active ingredients or mixture according to the invention needed to achieve an observable effect on growth, including the effects of necrosis, death, retardation, prevention, and removal, destruction, or otherwise diminishing the occurrence and activity of the target organism. The pesticidally effective amount can vary for the various mixtures/compositions used in the invention. A pesticidally effective amount of the compositions will also vary according to the prevailing conditions such as desired pesticidal effect and duration, weather, target species, locus, mode of application, and the like. In the case of foliar treatment, the quantity of active ingredient ranges from 0.0001 to 500 g per 100 m², preferably from 0.001 to 20 g per 100 m², or from 1 to 100 g per hectare, preferably from 10 to 50 g per hectare, or from 12 to 50 g per hectare, or from 10 to 30 g per hectare, or from 20 to 40 g per hectare, or from 10 to 20 g per hectare, or from 20 to 30 g per hectare, or from 30 to 40 g per hectare, or from 40 to 50 g per hectare.

In the case of soil treatment or of application to the pests dwelling place or nest, the quantity of active ingredient ranges from 0.0001 to 500 g per 100 m², preferably from 0.001 to 20 g per 100 m².

Customary application rates in the protection of materials are, for example, from 0.01 g to 1000 g of active compounds per m² treated material, desirably from 0.1 g to 50 g per m².

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds and mixtures according to the invention are effective through both contact (via soil, glass, wall, bed net, carpet, plant parts or animal parts), and ingestion (bait, or plant part).

The compounds and mixtures according to the invention may also be applied against non-crop insect pests, such as ants, termites, wasps, flies, mosquitos, crickets, or cockroaches. For use against said non-crop pests, the compounds and mixtures according to the invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredients is from 0.001 weight % to weight %, desirably from 0.001 weight % to 5% weight % of active compounds.

Formulations of compounds I or mixtures according to the invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound(s), solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds and mixtures according to the invention respective their compositions can also be used in mosquito and fumigating coils, smoke cartridges, vaporizer plates or long-term vaporizers and also in moth papers, moth pads or other heat-independent vaporizer systems. Methods to control infectious diseases transmitted by insects (e.g. malaria, dengue and yellow fever, lymphatic filariasis, and leishmaniasis) with compounds and mixtures according to the invention and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds and mixtures according to the invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds and mixtures according to the invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The details like the seed treatment application as given here in E1, including preferences and examples, are valid on their own and also in the embodiments E2 to E10.

The compounds and mixtures according to the invention are also suitable for the treatment of seeds in order to protect the seed from insect pest, in particular from soil-living insect pests and the resulting plant's roots and shoots against soil pests and foliar insects.

The compounds and mixtures according to the invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compounds and mixtures according to the invention. Particularly preferred is a method, wherein the plant's roots and shoots are protected, more preferably a method, wherein the plants shoots are protected from piercing and sucking insects, most preferably a method, wherein the plants shoots are protected from aphids. Also preferred ist a method, wherein the plant's roots and shoots are protected from chewing and biting insects, most preferably a method, wherein the plants shoots and roots are protected from Lepidoptera and/or Coleoptera, most preferably wherein the plant shoots and roots are protected from rice leaf beetle The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compounds and mixtures according to the invention.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

Particularly preferred is the application of the compounds and mixtures according to the invention and the compositions comprising them on rice.

In addition, the active compounds and mixtures according to the invention may also be used for the treatment of seeds from plants, which tolerate the action of herbicides or fungicides or insecticides owing to breeding, including genetic engineering methods.

For example, the active compounds and mixtures according to the invention can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compounds and mixtures according to the invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972). The seed treatment application of the active compounds is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds I, compounds II or the compounds and mixtures according to the invention, for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants. Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The details like the application pattern of Animal health given here in E1, including preferences and examples, are valid on their own and also in the embodiments E2 to E10.

The compounds and mixtures according to the invention are in particular also suitable for being used for combating parasites in and on animals.

An object of the present invention is therefore also to provide new methods to control parasites in and on animals. Another object of the invention is to provide safer pesticides for animals.

Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of the compounds and mixtures according to the invention and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a mixture according to the invention or a composition comprising it.

The invention also provides a process for the preparation of a composition for treating, controlling, preventing or protecting animals against infestation or infection by parasites which comprises a parasiticidally effective amount of a mixture according to the invention or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that the compounds and mixtures according to the invention are suitable for combating endo- and ectoparasites in and on animals.

Compounds and mixtures according to the invention and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds and mixtures according to the invention and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds and mixtures according to the invention and compositions comprising them are suitable for systemic and/or non-systemic control of ecto- and/or endoparasites. They are active against all or some stages of development.

The compounds and mixtures according to the invention are especially useful for combating ectoparasites.

The compounds and mixtures according to the invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria—Blattodea), e.g. *Battella germanica, Battella asahinae, Periplaneta americana, Periplaneta japonica, Periplaneta brunnea, Periplaneta fuliginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus,*

*Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necatoramericanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds and mixtures according to the invention and compositions containing them are particularly useful for the control of pests from the orders Diptera, Siphonaptera and Ixodida.

Moreover, the use of the compounds and mixtures according to the invention and compositions containing them for combating mosquitoes is especially preferred.

The use of the compounds and mixtures according to the invention and compositions containing them for combating flies is a further preferred embodiment of the present invention.

Furthermore, the use of the compounds I and compositions containing them for combating fleas is especially preferred.

The use of the compounds and mixtures according to the invention and compositions containing them for combating ticks is a further preferred embodiment of the present invention.

The compounds and mixtures according to the invention also are especially useful for combating endoparasites (roundworms nematoda, thorny headed worms and planarians).

Administration can be carried out both prophylactically and therapeutically.

Administration of the active compounds or mixtures is carried out directly or in the form of suitable preparations, orally, topically/dermally or parenterally.

For oral administration to warm-blooded animals, the compounds I, compounds II or the mixtures according to the invention may be formulated as animal feeds, animal feed premixes, animal feed concentrates, pills, solutions, pastes, suspensions, drenches, gels, tablets, boluses and capsules. In addition, the compounds I, compounds II or the mixtures according to the invention may be administered to the animals in their drinking water. For oral administration, the dosage form chosen should provide the animal with 0.01 mg/kg to 100 mg/kg of animal body weight per day of the compounds I, compounds II or the mixtures according to the invention, preferably with 0.5 mg/kg to 100 mg/kg of animal body weight per day.

Alternatively, the compounds I, compounds II or the mixtures according to the invention may be administered to animals parenterally, for example, by intraruminal, intramuscular, intravenous or subcutaneous injection. The compounds I, compounds II or the mixtures according to the invention may be dispersed or dissolved in a physiologically acceptable carrier for subcutaneous injection. Alternatively, the compounds I, compounds II or the mixtures according to the invention may be formulated into an implant for subcutaneous administration. In addition the compounds I, compounds II or the mixtures according to the invention may be transdermally administered to animals. For parenteral administration, the dosage form chosen should provide the animal with 0.01 mg/kg to 100 mg/kg of animal body weight per day of the compounds I, compounds II or the mixture according to the invention.

The compounds I, compounds II or the mixtures according to the invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds I, compounds II or the mixtures according to the invention. In addition, the compounds I, compounds II or the mixtures according to the invention may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/mixtures/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the the mixture according to the invention.

Generally it is favorable to apply the mixture according to the invention in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 per cent by weight, preferably from 0.1 to 65 per cent by weight, more preferably from 1 to 50 per cent by weight, most preferably from 5 to per cent by weight.

Preparations which are diluted before use contain the compounds acting against ectoparasites in concentrations of 0.5 to 90 per cent by weight, preferably of 1 to 50 per cent by weight.

Furthermore, the preparations comprise the compounds and mixtures according to the invention against endoparasites in concentrations of 10 ppm to 2 per cent by weight, preferably of 0.05 to 0.9 per cent by weight, very particularly preferably of 0.005 to 0.25 per cent by weight.

In a preferred embodiment of the present invention, the compositions comprising the compounds and mixtures according to the invention are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release the active compounds in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the active compounds. A detailed list of plastics and elastomers as well as preparation procedures for the shaped articles is given e.g. in WO 03/086075.

Embodiment E2

In embodiment E2, the invention relates to mixtures comprising the compounds according to the invention and a pesticide, preferably an insecticide.

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of pests which have developed natural or adapted resistance against the active compound in question. Therefore there is a need for pest control agents that help prevent or overcome resistance induced by pesticides.

Furthermore, there is a desire for pesticide compounds or combination of compounds, which when applied improve plants, which may result in "plant health", "vitality of plant propagation material" or "increased plant yield".

It is therefore an object of the present invention to provide agricultural combinations which solves one or more than one of the discussed problems as
- reducing the dosage rate,
- enhancing the spectrum of activity,
- combining knock-down activity with prolonged control,
- improving resistance management,
- Improved plant health;
- Improved vitality of plant propagation material, also termed seed vitality;
- Increased plant yield.

It was therefore an object of the present invention to provide pesticidal mixtures which solve at least one of the discussed problems as reducing the dosage rate, enhancing the spectrum of activity or combining knock-down activity with prolonged control or as to resistance management.

It has been found that this object is in part or in whole achieved by the combination of active compounds defined below.

The present invention relates to pesticidal mixtures comprising as active compounds
1) at least one pesticidally active anthranilamide compound I as described above, or a stereoisomer, salt, tautomer or N-oxide, or a polymorphic crystalline form, a co-crystal or a solvate of a compound or a stereoisomer, salt, tautomer or N-oxide thereof; and
2) at least one pesticidally active compound II selected from group M consisting of II-M.1 Acetylcholine esterase (AChE) inhibitors from the class of II-M.1A carbamates, including aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of II-M.1B organophosphates, including acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

II-M.2 GABA-gated chloride channel antagonists such as:

II-M.2A cyclodiene organochlorine compounds, including endosulfan or chlordane; or II-M.2B fiproles (phenylpyrazoles), including ethiprole, fipronil, flufiprole, pyrafluprole and pyriprole;

II-M.3 Sodium channel modulators from the class of

II-M.3A pyrethroids, including acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or II-M.3B sodium channel modulators such as DDT or methoxychlor;

II-M.4 Nicotinic acetylcholine receptor agonists (nAChR) from the class of

II-M.4A neonicotinoids, including acetamiprid, chlothianidin, dinotefuran, imidacloprid, nitenpyram, thiacloprid and thiamethoxam; or the compounds II-M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or II-M.4A.2: 1-[(6-chloro-3-pyridyl)methyl]-2-nitro-1-[(E)-pentylideneamino]guanidine; or II-M4A.3: 1-[(6-chloro-3-pyridyl)methyl]-7-methyl-8-nitro-5-propoxy-3,5,6,7-tetrahydro-2H-imidazo[1,2-a]pyridine; or II-M.4B nicotine.

II-M.5 Nicotinic acetylcholine receptor allosteric activators from the class of spinosyns, including spinosad or spinetoram;

II-M.6 Chloride channel activators from the class of avermectins and milbemycins, including abamectin, emamectin benzoate, ivermectin, lepimectin or milbemectin;

II-M.7 Juvenile hormone mimics, such as

II-M.7A juvenile hormone analogues as hydroprene, kinoprene and methoprene; or others as II-M.7B fenoxycarb, or II-M.7C pyriproxyfen;

II-M.8 miscellaneous non-specific (multi-site) inhibitors, including

II-M.8A alkyl halides as methyl bromide and other alkyl halides, or

II-M.8B chloropicrin, or
II-M.8C sulfuryl fluoride, or
II-M.8D borax, or
II-M.8E tartar emetic;
II-M.9 Selective homopteran feeding blockers, including
II-M.9B pymetrozine, or
II-M.9C flonicamid;
II-M.10 Mite growth inhibitors, including
II-M.10A clofentezine, hexythiazox and diflovidazin, or
II-M.10B etoxazole;
II-M.11 Microbial disruptors of insect midgut membranes, including *bacillus thuringiensis* or *bacillus sphaericus* and the insecticdal proteins they produce such as *bacillus thuringiensis* subsp. *israelensis*, *bacillus sphaericus*, *bacillus thuringiensis* subsp. *aizawai*, *bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;
II-M.12 Inhibitors of mitochondrial ATP synthase, including
II-M.12A diafenthiuron, or
II-M.12B organotin miticides such as azocyclotin, cyhexatin or fenbutatin oxide, or
II-M.12C propargite, or
II-M.12D tetradifon;
II-M.13 Uncouplers of oxidative phosphorylation via disruption of the proton gradient, including chlorfenapyr, DNOC or sulfluramid;
II-M.14 Nicotinic acetylcholine receptor (nAChR) channel blockers, including nereistoxin analogues as bensultap, cartap hydrochloride, thiocyclam or thiosultap sodium;
II-M.15 Inhibitors of the chitin biosynthesis type 0, such as benzoylure including bistrifluron, chlorfluazuron, diflubenzuron, flucycloxuron, flufenoxuron, hexaflumuron, lufenuron, novaluron, noviflumuron, teflubenzuron or triflumuron;
II-M.16 Inhibitors of the chitin biosynthesis type 1, including buprofezin;
II-M.17 Moulting disruptors, Dipteran, including cyromazine;
II-M.18 Ecdyson receptor agonists such as diacylhydrazines, including methoxyfenozide, tebufenozide, halofenozide, fufenozide or chromafenozide;
II-M.19 Octopamin receptor agonists, including amitraz;
II-M.20 Mitochondrial complex III electron transport inhibitors, including
II-M.20A hydramethylnon, or
II-M.20B acequinocyl, or
II-M.20C fluacrypyrim;
II-M.21 Mitochondrial complex I electron transport inhibitors, including
II-M.21A METI acaricides and insecticides such as fenazaquin, fenpyroximate, pyrimidifen, pyridaben, tebufenpyrad or tolfenpyrad, or
II-M.21B rotenone;
II-M.22 Voltage-dependent sodium channel blockers, including
II-M.22A indoxacarb, or
II-M.22B metaflumizone; or
II-M.22C 1-[(E)-[2-(4-cyanophenyl)-1-[3-(trifluoromethyl)phenyl]ethylidene]amino]-3-[4-(difluoromethoxy)phenyl]urea
II-M.23 Inhibitors of the acetyl CoA carboxylase, including Tetronic and Tetramic acid derivatives, including spirodiclofen, spiromesifen or spirotetramat;
II-M.24 Mitochondrial complex IV electron transport inhibitors, including
II-M.24A phosphine such as aluminium phosphide, calcium phosphide, phosphine or zinc phosphide, or
II-M.24B cyanide.
II-M.25 Mitochondrial complex II electron transport inhibitors, such as beta-ketonitrile derivatives, including cyenopyrafen or cyflumetofen;
II-M.26 Ryanodine receptor-modulators from the class of diamides, including flubendiamide, chlorantraniliprole (Rynaxypyr®), cyantraniliprole (Cyazypyr®), or the phthalamide compounds
II-M.26.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and
II-M.26.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound
II-M.26.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound
II-M.26.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from II-M.26.5a) to II-M.26.5d):
II-M.26.5a: N-[2-(5-amino-1,3,4-thiadiazol-2-yl)-4-chloro-6-methyl-phenyl]-5-bromo-2-(3-chloro-2-pyridyl)pyrazole-3-carboxamide;
II-M.26.5b: 5-chloro-2-(3-chloro-2-pyridyl)-N-[2,4-dichloro-6-[(1-cyano-1-methyl-ethyl)carbamoyl]phenyl]pyrazole-3-carboxamide;
II-M.26.5c: 5-bromo-N-[2,4-dichloro-6-(methylcarbamoyl)phenyl]-2-(3,5-dichloro-2-pyridyl)pyrazole-3-carboxamide;
II-M.26.5d: N-[2-(tert-butylcarbamoyl)-4-chloro-6-methyl-phenyl]-2-(3-chloro-2-pyridyl)-5-(fluoromethoxy)pyrazole-3-carboxamide; or
II-M.26.6: N2-(1-cyano-1-methyl-ethyl)-N1-(2,4-dimethylphenyl)-3-iodo-phthalamide; or
II-M.26.7: 3-chloro-N2-(1-cyano-1-methyl-ethyl)-N1-(2,4-dimethylphenyl)phthalamide
II-M.X insecticidal active compounds of unknown or uncertain mode of action, including afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds
II-M.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound
II-M.X.2: cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester, or the compound
II-M.X.3: 11-(4-chloro-2,6-dimethylphenyl)-12-hydroxy-1,4-dioxa-9-azadispiro[4.2.4.2]-tetradec-11-en-10-one, or the compound
II-M.X.4 3-(4'-fluoro-2,4-dimethylbiphenyl-3-yl)-4-hydroxy-8-oxa-1-azaspiro[4.5]dec-3-en-2-one, or the compound II-M.X.5: 1-[2-fluoro-4-methyl-5-[(2,2,2-trifluoroethyl)sufinyl]phenyl]-3-(trifluoromethyl)-1H-1,2,4-triazole-5-amine, or actives on basis of *bacillus firmus* (Votivo, I-1582), or II-M.X.6; a compound selected from the group of II-M.X.6a: (E/Z)—N-[1-[(6-chloro-3-pyridyl)methyl]-2-pyridylidene]-2,2,2-trifluoro-acetamide;

II-M.X.6b: (E/Z)—N-[1-[(6-chloro-5-fluoro-3-pyridyl)methyl]-2-pyridylidene]-2,2,2-trifluoro-acetamide;

II-M.X.6c: (E/Z)-2,2,2-trifluoro-N-[1-[(6-fluoro-3-pyridyl)methyl]-2-pyridylidene]acetamide;

II-M.X.6d: (E/Z)—N-[1-[(6-bromo-3-pyridyl)methyl]-2-pyridylidene]-2,2,2-trifluoro-acetamide;

II-M.X.6e: (E/Z)—N-[1-[1-(6-chloro-3-pyridyl)ethyl]-2-pyridylidene]-2,2,2-trifluoro-acetamide;

II-M.X.6f: (E/Z)—N-[1-[(6-chloro-3-pyridyl)methyl]-2-pyridylidene]-2,2-difluoro-acetamide;

II-M.X.6g: (E/Z)-2-chloro-N-[1-[(6-chloro-3-pyridyl)methyl]-2-pyridylidene]-2,2-difluoro-acetamide;

II-M.X.6h: (E/Z)—N-[1-[(2-chloropyrimidin-5-yl)methyl]-2-pyridylidene]-2,2,2-trifluoro-acetamide and II-M.X.6i: (E/Z)—N-[1-[(6-chloro-3-pyridyl)methyl]-2-pyridylidene]-2,2,3,3,3-pentafluoro-propanamide; or II-M.X.7: triflumezopyrim; or II-M.X.8: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or II-M.X.9: 3-[3-chloro-5-(trifluoromethyl)phenyl]-4-oxo-1-(pyrimidin-5-ylmethyl)pyrido[1,2-a]pyrimidin-1-ium-2-olate; or II-M.X.10: 8-chloro-N-[2-chloro-5-methoxyphenyl)sulfonyl]-6-trifluoromethyl)-imidazo[1,2-a]pyridine-2-carboxamide; or II-M.X.11: 4-[5-(3,5-dichlorophenyl)-5-(trifluoromethyl)-4H-isoxazol-3-yl]-2-methyl-N-(1-oxothietan-3-yl)benzamide; or II-M.X.12: 5-[3-[2,6-dichloro-4-(3,3-dichloroallyloxy)phenoxy]propoxy]-1H-pyrazole; or II-M.Y Biopesticides, e.g.

II-M.Y-1: Microbial pesticides with insecticidal, acaricidal, molluscidal and/or nematicidal activity: *Bacillus firmus*, *B. thuringiensis* ssp. *israelensis*, B. t. ssp. *galleriae*, B. t. ssp. *kurstaki*, *Beauveria bassiana*, *Burkholderia* sp., *Chromobacterium subtsugae*, *Cydia pomonella granulosis virus*, *Isaria fumosorosea*, *Lecanicillium longisporum*, *L. muscarium* (formerly *Verticillium lecanii*), *Metarhizium anisopliae*, *M. anisopliae* var. *acridum*, *Paecilomyces fumosoroseus*, *P. lilacinus*, *Paenibacillus poppiliae*, *Pasteuria* spp., *P. nishizawae*, *P. reneformis*, *P. usagae*, *Pseudomonas fluorescens*, *Steinernema feltiae*, *Streptomces galbus*;

II-M.Y-2) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodae*, Catnip oil, Neem oil, Quillay extract, *Tagetes* oil;

Some of the compounds may have a synergistic effect, e.g. the compounds described above under Embodiment A.

Moreover, it has been found that simultaneously, that is joint or separate, application of one or more active compound(s) I and one or more compound(s) II or successive application (that is immediately one after another and thereby creating the mixture "in-situ" on the desired location, as e.g. the plant) of one or more active compound(s) I and one or more active compound(s) II allows enhanced control of pests compared to the control rates that are possible with the individual compounds.

Therefore, the term "mixture" as used herein is intended to include also combinations.

The present invention also provides methods for the control of insects, acarids or nematodes comprising contacting the insect, acarid or nematode or their food supply, habitat, breeding grounds or their locus with a pesticidally effective amount of mixtures of at least one active compound I with at least one active compound II.

Moreover, the present invention also relates to a method of protecting plants from attack or infestation by insects, acarids or nematodes comprising contacting the plant, or the soil or water in which the plant is growing, with a pesticidally effective amount of a mixture of at least one active compound I with at least one active compound II.

The invention also provides a method for the protection of plant propagation material, preferably seeds, from soil insects and of the seedlings' roots and shoots from soil and foliar insects which comprises contacting the plant propagation material as e.g. the seeds before sowing and/or after pregermination with a pesticidally effective amount of a mixture of at least one active compound I with at least one active compound II.

The invention also provides seeds comprising a mixture of at least one active compound I with at least one active compound II.

The invention also provides pesticidal compositions, comprising a liquid or solid carrier and a mixture of at least one active compound I with at least one active compound II.

The invention also relates to the use of a mixture of at least one active compound I with at least one active compound II for combating insects, arachnids or nematodes.

The mixture(s) of at least one active compound I with at least one active compound II are herein referred to as "mixture(s) according to the invention".

In a specific embodiment, the mixture according to the invention is a mixture of one active compound I with one active compound II (binary mixture).

In another embodiment, the mixture according to the invention is a mixture of one active compound I with at least one active compound II.

In another embodiment, the mixture according to the invention is a mixture of one active compound I with two active compounds II, or with one active compound II and a further active compound, e.g. selected from group F, as described herein (ternary mixture).

In another embodiment, the mixture according to the invention is a mixture of one active compound I with three active compounds II, or with three active compounds selected from group M and group F, wherein at least one compound is selected from group M (4-way mixture).

In another embodiment, the mixture according to the invention is a mixture of one active compound I with four active compounds II or compounds selected from group M and group F, wherein at least one compound is selected from group M (5-way mixture).

Compounds II

The commercially available compounds II of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The pyrethroid momfluorothrin is known from U.S. Pat. No. 6,908,945. The pyrazole acaricide pyflubumide is known from WO2007/020986. The isoxazoline compound II-M.X.1 has been described in WO2005/085216, II-M.X.8 in WO2009/002809 and in WO2011/149749 and the isoxazoline II-M.X.11 in WO2013/050317. The pyripyropene derivative II-M.X.2 has been described in WO 2006/129714. The spiroketal-substituted cyclic ketoenol derivative II-M.X.3 is known from WO2006/089633 and the biphenyl-substituted spirocyclic ketoenol derivative II-M.X.4 from WO2008/067911. Triazoylphenylsulfide like II-M.X.5 have been described in WO2006/043635 and biological control agents on basis of *bacillus firmus* in WO2009/124707. The neonicotinoids II-M4A.1 is known from WO20120/069266 and WO2011/06946, the II-M.4A.2 from WO2013/003977, the II-M4A.3. from WO2010/069266. The metaflumizone analogue II-M.22C is described in CN 10171577. Cyantraniliprole (Cyazypyr) is known from e.g. WO 2004/067528. The phthalamides II-M.26.1 and II-M.26.2 are both known from WO 2007/101540. The anthranilamide II-M.26.3 has been described in WO 2005/077934. The hydrazide compound II-M.26.4 has been described in WO 2007/043677. The anthranilamide II-M.26.5a) is described in WO2011/085575, the II-M.26.5b) in WO2008/134969, the II-M.26.5c) in US2011/046186 and the II-M.26.5d in WO2012/034403. The diamide compounds II-M.26.6 and II-M.26.7 can be found in CN102613183.

The compounds II-M.X.6a) to II-M.X.6i) listed in II-M.X.6 have been described in WO2012/029672.

The mesoionic compound II-M.X.9 was described in WO2012/092115, the nematicide II-M.X.10 in WO2013/055584 and the Pyridalyl-type analogue II-M.X.12 in WO2010/060379.

Biopesticides

The biopesticides from group II-M.Y, and from group F.XIII) as described below, their preparation and their biological activity e.g. against harmful fungi, pests is known (e-Pesticide Manual V 5.2 (ISBN 978 1 901396 85 0) (2008-2011); www.epa.gov/opp00001/biopesticides/, see product lists therein; www.omri.org/omri-lists, see lists therein; Bio-Pesticides Database BPDB sitem.herts.ac.uk-laeru/bpdb/, see A to Z link therein). Many of these biopesticides are registered and/or are commercially available: aluminium silicate (SCREEN™ DUO from Certis LLC, USA), *Ampelomyces quisqualis* M-10 (e.g. AQ 10® from Intrachem Bio GmbH & Co. KG, Germany), *Ascophyllum nodosum* (Norwegian kelp, Brown kelp) extract (e.g. ORKA GOLD from Becker Underwood, South Africa), *Aspergillus flavus* NRRL 21882 (e.g. AFLA-GUARD® from Syngenta, CH), *Aureobasidium pullulans* (e.g. BOTECTOR® from bio-ferm GmbH, Germany), *Azospirillum brasilense* XOH (e.g. AZOS from Xtreme Gardening, USA USA or RTI Reforestation Technologies International; USA), *Bacillus amyloliquefaciens* IT-45 (CNCM I 3800, NCBI 1091041) (e.g. RHIZOCELL C from ITHEC, France), *B. amyloliquefaciens* subsp. *plantarum* MBI600 (NRRL B-50595, deposited at United States Department of Agriculture) (e.g. INTEGRAL®, CLARITY, SUBTILEX NG from Becker Underwood, USA), *B. pumilus* QST 2808 (NRRL Accession No. B 30087) (e.g. SONATA® and BALLAD® Plus from AgraQuest Inc., USA), *B. subtilis* GB03 (e.g. KODIAK from Gustafson, Inc., USA), *B. subtilis* GB07 (EPIC from Gustafson, Inc., USA), *B. subtilis* QST-713 (NRRL-Nr. B 21661 in RHAPSODY®, SERENADE® MAX and SERENADE® ASO from Agra-Quest Inc., USA), *B. subtilis* var. *amyloliqueᄀfaciens* FZB24 (e.g. TAEGRO® from Novozyme Biologicals, Inc., USA), *B. subtilis* var. *amyloliquefaciens* D747 (e.g. Double Nickel 55 from Certis LLC, USA), *Bacillus thuringiensis* ssp. *kurstaki* SB4 (e.g. BETA PRO® from Becker Underwood, South Africa), *Beauveria bassiana* GHA (BOTANIGARD® 22WGP from Laverlam Int. Corp., USA), *B. bassiana* 12256 (e.g. BIOEXPERT® SC from Live Sytems Technology S.A., Colombia), *B. bassiana* PRPI 5339 (ARSEF number 5339 in the USDA ARS collection of entomopathogenic fungal cultures) (e.g. BROADᄀBAND® from Becker Underwood, South Africa), *Bradyrhizobium* sp. (e.g. VAULT® from Becker Underwood, USA), *B. japonicum* (e.g. VAULT® from Becker Underwood, USA), *Candida oleophila* 1-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* CON/M/91-08 (e.g. Contans® WG from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Ecklonia maxima* (kelp) extract (e.g. KELPAK SL from Kelp Products Ltd, South Africa), *Fusarium oxysporum* (e.g. BIOFOX® from S.I.A.P.A., Italy, FUSACLEAN® from Natural Plant Protection, France), *Glomus intraradices* (e.g. MYC 4000 from ITHEC, France), *Glomus intraradices* RTI-801 (e.g. MYKOS from Xtreme Gardening, USA or RTI Reforestation Technologies International; USA), grapefruit seeds and pulp extract (e.g. BC-1000 from Chemie S.A., Chile), *Isaria fumosorosea* Apopka-97 (ATCC 20874) (PFR-97™ from Certis LLC, USA), *Lecanicillium muscarium* (formerly *Verticillium lecanii*) (e.g. MYCOTAL from Koppert BV, Netherlands), *Lecanicillium longisporum* KV42 and KV71 (e.g. VERTALEC® from Koppert BV, Netherlands), *Metarhizium anisopliae* var. *acridum* IMI 330189 (deposited in European Culture Collections CABI) (e.g. GREEN MUSCLE® from Becker Underwood, South Africa), *M. anisopliae* FI-1045 (e.g. BIOCANE® from Becker Underwood Pty Ltd, Australia), *M. anisopliae* var. *acridum* FI-985 (e.g. GREEN GUARD® SC from Becker Underwood Pty Ltd, Australia), *M. anisopliae* F52 (e.g. MET52® Novozymes Biologicals BioAg Group, Canada), *M. anisopliae* ICIPE 69 (e.g. METATHRIhPOL from ICIPE, Kenya), *Metschnikowia fructicola* (e.g. SHEMER® from Agrogreen, Israel), *Microdochium dimerum* (e.g. ANTIBOT® from Agrauxine, France), Neem oil (e.g. TRILOGY®, TRIACT® 70 EC from Certis LLC, USA), *Paecilomyces fumosoroseus* strain FE 9901 (e.g. NO FLY™ from Natural Industries, Inc., USA), *P. lilacinus* DSM 15169 (e.g. NEMATA® SC from Live Systems Technology S.A., Colombia), *P. lilacinus* BCP2 (e.g. PL GOLD from Becker Underwood BioAg SA Ltd, South Africa), mixture of *Paenibacillus alvei NAS6G6 and *Bacillus pumilis* (e.g. BAC-UP from Becker Underwood South Africa), *Penicillium bilaiae* (e.g. JUMP START® from Novozymes Biologicals BioAg Group, Canada), *Phlebiopsis gigantea* (e.g. ROT-STOP® from Verdera, Finland), potassium silicate (e.g. Sil-MATRIX™ from Certis LLC, USA), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* extract (e.g. REGALIA® from Marrone BioInnovations, USA), *Rhizobium leguminosarum* bv. *phaseolii* (e.g. RHIZO-STICK from Becker Underwood, USA), R. l. *trifolii* (e.g. DORMAL from Becker Underwood, USA), R. l. bv. *viciae* (e.g. NODULATOR from Becker Underwood, USA), *Sinorhizobium meliloti* (e.g. DORMAL ALFALFA from Becker Underwood, USA; NITRAGIN® Gold from Novozymes Biologicals BioAg Group, Canada), *Steinernema feltiae* (NEMA¬ SHIELD® from BioWorks, Inc., USA), *Streptomyces lydicus* WYEC 108 (e.g. Actinovate® from Natural Industries, Inc., USA, U.S. Pat. No. 5,403,584), *S. violaceusniger* YCED-9 (e.g. DT-9® from Natural Industries, Inc., USA, U.S. Pat. No. 5,968,503), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. fertile* JM41R (e.g. RICHPLUS™ from Becker Underwood Bio Ag SA Ltd, South Africa), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICO-VAB® from C.E.P.L.A.C., Brazil), *T. virens* GL-21 (also named *Gliocladium virens*) (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ), *Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. mojavensis* AP-209 (No. NRRL B-50616), *B. solisalsi* AP-217 (NRRL B-50617), *B. pumilus* strain INR-7 (otherwise referred to as BU-F22 (NRRL B-50153) and BU-F33 (NRRL B-50185)), *B. simplex* ABU 288 (NRRL B-50340) and *B.amyloliquefaciens* subsp. *plantarum* MBI600 (NRRL B-50595) have been mentioned i.a. in US patent appl. 20120149571, WO 2012/079073. *Beauveria bassiana* DSM 12256 is known from US200020031495. *Bradyrhizobium japonicum* USDA is known from U.S. Pat. No. 7,262,151.

*Sphaerodes mycoparasitica* IDAC 301008-01 (IDAC=International Depositary Authority of Canada Collection) is known from WO 2011/022809.

*Bacillus amyloliquefaciens* subsp. *plantarum* MBI600 having the accession number NRRL B-50595 is deposited with the United States Department of Agriculture on Nov. 10, 2011 under the strain designation *Bacillus subtilis* 1430. It has also been deposited at The National Collections of Industrial and Marine Bacteria Ltd. (NCIB), Torry Research Station, P.O. Box 31, 135 Abbey Road, Aberdeen, AB9 8DG, Scotland. under accession number 1237 on Dec. 22, 1986. *Bacillus amyloliquefaciens* MBI600 is known as plant growth-promoting rice seed treatment from Int. J. Microbiol. Res. ISSN 0975-5276, 3(2) (2011), 120-130 and further described e.g. in US 2012/0149571 A1. This strain MBI600 is commercially available as liquid formulation product Integral® (Becker-Underwood Inc., USA). Recently, the strain MBI 600 has been re-classified as *Bacillus amyloliquefaciens* subsp. *plantarum* based on polyphasic testing which combines classical microbiological methods relying on a mixture of traditional tools (such as culture-based methods) and molecular tools (such as genotyping and fatty acids analysis).

Thus, *Bacillus subtilis* MBI600 (or MBI 600 or MBI-600) is identical to *Bacillus amyloliquefaciens* subsp. *plantarum* MBI600, formerly *Bacillus subtilis* MBI600.

*Metarhizium anisopliae* IMI33 is commercially available from Becker Underwood as product Green Guard. *M. anisopliae* var *acridium* strain IMI 330189 (NRRL-50758) is commercially available from Becker Underwood as product Green Muscle.

*Bacillus subtilis* strain FB17 was originally isolated from red beet roots in North America (System Appl. Microbiol 27 (2004) 372-379). This *Bacillus subtilis* strain promotes plant health (US 2010/0260735 A1; WO 2011/109395 A2). *B. subtilis* FB17 has also been deposited at American Type Culture Collection (ATCC), Manassas, Va., USA, under accession number PTA-11857 on Apr. 26, 2011. *Bacillus subtilis* strain FB17 may also be referred to as UD1022 or UD10-22.

According to one embodiment of the inventive mixtures, the at least one biopesticide II is selected from the groups II-M.Y-1 to II-M.Y-2:

II-M.Y-1: Microbial pesticides with insecticidal, acaricidal, molluscidal and/or nematicidal activity: *Bacillus firmus* St 1582, *B. thuringiensis* ssp. *israelensis* SUM-6218, B. t. ssp. *galleriae* SDS-502, B. t. ssp. *kurstaki*, *Beauveria bassiana* GHA, *B. bassiana* H123, *B. bassiana* DSM 12256, *B. bassiana* PRPI 5339, *Burkholderia* sp. A396, *Chromobacterium subtsugae* PRAA4-1T, *Cydia pomonella granulosis* virus isolate V22, *Isaria fumosorosea* Apopka-97, *Lecanicillium longisporum* KV42, *L. longisporum* KV71, *L. muscarium* (formerly *Verticillium lecanii*), *Metarhizium anisopliae* FI-985, *M. anisopliae* FI-1045, *M. anisopliae* F52, *M. anisopliae* ICIPE 69, *M. anisopliae* var. *acridum* IMI 330189, *Paecilomyces fumosoroseus* FE 9901, *P. lilacinus* DSM 15169, *P. lilacinus* BCP2, *Paenibacillus poppiliae* Dutky-1940 (NRRL B-2309=ATCC 14706), *P. poppiliae* KLN 3, *P. poppiliae* Dutky 1, *Pasteuria* spp. Ph3, *P. nishizawae* PN-1, *P. reneformis* Pr-3, *P. usagae*, *Pseudomonas fluorescens* CL 145A, *Steinernema feltiae*, *Streptomces galbus*;

II-M.Y-2: Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia*

*negra* extract, extract of grapefruit seeds and pulp, extract of *Chenopodium ambrosiodae*, Catnip oil, Neem oil, Quillay extract, *Tagetes* oil;

According to one embodiment of the inventive mixtures, the at least one biopesticide II is selected from group II-M.Y-1.

According to one embodiment of the inventive mixtures, the at least one biopesticide II is selected from II-M.Y-2.

According to one embodiment of the inventive mixtures, the at least one biopesticide II is *Bacillus amyloliquefaciens* subsp. *plantarum* MBI600. These mixtures are particularly suitable in soybean.

According to another embodiment of the inventive mixtures, the at least one biopesticide II is *B. pumilus* strain INR-7 (otherwise referred to as BU-F22 (NRRL B-50153) and BU-F33 (NRRL B-50185; see WO 2012/079073). These mixtures are particularly suitable in soybean and corn.

According to another embodiment of the inventive mixtures, the at least one biopesticide II is *Bacillus pumilus*, preferably *B. pumilis* strain INR-7 (otherwise referred to as BU-F22 (NRRL B-50153) and BU-F33 (NRRL B-50185). These mixtures are particularly suitable in soybean and corn.

According to another embodiment of the inventive mixtures, the at least one biopesticide II is *Bacillus simplex*, preferably *B. simplex* strain ABU 288 (NRRL B-50340). These mixtures are particularly suitable in soybean and corn.

According to another embodiment of the inventive mixtures, the at least one biopesticide II is selected from *Trichoderma asperellum, T. atroviride, T. fertile, T. gamsii, T. harmatum*; mixture of *T. harzia¬ num* and *T. viride*; mixture of *T. polysporum* and *T. harzianum; T. stromaticum, T. virens* (also named *Gliocladium virens*) and *T. viride*; preferably *Trichoderma fertile*, in particular *T. fertile* strain JM41R. These mixtures are particularly suitable in soybean and corn.

According to another embodiment of the inventive mixtures, the at least one biopesticide II is *Sphaerodes mycoparasitica*, preferably *Sphaerodes mycoparasitica* strain IDAC 301008-01 (also referred to as strain SMCD2220-01). These mixtures are particularly suitable in soybean and corn.

According to another embodiment of the inventive mixtures, the at least one biopesticide II is *Beauveria bassiana*, preferably *Beauveria bassiana* strain PPR15339. These mixtures are particularly suitable in soybean and corn.

According to another embodiment of the inventive mixtures, the at least one biopesticide II is *Metarhizium anisopliae* or *M. anisopliae* var. *acridium*, preferably selectged from *M anisolpiae* strain IMI33 and *M. anisopliae* var. *acridium* strain IMI 330189. These mixtures are particularly suitable in soybean and corn.

According to another embodiment of the inventive mixtures, *Bradyrhizobium* sp. (meaning any *Bradyrhizobium* species and/or strain) as biopesticide II is *Bradyrhizobium japonicum* (*B. japonicum*). These mixtures are particularly suitable in soybean. Preferably *B. japonicum* is not one of the strains TA-11 or 532c. *B. japonicum* strains were cultivated using media and fermentation techniques known in the art, e.g. in yeast extract-mannitol broth (YEM) at 27° C. for about 5 days.

References for various *B. japonicum* strains are given e.g. in U.S. Pat. No. 7,262,151 (*B. japonicum* strains USDA 110 (=IITA 2121, SEMIA 5032, RCR 3427, ARS 1-110, Nitragin 61A89; isolated from *Glycine max* in Florida in 1959, Serogroup 110; Appl Environ Microbiol 60, 940-94, 1994), USDA 31 (=Nitragin 61A164; isolated from *Glycine max* in Wisoconsin in 1941, USA, Serogroup 31), USDA 76 (plant passage of strain USDA 74 which has been isolated from *Glycine max* in California, USA, in 1956, Serogroup 76), USDA 121 (isolated from *Glycine max* in Ohio, USA, in 1965), USDA 3 (isolated from *Glycine max* in Virginia, USA, in 1914, Serogroup 6) and USDA 136 (=CB 1809, SEMIA 586, Nitragin 61A136, RCR 3407; isolated from *Glycine max* in Beltsville, Md. in 1961; Appl Environ Microbiol 60, 940-94, 1994). USDA refers to United States Department of Agriculture Culture Collection, Beltsville, Md., USA (see e.g. Beltsville *Rhizobium* Culture Collection Catalog March 1987 ARS-30). Further suitable *B. japonicum* strain G49 (INRA, Angers, France) is described in Fernandez-Flouret, D. & Cleyet-Marel, J. C. (1987) C R Acad Agric Fr 73, 163-171), especially for soybean grown in Europe, in particular in France. Further suitable *B. japonicum* strain TA-11 (TA11 NOD+) (NRRL B-18466) is i.a. described in U.S. Pat. No. 5,021,076; Appl Environ Microbiol (1990) 56, 2399-2403 and commercially available as liquid inoculant for soybean (VAULT® NP, Becker Underwood, USA). Further *B. japonicum* strains as example for biopesticide II are described in US2012/0252672A. Further suitable and especially in Canada commercially available strain 532c (The Nitragin Company, Milwaukee, Wis., USA, field isolate from Wisconsin; Nitragin strain collection No. 61A152; Can J Plant Sci 70 (1990), 661-666).

Other suitable and commercially available *B. japonicum* strains (see e.g. Appl Environ Microbiol 2007, 73(8), 2635) are SEMIA 566 (isolated from North American inoculant in 1966 and used in Brazilian commercial inoculants from 1966 to 1978), SEMIA 586 (=CB 1809; originally isolated in Maryland, USA but received from Austrailia in 1966 and used in Brazilian inoculants in 1977), CPAC 15 (=SEMIA 5079; a natural varaiant of SEMIA 566 used in commercial inoculants since 1992) and CPAC 7 (=SEMIA 5080; a natural variant of SEMIA 586 used in commercial inoculants since 1992). These strains are especially suitable for soybean grown in Australia or South America, in particular in Brazil. Some of the abovementioned strains have been re-classified as a novel species *Bradyrhizobium elkanii*, e.g. strain USDA 76 (Can. J. Microbiol., 1992, 38, 501-505).

Another suitable and commercially available *B. japonicum* strain is E-109 (variant of strain USDA 138, see e.g. Eur. J. Soil Biol. 45 (2009) 28-35; Biol Fertil Soils (2011) 47:81-89, deposited at Agriculture Collection Laboratory of the Instituto de Microbiologia y Zoologia Agricola (IMYZA), Instituto Nacional de Tecnologi'a Agropecuaria (INTA), Castelar, Argentina). This strain is especially suitable for soybean grown in South America, in particular in Argentina. The present invention also relates to mixtures, wherein the at least one biopesticide II is selected from *Bradyrhizobium elkanii* and *Bradyrhizobium liaoningense* (*B. elkanii* and *B. liaoningense*), more preferably from *B. elkanii*. These mixtures are particularly suitable in soybean. *B. elkanii* and *liaoningense* were cultivated using media and fermentation techniques known in the art, e.g. in yeast extract-mannitol broth (YEM) at 27° C. for about 5 days.

Suitable and commercially available *B. elkanii* strains are SEMIA 587 and SEMIA 5019 (=29W) (see e.g. Appl Environ Microbiol 2007, 73(8), 2635) and USDA 3254 and USDA 76 and USDA 94. Further commercially available *B. elkanii* strains are U-1301 and U-1302 (e.g. product Nitroagin® Optimize from Novozymes Bio As S.A., Brazil or NITRASEC for soybean from LAGE y Cia, Brazil). These strains are especially suitable for soybean grown in Australia or South America, in particular in Brazil.

The present invention also relates to mixtures, wherein the at least one biopesticide II is selected from *Bradyrhizobium japonicum* (*B. japonicum*) and further comprises a compound III, wherein compound III is selected from jasmonic acid or salts or derivatives thereof including cis-jasmone, preferably methyl-jasmonate or cis-jasmone.

The present invention also relates to mixtures, wherein biopesticide II is selected from *Bradyrhizobium* sp. (*Arachis*) (B. sp. *Arachis*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*). This mixture comprising as biopesticide II B. sp. *Arachis* is especially suitable for use in peanut, Cowpea, Mung bean, Moth bean, Dune bean, Rice bean, Snake bean and Creeping vigna, in particular peanut.

Suitable and commercially available B. sp. (*Arachis*) strain is CB1015 (=IITA 1006, USDA 3446 presumably originally collected in India; from Australian Inoculants Research Group; see e.g. www.qaseeds.com.au/inoculant_applic.php; Beltsville *Rhizobium* Culture Collection Catalog March 1987 USDA-ARS ARS-30). These strains are especially suitable for peanut grown in Australia, North America or South America, in particular in Brazil. Further suitable strain is *bradyrhizobium* sp. PNLO1 (Becker Underwood; ISO Rep Marita McCreary, QC Manager Padma Somasageran; IDENTIFICATION OF *RHIZOBIA* SPECIES THAT CAN ESTABLISH NITROGEN-FIXING NODULES IN *CROTALARIA LONGIROSTRATA*. Apr. 29, 2010, University of Massachusetts Amherst: www.wpi.edu/Pubs/E-project/Available/E-project-042810-163614/unrestricted/Bisson.Mason._Identification_of_Rhizobia_Species_That_can_Establish_Nitrogen-Fixing_Nodules_in_Crotalia_Longirostrata.pdf).

Suitable and commercially available *Bradyrhizobium* sp. (*Arachis*) strains especially for cowpea and peanut but also for soybean are *Bradyrhizobium* SEMIA 6144, SEMIA 6462 (=BR 3267) and SEMIA 6464 (=BR 3262) (deposited at FEPAGRO-MIRCEN, R. Gonçalves Dias, 570 Porto Alegre-RS, 90130-060, Brazil; see e.g. FEMS Microbiology Letters (2010) 303(2), 123-131; Revista Brasileira de Ciencia do Solo (2011) 35(3); 739-742, ISSN 0100-0683).

The present invention also relates to mixtures wherein the at least one biopesticide II is selected from *Bradyrhizobium* sp. (*Arachis*) and further comprises a compound III, wherein compound III is selected from jasmonic acid or salts or derivatives thereof including cis-jasmone, preferably methyl-jasmonate or cis-jasmone.

The present invention also relates to mixtures, wherein the at least one biopesticide II is selected from *Bradyrhizobium* sp. (Lupine) (also called *B. lupini, B. lupines* or *Rhizobium lupini*).

This mixture is especially suitable for use in dry beans and lupins.

Suitable and commercially available *B. lupini* strain is LL13 (isolated from *Lupinus iuteus* nodules from French soils; deposited at INRA, Dijon and Angers, France; www.agriculture.gouv.fr/IMG/pdf/ch20060216.pdf). This strain is especially suitable for lupins grown in Australia, North America or Europe, in particular in Europe.

Further suitable and commercially available *B. lupini* strains WU425 (isolated in Esperance, Western Australia from a non-Australian legume *Ornthopus compressus*), WSM4024 (isolated from lupins in Australia by CRS during a 2005 survey) and WSM471 (isolated from *Ornithopus pinnatus* in Oyster Harbour, Western Australia) are described e.g. in Palta J. A. and Berger J. B. (eds), 2008, Proceedings 12th International Lupin Conference, 14-18 Sep. 2008, Fremantle, Western Australia. International Lupin Association, Canterbury, New Zealand, 47-50, ISBN 0-86476-153-8: www.lupins.org/pdf/conference/2008/Agronomy%20and%2Production/John%20Howies on%20and%20G%200Hara.pdf; Appl Environ Microbiol (2005) 71, 7041-7052 and Australian J. Exp. Agricult. (1996) 36(1), 63-70.

The present invention also relates to mixtures wherein the at least one biopesticide II is selected from *Bradyrhizobium* sp. (Lupine) (*B. lupini*) and further comprises a compound III, wherein compound III is selected from jasmonic acid or salts or derivatives thereof including cis-jasmone, preferably methyl-jasmonate or cis-jasmone.

The present invention also relates to mixtures, wherein the at least one biopesticide II is selected from *Mesorhizobium* sp. (meaning any *Mesorhizobium* species and/or strain), more preferably *Mesorhizobium ciceri*. These mixtures are particularly suitable in cowpea.

Suitable and commercially available M. sp. strains are e.g. *M. ciceri* CC1192 (=UPM 848, CECT 5549; from Horticultural Research Station, Gosford, Australia; collected in Israel from *Cicer arietinum* nodules; Can J Microbial (2002) 48, 279-284) and *Mesorhizobium* sp. strains WSM1271 (collected in Sardinia, Italy, from plant host *Biserrula pelecinus*), WSM 1497 (collected in Mykonos, Greece, from plant host *Biserrula pelecinus*), *M. loti* strains CC829 (commerical inoculant for *Lotus pedunculatus* and L. ulginosus in Australia, isolated from L. ulginosus nodules in USA) and SU343 (commercial inoculant for *Lotus corniculatus* in Australia; isolated from host nodules in USA) all of which are deposited at Western Australian Soil Microbiology (WSM) culture collection, Australia and/or CSIRO collection (CC), Canberra, Australian Capirtal Territory (see e.g. Soil Biol Biochem (2004) 36(8), 1309-1317; Plant and Soil (2011) 348(1-2), 231-243).

Suitable and commercially available *M. loti* strains are e.g. *M. loti* CC829 for *Lotus pedunculatus*.

The present invention also relates to mixtures wherein the at least one biopesticide II is selected from *Bradyrhizobium* sp. (Lupine) (*B. lupini*) and further comprises a compound III, wherein compound III is selected from jasmonic acid or salts or derivatives thereof including cis-jasmone, preferably methyl-jasmonate or cis-jasmone.

The present invention also relates to mixtures wherein the at least one biopesticide II is selected from *Mesorhizobium huakuii*, also referred to as *Rhizobium huakuii* (see e.g. Appl. Environ. Microbiol. 2011, 77(15), 5513-5516). These mixtures are particularly suitable in *Astralagus*, e.g. *Astalagus sinicus* (Chinese milkwetch), *Thermopsis*, e.g. *Thermopsis luinoides* (Goldenbanner) and alike.

Suitable and commercially available *M. huakuii* strain is HN3015 which was isolated from *Astralagus sinicus* in a rice-growing field of Southern China (see e.g. World J. Microbiol. Biotechn. (2007) 23(6), 845-851, ISSN 0959-3993).

The present invention also relates to mixtures wherein the at least one biopesticide II is selected from *Mesorhizobium huakuii* and further comprises a compound III, wherein compound III is selected from jasmonic acid or salts or derivatives thereof including cis-jasmone, preferably methyl-jasmonate or cis-jasmone.

The present invention also relates to mixtures, wherein the at least one biopesticide II is selected from *Azospirillum amazonense, A. brasilense, A. lipoferum, A. irakense, A. halopraeferens*, more preferably from *A. brasilense*, in particular selected from *A. brasilense* strains BR 11005 (SP 245) and AZ39 which are both commercially used in Brazil and are obtainable from EMBRAPA, Brazil. These mixtures are particularly suitable in soybean. Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

Salts of jasmonic acid (jasmonate) or derivatives include without limitation the jasmonate salts potassium jasmonate, sodium jasmonate, lithium jasmonate, ammonium jasmonate, dimethylammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-1-oxo-indane-4-carbonyl)-amino]-3-methyl-pentanoic acid methyl ester), linoleic acid or derivatives thereof and cis-jasmone, or combinations of any of the above.

According to one embodiment, the microbial pesticides embrace not only the isolated, pure cultures of the respective micro-organism as defined herein, but also its cell-free extract, its suspensions in a whole broth culture or as a metabolite-containing supernatant or a purified metabolite obtained from a whole broth culture of the microorganism or microorganism strain.

According to a further embodiment, the microbial pesticides embrace not only the isolated, pure cultures of the respective micro-organism as defined herein, but also a cell-free extract thereof or at least one metabolite thereof, and/or a mutant of the respective micro-organism having all the identifying characteristics thereof and also a cell-free extract or at least one metabolite of the mutant.

"Whole broth culture" refers to a liquid culture containing both cells and media.

"Supernatant" refers to the liquid broth remaining when cells grown in broth are removed by centrifugation, filtration, sedimentation, or other means well known in the art.

The term "metabolite" refers to any compound, substance or byproduct produced by a microorganism (such as fungi and bacteria) that has improves plant growth, water use efficiency of the plant, plant health, plant appearance, or the population of beneficial microorganisms in the soil around the plant activity.

The term "mutant" refers a microorganism obtained by direct mutant selection but also includes microorganisms that have been further mutagenized or otherwise manipulated (e.g., via the introduction of a plasmid). Accordingly, embodiments include mutants, variants, and or derivatives of the respective microorganism, both naturally occurring and artificially induced mutants. For example, mutants may be induced by subjecting the microorganism to known mutagens, such as N-methyl-nitrosoguanidine, using conventional methods.

According to the invention, the solid material (dry matter) of the biopesticides (with the exception of oils such as Neem oil, Tagetes oil, etc.) are considered as active components (e.g. to be obtained after drying or evaporation of the extraction medium or the suspension medium in case of liquid formulations of the microbial pesticides).

In accordance with the present invention, the weight ratios and percentages used herein for biological extract such as Quillay extract are based on the total weight of the dry content (solid material) of the respective extract(s).

For microbial pesticides, weight ratios and/or percentages refer to the total weight of a preparation of the respective biopesticide with at least $1 \times 10^6$ CFU/g ("colony forming units per gram total weight"), preferably with at least $1 \times 10^8$ CFU/g, even more preferably from $1 \times 10^8$ to $1 \times 10^{12}$ CFU/g dry matter. Colony forming unit is measure of viable microbial cells, in particular fungal and bacterial cells. In addition, here CFU may also be understood as number of (juvenile) individual nematodes in case of (entomo-pathogenic) nematode biopesticides, such as Steinernema feltiae.

Herein, microbial pesticides may be supplied in any physiological state such as active or dormant. Such dormant active component may be supplied for example frozen, dried, or lyophilized or partly desiccated (procedures to produce these partly desiccated organisms are given in WO2008/002371) or in form of spores.

Microbial pesticides used as organism in an active state can be delivered in a growth medium without any additional additives or materials or in combination with suitable nutrient mixtures. According to a further embodiment, microbial pesticides are delivered and formulated in a dormant stage, more preferably in form of spores.

The total weight ratios of compositions, which comprise a microbial pesticide as component 2, can be determined based on the total weight of the solid material (dry matter) of component 1) and using the amount of CFU of component 2) to calclulate the total weight of component 2) with the following equation that $1 \times 10^9$ CFU equals one gram of total weight of component 2).

According to one embodiment, the compositions, which comprise a microbial pesticide, comprise between 0.01 and 90% (w/w) of dry matter (solid material) of component 1) and from $1 \times 10^5$ CFU to $1 \times 10^{12}$ CFU of component 2) per gram total weight of the composition.

According to another embodiment, the compositions, which comprise a microbial pesticide, comprise between 5 and 70% (w/w) of dry matter (solid material) of component 1) and from $1 \times 10^6$ CFU to $1 \times 10^{10}$ CFU of component 2) per gram total weight of the composition.

According to another embodiment, the compositions, wherein one component is a microbial pesticide, comprise between 25 and 70% (w/w) of dry matter (solid material) of component 1) and from $1 \times 10^7$ CFU to $1 \times 10^9$ CFU of component 2) per gram total weight of the composition.

In the case of mixtures comprising a microbial pesticide, the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e.g. Steinernema feltiae), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e.g. in the form of eggs, juvenile or any other live stages, preferably in an infetive juvenile stage) per ha.

the case of mixtures comprising microbial pesticides, the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. In the case of microbial pesticides, the application rates with respect to plant propagation material also preferably range from about $1 \times 10^7$ to $1 \times 10^{14}$ (or more) CFU per 100 kg of seed, preferably from 1×109 to about 1×10$^{11}$ CFU per 100 kg of seed.

In one embodiment, the compound I in the mixtures according to the invention of E2 is selected from the compounds described in Embodiment A.

In one embodiment, the compound I in the mixtures according to the invention of E2 is selected from the compounds described in Embodiment B.

In one embodiment, the compound I in the mixtures according to the invention of E2 is selected from the compounds described in Embodiment C.

In one embodiment, the compound I in the mixtures according to the invention of E2 is selected from the compounds listed in Table ABC.

In one embodiment, I-A-1 is the compound I in the mixtures according to the invention of E2.

In one embodiment, I-A-28 is the compound I in the mixtures according to the invention of E2.

In one embodiment, I-B-115 is the compound I in the mixtures according to the invention of E2.

In one embodiment, I-B-131 is the compound I in the mixtures according to the invention of E2.

In one embodiment, I-B-132 is the compound I in the mixtures according to the invention of E2.

In one embodiment, I-C-19 is the compound I in the mixtures according to the invention of E2.

In one embodiment, I-C-35 is the compound I in the mixtures according to the invention of E2.

In one embodiment, I-C-36 is the compound I in the mixtures according to the invention of E2.

With respect to their use in the pesticidal mixtures of the present invention, particular preference is given to the compounds II as listed in the paragraphs below.

In one embodiment, the mixture according to the invention is a mixture of the compounds I with Acetylcholine esterase (AChE) inhibitors, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with an organophosphate, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

With regard to the use in a pesticidal mixture of the present invention, a compound II selected from group II-M.2 (GABA-gated chloride channel antagonists) as defined above is preferred, in particular group II-M.2B (fiproles), especially preferred ethiprole and fipronil.

Mixtures of compounds I as individualized herein, e.g. in Table ABC, with fipronil as compound II are particularly preferred, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

With regard to the use in a pesticidal mixture of the present invention, a compound II selected from group II-M.3 (Sodium channel modulators) as defined above is preferred, in particular group II-M.3A (pyrethroids), especially preferred alpha-cypermethrin and cyhalothrin.

Mixtures of compounds I as individualized herein, e.g. in Table ABC, with alpha-cypermethrin as compound II are particularly preferred; more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

Mixtures of compounds I as individualized herein, e.g. in Table ABC, with cyhalothrin as compound II are particularly preferred, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

With regard to the use in a pesticidal mixture of the present invention, a compound II selected from group II-M.4A (Neonicotinoids) as defined above is preferred, in particular clothianidin, dinotefuran, imidacloprid, thiacloprid, or thiamethoxam.

Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with thiamethoxam as compound II are especially preferred.

Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with clothianidin as compound II are also preferred. Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with dinotefuran as compound II are also preferred. Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with imidacloprid as compound II are also preferred. Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with thiacloprid as compound II are also preferred. Mixtures of compounds I with sulfoxaflor as compound II are also preferred.

Mixtures of compounds I with dinotefuran as compound II are especially preferred.

Mixtures of compounds I as individualized herein, e.g. in Table ABC, with dinotefuran as compound II are especially preferred.

Mixtures of compounds I with dinotefuran as compound II are especially preferred, wherein the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

With regard to the use in a pesticidal mixture of the present invention, in an embodiment of the invention, the compound II is selected from group II-M.5 (Nicotinic acetylcholine receptor allosteric activators) and is preferably spinosad or spinetoram.

With regard to the use in a pesticidal mixture of the present invention, in an embodiment of the invention, the compound II is selected from group II-M.6 (Chloride channel activators) and is preferably an avermectin.

Mixtures of compounds I as individualized herein, e.g. in Table ABC, with abamectin as compound II are especially preferred.

Mixtures of compounds I with abamectin as compound II are especially preferred, wherein the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

With regard to the use in a pesticidal mixture of the present invention, in an embodiment of the invention, the compound II is selected from group II-M.9 (Selective homopteran feeding blockers) and is preferably pymetrozine or flonicamid. Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with pymetrozine as compound II are especially preferred. Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with flonicamid as compound II are especially preferred.

With regard to the use in a pesticidal mixture of the present invention, in an embodiment of the invention, the compound II is selected from group II-M.13 (Uncouplers of oxidative phosphorylation via disruption of the proton gradient) and is preferably chlorfenapyr. Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with chlorfenapyr as compound II are especially preferred.

With regard to the use in a pesticidal mixture of the present invention, in an embodiment of the invention, the compound II is selected from group II-M.16 (Inhibitors of the chitin biosynthesis type 1) and is preferably buprofezin.

With regard to the use in a pesticidal mixture of the present invention, in an embodiment of the invention, the compound II is selected from group II-M.22 (Voltage-dependent sodium channel blockers) and is preferably metaflumizone.

With regard to the use in a pesticidal mixture of the present invention, in an embodiment of the invention, the compound II is selected from group II-M.23 (Inhibitors of the of acetyl CoA carboxylase) and is preferably a Tetronic or Tetramic acid derivative, spirodiclofen, spiromesifen or spirotetramat.

Mixtures of compounds I as individualized herein, e.g. in Table ABC (more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35), with Tetronic Acid as compound II are preferred. Mixtures of compounds I as individualized herein, e.g. in Table ABC, with Tetramic Acid as compound II are also preferred. Mixtures of compounds I as individualized herein, e.g. in Table ABC, with Tetramic Acid as compound II are also preferred.

With regard to the use in a pesticidal mixture of the present invention, in an embodiment of the invention, the compound II is selected from group II-M.26 (Ryanodine receptor-modulators) and is preferably chlorantraniliprole or cyantraniliprole.

With regard to the use in a pesticidal mixture of the present invention, in an embodiment of the invention, the compound II is sulfoxaflor. Mixtures of compounds I as individualized herein, e.g. in Table ABC, with sulfoxaflor as compound II are especially preferred.

Mixtures of compounds I with sulfoxaflor as compound II are especially preferred, wherein the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

With regard to the use in a pesticidal mixture of the present invention, in an embodiment of the invention, the compound II is a neonicotinoid. Mixtures of compounds I as individualized herein, e.g. in Table ABC, in particular a compound selected preferably from a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35, with a neonicotinoid as compound II are especially preferred.

With regard to the use in a pesticidal mixture of the present invention, in an embodiment of the invention, the compound II is dinotefuran. Mixtures of compounds I as individualized herein, e.g. in Table ABC, in particular a compound selected preferably from a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35, with dinotefuran as compound II are preferred.

In another embodiment of the invention, the compound II is compound II-M.X.2. Mixtures of compounds I as individualized herein, with compound II-M.X.2 as compound II are especially preferred.

Compound II-M.X.2 is cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester:

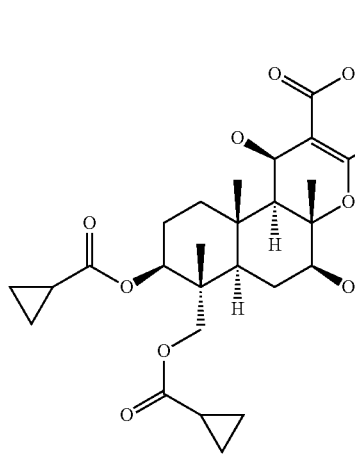

Especially preferred mixtures according to the invention are listed in the following table M:

TABLE M

| Mixture | Comp. I | Compound II |
|---|---|---|
| M.1 | I-A-1 | fipronil |
| M.2 | I-A-28 | fipronil |
| M.3 | I-B-33 | fipronil |
| M.4 | I-B-37 | fipronil |
| M.5 | I-B-115 | fipronil |
| M.6 | I-B-131 | fipronil |
| M.7 | I-B-132 | fipronil |
| M.8 | I-C-35 | fipronil |
| M.9 | I-C-36 | fipronil |
| M.10 | I-A-1 | thiamethoxam |
| M.11 | I-A-28 | thiamethoxam |
| M.12 | I-B-33 | thiamethoxam |
| M.13 | I-B-37 | thiamethoxam |
| M.14 | I-B-115 | thiamethoxam |
| M.15 | I-B-131 | thiamethoxam |
| M.16 | I-B-132 | thiamethoxam |
| M.17 | I-C-35 | thiamethoxam |
| M.18 | I-C-36 | thiamethoxam |
| M.19 | I-A-1 | abamectin |
| M.20 | I-A-28 | abamectin |
| M.21 | I-B-33 | abamectin |
| M.22 | I-B-37 | abamectin |
| M.23 | I-B-115 | abamectin |
| M.24 | I-B-131 | abamectin |
| M.25 | I-B-132 | abamectin |
| M.26 | I-C-35 | abamectin |
| M.27 | I-C-36 | abamectin |
| M.28 | I-A-1 | imidacloprid |
| M.29 | I-A-28 | imidacloprid |
| M.30 | I-B-33 | imidacloprid |
| M.31 | I-B-37 | imidacloprid |
| M.32 | I-B-115 | imidacloprid |
| M.33 | I-B-131 | imidacloprid |
| M.34 | I-B-132 | imidacloprid |
| M.35 | I-40 | imidacloprid |
| M.36 | I-C-35 | imidacloprid |
| M.37 | I-C-36 | imidacloprid |
| M.38 | I-A-1 | cyhalothrin |
| M.39 | I-A-28 | cyhalothrin |
| M.40 | I-B-33 | cyhalothrin |
| M.41 | I-B-37 | cyhalothrin |
| M.42 | I-B-115 | cyhalothrin |
| M.43 | I-B-131 | cyhalothrin |
| M.44 | I-B-132 | cyhalothrin |
| M.45 | I-C-35 | cyhalothrin |
| M.46 | I-C-36 | cyhalothrin |
| M.47 | I-A-1 | alpha-cypermethrin |
| M.48 | I-A-28 | alpha-cypermethrin |
| M.49 | I-B-33 | alpha-cypermethrin |
| M.50 | I-B-37 | alpha-cypermethrin |
| M.51 | I-B-115 | alpha-cypermethrin |
| M.52 | I-B-131 | alpha-cypermethrin |
| M.53 | I-B-132 | alpha-cypermethrin |
| M.54 | I-C-35 | alpha-cypermethrin |
| M.55 | I-C-36 | alpha-cypermethrin |
| M.56 | I-A-1 | Pymetrozine |
| M.57 | I-A-28 | Pymetrozine |
| M.58 | I-B-33 | Pymetrozine |
| M.59 | I-B-37 | Pymetrozine |
| M.60 | I-B-115 | Pymetrozine |
| M.61 | I-B-131 | Pymetrozine |
| M.62 | I-B-132 | Pymetrozine |
| M.63 | I-C-35 | Pymetrozine |
| M.64 | I-C-36 | Pymetrozine |
| M.65 | I-A-1 | Flonicamid |
| M.66 | I-A-28 | Flonicamid |
| M.67 | I-B-33 | Flonicamid |
| M.68 | I-B-37 | Flonicamid |
| M.69 | I-B-115 | Flonicamid |
| M.70 | I-B-131 | Flonicamid |
| M.71 | I-B-132 | Flonicamid |
| M.72 | I-C-35 | Flonicamid |
| M.73 | I-C-36 | Flonicamid |
| M.74 | I-A-1 | Spirotetramat |
| M.75 | I-A-28 | Spirotetramat |
| M.76 | I-B-33 | Spirotetramat |
| M.77 | I-B-37 | Spirotetramat |
| M.78 | I-B-115 | Spirotetramat |

TABLE M-continued

| Mixture | Comp. I | Compound II |
|---|---|---|
| M.79 | I-B-131 | Spirotetramat |
| M.80 | I-B-132 | Spirotetramat |
| M.81 | I-C-35 | Spirotetramat |
| M.82 | I-C-36 | Spirotetramat |
| M.83 | I-A-1 | Buprofezin |
| M.84 | I-A-28 | Buprofezin |
| M.85 | I-B-33 | Buprofezin |
| M.86 | I-B-37 | Buprofezin |
| M.87 | I-B-115 | Buprofezin |
| M.88 | I-B-131 | Buprofezin |
| M.89 | I-C-35 | Buprofezin |
| M.90 | I-C-36 | Buprofezin |
| M.91 | I-A-1 | Chlorfenapyr |
| M.92 | I-A-28 | Chlorfenapyr |
| M.93 | I-B-33 | Chlorfenapyr |
| M.94 | I-B-37 | Chlorfenapyr |
| M.95 | I-B-115 | Chlorfenapyr |
| M.96 | I-B-131 | Chlorfenapyr |
| M.97 | I-B-132 | Chlorfenapyr |
| M.98 | I-C-35 | Chlorfenapyr |
| M.99 | I-C-36 | Chlorfenapyr |
| M.100 | I-A-1 | Compound II-M.X.2 |
| M.101 | I-A-28 | Compound II-M.X.2 |
| M.102 | I-B-33 | Compound II-M.X.2 |
| M.103 | I-B-37 | Compound II-M.X.2 |
| M.104 | I-B-115 | Compound II-M.X.2 |
| M.105 | I-B-131 | Compound II-M.X.2 |
| M.106 | I-B-132 | Compound II-M.X.2 |
| M.107 | I-C-35 | Compound II-M.X.2 |
| M.108 | I-C-36 | Compound II-M.X.2 |
| M.109 | I-A-1 | sulfoxaflor |
| M.110 | I-A-28 | sulfoxaflor |
| M.111 | I-B-33 | sulfoxaflor |
| M.112 | I-B-37 | sulfoxaflor |
| M.113 | I-B-115 | sulfoxaflor |
| M.114 | I-B-131 | sulfoxaflor |
| M.115 | I-B-132 | sulfoxaflor |
| M.116 | I-C-35 | sulfoxaflor |
| M.117 | I-C-36 | sulfoxaflor |
| M.118 | I-A-1 | fluyradifurone |
| M.119 | I-A-28 | fluyradifurone |
| M.120 | I-B-33 | fluyradifurone |
| M.121 | I-B-37 | fluyradifurone |
| M.122 | I-B-115 | fluyradifurone |
| M.123 | I-B-131 | fluyradifurone |
| M.124 | I-B-132 | fluyradifurone |
| M.125 | I-C-35 | fluyradifurone |
| M.126 | I-C-36 | fluyradifurone |
| M.127 | I-A-1 | cycloxaprid |
| M.128 | I-A-28 | cycloxaprid |
| M.129 | I-B-33 | cycloxaprid |
| M.130 | I-B-37 | cycloxaprid |
| M.131 | I-B-115 | cycloxaprid |
| M.132 | I-B-131 | cycloxaprid |
| M.133 | I-B-132 | cycloxaprid |
| M.134 | I-C-35 | cycloxaprid |
| M.135 | I-C-36 | cycloxaprid |
| M.136 | I-A-1 | dinotefuran |
| M.137 | I-A-28 | dinotefuran |
| M.138 | I-B-33 | dinotefuran |
| M.139 | I-B-37 | dinotefuran |
| M.140 | I-B-115 | dinotefuran |
| M.141 | I-B-131 | dinotefuran |
| M.142 | I-B-132 | dinotefuran |
| M.143 | I-C-35 | dinotefuran |
| M.144 | I-C-36 | dinotefuran |
| M.145 | I-A-1 | metaflumizone |
| M.146 | I-A-28 | metaflumizone |
| M.147 | I-B-33 | metaflumizone |
| M.148 | I-B-37 | metaflumizone |
| M.149 | I-B-115 | metaflumizone |
| M.150 | I-B-131 | metaflumizone |
| M.151 | I-B-132 | metaflumizone |
| M.152 | I-C-35 | metaflumizone |
| M.153 | I-C-36 | metaflumizone |
| M.154 | I-A-1 | indoxacarb |
| M.155 | I-A-28 | indoxacarb |
| M.156 | I-B-33 | indoxacarb |

TABLE M-continued

| Mixture | Comp. I | Compound II |
|---|---|---|
| M.157 | I-B-37 | indoxacarb |
| M.158 | I-B-115 | indoxacarb |
| M.159 | I-B-131 | indoxacarb |
| M.160 | I-B-132 | indoxacarb |
| M.161 | I-C-35 | indoxacarb |
| M.162 | I-C-36 | indoxacarb |
| M.163 | I-A-1 | clothianidin |
| M.164 | I-A-28 | clothianidin |
| M.165 | I-B-33 | clothianidin |
| M.166 | I-B-37 | clothianidin |
| M.167 | I-B-115 | clothianidin |
| M.168 | I-B-131 | clothianidin |
| M.169 | I-B-132 | clothianidin |
| M.170 | I-C-35 | clothianidin |
| M.171 | I-C-36 | clothianidin |
| M.172 | I-A-1 | bifenthrin |
| M.173 | I-A-28 | bifenthrin |
| M.174 | I-B-33 | bifenthrin |
| M.175 | I-B-37 | bifenthrin |
| M.176 | I-B-115 | bifenthrin |
| M.177 | I-B-131 | bifenthrin |
| M.178 | I-B-132 | bifenthrin |
| M.179 | I-C-35 | bifenthrin |
| M.180 | I-C-36 | bifenthrin |
| M.181 | I-A-1 | acetamiprid |
| M.182 | I-A-28 | acetamiprid |
| M.183 | I-B-33 | acetamiprid |
| M.184 | I-B-37 | acetamiprid |
| M.185 | I-B-115 | acetamiprid |
| M.186 | I-B-131 | acetamiprid |
| M.187 | I-B-132 | acetamiprid |
| M.188 | I-C-35 | acetamiprid |
| M.189 | I-C-36 | acetamiprid |

Compound II-M.X.2 is cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester:

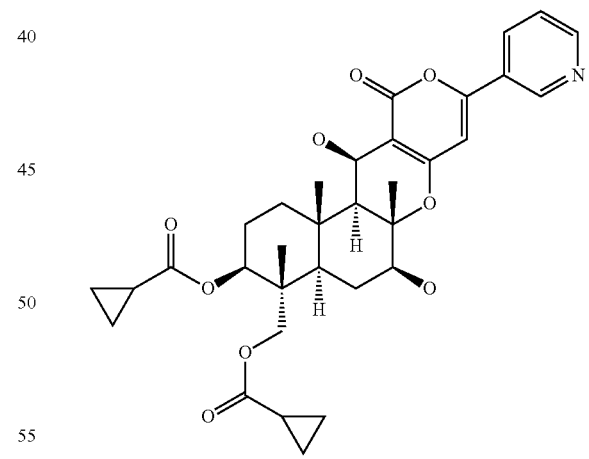

The pests that can be controlled or combatted are as described above or herein, e.g. in embodiment E1.

The formulations are as described herein, e.g. in embodiment E1.

The applications are as described herein, e.g. in embodiment E1.

Further active ingredients: Another aspect of the present invention is when preparing the mixtures, it is preferred to employ the mixture according to the invention or pure active compounds I and II, to which further active compounds, e.g.

against harmful fungi or having herbicidal activity, or growth-regulating agents or fertilizers can be added.

Compositions of this invention may further contain other active ingredients than those listed above. For example fungicides, herbicides, fertilizers such as ammonium nitrate, urea, potash, and superphosphate, phytotoxicants and plant growth regulators and safeners. These additional ingredients may be used sequentially or in combination with the above-described compositions, if appropriate also added only immediately prior to use (tank mix). For example, the plant(s) may be sprayed with a composition of this invention either before or after being treated with other active ingredients.

The further active ingredients may be selected from the group M as defined above for compounds II herein, or from the list F of active substances, as described below in Embodiment E3.

Biological Example

If present, synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, *Weeds*, 15, 20-22):

$$E = X + Y - \frac{XY}{100}$$

When the observed combined control effect is greater than the expected combined control effect (E), then the combined effect is synergistic.

The following tests demonstrate the control efficacy of compounds, mixtures or compositions of this invention on specific pests. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests.

The analysis of synergism or antagonism between the mixtures or compositions can be determined using Colby's equation.

Test 1

For evaluating control of green peach aphid (*Myzus persicae*) through systemic means the test unit consisted of 96-well-microtiter plates containing liquid artificial diet under an artificial membrane.

The compounds or mixtures were formulated using a solution containing 75% water and 25% DMSO. Different concentrations of formulated compounds or mixtures were pipetted into the aphid diet, using a custom built pipetter, at two replications.

For experimental mixtures in these tests identical volumes of both mixing partners at the desired concentrations respectively, were mixed together.

After application, 5-8 adult aphids were placed on the artificial membrane inside the microtiter plate wells. The aphids were then allowed to suck on the treated aphid diet and incubated at 23±10C, 50±5% RH for 3 days. Aphid mortality and fecundity was then visually assessed. For the mixture tested the results are listed in the tables for Example E2-1 and E2-2.

Example E2-1

| Green Peach Aphid | ppm | Average Control % |
|---|---|---|
| Pymetrozine | 80 | 0 |
| Compound I-A-1 | 0.4 | 0 |
| Pymetrozine + Compound I-A-1 | 80 + 0.4 | 50* |

*synergistic control effect according to Colby's equation

Example E2-2

| Green Peach Aphid | ppm | Average Control % |
|---|---|---|
| Chlorantraniliprole | 0.4 | 0 |
| Compound I-A-1 | 0.8 | 0 |
| Chlorantraniliprole + Compound I-A-1 | 0.4 + 0.08 | 100* |

*synergistic control effect according to Colby's equation

Embodiment E3

In embodiment E3, the invention relates to mixtures comprising the compounds according to the invention and a pesticide, preferably a fungicide.

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

There also exists the need for pest control agents that combine knock-down activity with prolonged control, that is, fast action with long lasting action.

The combating of harmful insects is in many regions not the only problem the farmer has to face. Also harmful phytopathogenic fungi can cause a great damage to crops and other plants. An efficient combination of insecticidal and fungicidal activity is desirable to overcome this problem. Thus, it is an object of the present invention to provide a combination which, on the one hand, has good insecticidal activity, and, on the other hand, good fungicidal activity. Moreover, it is desirable to have available pesticidal active agents which are effective against a broad spectrum of pests. Furthermore, application of the active ingredients should not damage crop plants.

Another difficulty in relation to the use of pesticides is that the repeated and exclusive application of an individual pesticidal compound leads in many cases to a rapid selection of pests which have developed natural or adapted resistance against the active compound in question. Therefore there is a need for pest control agents that help prevent or overcome resistance induced by pesticides.

Furthermore, there is a desire for pesiticide compounds or combination of compounds, which when applied improve plants, which may result in "plant health", "vitality of plant propagation material" or "increased plant yield".

It is therefore an object of the present invention to provide agricultural combinations which solves one or more than one of the discussed problems as reducing the dosage rate, enhancing the spectrum of activity, combining knock-down activity with prolonged control, improving resistance management,
Improved plant health;
Improved vitality of plant propagation material, also termed seed vitality;
Increased plant yield.

It was therefore an object of the present invention to provide pesticidal mixtures which solve at least one of the discussed problems as reducing the dosage rate, enhancing the spectrum of activity or combining knock-down activity with prolonged control or as to resistance management.

It has been found that this object is in part or in whole achieved by the combination of active compounds defined below.

The present invention relates to pesticidal mixtures comprising as active compounds 1) at least one pesticidally active anthranilamide compound I as described above, or a stereoisomer, salt, tautomer or N-oxide, or a polymorphic crystalline form, a co-crystal or a solvate of a compound or a stereoisomer, salt, tautomer or N-oxide thereof;
and
2) at least one pesticidally active compound II selected from the group consisting of the following list F:

F.I) Respiration Inhibitors

F.I-1) Inhibitors of complex III at Qo site selected from the group of strobilurins including azoxystrobin, coumethoxystrobin, coumoxystrobin, dimoxystrobin, enestroburin, fluoxastrobin, kresoxim-methyl, mandestrobin, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N methyl-acetamide;
oxazolidinediones and imidazolinones selected from famoxadone, fenamidone;

F.I-2) Inhibitors of complex II selected from the group of carboxamides, including carboxanilides selected from benodanil, benzovindiflupyr, bixafen, boscalid, carboxin, fenfuram, fenhexamid, fluopyram, flutolanil, furametpyr, isofetamid, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethyl-indan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl) pyrazole-4-carboxamide, 3-(trifluorometh-yl)-1,5-dimethyl-N-(1,1,3-trimethylindan-4-yl)-pyrazole-4-carboxamide, 1,3,5-tri-methyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxuamide, N-[2-(2,4-dichlorophenyl)-2-methoxy-1-methyl-ethyl]-3-(difluoromethyl)-1-methyl-pyrazole-4-carboxamide;

F.I-3) Inhibitors of complex III at Qi site including cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate, 3S,6S,7R,8R-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I uncouplers), including diflumetorim; (5,8-difluoro-quinazolin-4-yl)-{2-[2-fluoro-4-(4-trifluoromethylpyridin-2-yloxy)-phenyl]-ethyl}-amine; tecnazen; ametoctradin; silthiofam;
and including nitrophenyl derivates selected from binapacryl, dinobuton, dinocap, fluazinam, ferimzone; nitrthal-isopropyl,
and including organometal compounds selected from fentin salts, including fentin-acetate, fentin chloride or fentin hydroxide;

F.II) Sterol biosynthesis inhibitors (SBI fungicides)

F.II-1) C14 demethylase inhibitors,
including triazoles selected from azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, 1-[re/(2S;3R)-3-(2-chlorophenyl)-2-(2,4-difluorophenyl)-oxiranylmethyl]-5-thio-cyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol; 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl) butan-2-ol, 2-[2-chloro-4-(4-chlorophenoxyl) phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl) pentan-2-ol, 2-[4-(4-fluorophenoxy)-2-(trifluoromethyl)phenyl]-1-(1,2,4-triazol-1-yl) propan-2-ol;
and including imidazoles selected from imazalil, pefurazoate, oxpoconazole, prochloraz, triflumizole;

and including pyrimidines, pyridines and piperazines selected from fenarimol, nuarimol, pyrifenox, triforine, [3-(4-chloro-2-fluoro-phenyl)-5-(2,4-difluorophenyl)isoxazol-4-yl]-(3-pyridyl)methanol;

F.II-2) Delta14-reductase inhitors,
including morpholines selected from aldimorph, dodemorph, dodemorph-acetate, fenpropimorph, tridemorph;
and including piperidines selected from fenpropidin, piperalin;
and including spiroketalamines selected from spiroxamine;

F.II-3) Inhibitors of 3-keto reductase including hydroxyanilides selected from fenhexamid;

F.III) Nucleic acid synthesis inhibitors

F.III-1) RNA, DNA synthesis inhibitors,
including phenylamides or acyl amino acid fungicides selected from benalaxyl, benalaxyl-M, kiralaxyl, metalaxyl, metalaxyl-M (mefenoxam), ofurace, oxadixyl;
and including isoxazoles and iosothiazolones selected from hymexazole, octhilinone;

F.III-2) DNA topisomerase inhibitors selected from oxolinic acid;

F.III-3) Nucleotide metabolism inhibitors including hydroxy (2-amino)-pyrimidines selected from bupirimate;

F.IV) Inhibitors of cell division and or cytoskeleton

F.IV-1) Tubulin inhibitors:
including benzimidazoles and thiophanates selected from benomyl, carbendazim, fuberidazole, thiabendazole, thiophanate-methyl;
and including triazolopyrimidines selected from 5-chloro-7 (4-methylpiperidin-1-yl)-6-(2,4,6-trifluorophenyl)-[1,2,4]triazolo[1,5 a]pyrimidine F.IV-2) Other cell division inhibitors
including benzamides and phenyl acetamides selected from diethofencarb, ethaboxam, pencycuron, fluopicolide, zoxamide;

F.IV-3) Actin inhibitors including benzophenones selected from metrafenone; pyriofenone;

F.V) Inhibitors of amino acid and protein synthesis

F.V-1) Methionine synthesis inhibitors including anilino-pyrimidines selected from cyprodinil, mepanipyrim, nitrapyrin, pyrimethanil;

F.V-2) Protein synthesis inhibitors including antibiotics selected from blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors including dicarboximides selected from fluoroimid, iprodione, procymidone, vinclozolin;
and including phenylpyrroles selected from fenpiclonil, fludioxonil;

F.VI-2) G protein inhibitors including quinolines selected from quinoxyfen;

F.VII) Lipid and membrane synthesis inhibitors

F.VII-1) Phospholipid biosynthesis inhibitors including organophosphorus compounds selected from edifenphos, iprobenfos, pyrazophos;
and including dithiolanes selected from isoprothiolane;

F.VII-2) Lipid peroxidation
including aromatic hydrocarbons selected from dicloran, quintozene, tecnazene, tolclofos-methyl, biphenyl, chloroneb, etridiazole;

F.VII-3) Carboxyl acid amides (CAA fungicides)
including cinnamic or mandelic acid amides selected from dimethomorph, flumorph, mandiproamid, pyrimorph;
and including valinamide carbamates selected from benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acides including carbamates selected from propamocarb, propamocarb-hydrochlorid;

F.VII-5) fatty acid amide hydrolase inhibitors: 1-[4-[4-[5-(2,6-difluorophenyl)-4,5-dihydro-3 isoxazolyl]-2-thiazolyl]-1-piperidinyl]-2-[5-methyl-3-(trifluoromethyl)-1H-pyrazol-1 yl]ethanone;

F.VIII) Inhibitors with Multi Site Action

F.VIII-1) Inorganic active substances selected from Bordeaux mixture, copper acetate, copper hydroxide, copper oxychloride, basic copper sulfate, sulfur;

F.VIII-2) Thio- and dithiocarbamates selected from ferbam, mancozeb, maneb, metam, methasulphocarb, metiram, propineb, thiram, zineb, ziram;

F.VIII-3) Organochlorine compounds including phthalimides, sulfamides, chloronitriles selected from anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines selected from guanidine, dodine, dodine free base, guazatine, guazatine-acetate, iminoctadine, iminoctadine-triacetate, iminoctadine-tris (albesilate), dithianon, 2,6-dimethyl-1H,5H-[1,4] dithiino[2,3-c:5,6-c']dipyrrole-1,3,5,7(2H,6H)-tetraone;

F.VIII-5) Ahtraquinones selected from dithianon;

F.IX) Cell wall synthesis inhibitors

F.IX-1) Inhibitors of glucan synthesis selected from validamycin, polyoxin B;

F.IX-2) Melanin synthesis inhibitors selected from pyroquilon, tricyclazole, carpropamide, dicyclomet, fenoxanil;

F.X) Plant defence inducers

F.X-1) Salicylic acid pathway selected from acibenzolar-S-methyl;

F.X-2) Others selected from probenazole, isotianil, tiadinil, prohexadione-calcium; including phosphonates selected from fosetyl, fosetyl-aluminum, phosphorous acid and its salts;

F.XI) Unknown mode of action:
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yl-oxy)phenyl]-4,5-dihydro-1,2-oxazol-3-yl}-1,3-thi-azol-2-yl)piperidin-1-yl]ethanone, 2 [3,5-bis(difluoromethyl)-1H-pyrazol-1-yl]-1-[4-(4-{5-[2-chloro-6-(prop-2-yn-1-yl-oxy)phenyl]-4,5-dihydro-1,2-oxazol-3-yl}-1,3-thiazol-2 yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl) cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z) 3 amino-2-cyano-3-phenyl-prop-2-enoate, tert-butyl N-[6-[[(Z)-[(1-methyltetrazol-5-yl)-phenyl-methylene]amino]oxymethyl]-2-pyridyl]carbamate (picarbutrazox), pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroiso¬ quinolin-1-yl)quinoline, 3-(4,4-difluoro-3,3-dimethyl-3,4-dihydroisoquinolin-1-yl)-quinoline, 3-(4,4,5-trifluoro-3,3-dimethyl-3,4-dihydroisoquinolin-1-yl)quinoline;

F.XII) Growth regulators:
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XIII) Biopesticides
F.XIII-1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Fusarium oxysporum, Clonostachys rosea* f. *catenulate* (also named *Gliocladium catenulatum*), *Gliocladium roseum, Metschnikowia fructicola, Microdochium dimerum, Paenibacillus polymyxa, Pantoea agglomerans, Phlebiopsis gigantea, Pseudozyma flocculosa, Pythium oligandrum, Sphaerodes mycoparasitica, Streptomyces lydicus, S. violaceusniger, Talaromyces flavus, Trichoderma asperellum, T. atroviride, T. fertile, T. gamsii, T. harmatum*; mixture of *T. harzianum* and *T. viride*; mixture of *T. polysporum* and *T. harzianum; T. stromaticum, T. virens* (also named *Gliocladium virens*), *T. viride, Typhula phacorrhiza, Ulocladium oudema, U. oudemansii, Verticillium dahlia*, zucchini yellow mosaic virus (avirulent strain);

F.XIII-2) Biochemical pesticides with fungicidal, bactericidal, viricidal and/or plant defense activator activity: chitosan (hydrolysate), jasmonic acid or salts or derivatives thereof, laminarin, Menhaden fish oil, natamycin, Plum pox virus coat protein, *Reynoutria sachlinensis* extract, salicylic acid, tea tree oil;

F.XIII-3) Microbial pesticides with plant stress reducing, plant growth regulator, plant growth promoting and/or yield enhancing activity: *Azospirillum amazonense A. brasilense, A. lipoferum, A. irakense, A. halopraeferens, Bradyrhizobium* sp., *B. japonicum, Glomus intraradices, Mesorhizobium* sp., *Paenibacillus alvei, Penicillium bilaiae, Rhizobium leguminosarum* bv. *phaseolii, R. l. trifolii, R. l.* bv. *viciae, Sinorhizobium meliloti;*

F.XIII-4) Biochemical pesticides with plant stress reducing, plant growth regulator and/or plant yield enhancing activity: abscisic acid, aluminium silicate (kaolin), 3-decen-2-one, homobrassinlide, humates, lysophosphatidyl ethanolamine, polymeric polyhydroxy acid, *Ascophyllum nodosum* (Norwegian kelp, Brown kelp) extract and *Ecklonia maxima* (kelp) extract.

Some of the compounds may have a synergistic effect, e.g. the compounds described above under Embodiment A. Compounds II The commercially available compounds II of the group F listed above may be found in The Pesticide Manual, 15th Edition, C. D. S. Tomlin, British Crop Protection Council (2011) among other publications. Their preparation and their activity against harmful fungi is known (cf.: www.alanwood.net/pesticides/); these substances are commercially available. The compounds described by IUPAC nomenclature, their preparation and their fungicidal activity are also known (cf. Can. J. Plant Sci. 48(6), 587-94, 1968; EP A 141 317; EP-A 152 031; EP-A 226 917; EP A 243 970; EP A 256 503; EP-A 428 941; EP-A 532 022; EP-A 1 028 125; EP-A 1 035 122; EP A 1 201 648; EP A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

The biopesticides of group F.XIII are disclosed above in the paragraphs about biopesticides from group II-M.Y.

Moreover, it has been found that simultaneous, that is joint or separate, application of one or more active compound(s) I and one or more compound(s) II or successive application (that is immediately one after another and thereby creating the mixture "in-situ" on the desired location, as e.g. the plant) of one or more active compound(s) I and one or more active compound(s) II allows enhanced control of pests compared to the control rates that are possible with the individual compounds.

Therefore, the term "mixture" as used herein is intended to include also combinations.

In one embodiment, the compound I in the mixtures according to the invention of E3 is selected from the compounds described in Embodiment A.

In one embodiment, the compound I in the mixtures according to the invention of E3 is selected from the compounds described in Embodiment B.

In one embodiment, the compound I in the mixtures according to the invention of E3 is selected from the compounds described in Embodiment C.

In one embodiment, the compound I in the mixtures according to the invention of E3 is selected from the compounds listed in Table ABC.

In one embodiment, I-A-1 is the compound I in the mixtures according to the invention of E3.

In one embodiment, I-A-28 is the compound I in the mixtures according to the invention of E3.

In one embodiment, I-B-115 is the compound I in the mixtures according to the invention of E3.

In one embodiment, I-B-131 is the compound I in the mixtures according to the invention of E3.

In one embodiment, I-B-132 is the compound I in the mixtures according to the invention of E3.

In one embodiment, I-C-19 is the compound I in the mixtures according to the invention of E3.

In one embodiment, I-C-35 is the compound I in the mixtures according to the invention of E3.

In one embodiment, I-C-36 is the compound I in the mixtures according to the invention of E3.

With regard to the use in a pesticidal mixture of the present invention, a compound II selected from the group of the azoles is preferred, especially prochloraz, prothioconazole, tebuconazole and triticonazole, especially prothioconazole and triticonazole.

Mixtures of compounds I as individualized herein, e.g. in Table ABC, with triticonazole as compound II are particularly preferred. Mixtures of a compound selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35, with triticonazole as compound II are particularly preferred.

Mixtures of compounds I as individualized herein, e.g. in Table ABC, with prothioconazole as compound II are particularly preferred. Mixtures of a compound selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35, with prothioconazole as compound II are particularly preferred.

With regard to the use in a pesticidal mixture of the present invention, preferred is a compound II selected from the group of benomyl, carbendazim, epoxiconazole, fluquinconazole, flutriafol, flusilazole, metconazole, prochloraz, prothioconazole, tebuconazole, triticonazole, pyraclostrobin, trifloxystrobin, boscalid, dimethomorph, penthiopyrad, dodemorph, famoxadone, fenpropimorph, proquinazid, pyrimethanil, tridemorph, compound II-TFPTAP (5-chloro-7-(4-methylpiperidin-1-yl)-6-(2,4,6-trifluorophenyl)-[1,2,4]triazolo[1,5-a]pyrimidine), maneb, mancozeb, metiram, thiram, chlorothalonil, dithianon, flusulfamide, metrafenone, fluxapyroxad (N-(3',4',5' trifluorobiphenyl-2 yl)-3-difluoromethyl-1-methyl-1H-pyrazole-4 carboxamide), bixafen, penflufen, sedaxane, isopyrazam. Especially preferred is pyraclostrobin and fluxapyroxad.

In one embodiment, the mixture according to the invention is a mixture of the compounds I with a strobilurin, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with pyraclostrobin, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with kresoximmethyl, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with trifloxystrobin, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with a carboxamide, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with boscalid, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with fluopyram, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with penflufen, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with fluxapyroxad, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with bixafen, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with penthiopyrad, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with fluopyram, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with sedaxane, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with isopyrazam, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with benzovindiflupyr, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with isotianil, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with an azole, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with epoxiconazole, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with fluquinconazole, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with triticonazole, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with metconazole, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the mixture according to the invention is a mixture of the compounds I with prothioconazole, more preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

The present invention relates to agrochemical compositions comprising a mixture of at least one compound I (component 1) and at least one further active substance useful for plant protection, e. g. selected from the group F. (component 2).

Especially preferred mixtures according to the invention are listed in the following table M-F:

TABLE M-F

| Mixture | Comp. I | Compound II |
|---|---|---|
| M-F.1 | I-A-1 | benomyl |
| M-F.2 | I-A-28 | benomyl |
| M-F.3 | I-B-33 | benomyl |
| M-F.4 | I-B-37 | benomyl |
| M-F.5 | I-B-115 | benomyl |
| M-F.6 | I-B-131 | benomyl |
| M-F.7 | I-B-132 | benomyl |
| M-F.8 | I-C-35 | benomyl |
| M-F.9 | I-C-36 | benomyl |
| M-F.10 | I-A-1 | carbendazim |
| M-F.11 | I-A-28 | carbendazim |
| M-F.12 | I-B-33 | carbendazim |
| M-F.13 | I-B-37 | carbendazim |
| M-F.14 | I-B-115 | carbendazim |
| M-F.15 | I-B-131 | carbendazim |
| M-F.16 | I-B-132 | carbendazim |
| M-F.17 | I-C-35 | carbendazim |
| M-F.18 | I-C-36 | carbendazim |
| M-F.19 | I-A-1 | epoxiconazole |
| M-F.20 | I-A-28 | epoxiconazole |
| M-F.21 | I-B-33 | epoxiconazole |
| M-F.22 | I-B-37 | epoxiconazole |
| M-F.23 | I-B-115 | epoxiconazole |
| M-F.24 | I-B-131 | epoxiconazole |
| M-F.25 | I-B-132 | epoxiconazole |
| M-F.26 | I-C-35 | epoxiconazole |
| M-F.27 | I-C-36 | epoxiconazole |
| M-F.28 | I-A-1 | fluquinconazole |
| M-F.29 | I-A-28 | fluquinconazole |
| M-F.30 | I-B-33 | fluquinconazole |

TABLE M-F-continued

| Mixture | Comp. I | Compound II |
|---|---|---|
| M-F.31 | I-B-37 | fluquinconazole |
| M-F.32 | I-B-115 | fluquinconazole |
| M-F.33 | I-B-131 | fluquinconazole |
| M-F.34 | I-B-132 | fluquinconazole |
| M-F.35 | I-C-35 | fluquinconazole |
| M-F.36 | I-C-36 | fluquinconazole |
| M-F.37 | I-A-1 | flutriafol |
| M-F.38 | I-A-28 | flutriafol |
| M-F.39 | I-B-33 | flutriafol |
| M-F.40 | I-B-37 | flutriafol |
| M-F.41 | I-B-115 | flutriafol |
| M-F.42 | I-B-131 | flutriafol |
| M-F.43 | I-B-132 | flutriafol |
| M-F.44 | I-C-35 | flutriafol |
| M-F.45 | I-C-36 | flutriafol |
| M-F.46 | I-A-1 | flusilazole |
| M-F.47 | I-A-28 | flusilazole |
| M-F.48 | I-B-33 | flusilazole |
| M-F.49 | I-B-37 | flusilazole |
| M-F.50 | I-B-115 | flusilazole |
| M-F.51 | I-B-131 | flusilazole |
| M-F.52 | I-B-132 | flusilazole |
| M-F.53 | I-C-35 | flusilazole |
| M-F.54 | I-C-36 | flusilazole |
| M-F.55 | I-A-1 | metconazole |
| M-F.56 | I-A-28 | metconazole |
| M-F.57 | I-B-33 | metconazole |
| M-F.58 | I-B-37 | metconazole |
| M-F.59 | I-B-115 | metconazole |
| M-F.60 | I-B-131 | metconazole |
| M-F.61 | I-B-132 | metconazole |
| M-F.62 | I-C-35 | metconazole |
| M-F.63 | I-C-36 | metconazole |
| M-F.64 | I-A-1 | prochloraz |
| M-F.65 | I-A-28 | prochloraz |
| M-F.66 | I-B-33 | prochloraz |
| M-F.67 | I-B-37 | prochloraz |
| M-F.68 | I-B-115 | prochloraz |
| M-F.69 | I-B-131 | prochloraz |
| M-F.70 | I-B-132 | prochloraz |
| M-F.71 | I-C-35 | prochloraz |
| M-F.72 | I-C-36 | prochloraz |
| M-F.73 | I-A-1 | prothioconazole |
| M-F.74 | I-A-28 | prothioconazole |
| M-F.75 | I-B-33 | prothioconazole |
| M-F.76 | I-B-37 | prothioconazole |
| M-F.77 | I-B-115 | prothioconazole |
| M-F.78 | I-B-131 | prothioconazole |
| M-F.79 | I-B-132 | prothioconazole |
| M-F.80 | I-C-35 | prothioconazole |
| M-F.81 | I-C-36 | prothioconazole |
| M-F.82 | I-A-1 | tebuconazole |
| M-F.83 | I-A-28 | tebuconazole |
| M-F.84 | I-B-33 | tebuconazole |
| M-F.85 | I-B-37 | tebuconazole |
| M-F.86 | I-B-115 | tebuconazole |
| M-F.87 | I-B-131 | tebuconazole |
| M-F.88 | I-B-132 | tebuconazole |
| M-F.89 | I-C-35 | tebuconazole |
| M-F.90 | I-C-36 | tebuconazole |
| M-F.91 | I-A-1 | triticonazole |
| M-F.92 | I-A-28 | triticonazole |
| M-F.93 | I-B-33 | triticonazole |
| M-F.94 | I-B-37 | triticonazole |
| M-F.95 | I-B-115 | triticonazole |
| M-F.96 | I-B-131 | triticonazole |
| M-F.97 | I-B-132 | triticonazole |
| M-F.98 | I-C-35 | triticonazole |
| M-F.99 | I-C-36 | triticonazole |
| M-F.100 | I-A-1 | pyraclostrobin |
| M-F.101 | I-A-28 | pyraclostrobin |
| M-F.102 | I-B-33 | pyraclostrobin |
| M-F.103 | I-B-37 | pyraclostrobin |
| M-F.104 | I-B-115 | pyraclostrobin |
| M-F.105 | I-B-131 | pyraclostrobin |
| M-F.106 | I-B-132 | pyraclostrobin |
| M-F.107 | I-C-35 | pyraclostrobin |
| M-F.108 | I-C-36 | pyraclostrobin |

TABLE M-F-continued

| Mixture | Comp. I | Compound II |
|---|---|---|
| M-F.109 | I-A-1 | trifloxystrobin |
| M-F.110 | I-A-28 | trifloxystrobin |
| M-F.111 | I-B-33 | trifloxystrobin |
| M-F.112 | I-B-37 | trifloxystrobin |
| M-F.113 | I-B-115 | trifloxystrobin |
| M-F.114 | I-B-131 | trifloxystrobin |
| M-F.115 | I-B-132 | trifloxystrobin |
| M-F.116 | I-C-35 | trifloxystrobin |
| M-F.117 | I-C-36 | trifloxystrobin |
| M-F.118 | I-A-1 | boscalid |
| M-F.119 | I-A-28 | boscalid |
| M-F.120 | I-B-33 | boscalid |
| M-F.121 | I-B-37 | boscalid |
| M-F.122 | I-B-115 | boscalid |
| M-F.123 | I-B-131 | boscalid |
| M-F.124 | I-B-132 | boscalid |
| M-F.125 | I-C-35 | boscalid |
| M-F.126 | I-C-36 | boscalid |
| M-F.127 | I-A-1 | dimethomorph |
| M-F.128 | I-A-28 | dimethomorph |
| M-F.129 | I-B-33 | dimethomorph |
| M-F.130 | I-B-37 | dimethomorph |
| M-F.131 | I-B-115 | dimethomorph |
| M-F.132 | I-B-131 | dimethomorph |
| M-F.133 | I-B-132 | dimethomorph |
| M-F.134 | I-C-35 | dimethomorph |
| M-F.135 | I-C-36 | dimethomorph |
| M-F.136 | I-A-1 | penthiopyrad |
| M-F.137 | I-A-28 | penthiopyrad |
| M-F.138 | I-B-33 | penthiopyrad |
| M-F.139 | I-B-37 | penthiopyrad |
| M-F.140 | I-B-115 | penthiopyrad |
| M-F.141 | I-B-131 | penthiopyrad |
| M-F.142 | I-B-132 | penthiopyrad |
| M-F.143 | I-C-35 | penthiopyrad |
| M-F.144 | I-C-36 | penthiopyrad |
| M-F.145 | I-A-1 | dodemorph |
| M-F.146 | I-A-28 | dodemorph |
| M-F.147 | I-B-33 | dodemorph |
| M-F.148 | I-B-37 | dodemorph |
| M-F.149 | I-B-115 | dodemorph |
| M-F.150 | I-B-131 | dodemorph |
| M-F.151 | I-B-132 | dodemorph |
| M-F.152 | I-C-35 | dodemorph |
| M-F.153 | I-C-36 | dodemorph |
| M-F.154 | I-A-1 | famoxadone |
| M-F.155 | I-A-28 | famoxadone |
| M-F.156 | I-B-33 | famoxadone |
| M-F.157 | I-B-37 | famoxadone |
| M-F.158 | I-B-115 | famoxadone |
| M-F.159 | I-B-131 | famoxadone |
| M-F.160 | I-B-132 | famoxadone |
| M-F.161 | I-C-35 | famoxadone |
| M-F.162 | I-C-36 | famoxadone |
| M-F.163 | I-A-1 | fenpropimorph |
| M-F.164 | I-A-28 | fenpropimorph |
| M-F.165 | I-B-33 | fenpropimorph |
| M-F.166 | I-B-37 | fenpropimorph |
| M-F.167 | I-B-115 | fenpropimorph |
| M-F.168 | I-B-131 | fenpropimorph |
| M-F.169 | I-B-132 | fenpropimorph |
| M-F.170 | I-C-35 | fenpropimorph |
| M-F.171 | I-C-36 | fenpropimorph |
| M-F.172 | I-A-1 | proquinazid |
| M-F.173 | I-A-28 | proquinazid |
| M-F.174 | I-B-33 | proquinazid |
| M-F.175 | I-B-37 | proquinazid |
| M-F.176 | I-B-115 | proquinazid |
| M-F.177 | I-B-131 | proquinazid |
| M-F.178 | I-B-132 | proquinazid |
| M-F.179 | I-C-35 | proquinazid |
| M-F.180 | I-C-36 | proquinazid |
| M-F.181 | I-A-1 | pyrimethanil |
| M-F.182 | I-A-28 | pyrimethanil |
| M-F.183 | I-B-33 | pyrimethanil |
| M-F.184 | I-B-37 | pyrimethanil |
| M-F.185 | I-B-115 | pyrimethanil |
| M-F.186 | I-B-131 | pyrimethanil |
| M-F.187 | I-B-132 | pyrimethanil |
| M-F.188 | I-C-35 | pyrimethanil |
| M-F.189 | I-C-36 | pyrimethanil |
| M-F.190 | I-A-1 | tridemorph |
| M-F.191 | I-A-28 | tridemorph |
| M-F.192 | I-B-33 | tridemorph |
| M-F.193 | I-B-37 | tridemorph |
| M-F.194 | I-B-115 | tridemorph |
| M-F.195 | I-B-131 | tridemorph |
| M-F.196 | I-B-132 | tridemorph |
| M-F.197 | I-C-35 | tridemorph |
| M-F.198 | I-C-36 | tridemorph |
| M-F.199 | I-A-1 | II-TFPTAP |
| M-F.200 | I-A-28 | II-TFPTAP |
| M-F.201 | I-B-33 | II-TFPTAP |
| M-F.202 | I-B-37 | II-TFPTAP |
| M-F.203 | I-B-115 | II-TFPTAP |
| M-F.204 | I-B-131 | II-TFPTAP |
| M-F.205 | I-B-132 | II-TFPTAP |
| M-F.206 | I-C-35 | II-TFPTAP |
| M-F.207 | I-C-36 | II-TFPTAP |
| M-F.208 | I-A-1 | maneb |
| M-F.209 | I-A-28 | maneb |
| M-F.210 | I-B-33 | maneb |
| M-F.211 | I-B-37 | maneb |
| M-F.212 | I-B-115 | maneb |
| M-F.213 | I-B-131 | maneb |
| M-F.214 | I-B-132 | maneb |
| M-F.215 | I-C-35 | maneb |
| M-F.216 | I-C-36 | maneb |
| M-F.217 | I-A-1 | mancozeb |
| M-F.218 | I-A-28 | mancozeb |
| M-F.219 | I-B-33 | mancozeb |
| M-F.220 | I-B-37 | mancozeb |
| M-F.221 | I-B-115 | mancozeb |
| M-F.222 | I-B-131 | mancozeb |
| M-F.223 | I-B-132 | mancozeb |
| M-F.224 | I-C-35 | mancozeb |
| M-F.225 | I-C-36 | mancozeb |
| M-F.226 | I-A-1 | metiram |
| M-F.227 | I-A-28 | metiram |
| M-F.228 | I-B-33 | metiram |
| M-F.229 | I-B-37 | metiram |
| M-F.230 | I-B-115 | metiram |
| M-F.231 | I-B-131 | metiram |
| M-F.232 | I-B-132 | metiram |
| M-F.233 | I-C-35 | metiram |
| M-F.234 | I-C-36 | metiram |
| M-F.235 | I-A-1 | thiram |
| M-F.236 | I-A-28 | thiram |
| M-F.237 | I-B-33 | thiram |
| M-F.238 | I-B-37 | thiram |
| M-F.239 | I-B-115 | thiram |
| M-F.240 | I-B-131 | thiram |
| M-F.241 | I-B-132 | thiram |
| M-F.242 | I-C-35 | thiram |
| M-F.243 | I-C-36 | thiram |
| M-F.244 | I-A-1 | chlorothalonil |
| M-F.245 | I-A-28 | chlorothalonil |
| M-F.246 | I-B-33 | chlorothalonil |
| M-F.247 | I-B-37 | chlorothalonil |
| M-F.248 | I-B-115 | chlorothalonil |
| M-F.249 | I-B-131 | chlorothalonil |
| M-F.250 | I-B-132 | chlorothalonil |
| M-F.251 | I-C-35 | chlorothalonil |
| M-F.252 | I-C-36 | chlorothalonil |
| M-F.253 | I-A-1 | dithianon |
| M-F.254 | I-A-28 | dithianon |
| M-F.255 | I-B-33 | dithianon |
| M-F.256 | I-B-37 | dithianon |
| M-F.257 | I-B-115 | dithianon |
| M-F.258 | I-B-131 | dithianon |
| M-F.259 | I-B-132 | dithianon |
| M-F.260 | I-C-35 | dithianon |
| M-F.261 | I-C-36 | dithianon |
| M-F.262 | I-A-1 | flusulfamide |
| M-F.263 | I-A-28 | flusulfamide |
| M-F.264 | I-B-33 | flusulfamide |

TABLE M-F-continued

| Mixture | Comp. I | Compound II |
|---|---|---|
| M-F.265 | I-B-37 | flusulfamide |
| M-F.266 | I-B-115 | flusulfamide |
| M-F.267 | I-B-131 | flusulfamide |
| M-F.268 | I-B-132 | flusulfamide |
| M-F.269 | I-C-35 | flusulfamide |
| M-F.270 | I-C-36 | flusulfamide |
| M-F.271 | I-A-1 | metrafenone |
| M-F.272 | I-A-28 | metrafenone |
| M-F.273 | I-B-33 | metrafenone |
| M-F.274 | I-B-37 | metrafenone |
| M-F.275 | I-B-115 | metrafenone |
| M-F.276 | I-B-131 | metrafenone |
| M-F.277 | I-B-132 | metrafenone |
| M-F.278 | I-C-35 | metrafenone |
| M-F.279 | I-C-36 | metrafenone |
| M-F.280 | I-A-1 | fluxapyroxad |
| M-F.281 | I-A-28 | fluxapyroxad |
| M-F.282 | I-B-33 | fluxapyroxad |
| M-F.283 | I-B-37 | fluxapyroxad |
| M-F.284 | I-B-115 | fluxapyroxad |
| M-F.285 | I-B-131 | fluxapyroxad |
| M-F.286 | I-B-132 | fluxapyroxad |
| M-F.287 | I-C-35 | fluxapyroxad |
| M-F.288 | I-C-36 | fluxapyroxad |
| M-F.289 | I-A-1 | bixafen |
| M-F.290 | I-A-28 | bixafen |
| M-F.291 | I-B-33 | bixafen |
| M-F.292 | I-B-37 | bixafen |
| M-F.293 | I-B-115 | bixafen |
| M-F.294 | I-B-131 | bixafen |
| M-F.295 | I-B-132 | bixafen |
| M-F.296 | I-C-35 | bixafen |
| M-F.297 | I-C-36 | bixafen |
| M-F.298 | I-A-1 | penflufen |
| M-F.299 | I-A-28 | penflufen |
| M-F.300 | I-B-33 | penflufen |
| M-F.301 | I-B-37 | penflufen |
| M-F.302 | I-B-115 | penflufen |
| M-F.303 | I-B-131 | penflufen |
| M-F.304 | I-B-132 | penflufen |
| M-F.305 | I-C-35 | penflufen |
| M-F.306 | I-C-36 | penflufen |
| M-F.307 | I-A-1 | sedaxane |
| M-F.308 | I-A-28 | sedaxane |
| M-F.309 | I-B-33 | sedaxane |
| M-F.310 | I-B-37 | sedaxane |
| M-F.311 | I-B-115 | sedaxane |
| M-F.312 | I-B-131 | sedaxane |
| M-F.313 | I-B-132 | sedaxane |
| M-F.314 | I-C-35 | sedaxane |
| M-F.315 | I-C-36 | sedaxane |
| M-F.316 | I-A-1 | isopyrazam |
| M-F.317 | I-A-28 | isopyrazam |
| M-F.318 | I-B-33 | isopyrazam |
| M-F.319 | I-B-37 | isopyrazam |
| M-F.320 | I-B-115 | isopyrazam |
| M-F.321 | I-B-131 | isopyrazam |
| M-F.322 | I-B-132 | isopyrazam |
| M-F.323 | I-C-35 | isopyrazam |
| M-F.324 | I-C-36 | isopyrazam |

Compound II-TFPTAP is 5-chloro-7-(4-methylpiperidin-1-yl)-6-(2,4,6-trifluorophenyl)-[1,2,4]triazolo[1,5-a]pyrimidine.

Fluxapyroxad is N-(3',4',5' trifluorobiphenyl-2 yl)-3-difluoromethyl-1-methyl-1H-pyrazole-4 carboxamide.

In one embodiment of the invention, the component 2 is a fungicide, preferably selected from group F.I) to F.XI).

In one embodiment of the invention, the component 2 is a growth regulator, preferably selected from group F.XII).

The present invention furthermore relates to agrochemical compositions comprising a mixture of at least one compound I (component 1) and at least one further active substance useful for plant protection, e. g. selected from the group F.XIII) (component 2), in particular at least one further fungicidal biopesticide selected from the groups F.XIII-1) and F.XIII-2), as described above, and if desired one suitable solvent or solid carrier. Preference is also given to mixtures comprise as biopesticide II (component 3) a biopesticide from group F.XIII-1), preferably selected from Bacillus amyloliquefaciens AP-136 (NRRL B-50614), B. amyloliquefaciens AP-188 (NRRL B-50615), B. amyloliquefaciens AP-218 (NRRL B-50618), B. amyloliquefaciens AP-219 (NRRL B-50619), B. amyloliquefaciens AP-295 (NRRL B-50620), B. amyloliquefaciens IT-45 (CNCM 1-3800, NCBI 1091041), B. amyloliquefaciens subsp. plantarum MBI600 (NRRL B-50595), B. mojavensis AP-209 (No. NRRL B-50616), B. pumilus INR-7 (otherwise referred to as BU-F22 (NRRL B-50153) and BU-F33 (NRRL B-50185)), B. pumilus KFP9F, B. pumilus QST 2808 (NRRL B-30087), B. pumilus GHA 181, B. simplex ABU 288 (NRRL B-50340), B. solisalsi AP-217 (NRRL B-50617), B. subtilis CX-9060, B. subtilis GB03, B. subtilis GB07, B. subtilis QST-713 (NRRL B-21661), B. subtilis var. amyloliquefaciens FZB23, B. subtilis var. amyloliquefaciens D747, Paenibacillus alvei NAS6G6, Paenibacillus polymyxa PKB1 (ATCC No. 202127), Sphaerodes mycoparasitica IDAC 301008-01 and Trichoderma fertile JM41R, even more preferably from Bacillus amyloliquefaciens AP-136 (NRRL B-50614), B. amyloliquefaciens AP-188 (NRRL B-50615), B. amyloliquefaciens AP-218 (NRRL B-50618), B. amyloliquefaciens AP-219 (NRRL B-50619), B. amyloliquefaciens AP-295 (NRRL B-50620), B. amyloliquefaciens IT-45 (CNCM 1-3800, NCBI 1091041), B. mojavensis AP-209 (No. NRRL B-50616), B. pumilus INR-7 (otherwise referred to as BU-F22 (NRRL B-50153) and BU-F33 (NRRL B-50185)), B. pumilus QST 2808 (NRRL B-30087), B. simplex ABU 288 (NRRL B-50340), B. subtilis QST-713 (NRRL B-21661), B. subtilis MBI600 (NRRL B-50595), Paenibacillus alvei NAS6G6, Sphaerodes mycoparasitica IDAC 301008-01 and Trichoderma fertile JM41R.

Preference is also given to mixtures comprise as biopesticide II (component 3) a biopesticide from group L2), preferably selected from chitosan (hydrolysate), methyljasmonate, cis-jasmone, laminarin, Reynoutria sachlinensis extract and tea tree oil.

Preference is also given to mixtures comprise as biopesticide II (component 3) a biopesticide from group L3), preferably selected from Bacillus firmus St 1582, Bacillus thuringiensis ssp. kurstaki SB4, Beauveria bassiana GHA, B. bassiana H123, B. bassiana DSM 12256, B. bassiana PRPI 5339, Metarhizium anisopliae var. acridum IMI 330189, M. anisopliae FI-985, M. anisopliae FI-1045, M. anisopliae F52, M. anisopliae ICIPE 69, Paecilomyces lilacinus DSM 15169, P. lilacinus BCP2, Paenibacillus poppiliae Dutky-1940 (NRRL B-2309=ATCC 14706), P. poppiliae KLN 3 and P. poppiliae Dutky 1, even more preferably from Bacillus thuringiensis ssp. kurstaki SB4 B. bassiana DSM 12256, B. bassiana PRPI 5339, Metarhizium anisopliae var. acridum IMI 330189, M. anisopliae FI-985, M. anisopliae FI-1045, Paecilomyces lilacinus DSM 15169, P. lilacinus BCP2, Paenibacillus poppiliae Dutky-1940 (NRRL B-2309=ATCC 14706), P. poppiliae KLN 3 and P. poppiliae Dutky 1.

Preference is also given to mixtures comprise as biopesticide II (component 3) a biopesticide from group L4), preferably selected from methyl jasmonate, Acacia negraq extract, extract of grapefruit seeds and pulp, Catnip oil, Neem oil, Quillay extract and Tagetes oil.

Preference is also given to mixtures comprise as biopesticide II (component 3) a biopesticide from group L5), preferably selected from *Azospirillum amazonense* BR 11140 (SpY2T), *A. brasilense* XOH, *A. brasilense* BR 11005 (Sp245), *A. brasilense* BR 11002, *A. lipoferum* BR 11646 (Sp31), *A. irakense, A. halopraeferens, Bacillus amyloliquefaciens* AP-136 (NRRL B-50614), *Bradyrhizobium* sp. (*Vigna*), *B. japonicum* USDA 3, *B. japonicum* USDA 31, *B. japonicum* USDA 76, *B. japonicum* USDA 110, *B. japonicum* USDA 121, *Glomus intraradices* RTI-801, *Paenibacillus alvei* NAS6G6, *Penicillium bilaiae, Rhizobium leguminosarum* bv. *phaseolii*, R. 1. *trifolii*, R. 1. bv. *viciae*, and *Sinorhizobium meliloti*, more preferably selected from *Azospirillum brasilense* BR 11005 (Sp245), *Bradyrhizobium* sp. (*Vigna*), *B. japonicum* USDA 3, *B. japonicum* USDA 31, *B. japonicum* USDA 76, *B. japonicum* USDA 110, *B. japonicum* USDA 121, *Rhizobium leguminosarum* bv. *phaseolii*, R. 1. *trifolii*, R. 1. bv. *viciae*, and *Sinorhizobium meliloti*.

Preference is also given to mixtures comprise as biopesticide II (component 3) a biopesticide from group L6), preferably selected from abscisic acid, aluminium silicate (kaolin), humates, *Ascophyllum nodosum* (Norwegian kelp, Brown kelp) extract and *Ecklonia maxima* (kelp) extract.

The inventive mixtures comprising as biopesticide II a microbial pesticide from groups L1), L3) and L5) may be formulated as an inoculant for a plant. The term "inoculant" means a preparation that includes an isolated culture of a microbial pesticide and optionally a carrier, which may include a biologically acceptable medium.

If present, synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, *Weeds*, 15, 20-22):

$$E = X + Y - \frac{XY}{100}$$

When the observed combined control effect is greater than the expected combined control effect (E), then the combined effect is synergistic.

The tests demonstrate the control efficacy of compounds, mixtures or compositions of this invention on specific pests. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests.

The analysis of synergism or antagonism between the mixtures or compositions can be determined using Colby's equation.

Embodiment E4

The present invention relates to new uses of anthranilamide compounds according to the invention, and their mixtures with selected other pesticides in soil and seed treatment application methods.

Invertebrate pests, arthropods and nematodes, and in particular insects and arachnids, destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes.

Especially soil-living pests, arthropod pests, including soil-living insects and arachnids, and especially spider mites, and nematodes, are often controlled and combated by applying an effective amount of a suitable pesticide compound to the soil, e.g. by drenching, drip application, dip application or soil injection. The pesticidal compounds may further be applied as a solid or liquid composition, e.g. such as a dust or granule formulation comprising an inert carrier, e.g. such as clay.

Methods of soil application can suffer from several problems. Pesticidal compounds are not always especially suitable for being applied by different soil application methods such as by drenching, drip application, dip application or soil injection. Their pesticidal activity may be affected in some cases.

It is therefore an object of the present invention to provide compounds having a good pesticidal activity and a good applicability in techniques of soil treatment against a large number of different invertebrate pests, especially against soil-living pests, which are difficult to control.

Some soil-applied pesticides compositions may also have potential for leaching. Therefore, care must be taken to minimize both surface and ground water contamination. Moreover, the effectiveness of the pesticide may vary depending on environmental conditions—e.g. properly timed rain is needed for the successful functioning of the chemistry in the soil, but too much rain may reduce the effectiveness and may cause leaching.

It is therefore also an object of the present invention to provide compositions which are suitable for combating soil-living pests and which overcome the problems associated with the known techniques. In particular the compositions should be applicable easily and provide a long-lasting action on soil-living pests. Moreover, environmental conditions should not have an adverse effect on the effectiveness of the pesticide.

It is therefore also an object of the present invention to provide methods of application, which are suitable for combating soil-living pests Soil application methods are considered as different techniques of applying pesticidal compounds directly or indirectly to the soil and/or ground, such as drip applications or drip irrigations (onto the soil), or soil injection, further methods of drenching the soil.

Furthermore, object of the present inventions are methods of application by dipping roots, tubers or bulbs (referred to as dip application), by hydroponic systems or also by seed treatment.

Another of the problems the farmer is faced with in this context is, that seeds and plant roots and shoots are constantly threatened by foliar and soil insects and other pests.

Thus a further difficulty in relation to the use of such seed protection pesticides is that the repeated and exclusive application of an individual pesticidal compound leads also here in many cases to a rapid selection of soil pests, which have developed natural or adapted resistance against the active compound in question. Therefore there is a need for seed protection agents that help prevent or overcome resistance.

It is therefore a further object of the present invention to provide compounds which solve the problems of protection of the protection of seeds and growing plants, reducing the dosage rate, enhancing the spectrum of activity and/or to manage pest resistance.

The present invention therefore also provides methods for the protection of plant propagation material, especially seeds, from soil insects and of the resulting plant's roots and shoots from soil and foliar insects.

The invention also relates to plant propagation material, especially seeds, which is protected from soil and foliar insects.

Surprisingly, it has now been found that anthranilamide compounds I as described above, or a stereoisomer, salt, tautomer or N-oxide, or a polymorphic crystalline form, a co-crystal or a solvate of a compound or a stereoisomer, salt, tautomer or N-oxide thereof; are, alone or in combination with other selected pesticidal compounds (II), highly suitable for addressing such needs in agriculture. It has been found that these objects as mentioned above are in part or in whole achieved by soil application techniques and seed treatment methods for the control, the protection and the combat from soil insects. This relates especially to seeds and to the resulting plant's roots and shoots.

Thus, in one embodiment, the invention relates to the use of these compounds I (or a stereoisomer, salt, tautomer or N-oxide, or a polymorphic crystalline form, a co-crystal or a solvate of a compound or a stereoisomer, salt, tautomer or N-oxide thereof) for controlling and/or combating animal pests in soil application methods and seed treatment methods.

In one embodiment, the invention relates to said use for controlling and/or combating animal pests in soil application methods and seed treatment methods.

Furthermore, in this context, it has also been found that the compounds I and their mixtures with other pesticides, are especially suitable for the protection of seeds from soil insects and of the resulting plant's roots and shoots from soil and foliar insects.

In seed and soil treatment, there are certain pests which represent a big threat to plants during the stage from shoot/seedling to a small plant. Some pests which are especially known to represent a risk for the shoot/seedling or small plant, include rootworms, wireworms (e.g. in potatoe crop protection) and maggots like seedcorn maggot (e.g. *Delia platura*), western corn rootworm, black cutworm, mites, spider mites. These are only some examples; there are more pests specifically interesting in seed and soil treatment, which the person skilled in the art knows.

In one embodiment, the compound I in the methods and uses according to the invention of E4 is selected from the compounds described in Embodiment A.

In one embodiment, the compound I in the methods and uses according to the invention of E4 is selected from the compounds described in Embodiment B.

In one embodiment, the compound I in the methods and uses according to the invention of E4 is selected from the compounds described in Embodiment C.

In one embodiment, the compound I in the methods and uses according to the invention of E4 is selected from the compounds listed in Table ABC.

In one embodiment, I-A-1 is the compound I in the methods and uses according to the invention of E4.

In one embodiment, I-A-28 is the compound I in the methods and uses according to the invention of E4.

In one embodiment, I-B-115 is the compound I in the methods and uses according to the invention of E4.

In one embodiment, I-B-131 is the compound I in the methods and uses according to the invention of E4.

In one embodiment, I-B-132 is the compound I in the methods and uses according to the invention of E4.

In one embodiment, I-C-19 is the compound I in the methods and uses according to the invention of E4.

In one embodiment, I-C-35 is the compound I in the methods and uses according to the invention of E4.

In one embodiment, I-C-36 is the compound I in the methods and uses according to the invention of E4.

In a further embodiment, the invention relates to the methods and uses of the compounds according to the invention (as defined in Embodiment A, B or C) in combination with other selected pesticidal compounds (II), as defined and specified in Embodiments 2 and 3.

Thus, the compounds I or their agriculturally acceptable salts, and/or their mixtures with other selected pesticides, are highly suitable for methods for controlling and/or combating insects, acarids and/or nematodes, and especially spider mites, by soil application methods.

According to the present invention, the compounds I and/or their mixtures are used for controlling arthropds, especially insects and arachnids, more especially (spider) mites, and/or nematodes by soil application methods such as drenching, drip application, dip application or soil injection or by seed treatment.

Seed treatment methods comprise e.g contacting the seeds before sowing and/or after pregermination with comprising the compounds I and their mixtures with other pesticides.

The invention in particular relates to soil application methods for combating soil-living arthropod pests, and nematode pests, which comprises applying to the soil a pesticidally effective amount of a compound of the present invention.

The pests that can be controlled or combatted are as described herein. e.g. in Embodiment E1, which include soil-living pests.

The term "soil-living" means that the habitat, breeding ground, area or environment in which a pest or parasite is growing or may grow is the soil.

As stated above, in seed and soil treatment, there are certain pests which represent a big threat to plants during the stage from shoot/seedling to a small plant. There are pests which represent a threat, because they cause damage to plant roots, bulbs etc. There are pests which represent a threat, because, although they do not cause damage to roots and the such, they are merely developing in the soil so they can once again rise and become above-ground phytophagous or plant-eating pests. The soil-living pests especially include Coleoptera, which are beetles; Lepidoptera, which are moths and butterflies; Diptera, which are flies (especially *Lycoriella, Sciara, Bradysia* spp.); leafminers, cutworms, caterpillars, fungus gnats, mushroom flies, shore flies, black vine, carrot and strawberry-root weevils; sod webworms, wire- and potato-tuber worms; apple, carrot-rust fly, onion and cabbage maggots; and flea, June/May and cucumber beetle larvae.

Some pests which are especially known to represent a risk for the shoot/seedling or small plant, include rootworms, wireworms (e.g. in potatoe crop protection) and maggots like seedcorn maggot (e.g. *Delia platura*), western corn rootworm, black cutworm, mites, spider mites. These are only some examples; there are more pests specifically interesting in seed and soil treatment, which the person skilled in the art knows.

In an embodiment of the invention, the methods of the present invention are used for controlling pests from the family Aphididae.

In an embodiment of the invention, the methods of the present invention are used for controlling pests from the family Phemphigidae.

In an embodiment of the invention, the methods of the present invention are used for controlling pests from the family Phemphigidae.

In an embodiment of the invention, the methods of the present invention are used for controlling pests from the family Tetranychidae.

In an embodiment of the invention, the methods of the present invention are used for controlling pests from the family Tarsonemidae.

In an embodiment of the invention, the methods of the present invention are used for controlling pests from the family Thripidae.

In an embodiment of the invention, the methods of the present invention are used for controlling pests from the family Aleyrodidae In an embodiment of the invention, the methods of the present invention are used for controlling pests from the family Coccidae.

In an embodiment of the invention, the methods of the present invention are used for controlling pests from the family Pseudococcidae.

In an embodiment of the invention, the methods of the present invention are used for controlling pests from the family Agromyzidae.

In an embodiment of the invention, the methods of the present invention are used for controlling pests from the family Aphelenchoididae.

In a preferred embodiment of the invention, the methods of the present invention are used for controlling pests from the family Coleoptera.

In a preferred embodiment of the invention, the methods of the present invention are used for controlling pests from the family Lepidoptera.

In a preferred embodiment of the invention, the methods of the present invention are used for controlling pests from the family Orthoptera.

In a preferred embodiment of the invention, the methods of the present invention are used for controlling pests from the family Hemiptera.

In a preferred embodiment of the invention, the methods of the present invention are used for controlling pests from the family Isoptera.

In a preferred embodiment of the invention, the methods of the present invention are used for controlling pests from the family Diptera.

In a preferred embodiment of the invention, the methods of the present invention are used for controlling pests from the family Thipidae.

In a further embodiment, the invention relates to the use of the compounds according to the invention (as defined in Embodiment A, B or C) in combination with other selected pesticidal compounds (II), as defined and specified in Embodiments 2 and 3.

The formulations are as described herein, e.g. in embodiment E1.

The applications are as described herein, e.g. in embodiment E1.

Further active ingredients: Another aspect of the present invention is when preparing the mixtures, it is preferred to employ the mixture according to the invention or pure active compounds I and II, to which further active compounds, e.g. against harmful fungi or having herbicidal activity, or growth-regulating agents or fertilizers can be added.

Compositions of this invention may further contain other active ingredients, for example fungicides, herbicides, fertilizers such as ammonium nitrate, urea, potash, and superphosphate, phytotoxicants and plant growth regulators and safeners, as described herein, e.g. in Embodiments E2 and E3. These additional ingredients may be used sequentially or in combination with the above-described compositions, if appropriate also added only immediately prior to use (tank mix). For example, the plant(s) may be sprayed with a composition of this invention either before or after being treated with other active ingredients.

The further active ingredients may be selected from the group M, or from the list F of active substances, as described herein in Embodiment E2 or E3.

Applications: Soil Treatment

The present invention relates to the methods by use on natural substrates (soil) or artificial (growth) substrates (e.g. rock wool, glass wool, quartz sand, gravel, expanded clay, vermiculite), in the open or in closed systems (e.g. greenhouses or under film mulch) and in annual crops (such as vegetables, spices, ornamentals) or perennial crops (such as citrus plants, fruits, tropical crops, spices, nuts, grapevines, conifers and ornamentals).

It has now been found that the problems associated with combating soil-living pests by pesticide treatment of the soil can be overcome by such application methods using compounds of the present invention.

The animal pest, i.e. the insects, arachnids and nematodes, the plant, the water or the soil in which the plant is growing can be contacted with the present compounds I or composition(s) containing them by any application method known in the art. As such, "contacting" includes both direct contact (applying the compounds/compositions directly on the animal pest or plant) and indirect contact (applying the compounds/compositions to the locus of the animal pest or plant). When the plant is contacted, typically the tuber, bulbs or roots of the plant are contacted.

Soil application techniques and soil application methods according to the present invention, are methods wherein the active compound(s) are applied by drenching the soil, applied by drip irrigation, applied by soil injection.

Another soil application technique in the sense of the present invention is a method, wherein the active compound(s) are applied by dipping roots, tubers or bulbs.

An alternative method of soil application technique is that the active compound(s) are applied with drip application systems.

In the case of soil treatment or of application to the pests dwelling place or nest, the quantity of active ingredient ranges from 0.0001 to 500 g per 100 m$^2$, preferably from 0.001 to 20 g per 100 m$^2$.

Seed Treatment

The compounds I are especially also suitable for the treatment of seeds in order to protect the seed from insect pest, in particular from soil-living insect pests and the resulting plant's roots and shoots against soil pests and foliar insects.

The compounds I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

Consequently, the present invention relates to methods for the protection of seeds, from soil insects and of the resulting plant's roots and shoots from soil and foliar insects wherein the seeds are contacted before sowing and/or after pregermination with the neonicotinoid insecticide cycloxaprid alone or in combination with a selected pesticidal active compound II.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In general, suitable seeds are seeds of cereals, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The seed treatment application of the active compound is carried out by spraying or by dusting the seeds before sowing of the plants and before emergence of the plants.

Compositions which are especially useful for seed treatment are described above.
Biology
B.1.1 Soil Drench Assay in Lima Bean Test solution comprising a compound of the present invention is prepared at desired concentration using water and an organic solvent. Potted lima bean plants are treated with test solution by means of soil drenching. After the desired time, a mixed population of two spotted spider mites is released onto the leaves.

After the desired time after the release of spider mites, the acaricidal efficacy is measured by means of the rating of the damage caused by spider mites or the spider mite mortality.
B.1.2 Seed Treatment Assay in Cotton Test solution comprising a compound of the present invention is prepared at desired concentration using water and an organic solvent. Cotton seeds are coated with such prepared test solution and sown to the pots. After plant emergence, a mixed population of two spotted spider mites is released onto the leaves.

After the desired time after the release of spider mites, the acaricidal efficacy is measured by means of the rating of the damage caused by spider mites or the spider mite mortality.

B.1.3 Seed Treatment Assay in Cucumber

Test solution comprising a compound of the present invention is prepared at desired concentration using water and an organic solvent. Cucumber seeds are coated with such prepared stest olution and sown to the pots. After plant emergence, a mixed population of two spotted spider mites is released onto the leaves.

After the desired time after the release of spider mites, the acaricidal efficacy is measured by means of the rating of the damage caused by spider mites or the spider mite mortality.
B. 1.4 Soil Incorporation Against Western Corn Rootworm (*Diabrotica virgifera virgifera*)

The active compound is applied in acetone at rates of 5 and 50 ppm a.i./soil (w/w). Treatments are applied in solution to sifted, North Carolina loamy sand (Sandhill soil) in a plastic bag. Treatments are thoroughly incorporated by sealing and shaking each bag by hand and allowing the solution to soak through the soil mass for at least 10 minutes before unsealing. The bags are then kept open in a fume hood overnight to evaporate the solvent from the soil. One day after treatment (DAT) distilled water for moisture and water-soaked millet seed (*Panicum miliaceum* 'white millet') as a food source are added to each bag and mixed in thoroughly. 11 cm$^3$ of millet and soil mixture are dispensed into a 1 oz. plastic cup. Each cup is infested with 10 western corn rootworm second-instar larvae. Each cup or group of four cells is a replicate, and replication is 3×. The test is maintained in incubators at 26° C. in the dark. Mortality is evaluated 3 days after infestation (DAI) and mean percent mortality is calculated.
B.1.5 Soil Incorporation Against Black Cutworm (*Agrotis ipsilon*)

The active compound is applied in acetone at rates of 5 and 50 ppm a.i./soil (w/w). Treatments are applied in solution to sifted, North Carolina loamy sand (Sandhill soil) in a plastic bag. Treatments are thoroughly incorporated by sealing and shaking each bag by hand and allowing the solution to soak through the soil mass for at least 10 minutes before unsealing. The bags are then kept open in a fume hood overnight to evaporate the solvent from the soil. One day after treatment (DAT) distilled water for moisture and water-soaked millet seed (*Panicum miliaceum* 'white millet') as a food source are added to each bag and mixed in thoroughly. 11 cm$^3$ of millet and soil mixture are dispensed into a 1 oz. plastic cup. Each cup is infested with one black cutworm second-instar larva. Each cup or group of four cells is a replicate, and replication is 3×. The test is maintained in incubators at 26° C. with 14 hours. Mortality is evaluated 3 days after infestation (DAI) and mean percent mortality relative to the solvent blank is calculated.

Each cup is infested with 10 western corn rootworm second-instar larvae, and each cell is infested with one black cutworm second-instar larva. Each cup or group of four cells is a replicate, and replication is 3×. The test is maintained in incubators at 26° C. in the dark for western corn rootworm and at 26° C. with 14 hours light for black cutworm. Mortality is evaluated 3 days after infestation (DAI) and mean percent mortality relative to the solvent blank is calculated.
B.2.1 Root Length in Treatment Against Seedcorn Maggot (Anthomyiidae: *Delia platura*).

The compounds according to the invention and other diamide compounds (cyantraniliprole and chlorantraniliprole) are tested for activity against seedcorn maggot. The compound is dissolved in acetone, and then water is added to achieve a final concentration of 0.5% acetone. Rates are 1 and 10 ppm. Four cucumber seeds (*Cucumis sativus*

'National Pickling') are placed in a germination pouch and 18 ml of solution is added. Pouches are held upright in an incubator (22° C., 14L:10D). At 2 days after treatment (DAT), approximately 50 seedcorn maggot eggs are applied to each germination pouch in 0.5 ml of distilled water. Root length of each cucumber plant is measured 7 days after infestation (DAI). Five replicates (pouches) are prepared for each treatment. Analysis of variance is conducted, and mean separation is performed using Student-Newman-Keul's HSD ($\alpha=0.05$). Percent control is calculated as the mean root length relative to that of the infested and uninfested solvent blank treatments.

B.2.2 Plant Emergence, Shoot Height and Root Mass in Treatment Against Western Corn Rootworm (Chrysomelidae: *Diabrotica virgifera virgifera*).

The compounds according to the invention, in formulated form, and other diamide compounds (chlorantraniliprole: Altacor® and Coragen®) are tested for activity against western corn rootworm. Pots are filled with soil mixture (1:1 loamy sand:sand) and watered prior to treatment and planting. Formulations are diluted in distilled water and then applied to 20 g corn seed in a volume of 188 µl in a Hege 11 liquid seed treater and spun for 30 s. One seed is planted per pot 1-3 days after treatment. Five replicates (pots) are prepared for each treatment. Pots are arranged in a randomized complete block design in the greenhouse and top watered daily. At 5-6 days after planting (DAP), 12 western corn rootworm larvae (2nd instar) are infested in each pot. After infestation, pots are maintained in a growth chamber (26° C., 10 hours light:14 hours dark) and bottom-watered as needed. Plant emergence and shoot phytotoxicity are evaluated 5 DAP. Shoot height and fresh root mass are evaluated 7 days after infestation (DAI). Analysis of variance is conducted, and mean separation is performed using Student-Newman-Keul's HSD ($\alpha=0.05$).

Embodiment E5

The present invention relates to a method for controlling pests and/or increasing the plant health of a cultivated plant with at least one modification (hereinafter abbreviated as "cultivated plant") as compared to the respective non-modified control plant, comprising the application of a pesticidally active compound I as described herein.

In one embodiment, the compound I in the methods and uses according to the invention of E5 is selected from the compounds described in Embodiment A.

In one embodiment, the compound I in the methods and uses according to the invention of E5 is selected from the compounds described in Embodiment B.

In one embodiment, the compound I in the methods and uses according to the invention of E5 is selected from the compounds described in Embodiment C.

In one embodiment, the compound I in the methods and uses according to the invention of E5 is selected from the compounds listed in Table ABC.

In some embodiments, the invention relates to methods and uses, wherein the compound I is applied in an application type which corresponds in each case to one row of Table AP-T.

In one embodiment, the compound I in the methods and uses according to the invention of E5 is selected from the compounds described in Embodiment A.

In one embodiment, the compound I in the methods and uses according to the invention of E5 is selected from the compounds described in Embodiment B.

In one embodiment, the compound I in the methods and uses according to the invention of E5 is selected from the compounds described in Embodiment C.

In one embodiment, the compound I in the methods and uses according to the invention of E5 is selected from the compounds listed in Table ABC.

In one embodiment, I-A-1 is the compound I in the methods and uses according to the invention of E5.

In one embodiment, I-A-28 is the compound I in the methods and uses according to the invention of E5.

In one embodiment, I-B-115 is the compound I in the methods and uses according to the invention of E5.

In one embodiment, I-B-131 is the compound I in the methods and uses according to the invention of E5.

In one embodiment, I-B-132 is the compound I in the methods and uses according to the invention of E5.

In one embodiment, I-C-19 is the compound I in the methods and uses according to the invention of E5.

In one embodiment, I-C-35 is the compound I in the methods and uses according to the invention of E5.

In one embodiment, I-C-36 is the compound I in the methods and uses according to the invention of E5.

In a further embodiment, the invention relates to the methods and uses of the compounds according to the invention (as defined in Embodiment A, B or C) in combination with other selected pesticidal compounds (II), as defined and specified in Embodiments 2 and 3.

The pests that can be controlled or combatted are as described above or herein, e.g. in embodiment E1.

The plants or crops to be protected are as described above or herein, e.g. in embodiment E1.

The formulations are as described herein, e.g. in embodiment E1.

The applications are as described herein, e.g. in embodiment E1.

The mixtures and preferred mixtures are as described herein.

In one embodiment the methods of the present invention effectuate an increased yield of a cultivated plant or its product.

In another embodiment the the methods of the present invention effectuate an increased vigor of a cultivated plant or its product.

In another embodiment the the methods of the present invention effectuate in an increased quality of a cultivated plant or its product.

In yet another embodiment the the methods of the present invention effectuate an increased tolerance and/or resistance of a cultivated plant or its product against biotic stress.

In yet another embodiment the the methods of the present invention effectuate an increased tolerance and/or resistance of a cultivated plant or its product against abiotic stress.

In a preferred embodiment of the invention, the methods of the present invention increase the yield of cultivated plants.

In a preferred embodiment of the invention, embodiment of the invention, the the methods of the present invention increase the yield of cultivated plants such as the plant weight and/or the plant biomass (e.g. overall fresh weight) and/or the grain yield and/or the number of tillers.

In another preferred embodiment of the invention, embodiment of the invention, the the methods of the present invention increase the plant vigor of cultivated plants.

In a more preferred embodiment of the invention, the methods of the present invention increase the yield of cultivated plants.

In a most preferred embodiment of the invention, the methods of the present invention increase the yield of cultivated plants such as the plant weight and/or the plant biomass (e.g. overall fresh weight) and/or the grain yield and/or the number of tillers.

Thus, the present invention relates to methods for controlling pests of a cultivated plant as compared to the respective non-modified control plant, comprising the application of compounds I and their mixtures to a cultivated plant, parts of such plant, plant propagation material, or at its locus of growth.

Thus, the present invention also relates to methods for increasing the plant health, in particular the yield of a cultivated plant as compared to the respective non-modified control plant, comprising the application of compounds I and their mixtures to a cultivated plant, parts of such plant, plant propagation material, or at its locus of growth.

The term "plant propagation material" is to be understood to denote all the generative parts of a plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. Preferably, the term plant propagation material denotes seeds.

In a preferred embodiment, the present invention relates to a method of controlling harmful insects and/or increasing the health of a cultivated plant, in particular the yield of a cultivated plant, by treating plant propagation material, preferably seeds with compounds I and their mixtures.

The present invention also comprises plant propagation material, preferably seed, of a cultivated plant treated with compounds I and their mixtures In another preferred embodiment, the present invention relates to a method of controlling harmful insects and/or increasing the health of a cultivated plant, in particular the yield of a cultivated plant by treating the cultivated plant, part(s) of such plant or at its locus of growth with compounds I and their mixtures. compounds I or their mixtures The term cultivated plant(s) includes to "modified plant(s)" and "transgenic plant(s)".

In one embodiment of the invention, the term "cultivated plants" refers to "modified plants". In one embodiment of the invention, the term "cultivated plants" refers to "transgenic plants".

"Modified plants" are those which have been modified by conventional breeding techniques. The term "modification" means in relation to modified plants a change in the genome, epigenome, transcriptome or proteome of the modified plant, as compared to the control, wild type, mother or parent plant whereby the modification confers a trait (or more than one trait) or confers the increase of a trait (or more than one trait) as listed below.

The modification may result in the modified plant to be a different, for example a new plant variety than the parental plant.

"Transgenic plants" are those, which genetic material has been modified by the use of recombinant DNA techniques that under natural circumstances can not readily be obtained by cross breeding, mutations or natural recombination, whereby the modification confers a trait (or more than one trait) or confers the increase of a trait (or more than one trait) as listed below as compared to the wild-type plant.

In one embodiment, one or more genes have been integrated into the genetic material of a genetically modified plant in order to improve certain properties of the plant, preferably increase a trait as listed below as compared to the wild-type plant. Such genetic modifications also include but are not limited to targeted post-translational modification of protein(s), or to post-transcriptional modifications of oligo- or polypeptides e.g. by glycosylation or polymer additions such as prenylated, acetylated, phosphorylated or farnesylated moieties or PEG moieties.

In one embodiment under the term "modification" when reffering to a transgenic plant or parts thereof is understood that the activity, expression level or amount of a gene product or the metabolite content is changed, e.g. increased or decreased, in a specific volume relative to a corresponding volume of a control, reference or wild-type plant or plant cell, including the de novo creation of the activity or expression.

In one embodiment the activity of a polypeptide is increased or generated by expression or overexpresion of the gene coding for said polypeptide which confers a trait or confers the increase of a trait as listed below as compared to the control plant. The term "expression" or "gene expression" means the transcription of a specific gene or specific genes or specific genetic construct. The term "expression" or "gene expression" in particular means the transcription of a gene or genes or genetic construct into structural RNA (rRNA, tRNA), regulatory RNA (e.g. miRNA, RNAi, RNAa) or mRNA with or without subsequent translation of the latter into a protein. In another embodiment the term "expression" or "gene expression" in particular means the transcription of a gene or genes or genetic construct into structural RNA (rRNA, tRNA) or mRNA with or without subsequent translation of the latter into a protein. In yet another embodiment it means the transcription of a gene or genes or genetic construct into mRNA.

The process includes transcription of DNA and processing of the resulting mRNA product. The term "increased expression" or "overexpression" as used herein means any form of expression that is additional to the original wild-type expression level.

The term "expression of a polypeptide" is understood in one embodiment to mean the level of said protein or polypeptide, preferably in an active form, in a cell or organism.

In one embodiment the activity of a polypeptide is decreased by decreased expression of the gene coding for said polypeptide which confers a trait or confers the increase of a trait as listed below as compared to the control plant. Reference herein to "decreased expression" or "reduction or substantial elimination" of expression is taken to mean a decrease in endogenous gene expression and/or polypeptide levels and/or polypeptide activity relative to control plants. It comprises further reducing, repressing, decreasing or deleting of an expression product of a nucleic acid molecule.

The terms "reduction", "repression", "decrease" or "deletion" relate to a corresponding change of a property in an organism, a part of an organism such as a tissue, seed, root, tuber, fruit, leave, flower etc. or in a cell. Under "change of a property" it is understood that the activity, expression level or amount of a gene product or the metabolite content is changed in a specific volume or in a specific amount of protein relative to a corresponding volume or amount of protein of a control, reference or wild type. Preferably, the overall activity in the volume is reduced, decreased or deleted in cases if the reduction, decrease or deletion is related to the reduction, decrease or deletion of an activity of a gene product, independent whether the amount of gene product or the specific activity of the gene product or both is reduced, decreased or deleted or whether the amount, stability or translation efficacy of the nucleic acid sequence or gene encoding for the gene product is reduced, decreased or deleted.

The terms "reduction", "repression", "decrease" or "deletion" include the change of said property in only parts of the subject of the present invention, for example, the modification can be found in compartment of a cell, like an organelle, or in a part of a plant, like tissue, seed, root, leave, tuber, fruit, flower etc. but is not detectable if the overall subject, i.e. complete cell or plant, is tested. Preferably, the "reduction", "repression", "decrease" or "deletion" is found cellular, thus the term "reduction, decrease or deletion of an activity" or "reduction, decrease or deletion of a metabolite content" relates to the cellular reduction, decrease or deletion compared to the wild type cell. In addition the terms "reduction", "repression", "decrease" or "deletion" include the change of said property only during different growth phases of the organism used in the inventive process, for example the reduction, repression, decrease or deletion takes place only during the seed growth or during blooming. Furthermore the terms include a transitional reduction, decrease or deletion for example because the used method, e.g. the antisense, RNAi, snRNA, dsRNA, siRNA, miRNA, ta-siRNA, cosuppression molecule, or ribozyme, is not stable integrated in the genome of the organism or the reduction, decrease, repression or deletion is under control of a regulatory or inducible element, e.g. a chemical or otherwise inducible promoter, and has therefore only a transient effect.

Methods to achieve said reduction, decrease or deletion in an expression product are known in the art, for example from the international patent application WO 2008/034648, particularly in paragraphs [0020.1.1.1], [0040.1.1.1], [0040.2.1.1] and [0041.1.1.1].

Reducing, repressing, decreasing or deleting of an expression product of a nucleic acid molecule in modified plants is known. Examples are canola i.e. double nill oilseed rape with reduced amounts of erucic acid and sinapins.

Such a decrease can also be achieved for example by the use of recombinant DNA technology, such as antisense or regulatory RNA (e.g. miRNA, RNAi, RNAa) or siRNA approaches. In particular RNAi, snRNA, dsRNA, siRNA, miRNA, ta-siRNA, cosuppression molecule, ribozyme, or antisense nucleic acid molecule, a nucleic acid molecule conferring the expression of a dominant-negative mutant of a protein or a nucleic acid construct capable to recombine with and silence, inactivate, repress or reduces the activity of an endogenous gene may be used to decrease the activity of a polypeptide in a transgenic plant or parts thereof or a plant cell thereof used in one embodiment of the methods of the invention. Examples of transgenic plants with reduced, repressed, decreased or deleted expression product of a nucleic acid molecule are *Carica papaya* (Papaya plants) with the event name X17-2 of the University of Florida, *Prunus domestica* (Plum) with the event name C5 of the United States Department of Agriculture—Agricultural Research Service, or those listed in rows T9-48 and T9-49 of table 9 below. Also known are plants with increased resistance to nematodes for example by reducing, repressing, decreasing or deleting of an expression product of a nucleic acid molecule, e.g. from the PCT publication WO 2008/095886.

The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants. Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene.

The terms "control" or "reference" are exchangeable and can be a cell or a part of a plant such as an organelle like a chloroplast or a tissue, in particular a plant, which was not modified or treated according to the herein described process according to the invention. Accordingly, the plant used as control or reference corresponds to the plant as much as possible and is as identical to the subject matter of the invention as possible. Thus, the control or reference is treated identically or as identical as possible, saying that only conditions or properties might be different which do not influence the quality of the tested property other than the treatment of the present invention.

It is possible that control or reference plants are wild-type plants. However, "control" or "reference" may refer to plants carrying at least one genetic modification, when the plants employed in the process of the present invention carry at least one genetic modification more than said control or reference plants. In one embodiment control or reference plants may be transgenic but differ from transgenic plants employed in the process of the present invention only by said modification contained in the transgenic plants employed in the process of the present invention.

The term "wild type" or "wild-type plants" refers to a plant without said genetic modification. These terms can refer to a cell or a part of a plant such as an organelle like a chloroplast or a tissue, in particular a plant, which lacks said genetic modification but is otherwise as identical as possible to the plants with at least one genetic modification employed in the present invention. In a particular embodiment the "wild-type" plant is not transgenic.

Preferably, the wild type is identically treated according to the herein described process according to the invention. The person skilled in the art will recognize if wild-type plants will not require certain treatments in advance to the process of the present invention, e.g. non-transgenic wild-type plants will not need selection for transgenic plants for example by treatment with a selecting agent such as a herbicide.

The control plant may also be a nullizygote of the plant to be assessed. The term "nullizygotes" refers to a plant that has undergone the same production process as a transgenic, yet has lost the once acquired genetic modification (e.g. due to mendelian segregation) as the corresponding transgenic. If the starting material of said production process is transgenic, then nullizygotes are also transgenic but lack the additional genetic modification introduced by the production process. In the process of the present invention the purpose of wild-type and nullizygotes is the same as the one for control and reference or parts thereof. All of these serve as controls in any comparison to provide evidence of the advantageous effect of the present invention.

Preferably, any comparison is carried out under analogous conditions. The term "analogous conditions" means that all conditions such as, for example, culture or growing conditions, soil, nutrient, water content of the soil, temperature, humidity or surrounding air or soil, assay conditions (such as buffer composition, temperature, substrates, pathogen strain, concentrations and the like) are kept identical between the experiments to be compared. The person skilled in the art will recognize if wild-type, control or reference plants will not require certain treatments in advance to the process of the present invention, e.g. non-transgenic wild-type plants will not need selection for transgenic plants for example by treatment with herbicide.

In case that the conditions are not analogous the results can be normalized or standardized based on the control.

The "reference", "control", or "wild type" is preferably a plant, which was not modified or treated according to the herein described process of the invention and is in any other property as similar to a plant, employed in the process of the present invention of the invention as possible.

The reference, control or wild type is in its genome, transcriptome, proteome or metabolome as similar as possible to a plant, employed in the process of the present invention of the present invention. Preferably, the term "reference-" "control-" or "wild-type-" plant, relates to a plant, which is nearly genetically identical to the organelle, cell, tissue or organism, in particular plant, of the present invention or a part thereof preferably 90% or more, e.g. 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a plant, which is genetically identical to the plant, cell, a tissue or organelle used according to the process of the invention except that the responsible or activity conferring nucleic acid molecules or the gene product encoded by them have been amended, manipulated, exchanged or introduced in the organelle, cell, tissue, plant, employed in the process of the present invention.

Preferably, the reference and the subject matter of the invention are compared after standardization and normalization, e.g. to the amount of total RNA, DNA, or protein or activity or expression of reference genes, like housekeeping genes, such as ubiquitin, actin or ribosomal proteins.

The genetic modification carried in the organelle, cell, tissue, in particular plant used in the process of the present invention is in one embodiment stable e.g. due to a stable transgenic integration or to a stable mutation in the corresponding endogenous gene or to a modulation of the expression or of the behaviour of a gene, or transient, e.g. due to an transient transformation or temporary addition of a modulator such as an agonist or antagonist or inducible, e.g. after transformation with a inducible construct carrying a nucleic acid molecule under control of a inducible promoter and adding the inducer, e.g. tetracycline.

In one embodiment preferred plants, from which "modified plants" and/or "transgenic plants" are be selected from the group consisting of cereals, such as maize (corn), wheat, barley *sorghum*, rice, rye, millet, triticale, oat, pseudocereals (such as buckwheat and *quinoa*), alfalfa, apples, banana, beet, broccoli, Brussels sprouts, cabbage, canola (rapeseed), carrot, cauliflower, cherries, chickpea, Chinese cabbage, Chinese mustard, collard, cotton, cranberries, creeping bentgrass, cucumber, eggplant, flax, grape, grapefruit, kale, kiwi, kohlrabi, melon, mizuna, mustard, *papaya*, peanut, pears, pepper, persimmons, pigeonpea, pineapple, plum, potato, raspberry, rutabaga, soybean, squash, strawberries, sugar beet, sugarcane, sunflower, sweet corn, tobacco, tomato, turnip, walnut, watermelon and winter squash,
more preferably from the group consisting of alfalfa, canola (rapeseed), cotton, rice, maize, cerals (such as wheat, barley, rye, oat), soybean, fruits and vegetables (such as potato, tomato, melon, *papaya*), pome fruits (such as apple and pear), vine, sugarbeet, sugarcane, rape, citrus fruits (such as citron, lime, orange, pomelo, grapefruit, and mandarin) and stone fruits (such as cherry, apricot and peach), most preferably from cotton, rice, maize, cerals (such as wheat, barley, rye, oat), *sorghum*, squash, soybean, potato, vine, pome fruits (such as apple), citrus fruits (such as citron and orange), sugarbeet, sugarcane, rape, oilseed rape and tomatoes, utmost preferably from cotton, rice, maize, wheat, barley, rye, oat, soybean, potato, vine, apple, pear, citron and orange.

In another embodiment of the invention the cultivated plant is a gymnosperm plant, especially a spruce, pine or fir.

In one embodiment, the cultivated plant is selected from the families Aceraceae, Anacardiaceae, Apiaceae, Asteraceae, Brassicaceae, Cactaceae, Cucurbitaceae, Euphor-biaceae, Fabaceae, Malvaceae, Nymphaeaceae, Papaveraceae, Rosaceae, Salicaceae, Solanaceae, Arecaceae, Bromeliaceae, Cyperaceae, lridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, As-teraceae, Brassicaceae, Cucurbitaceae, Fabaceae, Papaveraceae, Rosaceae, Solanaceae, Liliaceae or Poaceae.

Preferred are crop plants and in particular plants selected from the families and genera mentioned above for example preferred the species *Anacardium occidentale, Calendula officinalis, Carthamus tinctorius, Cichorium intybus, Cynara scolymus, Helianthus annus, Tagetes lucida, Tagetes erecta, Tagetes tenuifolia; Daucus carota; Corylus avellana, Corylus colurna, Borago officinalis; Brassica napus, Brassica rapa* ssp., *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis, Brassica oleracea, Arabidopsis thaliana, Anana comosus, Ananas ananas, Bromelia comosa, Carica papaya, Cannabis sative, Ipomoea batatus, Ipomoea pandurata, Convolvulus batatas, Convolvulus tiliaceus, Ipomoea fas-tigiata, Ipomoea tiliacea, Ipomoea triloba, Convolvulus panduratus, Beta vulgaris, Beta vul-garis* var. *altissima, Beta vulgaris* var. *vulgaris, Beta maritima, Beta vulgaris* var. *perennis, Beta vulgaris* var. *conditiva, Beta vulgaris* var. *esculenta, Cucurbita maxima, Cucurbita mixta, Cucurbita pepo, Cucurbita moschata, Olea europaea, Manihot utilissima, Janipha manihot, Jatropha manihot., Manihot aipil, Manihot dulcis, Manihot manihot, Manihot melanobasis, Manihot esculenta, Ricinus communis, Pisum sativum, Pisum arvense, Pisum humile, Medicago sativa, Medicago falcata, Medicago varia, Glycine max Dolichos soja, Glycine gracilis, Glycine hispida, Phaseolus max, Soja hispida, Soja max, Cocos nucifera, Pelargonium grossularioides, Oleum cocoas, Laurus nobilis, Persea americana, Arachis hypogaea, Linum usitatissimum, Linum humile, Linum austriacum, Linum bienne, Linum angustifolium, Linum catharticum, Linum flavum, Linum grandiflorum, Adenolinum grandiflo-rum, Linum lewisii, Linum narbonense, Linum perenne, Linum perenne* var. *lewisii, Linum pratense, Linum trigynum, Punica granatum, Gossypium hirsutum, Gossypium arboreum, Gossypium barbadense, Gossypium herbaceum, Gossypium thurberi, Musa nana, Musa acuminata, Musa paradisiaca, Musa* spp., *Elaeis guineensis, Papaver orientale, Papaver rhoeas, Papaver dubium, Sesamum indicum, Piper aduncum, Piper amalago, Piper angus-tifolium, Piper auritum, Piper betel, Piper cubeba, Piper longum, Piper nigrum, Piper ret-rofractum, Artanthe adunca, Artanthe elongata, Peperomia elongata, Piper elongatum, Steffensia elongata, Hordeum vulgare, Hordeum jubatum, Hordeum murinum, Hordeum secalinum, Hordeum distichon Hordeum aegiceras, Hordeum hexas-* tichon, *Hordeum hexa-stichum, Hordeum irregulare, Hordeum sativum, Hordeum secalinum, Avena sativa, Avena fatua, Avena byzantina, Avena fatua* var. *sativa, Avena hybrida, Sorghum bicolor, Sorghum halepense, Sorghum saccharatum, Sorghum vulgare, Andropogon drummondii, Holcus bi-color, Holcus sorghum, Sorghum aethiopicum, Sorghum arundinaceum, Sorghum caf-frorum, Sorghum cernuum, Sorghum dochna, Sorghum drummondii, Sorghum durra, Sor-ghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum, Zea mays, Triticum aestivum, Triticum durum, Triticum turgidum, Triticum hybernum, Triticum macha, Triticum sativum* or *Triticum vulgare, Cofea* spp., *Coffea arabica, Coffea canephora, Coffea liberica, Capsicum annuum, Capsi-cum annuum* var. *glabriusculum, Capsicum frutescens, Capsicum annuum, Nicotiana tabacum, Solanum tuberosum, Solanum melongena, Lycopersicon esculentum, Lycopersicon lycopersicum, Lycopersicon pyriforme, Solanum integrifolium, Solanum lycopersicum Theobroma cacao* and *Camellia sinensis*.

Anacardiaceae such as the genera *Pistacia, Mangifera, Anacardium* e.g. the species *Pistacia vera* [pistachios, Pistazie], *Mangifer indica* [Mango] or *Anacardium occidentale* [Cashew], Asteraceae such as the genera *Calendula, Carthamus, Centaurea, Cichorium, Cynara, Helianthus, Lactuca, Locusta, Tagetes, Valeriana* e.g. the species *Calendula officinalis* [Marigold], *Carthamus tinctorius* [safflower], *Centaurea cyanus* [corn-flower], *Cichorium intybus* [blue daisy], *Cynara scolymus* [Artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [lettuce], *Tagetes lucida, Tagetes erecta* or *Tagetes tenuifolia* [Marigold]; Apiaceae such as the genera *Daucus* e.g. the species *Daucus carota* [carrot]; Betulaceae such as the genera *Corylus* e.g. the species *Corylus avellana* or *Corylus colurna* [hazelnut]; Boraginaceae such as the genera *Borago* e.g. the species *Borago officinalis* [borage]; Brassicaceae such as the genera *Brassica, Melanosinapis, Sinapis, Arabadopsis* e.g. the species *Brassica napus, Brassica rapa* ssp. [canola, oilseed rape, turnip rape], *Sinapis arvensis Brassica juncea, Brassica juncea* var. *juncea, Brassica juncea* var. *crispifolia, Brassica juncea* var. *foliosa, Brassica nigra, Bras-sica sinapioides, Melanosinapis communis* [mustard], *Brassica oleracea* [fodder beet] or *Arabidopsis thaliana*, Bromeliaceae such as the genera *Anana, Bromelia* e.g. the species *Anana comosus, Ananas ananas* or *Bromela comosa* [pineapple]; Caricaceae such as the genera *Carica* e.g. the species *Carica papaya [papaya]*; Cannabaceae such as the genera *Cannabis* e.g. the species *Cannabis sative* [hemp], Convolvulaceae such as the genera *Ipomea, Convolvulus* e.g. the species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, Man of the Earth, wild potato], Chenopodiaceae such as the genera *Beta*, i.e. the species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugar beet]; Cucurbitaceae such as the genera *Cucubita* e.g. the species *Cucurbita maxima, Cucurbita mixta, Cucurbita pepo* or *Cucurbita mo-schata* [pumpkin, squash]; Elaeagnaceae such as the genera *Elaeagnus* e.g. the species *Olea europaea* [olive]; Ericaceae such as the genera *Kalmia* e.g. the species *Kalmia latifolia, Kalmia angustifolia, Kalmia microphylla, Kalmia polifolia, Kalmia occidentalis, Cistus chamaerhodendros* or *Kalmia lucida* [American laurel, broad-leafed *laurel*, calico bush, spoon wood, sheep *laurel*, alpine *laurel*, bog *laurel*, western bog-*laurel*, swamp-*laurel*]; Euphorbiaceae such as the genera *Manihot, Janipha, Jatropha, Ricinus* e.g. the species *Manihot utilissima, Janipha manihot, Jatropha manihot., Manihot aipil, Manihot dulcis, Manihot manihot, Manihot melanobasis, Manihot esculenta [manihot*, arrowroot, tapioca, *cassava*] or *Ricinus communis* [castor bean, Castor Oil Bush, Castor Oil Plant, Palma Christi, Wonder Tree]; Fabaceae such as the genera *Pisum, Albizia, Cathormion, Feuillea, Inga, Pithecolobium, Acacia, Mimosa, Medicajo, Glycine, Dolichos, Phaseolus, Soja* e.g. the species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [bastard logwood, silk tree, East Indian Walnut], *Medicago sativa, Medicago falcata, Medicago varia* [alfalfa]*Glycine max Dolichos soja, Glycine gracilis, Glycine hispida, Phaseolus max, Soja hispida* or *Soja max* [soy-bean]; Geraniaceae such as the genera *Pelargonium, Cocos, Oleum* e.g. the species *Cocos nucifera, Pelargonium grossularioides* or *Oleum cocois* [coconut]; Gramineae such as the genera *Saccharum* e.g. the species *Saccharum officinarum*, Juglandaceae such as the genera *Juglans, Wallia* e.g. the species *Juglans regia, Juglans ailanthifolia, Juglans sie-boldiana, Juglans cinerea, Wallia cinerea, Juglans bixbyi, Juglans californica, Juglans hindsi, Juglans intermedia, Juglans jamaicensis, Juglans major, Juglans microcarpa, Juglans nigra* or *Wallia nigra* [walnut, black walnut, common walnut, persian walnut, white walnut, butternut, black walnut]; Lauraceae such as the genera *Persea, Laurus* e.g. the species *laurel Laurus nobilis* [bay, laurel, bay *laurel*, sweet bay], *Persea americana, Persea gratissima* or *Persea persea* [avocado]; Leguminosae such as the genera *Arachis* e.g. the species *Arachis hypogaea* [peanut]; Linaceae such as the genera *Linum, Adenolinum* e.g. the species *Linum usitatissimum, Linum humile, Linum austriacum, Linum bienne, Linum angustifolium, Linum catharticum, Linum flavum, Linum grandiflorum, Adenolinum grandiflorum, Linum lewisil, Linum narbonense, Linum perenne, Linum perenne* var. *lewisil, Linum pratense* or *Linum trigynum* [flax, linseed]; Lythrarieae such as the genera *Punica* e.g. the species *Punica granatum* [pomegranate]; Malvaceae such as the genera *Gossypium* e.g. the species *Gossypium hirsutum, Gossypium arboreum, Gossypium barbadense, Gossypium herbaceum* or *Gossypium thurberi* [cotton]; Musaceae such as the genera *Musa* e.g. the species *Musa nana, Musa acuminata, Musa paradisiaca, Musa* spp. [banana]; Onagraceae such as the genera *Camissonia, Oenothera* e.g. the species *Oeno-thera biennis* or *Camissonia brevipes* [primrose, evening primrose]; Palmae such as the genera *Elacis* e.g. the species *Elaeis guineensis* [oil plam]; Papaveraceae such as the genera *Papaver* e.g. the species *Papaver orientale, Papaver rhoeas, Papaver dubium* [poppy, oriental poppy, corn poppy, field poppy, shirley poppies, field poppy, long-headed poppy, long-pod poppy]; Pedaliaceae such as the genera *Sesamum* e.g. the species *Sesamum indicum* [sesame]; Piperaceae such as the genera *Piper, Artanthe, Peperomia, Steffensia* e.g. the species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata*. [Cayenne pepper, wild pepper]; Poaceae such as the genera *Hordeum, Secale, Avena, Sorghum, Andropogon, Holcus, Panicum, Oryza, Zea, Triticum* e.g. the species *Hordeum vulgare, Hordeum jubatum, Hordeum murinum, Hordeum secalinum, Hordeum distichon Hordeum aegiceras, Hordeum hexastichon., Hordeum hexastichum, Hordeum irregulare, Hordeum sativum, Hordeum secalinum* [barley, pearl barley, foxtail barley, wall barley, meadow barley], *Secale cereale* [rye], *Avena sativa, Avena fatua, Avena byzantina, Avena fatua* var. *sativa, Avena hybrida* [oat], *Sorghum bicolor, Sorghum halepense, Sorghum saccharatum, Sorghum vulgare, Andropogon drummondi, Holcus bicolor, Holcus sorghum, Sorghum aethiopicum, Sorghum arundinaceum, Sorghum caffrorum, Sorghum cernuum, Sorghum dochna, Sorghum drummondi, Sorghum durra, Sorghum guineense, Sorghum lanceola-tum, Sorghum nervosum, Sorghum saccharatum, Sorghum subglabrescens, Sorghum ver-ticilliflorum, Sorghum vulgare, Holcus halepensis, Sorghum miliaceum millet, Panicum miliaceum [Sorghum, millet], Oryza sativa, Oryza latifolia* [rice], *Zea mays* [corn, maize]*Triticum aestivum, Triticum durum, Triticum turgidum, Triticum hybernum, Triticum macha, Triti-cum sativum* or *Triticum vulgare* [wheat, bread wheat, common wheat], Proteaceae such as the genera *Macadamia* e.g. the species *Macadamia intergrifolia* [macadamia]; Rubiaceae such as the genera *Coffea* e.g. the species *Cofea* spp., *Coffea arabica, Coffea canephora* or *Coffea liberica* [coffee]; Scrophulariaceae such as the genera *Verbascum* e.g. the species *Verbascum blattaria, Verbascum chaixil, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein, white moth mullein, nettle-leaved mullein, dense-flowered mullein, silver mullein, long-leaved mullein, white mullein, dark mullein, greek mullein, orange mullein, purple mullein, hoary mullein, great mullein]; Solanaceae such as the genera *Capsicum, Nicotiana, Solanum, Lycopersicon* e.g. the species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffi, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [egg-plant], *Lycopersicon esculentum, Lycopersicon lycopersicum., Lycopersicon pyriforme, Solanum integrifolium* or *Solanum lycopersicum* [tomato]; Sterculiaceae such as the genera *Theobroma* e.g. the species *Theobroma cacao* [cacao]; Theaceae such as the genera *Camellia* e.g. the species *Camellia sinensis* [tea].

In one embodiment, the cultivated plant is selected from the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Annona* spp., *Apium graveolens, Arachis* spp, *Artocarpus* spp., *Asparagus officinalis, Avena* spp., *Averrhoa carambola, Bambusa* sp., *Benincasa hispida, Bertholletia excelsea, Beta vulgaris, Brassica* spp. *Cadaba farinosa, Canna indica, Capsicum* spp., *Carex elata, Carissa macrocarpa, Carya* spp., *Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis oleifera*), *Eleusine coracana, Eragrostis tef Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Hemerocallis fulva, Hibiscus* spp., *Hordeum* spp., *Lathyrus* spp., *Lens culinaris, Litchi chinensis, Lotus* spp., *Luffa acutangula, Lupinus* spp., *Luzula sylvatica, Lycopersicon* spp. *Macrotyloma* spp., *Malus* spp., *Malpighia emarginata, Mammea americana, Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp, *Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pisum* spp., *Poa* spp., *Populus* spp., *Prosopis* spp., *Prunus* spp., *Psidium* spp., *Pyrus communis, Quercus* spp., *Raphanus sativus, Rheum rhabarbarum, Ribes* spp., *Rubus* spp., *Saccharum* spp., *Salix* sp., *Sambucus* spp., *Secale cereale, Sesamum* spp., *Sinapis* sp., *Solanum* spp., *Spinacia* spp., *Syzygium* spp., *Tagetes* spp., *Tamarindus indica, Theobroma cacao, Trifolium* spp., *Tripsacum dactyloldes, Triticosecale rimpaui, Triticum* spp. (e.g. *Triticum monococcum*), *Tropaeolum minus, Tropaeolum majus, Vaccinium* spp., *Vicia* spp., *Vigna* spp., *Viola odorata, Vitis* spp., *Zizania palustris, Ziziphus* spp., amongst others.

The cultivated plants are plants, which comprise at least one trait. The term "trait" refers to a property, which is present in the plant either by genetic engineering or by conventional breeding techniques. Each trait has to be assessed in relation to its respective control. Examples of traits are:

herbicide tolerance,
insect resistance by expression of bacterial toxins,
fungal resistance or viral resistance or bacterial resistance,
antibiotic resistance,
stress tolerance,
maturation alteration,
content modification of chemicals present in the cultivated plant, preferably increasing the content of fine chemicals advantageous for applications in the field of the food and/or feed industry, the cosmetics industry and/or the pharmaceutical industry,
modified nutrient uptake, preferably an increased nutrient use efficiency and/or resistance to conditions of nutrient deficiency,
improved fiber quality,
plant vigor,
modified colour,
fertility restoration, and male sterility.

Principally, cultivated plants may also comprise combinations of the aforementioned traits, e.g. they may be tolerant to the action of herbicides and express bacertial toxins.

Principally, all cultivated plants may also provide combinations of the aforementioned properties, e.g. they may be tolerant to the action of herbicides and express bacertial toxins.

In the detailed description below, the term "plant" refers to a cultivated plant.

Tolerance to herbicides can be obtained by creating insensitivity at the site of action of the herbicide by expression of a target enzyme which is resistant to herbicide; rapid metabolism (conjugation or degradation) of the herbicide by expression of enzymes which inactivate herbicide; or poor uptake and translocation of the herbicide. Examples are the expression of enzymes which are tolerant to the herbicide in comparison to wild type enzymes, such as the expression of 5-enolpyruvylshikimate-3-phosphate synthase (EPSPS), which is tolerant to glyphosate (see e.g. Heck et. al, Crop Sci. 45, 2005, 329-339; Funke et. al, PNAS 103, 2006, 13010-13015; U.S. Pat. Nos. 5,188,642, 4,940,835, 5,633, 435, 5,804,425, 5,627,061), the expression of glutamine synthase which is tolerant to glufosinate and bialaphos (see e.g. U.S. Pat. Nos. 5,646,024, 5,561,236) and DNA constructs coding for dicamba-degrading enzymes (see e.g. U.S. Pat. No. 7,105,724). Gene constructs can be obtained, for example, from micro-organism or plants, which are tolerant to said herbicides, such as the *Agrobacterium* strain CP4 EPSPS which is resistant to glyphosate; *Streptomyces* bacteria which are resistance to glufosinate; *Arabidopsis, Daucus carota, Pseudomonoas* spp. or *Zea mais* with chimeric gene sequences coding for HDDP (see e.g. WO 1996/38567, WO 2004/55191); *Arabidopsis thaliana* which is resistant to protox inhibitors (see e.g. US 2002/0073443).

Preferably, the herbicide tolerant plant can be selected from cereals such as wheat, barley, rye, oat; canola, *sorghum*, soybean, rice, oil seed rape, sugar beet, sugarcane, grapes, lentils, sunflowers, alfalfa, pome fruits; stone fruits; peanuts; coffee; tea; strawberries; turf; vegetables, such as tomatoes, potatoes, cucurbits and lettuce, more preferably, the plant is selected from soybean, maize (corn), rice, cotton, oilseed rape in particular canola, tomatoes, potatoes, sugarcane, vine, apple, pear, citron, orange and cereals such as wheat, barley, rye and oat.

In one embodiment, the plant is soybean.

In one embodiment, the invention relates to a method for controlling pests and/or increasing the plant health of a cultivated plant with at least one modification as compared to the respective non-modified control plant, wherein the plant is soybean, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

Examples of commercial available transgenic plants with tolerance to herbicides, are the corn varieties "Roundup Ready Corn", "Roundup Ready 2" (Monsanto), "Agrisure GT", "Agrisure GT/CB/LL", "Agrisure GT/RW", "Agrisure 3000GT" (Syngenta), "YieldGard VT Rootworm/RR2" and "YieldGard VT Triple" (Monsanto) with tolerance to glyphosate; the corn varieties "Liberty Link" (Bayer), "Herculex I", "Herculex RW", "Herculex Xtra" (Dow, Pioneer), "Agrisure GT/CB/LL" and "Agrisure CB/LL/RW" (Syngenta) with tolerance to glufosinate; the soybean varieties "Roundup Ready Soybean" (Monsanto) and "Optimum GAT" (DuPont, Pioneer) with tolerance to glyphosate; the cotton varieties "Roundup Ready Cotton" and "Roundup Ready Flex" (Monsanto) with tolerance to glyphosate; the cotton variety "FiberMax Liberty Link" (Bayer) with tolerance to glufosinate; the cotton variety "BXN" (Calgene) with tolerance to bromoxynil; the canola varieties "Navigator" und "Compass" (Rhone-Poulenc) with bromoxynil tolerance; the canola varierty "Roundup Ready Canola" (Monsanto) with glyphosate tolerance; the canola variety "InVigor" (Bayer) with glufosinate tolerance; the rice variety "Liberty Link Rice" (Bayer) with glulfosinate tolerance and the alfalfa variety "Roundup Ready Alfalfa" with glyphosate tolerance. Further transgenic plants with herbicide tolerance are commonly known, for instance alfalfa, apple, *eucalyptus*, flax, grape, lentils, oil seed rape, peas, potato, rice, sugar beet, sunflower, tobacco, tomatom turf grass and wheat with tolerance to glyphosate (see e.g. U.S. Pat. Nos. 5,188,642, 4,940,835, 5,633,435, 5,804,425, 5,627,061); beans, soybean, cotton, peas, potato, sunflower, tomato, tobacco, corn, *sorghum* and sugarcane with tolerance to dicamba (see e.g. U.S. Pat. Nos. 7,105,724 and 5,670,454); pepper, apple, tomato, millet, sunflower, tobacco, potato, corn, cucumber, wheat and *sorghum* with tolerance to 2,4-D (see e.g. U.S. Pat. Nos. 6,153,401, 6,100,446, WO 2005107437, U.S. Pat. Nos. 5,608,147 and 5,670,454); sugarbeet, potato, tomato and tobacco with tolerance to glufosinate (see e.g. U.S. Pat. Nos. 5,646,024, 5,561,236); canola, barley, cotton, lettuce, melon, millet, oats, potato, rice, rye, *sorghum*, soybean, sugarbeet, sunflower, tobacco, tomato and wheat with tolerance to acetolactate synthase (ALS) inhibiting herbicides, such as triazolopyrimidine sulfonamides, sulfonylureas and imidazolinones (see e.g. U.S. Pat. No. 5,013,659, WO 2006060634, U.S. Pat. Nos. 4,761, 373, 5,304,732, 6,211,438, 6,211,439 and 6,222,100); cereals, sugar cane, rice, corn, tobacco, soybean, cotton, rapeseed, sugar beet and potato with tolerance to HPPD inhibitor herbicides (see e.g. WO 2004/055191, WO 199638567, WO 1997049816 and U.S. Pat. No. 6,791,014); wheat, soybean, cotton, sugar beet, rape, rice, *sorghum* and sugar cane with tolerance to protoporphyrinogen oxidase (PPO) inhibitor herbicides (see e.g. US 2002/0073443, US 20080052798, Pest Management Science, 61, 2005, 277-285). The methods of producing such transgenic plants are generally known to the person skilled in the art and are described, for example, in the publications mentioned above.

Plants, which are capable of synthesising one or more selectively acting bacterial toxins, comprise for example at least one toxin from toxin-producing bacteria, especially those of the genus *Bacillus*, in particular plants capable of synthesising one or more insecticidal proteins from *Bacillus cereus* or *Bacillus popliae*; or insecticidal proteins from *Bacillus thuringiensis*, such as delta.-endotoxins, e.g. CryIA (b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In one embodiment a plant is capable of producing a toxin, lectin or inhibitor if it contains at least one cell comprising a nucleic acid sequence encoding said toxin, lectin, inhibitor or inhibitor producing enzyme, and said nucleic acid sequence is transcribed and translated and if appropriate the resulting protein processed and/or secreted in a constitutive manner or subject to developmental, inducible or tissue-specific regulation.

In the context of the present invention there are to be understood delta.-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 2003/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 2003/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 1990/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Preferably, the plant capable of expression of bacterial toxins is selected from cereals such as wheat, barley, rye, oat; canola, cotton, eggplant, lettuce, *sorghum*, soybean, rice, oil seed rape, sugar beet, sugarcane, grapes, lentils, sunflowers, alfalfa, pome fruits; stone fruits; peanuts; coffee; tea; strawberries; turf; vegetables, such as tomatoes, potatoes, cucurbits and lettuce, more preferably, the plant is selected from cotton, soybean, maize (corn), rice, tomatoes, potatoes, oilseed rape and cereals such as wheat, barley, rye and oat, most preferably from cotton, soybean, maize, vine, apple, pear, citron, orange and cereals such as wheat, barley, rye and oat.

Examples of commercial available transgenic plants capable of expression of bacterial toxins are the corn varieties "YieldGard corn rootworm" (Monsanto), "YieldGard VT" (Monsanto), "Herculex RW" (Dow, Pioneer), "Herculex Rootworm" (Dow, Pioneer) and "Agrisure CRW" (Syngenta) with resistance against corn rootworm; the corn varieties "YieldGard corn borer" (Monsanto), "YieldGard VT Pro" (Monsanto), "Agrisure CB/LL" (Syngenta), "Agrisure 3000GT" (Syngenta), "Hercules I", "Hercules II" (Dow, Pioneer), "KnockOut" (Novartis), "NatureGard" (Mycogen) and "StarLink" (Aventis) with resistance against corn borer, the corn varieties "Herculex I" (Dow, Pioneer) and "Herculex Xtra" (Dow, Pioneer) with resistance against western bean cutworm, corn borer, black cutworm and fall armyworm; the corn variety "YieldGard Plus" (Monsanto) with resistance against corn borer and corn rootworm; the cotton variety "Bollgard I"" (Monsanto) with resistance against tobacco budworm; the cotton varieties "Bollgard II" (Monsanto), "WideStrike" (Dow) and "VipCot" (Syngenta) with resistance against tobacco budworm, cotton bollworm, fall armyworm, beet armyworm, cabbage looper, soybean lopper and pink bollworm; the potato varieties "NewLeaf", "NewLeaf Y" and "NewLeaf Plus" (Monsanto) with tobacco hornworm resistance and the eggplant varieties "Bt brinjal", "Dumaguete Long Purple", "Mara" with resistance against brinjal fruit and shoot borer, bruit borer and cotton bollworm (see e.g. U.S. Pat. No. 5,128,130). Further transgenic plants with insect resistance are commonly known, such as yellow stemborer resistant rice (see e.g. Molecular Breeding, Volume 18, 2006, Number 1), lepidopteran resistant lettuce (see e.g. U.S. Pat. No. 5,349,124), resistant soybean (see e.g. U.S. Pat. No. 7,432,421) and rice with resistance against Lepidopterans, such as rice stemborer, rice skipper, rice cutworm, rice caseworm, rice leaffolder and rice armyworm (see e.g. WO 2001021821). The methods of producing such transgenic plants are generally known to the person skilled in the art and are described, for example, in the publications mentioned above.

Preferably, plants, which are capable of synthesising antipathogenic substances are selected from soybean, maize (corn), rice, tomatoes, potato, banana, *papaya*, tobacco, grape, plum and cereals such as wheat, barley, rye and oat, most preferably from soybean, maize (corn), rice, cotton, tomatoes, potato, banana, *papaya*, oil seed rape, vine, apple, pear, citron, orange and cereals such as wheat, barley, rye and oat.

Plants, which are capable of synthesising antipathogenic substances having a selective action are for example plants expressing the so-called "pathogenesis-related proteins" (PRPs, see e.g. EP-A-0 392 225) or so-called "antifungal proteins" (AFPs, see e.g. U.S. Pat. No. 6,864,068). A wide range of antifungal proteins with activity against plant pathogenic fungi have been isolated from certain plant species and are common knowledge. Examples of such antipathogenic substances and transgenic plants capable of synthesising such antipathogenic substances are known, for example, from EP-A-0 392 225, WO 93/05153, WO 95/33818, and EP-A-0 353 191. Transgenic plants which are resistant against fungal, viral and bacterial pathogens are produced by introducing plant resistance genes. Numerous resistant genes have been identified, isolated and were used to improve plant resistant, such as the N gene which was introduced into tobacco lines that are susceptible to Tobacco Mosaic Virus (TMV) in order to produce TMV-resistant tobacco plants (see e.g. U.S. Pat. No. 5,571,706), the Prf gene, which was introduced into plants to obtain enhanced pathogen resistance (see e.g. WO 199802545) and the Rps2 gene from *Arabidopsis thaliana*, which was used to create resistance to bacterial pathogens including *Pseudomonas syringae* (see e.g. WO 199528423). Plants exhibiting systemic acquired resistance response were obtained by introducing a nucleic acid molecule encoding the TIR domain of the N gene (see e.g. U.S. Pat. No. 6,630,618). Further examples of known resistance genes are the Xa21 gene, which has been introduced into a number of rice cultivars (see e.g. U.S. Pat. Nos. 5,952,485, 5,977,434, WO 1999/

09151, WO 1996/22375), the Rcg1 gene for colletotrichum resistance (see e.g. US 2006/225152), the prp1 gene (see e.g. U.S. Pat. No. 5,859,332, WO 2008/017706), the ppv-cp gene to introduce resistance against plum pox virus (see e.g. US PP15,154Ps), the P1 gene (see e.g. U.S. Pat. No. 5,968,828), genes such as Blb1, Blb2, Blb3 and RB2 to introduce resistance against *Phytophthora infestans* in potato (see e.g. U.S. Pat. No. 7,148,397), the LRPKml gene (see e.g. WO1999064600), the P1 gene for potato virus Y resistance (see e.g. U.S. Pat. No. 5,968,828), the HA5-1 gene (see e.g. U.S. Pat. Nos. 5,877,403 and 6,046,384), the PIP gene to introduce a broad resistant to viruses, such as potato virus X (PVX), potato virus Y (PVY), potato leafroll virus (PLRV) (see e.g. EP 0707069) and genes such as *Arabidopsis* N116, ScaM4 and ScaM5 genes to obtain fungal resistance (see e.g. U.S. Pat. No. 6,706,952 and EP 1018553). The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins'" (PRPs; see e.g. EP-A-0 392 225); antipathogenic substances produced by microorganisms, for example peptide antibiotics or heterocyclic antibiotics (see e.g. WO 1995/33818) or protein or polypeptide factors involved in plant pathogen defense (so-called "plant disease resistance genes", as described in WO 2003/000906).

Antipathogenic substances produced by the plants are able to protect the plants against a variety of pathogens, such as fungi, viruses and bacteria. Useful plants of elevated interest in connection with present invention are cereals, such as wheat, barley, rye and oat; soybean; maize; rice; alfalfa, cotton, sugar beet, sugarcane, tobacco, potato, banana, oil seed rape; pome fruits; stone fruits; peanuts; coffee; tea; strawberries; turf; vines and vegetables, such as tomatoes, potatoes, cucurbits, *papaya*, melon, lenses and lettuce, more preferably selected from soybean, maize (corn), alfalfa, cotton, potato, banana, *papaya*, rice, tomatoes and cereals such as wheat, barley, rye and oat, most preferably from soybean, maize (corn), rice, cotton, potato, tomato, oilseed rape, vine, apple, pear, citron, orange and cereals such as wheat, barley, rye and oat.

Transgenic plants with resistance against fungal pathogens, are, for examples, soybeans with resistance against Asian soybean rust (see e.g. WO 2008/017706); plants such as alfalfa, corn, cotton, sugar beet, oileed, rape, tomato, soybean, wheat, potato and tobacco with resistance against *Phytophtora infestans* (see e.g. U.S. Pat. Nos. 5,859,332, 7,148,397, EP 1334979); corn with resistance against leaf blights, ear rots and stalk rots (such as anthracnose leaf bligh, anthracnose stalk rot, *diplodia* ear rot, *Fusarium verticilioides, Gibberella zeae* and top dieback, see e.g. US 2006/225152); apples with resistance against apple scab (*Venturia inaequalis*, see e.g. WO 1999064600); plants such as rice, wheat, barley, rye, corn, oats, potato, melon, soybean and *sorghum* with resistance against *fusarium* diseases, such as *Fusarium graminearum, Fusarium sporotrichioides, Fusarium lateritium, Fusarium pseudograminearum Fusarium sambucinum, Fusarium culmorum, Fusarium poae, Fusarium acuminatum, Fusarium equiseti* (see e.g. U.S. Pat. No. 6,646,184, EP 1477557); plants, such as corn, soybean, cereals (in particular wheat, rye, barley, oats, rye, rice), tobacco, *sorghum*, sugarcane and potatoes with broad fungal resistance (see e.g. U.S. Pat. Nos. 5,689,046, 6,706, 952, EP 1018553 and U.S. Pat. No. 6,020,129).

Transgenic plants with resistance against bacterial pathogens and which are covered by the present invention, are, for examples, rice with resistance against *Xylella fastidiosa* (see e.g. U.S. Pat. No. 6,232,528); plants, such as rice, cotton, soybean, potato, *sorghum*, corn, wheat, balrey, sugarcane, tomato and pepper, with resistance against bacterial blight (see e.g. WO 2006/42145, U.S. Pat. Nos. 5,952,485, 5,977, 434, WO 1999/09151, WO 1996/22375); tomato with resistance against *Pseudomonas syringae* (see e.g. Can. J. Plant Path., 1983, 5: 251-255).

Transgenic plants with resistance against viral pathogens, are, for examples, stone fruits, such as plum, almond, apricot, cherry, peach, nectarine, with resistance against plum pox virus (PPV, see e.g. US PP15,154Ps, EP 0626449); potatoes with resistance against potato virus Y (see e.g. U.S. Pat. No. 5,968,828); plants such as potato, tomato, cucumber and leguminosaes which are resistant against tomato spotted wilt virus (TSWV, see e.g. EP 0626449, U.S. Pat. No. 5,973,135); corn with resistance against maize streak virus (see e.g. U.S. Pat. No. 6,040,496); *papaya* with resistance against *papaya* ring spot virus (PRSV, see e.g. U.S. Pat. Nos. 5,877,403, 6,046,384); cucurbitaceae, such as cucumber, melon, watermelon and pumpkin, and solanaceae, such as potato, tobacco, tomato, eggplant, paprika and pepper, with resistance against cucumber mosaic virus (CMV, see e.g. U.S. Pat. No. 6,849,780); cucurbitaceae, such as cucumber, melon, watermelon and pumpkin, with resistance against watermelon mosaic virus and zucchini yellow mosaic virus (see e.g. U.S. Pat. No. 6,015,942); potatoes with resistance against potato leafroll virus (PLRV, see e.g. U.S. Pat. No. 5,576,202); potatoes with a broad resistance to viruses, such as potato virus X (PVX), potato virus Y (PVY), potato leafroll virus (PLRV) (see e.g. EP 0707069).

Further examples of deregulated orcommercially available transgenic plants with modified genetic material capable of expression of antipathogenic substances are the following plants: *Carica papaya* (*papaya*), Event: 55-1/63-1; Cornell University, *Carica papaya* (*Papaya*); Event: (X17-2); University of Florida, *Cucurbita pepo* (Squash); Event: (CZW-3); Asgrow (USA); Seminis Vegetable Inc. (Canada), *Cucurbita pepo* (Squash); Event: (ZW20); Upjohn (USA); Seminis Vegetable Inc. (Canada), *Prunus domestica* (Plum); Event: (C5); United States Department of Agriculture—Agricultural Research Service, *Solanum tuberosum* L. (Potato); Event: (RBMT15-101, SEMT15-02, SEMT15-15); Monsanto Company and *Solanum tuberosum* L. (Potato); Event: (RBMT21-129, RBMT21-350, RBMT22-082); Monsanto Company.

Transgenic plants with resistance against nematodes and which may be used in the methods of the present invention are, for examples, soybean plants with resistance to soybean cyst nematodes.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode.

Also known in the art are transgenic plants with reduced feeding structures for parasitic nematodes, e.g. plants resistant to herbicides except of those parts or those cells that are nematode feeding sites and treating such plant with a herbicide to prevent, reduce or limit nematode feeding by damaging or destroying feeding sites (e.g. U.S. Pat. No. 5,866,777).

Use of RNAi to target essential nematode genes has been proposed, for example, in PCT Publication WO 2001/96584, WO 2001/17654, US 2004/0098761, US 2005/0091713, US 2005/0188438, US 2006/0037101, US 2006/0080749, US 2007/0199100, and US 2007/0250947.

Transgenic nematode resistant plants have been disclosed, for example in the PCT publications WO 2008/095886 and WO 2008/095889.

Plants which are resistant to antibiotics, such as kanamycin, neomycin and ampicillin. The naturally occurring bacterial nptII gene expresses the enzyme that blocks the effects of the antibiotics kanamycin and neomycin. The ampicillin resistance gene ampR (also known as blaTEM1) is derived from the bacterium *Salmonella paratyphi* and is used as a marker gene in the transformation of micro-organisms and plants. It is responsible for the synthesis of the enzyme beta-lactamase, which neutralises antibiotics in the penicillin group, including ampicillin. Transgenic plants with resistance against antibiotics, are, for examples potato, tomato, flax, canola, oilseed rape and corn (see e.g. Plant Cell Reports, 20, 2001, 610-615. Trends in Plant Science, 11, 2006, 317-319. Plant Molecular Biology, 37, 1998, 287-296. Mol Gen Genet., 257, 1998, 606-13.). Plant Cell Reports, 6, 1987, 333-336. Federal Register (USA), Vol. 60, No. 113, 1995, page 31139. Federal Register (USA), Vol. 67, No. 226, 2002, page 70392. Federal Register (USA), Vol. 63, No. 88, 1998, page 25194. Federal Register (USA), Vol. 60, No. 141, 1995, page 37870. Canadian Food Inspection Agency, FD/OFB-095-264-A, October 1999, FD/OFB-099-127-A, October 1999. Preferably, the plant is selected from soybean, maize (corn), rice, cotton, oilseed rape, potato, sugarcane, alfalfa, tomatoes and cereals, such as wheat, barley, rye and oat, most preferably from soybean, maize (corn), rice, cotton, oilseed rape, tomato, potato, vine, apple, pear, citron, orange and cereals such as wheat, barley, rye and oat.

Plants which are tolerant to stress conditions (see e.g. WO 2000/04173, WO 2007/131699, CA 2521729 and US 2008/0229448) are plants, which show increased tolerance to abiotic stress conditions such as drought, high salinity, high light intensities, high UV irradiation, chemical pollution (such as high heavy metal concentration), low or high temperatures, limited supply of nutrients (i.e. nitrogen, phosphorous) and population stress. Preferably, transgenic plants with resistance to stress conditions, are selected from rice, corn, soybean, sugarcane, alfalfa, wheat, tomato, potato, barley, rapeseed, beans, oats, *sorghum* and cotton with tolerance to drought (see e.g. WO 2005/048693, WO 2008/002480 and WO 2007/030001); corn, soybean, wheat, cotton, rice, rapeseed and alfalfa with tolerance to low temperatures (see e.g. U.S. Pat. No. 4,731,499 and WO 2007/112122); rice, cotton, potato, soybean, wheat, barley, rye, *sorghum*, alfalfa, grape, tomato, sunflower and tobacco with tolerance to high salinity (see e.g. U.S. Pat. Nos. 7,256,326, 7,034,139, WO 2001/030990). The methods of producing such transgenic plants are generally known to the person skilled in the art and are described, for example, in the publications mentioned above. Preferably, the plant is selected from soybean, maize (corn), rice, cotton, sugarcane, alfalfa, sugar beet, potato, oilseed rape, tomatoes and cereals such as wheat, barley, rye and oat, most preferably from soybean, maize (corn), rice, cotton, oilseed rape, tomato, potato, sugarcane, vine, apple, pear, citron, orange and cereals such as wheat, barley, rye and oat.

Altered maturation properties, are for example delayed ripening, delayed softening and early maturity. Preferably, transgenic plants with modified maturation properties, are, selected from tomato, melon, raspberry, strawberry, muskmelon, pepper and *papaya* with delayed ripening (see e.g. U.S. Pat. Nos. 5,767,376, 7,084,321, 6,107,548, 5,981,831, WO 1995035387, U.S. Pat. Nos. 5,952,546, 5,512,466, WO 1997001952, WO 1992/008798, Plant Cell. 1989, 53-63. Plant Molecular Biology, 50, 2002). The methods of producing such transgenic plants are generally known to the person skilled in the art and are described, for example, in the publications mentioned above. Preferably, the plant is selected from fruits, such as tomato, vine, melon, *papaya*, banana, pepper, raspberry and strawberry; stone fruits, such as cherry, apricot and peach; pome fruits, such as apple and pear; and citrus fruits, such as citron, lime, orange, pomelo, grapefruit, and mandarin, more preferably from tomato, vine, apple, banana, orange and strawberry, most preferably tomatoes.

Content modification is synthesis of modified chemical compounds (if compared to the corresponding control plant) or synthesis of enhanced amounts of chemical (if compounds compared to the corresponding control plant) and corresponds to an increased or reduced amount of vitamins, amino acids, proteins and starch, different oils and a reduced amount of nicotine.

Commercial examples are the soybean varieties "Vistive II" and "Visitive III" with low-linolenic/medium oleic content; the corn variety "Mavera high-value corn" with increased lysine content; and the soybean variety "Mavera high value soybean" with yielding 5% more protein compared to conventional varieties when processed into soybean meal. Further transgenic plants with altered content are, for example, potato and corn with modified amylopectin content (see e.g. U.S. Pat. No. 6,784,338, US 20070261136); canola, corn, cotton, grape, *catalpa*, cattail, rice, soybean, wheat, sunflower, balsam pear and vernonia with a modified oil content (see e.g. U.S. Pat. Nos. 7,294,759, 7,157,621, 5,850,026, 6,441,278, 6,380,462, 6,365,802, 6,974,898, WO 2001/079499, US 2006/0075515 and U.S. Pat. No. 7,294,759); sunflower with increased fatty acid content (see e.g. U.S. Pat. No. 6,084,164); soybeans with modified allergens content (so called "hypoallergenic soybean, see e.g. U.S. Pat. No. 6,864,362); tobacco with reduced nicotine content (see e.g. US 20060185684, WO 2005000352 and WO 2007064636); canola and soybean with increased lysine content (see e.g. Bio/Technology 13, 1995, 577-582); corn and soybean with altered composition of methionine, leucine, isoleucine and valine (see e.g. U.S. Pat. Nos. 6,946, 589, 6,905,877); soybean with enhanced sulfur amino acid content (see e.g. EP 0929685, WO 1997041239); tomato with increased free amino acid contents, such as asparagine, aspartic acid, serine, threonine, alanine, histidine and glutamic acid (see e.g. U.S. Pat. No. 6,727,411); corn with enhanced amino acid content (see e.g. WO 05077117); potato, corn and rice with modified starch content (see e.g. WO 1997044471 and U.S. Pat. No. 7,317,146); tomato, corn, grape, alfalfa, apple, beans and peas with modified flavonoid content (see e.g. WO 2000/04175); corn, rice, *sorghum*, cotton, soybeans with altered content of phenolic compounds (see e.g. US 20080235829). The methods of producing such transgenic plants are generally known to the person skilled in the art and are described, for example, in the publications mentioned above. Preferably, the plant is selected from soybean, maize (corn), rice, cotton, sugarcane, potato, tomato, oilseed rape, flax and cereals such as wheat, barley, rye and oat, most preferably soybean, maize (corn), rice, oilseed rape, potato, tomato, cotton, vine, apple, pear, citron, orange and cereals such as wheat, barley, rye and oat.

Enhanced nutrient utilization is e.g. assimilation or metabolism of nitrogen or phosphorous. Preferably, transgenic plants with enhanced nitrogen assimilatory and utilization capacities are selected from for example, canola, corn, wheat, sunflower, rice, tobacco, soybean, cotton, alfalfa, tomato, wheat, potato, sugar beet, sugar cane and rapeseed (see e.g. WO 1995/009911, WO 1997/030163, U.S. Pat. Nos. 6,084,153, 5,955,651 and 6,864,405). Plants with improved phosphorous uptake are, for example, tomato and potato (see e.g. U.S. Pat. No. 7,417,181). The methods of producing such transgenic plants are generally known to the person skilled in the art and are described, for example, in the publications mentioned above. Preferably, the plant is selected from soybean, maize (corn), rice, cotton, sugarcane, alfalfa, potato, oilseed rape and cereals such as wheat, barley, rye and oat, most preferably from soybean, maize (corn), rice, cotton, oilseed rape, tomato, potato, vine, apple, pear, citron, orange and cereals such as wheat, barley.

Transgenic plants with male sterility are preferably selected from canola, corn, tomato, rice, Indian mustard, wheat, soybean and sunflower (see e.g. U.S. Pat. Nos. 6,720,481, 6,281,348, 5,659,124, 6,399,856, 7,345,222, 7,230,168, 6,072,102, EP1 135982, WO 2001/092544 and WO 1996/040949). The methods of producing such transgenic plants are generally known to the person skilled in the art and are described, for example, in the publications mentioned above. Preferably, the plant is selected from soybean, maize (corn), rice, cotton, oilseed rape, tomato, potato, vine, apple, pear, citron, orange and cereals such as wheat, barley.

Further examples of deregulated or commercially available transgenic plants with modified genetic material being male sterile are

*Brassica napus* (Argentine Canola: (Event: MS1, RF1=>PGS1; Bayer CropScience (formerly Plant Genetic Systems); *Brassica napus* (Event: MS1, RF2=>PGS2; Bayer CropScience (formerly Plant Genetic Systems); *Brassica napus* (Event: MS8xRF3; Bayer CropScience (Aventis CropScience(AgrEvo)); *Brassica napus* (Event: PHY14, PHY35; Bayer CropScience (formerly Plant Genetic Systems); *Brassica napus* (Event: PHY36; Bayer CropScience (formerly Plant Genetic Systems); *Cichorium intybus* (Chicory: (Event: RM3-3, RM3-4, RM3-6; Bejo Zaden BV; *Zea mays* L. (Maize: (Event: 676, 678, 680; Pioneer Hi-Bred International Inc.; *Zea mays* L. (Event: MS3; Bayer CropScience (Aventis CropScience(AgrEvo)) and *Zea mays* L. (Event: MS6; Bayer CropScience (Aventis CropScience (AgrEvo)).

Plants, which produce higher quality fiber are e.g. transgenic cotton plants. The such improved quality of the fiber is related to improved micronaire of the fiber, increased strength, improved staple length, improved length uniformity and color of the fibers (see e.g. WO 1996/26639, U.S. Pat. Nos. 7,329,802, 6,472,588 and WO 2001/17333). The methods of producing such transgenic plants are generally known to the person skilled in the art and are described, for example, in the publications mentioned above.

As set forth above, cultivated plants may comprise one or more traits, e.g. selected from the group consisting of herbicide tolerance, insect resistance, fungal resistance, viral resistance, bacterial resistance, stress tolerance, maturation alteration, content modification, modified nutrient uptake and male sterility (see e.g. WO 2005033319 and U.S. Pat. No. 6,376,754).

Examples of commercial available transgenic plants with two combined properties are the corn varieties "YieldGard Roundup Ready" and YieldGard Roundup Ready 2" (Monsanto) with glyphosate tolerance and resistance to corn borer; the corn variety "Agrisure CB/LL" (Syntenta) with glufosinate tolerance and corn borer resistance; the corn variety "Yield Gard VT Rootworm/RR2" with glyphosate tolerance and corn rootworm resistance; the corn variety "Yield Gard VT Triple" with glyphosate tolerance and resistance against corn rootworm and corn borer; the corn variety "Herculex I" with glufosinate tolerance and lepidopteran resistance (Cry1F), i.e. against western bean cutworm, corn borer, black cutworm and fall armyworm; the corn variety "YieldGard Corn Rootworm/Roundup Ready 2" (Monsanto) with glyphosate tolerance and corn rootworm resistance; the corn variety "Agrisure GT/RW" (Syngenta) with gluphosinate tolerance and lepidopteran resistance (Cry3A), i.e. against western corn rootworm, northern corn rootworm and Mexican corn rootworm; the corn variety "Herculex RW" (Dow, Pioneer) with glufosinate tolerance and lepidopteran resistance (Cry34/35Ab1), i.e. against western corn rootworm, northern corn rootworm and Mexican corn rootworm; the corn variety "Yield Gard VT Rootworm/RR2" with glyphosate tolerance and corn rootworm resistance; the soybean variety "Optimum GAT" (DuPont, Pioneer) with glyphosate tolerance and ALS herbicide tolerance; the corn variety "Mavera high-value corn" with glyphosate tolerance, resistance to corn rootworm and European corn borer and high lysine trait.

Examples of commercial available transgenic plants with three traits are the corn variety "Herculex I/Roundup Ready 2" with glyphosate tolerance, gluphosinate tolerance and lepidopteran resistance (Cry1F), i.e. against western bean cutworm, corn borer, black cutworm and fall armyworm; the corn variety "YieldGard Plus/Roundup Ready 2" (Monsanto) with glyphosate tolerance, corn rootworm resistance and corn borer resistance; the corn variety "Agrisure GT/CB/LL" (Syngenta) with tolerance to glyphosate tolerance, tolerance to gluphosinate and corn borer resistance; the corn variety "Herculex Xtra" (Dow, Pioneer) with glufosinate tolerance and lepidopteran resistance (Cry1F+Cry34/35Ab1), i.e. against western corn rootworm, northern corn rootworm, Mexican corn rootworm, western bean cutworm, corn borer, black cutworm and fall armyworm; the corn varieties "Agrisure CB/LL/RW" (Syngenta) with glufosinate tolerance, corn borer resistance (Cry1Ab) and lepidopteran resistance (Cry3A), i.e. against western corn rootworm, northern corn rootworm and Mexican corn rootworm; the corn variety "Agrisure 3000GT" (Syngenta) with glyphosate tolerance+corn borer resistance (Cry1Ab) and lepidopteran resistance (Cry3A), i.e. against western corn rootworm, northern corn rootworm and Mexican corn rootworm. The methods of producing such transgenic plants are generally known to the person skilled in the art.

An example of a commercial available transgenic plant with four traits is "Hercules Quad-Stack" with glyphosate tolerance, glufosinate tolerance, corn borer resistance and corn rootworm resistance.

Preferably, the cultivated plants are plants, which comprise at least one trait selected from herbicide tolerance, insect resistance by expression of bacertial toxins, fungal resistance or viral resistance or bacterial resistance by expression of antipathogenic substances
stress tolerance,
content modification of chemicals present in the cultivated plant compared to the corresponding control plant.

Most preferably, the cultivated plants are plants, which are tolerant to the action of herbicides and plants, which express bacterial toxins, which provides resistance against animal pests (such as insects or arachnids or nematodes), wherein the bacterial toxin is preferably a toxin from *Bacillus thuriginensis*. Herein, the plant is preferably selected from cotton, rice, maize, wheat, barley, rye, oat, soybean, potato, vine, apple, pear, citron and orange.

In an utmost preferred embodiment, the cultivated plants are plants, which are tolerant to the action of herbicides. Further guidance for specific combinations within this utmost preferred embodiment can be found in tables 1, 2, 14 and tables A, B and C.

If such plants are used in the methods according to the present invention, compounds I and their mixtures may additionally comprise a herbicide III, to which the plant is tolerant.

For example, if the cultivated plant is a cultivated plant tolerant to glyphosate, compounds I and their mixtures may additionally comprise glyphosate.

For example, if the cultivated plant is a cultivated plant tolerant to glufonsinate, compounds I and their mixtures may additionally comprise glufonisate.

For example, if the cultivated plant is a cultivated plant tolerant to a imidazolione herbicide, compounds I and their mixtures may additionally comprise at least one imidazolione-herbicide.

Herein, the imidazolionone-herbicide is selected from imazamox, imazethapyr, imazapic, imazapyr, imazamethabenz or imazaquin.

For example, if the cultivated plant is a cultivated plant tolerant to dicamba, compounds I and their mixtures may additionally comprise dicamba.

For example, if the cultivated plant is a cultivated plant tolerant to sethoxidim, compounds I and their mixtures may additionally comprise sethoxidim.

For example, if the cultivated plant is a cultivated plant tolerant to cycloxidim, compounds I and their mixtures may additionally comprise cyloxidim.

Thus, the present invention also relates to ternary mixtures, comprising a compound I, an insecticide II and a herbicide III. In particular, the present invention also relates to ternary mixtures comprising two insecticides and a fungicide.

In another particular embodiment, the present invention also relates to ternary mixtures comprising two fungicides and one insecticide.

In another particular embodiment, the present invention also relates to ternary mixtures comprising an insecticide, a fungicides and a herbicide.

In one embodiment of the invention the cultivated plant is selected from the group of plants as mentioned in the paragraphs and tables of this disclosure, preferably as mentioned above.

Preferably, the cultivated plants are plants, which comprise at least one trait selected from herbicide tolerance, insect resistance for example by expression of one or more bacterial toxins, fungal resistance or viral resistance or bacterial resistance by expression of one or more antipathogenic substances, stress tolerance, nutrient uptake, nutrient use efficiency, content modification of chemicals present in the cultivated plant compared to the corresponding control plant.

More preferably, the cultivated plants are plants, which comprise at least one trait selected from herbicide tolerance, insect resistance by expression of one or more bacterial toxins, fungal resistance or viral resistance or bacterial resistance by expression of one or more antipathogenic substances, stress tolerance, content modification of one or more chemicals present in the cultivated plant compared to the corresponding control plant.

Most preferably, the cultivated plants are plants, which are tolerant to the action of herbicides and plants, which express one or more bacterial toxins, which provides resistance against one or more animal pests (such as insects or arachnids or nematodes), wherein the bacterial toxin is preferably a toxin from *Bacillus thuriginensis*. Herein, the cultivated plant is preferably selected from soybean, maize (corn), rice, cotton, sugarcane, alfalfa, potato, oilseed rape, tomatoes and cereals such as wheat, barley, rye and oat, most preferably from soybean, maize (corn), cotton, rice and cereals such as wheat, barley, rye and oat.

Utmost preference is given to cultivated plants, which are tolerant to the action of herbicides.

In another utmost preference, the cultivated plants are plants, which are given in table A. Sources: AgBios database and GMO-compass database (AG BIOS, P.O. Box 475, 106 St. John St. Merrickville, Ontario KOG1NO, Canada, access: www.cera-gmc.org/, also see BioTechniques, Volume 35, No. 3, September 2008, p. 213, and www.gmo-compass.org/eng/gmo/db/).

Thus, in one preferred embodiment, the present invention relates to a method of controlling harmful insects and/or increasing the health of cultivated plants by treating cultivated plants, parts of such plants, plant propagation materials, or at their locus of growth with compounds I and their mixtures, wherein the plant is a plant, which is rendered tolerant to herbicides, more preferably to herbicides such as glutamine synthetase inhibitors, 5-enol-pyrovyl-shikimate-3-phosphate-synthase inhibitors, acetolactate synthase (ALS) inhibitors, protoporphyrinogen oxidase (PPO) inhibitors, auxine type herbicides, most preferably to herbicides such as glyphosate, glufosinate, imazapyr, imazapic, imazamox, imazethapyr, imazaquin, imazamethabenz methyl, dicamba and 2,4-D.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures compounds I, wherein the plant corresponds to a row of table A1. In this embodiment, the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a more preferred embodiment, the present invention relates to a method of controlling harmful insects and/or increasing the health of cultivated plants by treating plant propagation materials, preferably seeds, with compounds I or their mixtures with a combination partner selected from endosulfan, ethiprole and fipronil, wherein the plant corresponds to row of table A1. In this embodiment, the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In another more preferred embodiment, the present invention relates to a method of controlling harmful insects and/or increasing the health of cultivated plants by treating cultivated plants, parts of such plants or at their locus of growth with compounds I or their mixtures, wherein the plant corresponds to row of table A1. In this embodiment, the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or at their locus of growth with compounds I, wherein the plant corresponds to a row of table A1. In this embodiment, the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating plant propagation materials, preferably seeds of cultivated plants of cultivated crops with compounds I and their mixtures, wherein the plant corresponds to a row of table A1. In this embodiment, the compound I is preferably a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

TABLE A1

| No | description | transgenic event | plant | literature/commercial plants |
|---|---|---|---|---|
| A1-1 | Glyphosate tolerance | ASR368 | *Agrostis stolonifera* (creeping bentgrass) | available, Scotts Seeds |
| A1-2 | Glyphosate tolerance | A5-15 | *Beta vulgaris* (sugar beet) | available, Danisco Seeds/DLF Trifolium |
| A1-3 | Glyphosate tolerance | GTSB77 | *Beta vulgaris* (sugar beet) | available, Novartis Seeds; Monsanto Company |
| A1-4 | Glyphosate tolerance | H7-1 | *Beta vulgaris* (sugar beet) | available, Monsanto Company |
| A1-5 | Glyphosate tolerance | T120-7 | *Beta vulgaris* (sugar beet) | available, Bayer CropScience (Aventis CropScience(AgrEvo)) |
| A1-6 | Glyphosate tolerance | GT200 | *Brassica napus* (Argentine canola) | available, Monsanto Company |
| A1-7 | Glyphosate tolerance | GT73, RT73 | *Brassica napus* (Argentine canola) | available, Monsanto Company |
| A1-8 | Glyphosate tolerance | HCN10 | *Brassica napus* (Argentine canola) | available, Aventis CropScience |
| A1-9 | Glyphosate tolerance | HCN92 | *Brassica napus* (Argentine canola) | available, Bayer CropScience (Aventis CropScience(AgrEvo)) |
| A1-10 | Glyphosate tolerance | T45 (HCN28) | *Brassica napus* (Argentine canola) | available, Bayer CropScience (Aventis CropScience(AgrEvo)) |
| A1-11 | Glyphosate tolerance | ZSR500/502 | *Brassica rapa* (Polish canola) | available, Monsanto Company |
| A1-12 | Glyphosate tolerance | GTS 40-3-2 | *Glycine max L.* (soybean) | available, Monsanto Company |
| A1-13 | Glyphosate tolerance | MON40-3-2 | *Glycine max L.* (soybean) | available, Monsanto Company |
| A1-14 | Glyphosate tolerance | MON89788 | *Glycine max L.* (soybean) | available, Monsanto Company |
| A1-15 | Glyphosate | GHB614 | *Gossypium* | available, Bayer |
| A1-16 | Glyphosate tolerance | MON1445 | *Gossypium hirsutum L.* (cotton) | available, Monsanto Company |
| A1-17 | Glyphosate | MON1445 | *Gossypium* | available, Monsanto |
| A1-18 | Glyphosate | MON8891 | *Gossypium* | available, Monsanto |
| A1-19 | Glyphosate tolerance | MON-00101-8, MON-00163-7 (J101, J163) | *Medicago sativa* (alfalfa) | available, Monsanto and Forage Genetics International |
| A1-20 | Glyphosate tolerance | MON71800 | *Triticum aestivum* (wheat) | available, Monsanto Company |
| A1-21 | Glyphosate | NK603 | *Zea mays L.* (corn, | available, Monsanto |
| A1-22 | Glyphosate | GA21 | *Zea mays L.* (corn, | available, Syngenta |

TABLE A1-continued

| No | description | transgenic event | plant | literature/commercial plants |
|---|---|---|---|---|
| A1-23 | Glyphosate | MON832 | Zea mays L. (corn, | Monsanto Company |
| A1-24 | Glufosinate tolerance | GS40/ 90pHoe6/ Ac | Brassica napus (Argentine canola) | available, Bayer CropScience |
| A1-25 | Glufosinate tolerance | Liberator pHoe6/Ac | Brassica napus (Argentine canola) | available, Bayer CropScience |
| A1-26 | Glufosinate tolerance | TOPAS 19/2 | Brassica napus (Argentine canola) | available, Bayer CropScience |
| A1-27 | Glufosinate tolerance | T14, T25 (ACS-ZM002-1/ ACS- | Zea mays L. (corn, maize) | Bayer CropScience (Aventis CropScience(AgrEvo)) |
| A1-28 | Glufosinate ammonium tolerance | PHY14, PHY35 | Brassica napus (Argentine canola) | available, Aventis CropScience (formerly Plant Genetic Systems) |
| A1-29 | Glufosinate ammonium tolerance | PHY36 | Brassica napus (Argentine canola) | available, Aventis CropScience (formerly Plant Genetic Systems) |
| A1-30 | Glufosinate ammonium tolerance | HCR-1 | Brassica rapa (Polish canola) | available, Bayer CropScience (Aventis CropScience(AgrEvo)) |
| A1-31 | Glufosinate ammonium tolerance | RM3-3, RM3-4, RM3-6 | Cichorium intybus (Chicory) | available, Bejo Zaden BV |
| A1-32 | Glufosinate ammonium tolerance | A2704-12, A2704-21, A5547-35 | Glycine max L. (soybean) | available, Bayer CropScience (Aventis CropScience(AgrEvo)) |
| A1-33 | Glufosinate ammonium tolerance | A5547-127 | Glycine max L. (soybean) | available, Bayer CropScience (Aventis CropScience(AgrEvo)) |
| A1-34 | Glufosinate ammonium tolerance | GU262 | Glycine max L. (soybean) | available, Bayer CropScience (Aventis CropScience(AgrEvo)) |
| A1-35 | Glufosinate ammonium tolerance | W62, W98 | Glycine max L. (soybean) | available, Bayer CropScience (Aventis CropScience(AgrEvo)) |
| A1-36 | Glufosinate ammonium | LLCotton25 | Gossypium hirsutum L. (cotton) | available, Bayer CropScience (Aventis |
| A1-37 | Glufosinate ammonium tolerance | LL RICE 62 | Oryza sativa (rice) | available, Bayer CropScience |
| A1-38 | Glufosinate ammonium tolerance | LLrice06 LLrice 62 | Oryza sativa (rice) | available, Bayer CropScience |
| A1-39 | Glufosinate ammonium tolerance | LLrice601 | Oryza sativa (rice) | available, Bayer CropScience |
| A1-40 | Glufosinate | 676, 678, | Zea mays L. (corn, | available, Pioneer Hi- |
| A1-41 | Glufosinate | B16 | Zea mays L. (corn, | available, Dekalb |
| A1-42 | Imidazolinone tolerance | NS738, NS1471, | Brassica napus (Argentine canola) | available, Pioneer Hi-Bred International Inc. |
| A1-43 | Imidazolinone tolerance | X81359 | Helianthus annuus (sunflower) | available, BASF |
| A1-44 | Imidazolinone tolerance | RH44 | Lens culinaris (lentil) | available, BASF |
| A1-45 | Imidazolinone tolerance | CFX51 | Oryza sativa (rice) | available, BASF |
| A1-46 | Imidazolinone tolerance | IMINTA-1, IMINTA-4 | Oryza sativa (rice) | available, BASF |
| A1-47 | Imidazolinone tolerance | PWC16 | Oryza sativa (rice) | available, BASF |
| A1-48 | Imidazolinone tolerance | AP205CL | Triticum aestivum (wheat) | available, BASF Inc. |
| A1-49 | Imidazolinone | AP602CL | Triticum aestivum | available, BASF Inc. |
| A1-50 | Imidazolinone | BW255-2, | Triticum aestivum | available, BASF Inc. |
| A1-51 | Imidazolinone | BW7 | Triticum aestivum | available, BASF Inc. |
| A1-52 | Imidazolinone | SWP9650 | Triticum aestivum | available, Cyanamid |
| A1-53 | Imidazolinone | Teal 11A | Triticum aestivum | available, BASF Inc. |
| A1-54 | Imidazolinone | 3751IR | Zea mays L. (corn, | available, Pioneer Hi- |
| A1-55 | Imidazolinone | EXP1910I | Zea mays L. (corn, | available, Syngenta |
| A1-56 | Imidazolinone | IT | Zea mays L. (corn, | available, Pioneer Hi- |
| A1-57 | sulfonyl urea | 19-51A | Gossypium | available, DuPont |
| A1-58 | sulfonyl urea tolerance | CDC-FL001-2 (FP967) | University of Saskatchewan, Crop Dev. Centre | available, Linum usitatissimum L. (flax, linseed) |

TABLE A1-continued

| No | description | transgenic event | plant | literature/commercial plants |
|---|---|---|---|---|
| A1-59 | Bromoxynil and loxynil tolerance | OXY-235 | *Brassica napus* (Argentine canola) | available, Aventis CropScience (formerly Rhône Poulenc Inc.) |
| A1-60 | Bromoxynil and | BXN | *Gossypium* | available, Calgene Inc. |
| A1-61 | Bromoxynil and loxynil tolerance | C/F/93/08-02 | *Nicotiana tabacum L.* (tobacco) | available, Societe National d'Exploitation des Tabacs et Allumettes |
| A1-62 | Cyclohexanone tolerance | DK404SR | *Zea mays L.* (corn, maize) | available, BASF Inc. |

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 1, wherein the compound I is compound I-C-36.

TABLE 1

| No | detailed description [Event] | plant | Literature/commercial plants |
|---|---|---|---|
| T1-1 | imidazolinone tolerance | canola | B* |
| T1-2 | imidazolinone tolerance | maize | A*, B* |
| T1-3 | imidazolinone tolerance | rice | A*, C* |
| T1-4 | imidazolinone tolerance | millet | A* |
| T1-5 | imidazolinone tolerance | barley | A* |
| T1-6 | imidazolinone tolerance | wheat | A* |
| T1-7 | imidazolinone tolerance | *sorghum* | A* |
| T1-8 | imidazolinone tolerance | oats | A* |
| T1-9 | imidazolinone tolerance | rye | A* |
| T1-10 | imidazolinone tolerance | sugar beet | WO 1998/02526/WO 1998/02527 |
| T1-11 | imidazolinone tolerance | lentils | US2004/0187178 |
| T1-12 | imidazolinone tolerance | sunflowers | B* |
| T1-13 | imidazolinone tolerance | wheat | D* |
| T1-14 | glyphosate tolerance | alfalfa | E*; "Roundup Ready Alfalfa" |
| T1-15 | glyphosate tolerance | apple | E* |
| T1-16 | glyphosate tolerance | barley | E* |
| T1-17 | glyphosate tolerance | canola | E*; V* |
| T1-18 | glyphosate tolerance | maize | E*; W* |
| T1-19 | glyphosate tolerance | cotton | E*; X* |
| T1-20 | glyphosate tolerance | flax | E* |
| T1-21 | glyphosate tolerance | grape | E* |
| T1-22 | glyphosate tolerance | lentil | E* |
| T1-23 | glyphosate tolerance | oil seed rape | E* |
| T1-24 | glyphosate tolerance | pea | E* |
| T1-25 | glyphosate tolerance | potato | E* |
| T1-26 | glyphosate tolerance | rice | "Roundup Ready Rice" (Monsanto) |
| T1-27 | glyphosate tolerance | soybean | E*; Y* |
| T1-28 | glyphosate tolerance | sugar beet | E* |
| T1-29 | glyphosate tolerance | sunflower | E* |

TABLE 1-continued

| | | | |
|---|---|---|---|
| T1-30 | glyphosate tolerance | tobacco | E* |
| T1-31 | glyphosate tolerance | tomato | E* |
| T1-32 | glyphosate tolerance | turf grass | E* |
| T1-33 | glyphosate tolerance | wheat | E* |
| T1-34 | gluphosinate tolerance | canola | F*; U* |
| T1-35 | gluphosinate tolerance | maize | F*; Z* |
| T1-36 | gluphosinate tolerance | cotton | F*; "FiberMax Liberty Link" (Bayer), |
| T1-37 | gluphosinate tolerance | potato | F* |
| T1-38 | gluphosinate tolerance | rice | F*, G*; "Liberty Link Rice" (Bayer), |
| T1-39 | gluphosinate tolerance | sugar beet | F* |
| T1-40 | gluphosinate tolerance | soybean | U.S. Pat. No. 6,376,754 |
| T1-41 | gluphosinate tolerance | tobacco | F* |
| T1-42 | gluphosinate tolerance | tomato | F* |
| T1-43 | dicamba tolerance | bean | U.S. Pat. No. 7,105,724 |
| T1-44 | dicamba tolerance | maize | U.S. Pat. No. 7,105,724, WO2008051633 |
| T1-45 | dicamba tolerance | cotton | U.S. Pat. No. 7,105,724, U.S. Pat. No. 5,670,454 |
| T1-46 | dicamba tolerance | pea | U.S. Pat. No. 7,105,724 |
| T1-47 | dicamba tolerance | potato | U.S. Pat. No. 7,105,724 |
| T1-48 | dicamba tolerance | *sorghum* | U.S. Pat. No. 7,105,724 |
| T1-49 | dicamba tolerance | soybean | U.S. Pat. No. 7,105,724, U.S. Pat. No. 5,670,454 |
| T1-50 | dicamba tolerance | sunflower | U.S. Pat. No. 7,105,724 |
| T1-51 | dicamba tolerance | tobacco | U.S. Pat. No. 7,105,724 |
| T1-52 | dicamba tolerance | tomato | U.S. Pat. No. 7,105,724, U.S. Pat. No. 5,670,454 |
| T1-53 | bromoxynil tolerance | canola | "Navigator", "Compass" (Rhone-Poulenc) |
| T1-54 | bromoxynil tolerance | cotton | "BXN" (calgene) |
| T1-55 | 2,4-D tolerance | apple | H* |
| T1-56 | 2,4-D tolerance | maize | H* |
| T1-57 | 2,4-D tolerance | cotton | U.S. Pat. No. 5,670,454 |
| T1-58 | 2,4-D tolerance | cucumber | H* |
| T1-59 | 2,4-D tolerance | pepper | H* |
| T1-60 | 2,4-D tolerance | potato | H* |
| T1-61 | 2,4-D tolerance | *sorghum* | H* |
| T1-62 | 2,4-D tolerance | soybean | H* |
| T1-63 | 2,4-D tolerance | sunflower | H* |
| T1-64 | 2,4-D tolerance | tobacco | H* |
| T1-65 | 2,4-D tolerance | tomato | H* |
| T1-66 | 2,4-D tolerance | wheat | H* |
| T1-67 | HPPD inhibitor tolerance (K*) | barley | I* |
| T1-68 | HPPD inhibitor tolerance (K*) | maizef | I* |
| T1-69 | HPPD inhibitor tolerance (K*) | cotton | I* |
| T1-70 | HPPD inhibitor tolerance (K*) | potato | I* |
| T1-71 | HPPD inhibitor tolerance (K*) | rapeseed | I* |
| T1-72 | HPPD inhibitor tolerance (K*) | rice | I* |
| T1-73 | HPPD inhibitor tolerance (K*) | soybean | I* |
| T1-74 | HPPD inhibitor tolerance (K*) | sutarbeet | I* |
| T1-75 | HPPD inhibitor tolerance (K*) | sugarcane | I* |
| T1-76 | HPPD inhibitor tolerance (K*) | tobacco | I* |
| T1-77 | HPPD inhibitor tolerance (K*) | wheat | I* |
| T1-78 | Protox inhibitor tolerance (L*) | cotton | M* |
| T1-79 | Protox inhibitor tolerance (L*) | rape | M* |
| T1-80 | Protox inhibitor tolerance (L*) | rice | M* |
| T1-81 | Protox inhibitor tolerance (L*) | *sorghum* | M* |
| T1-82 | Protox inhibitor tolerance (L*) | soybean | M* |
| T1-83 | Protox inhibitor tolerance (L*) | sugarbeet | M* |
| T1-84 | Protox inhibitor tolerance (L*) | sugar cane | M* |

TABLE 1-continued

| | | | | |
|---|---|---|---|---|
| T1-85 | Protox inhibitor tolerance (L*) | | wheat | M* |
| T1-86 | imidazolinone tolerance | | soybean | N* |

| | description | Event | | |
|---|---|---|---|---|
| T1-87 | Glyphosate tolerance | ASR368 | *Agrostis stolonifera* (creeping bentgrass) | available, Scotts Seeds |
| T1-88 | Glyphosate tolerance | A5-15 | *Beta vulgaris* (sugar beet) | available, Danisco Seeds/DLF Trifolium |
| T1-89 | Glyphosate tolerance | GTSB77 | *Beta vulgaris* (sugar beet) | available, Novartis Seeds; Monsanto Company |
| T1-90 | Glyphosate tolerance | H7-1 | *Beta vulgaris* (sugar beet) | available, Monsanto Company |
| T1-91 | Glyphosate tolerance | T120-7 | *Beta vulgaris* (sugar beet) | available, Bayer CropScience (Aventis CropScience(AgrEvo) |
| T1-92 | Glyphosate tolerance | GT200 | *Brassica napus* (Argentine canola) | available, Monsanto Company |
| T1-93 | Glyphosate tolerance | GT73, RT73 | *Brassica napus* (Argentine canola) | available, Monsanto Company |
| T1-94 | Glyphosate tolerance | HCN10 | *Brassica napus* (Argentine canola) | available, Aventis CropScience |
| T1-95 | Glyphosate tolerance | HCN92 | *Brassica napus* (Argentine canola) | available, Bayer CropScience (Aventis CropScience(AgrEvo) |
| T1-96 | Glyphosate tolerance | T45 (HCN28) | *Brassica napus* (Argentine canola) | available, Bayer CropScience (Aventis CropScience(AgrEvo) |
| T1-97 | Glyphosate tolerance | ZSR500/ 502 | *Brassica rapa* (Polish canola) | available, Monsanto Company |
| T1-98 | Glyphosate tolerance | GTS 40-3-2 | *Glycine max L.* (soybean) | available, Monsanto Company |
| T1-99 | Glyphosate tolerance | MON40-3-2 | *Glycine max L.* (soybean) | available, Monsanto Company |
| T1-100 | Glyphosate tolerance | MON89788 | *Glycine max L.* (soybean) | available, Monsanto Company |
| T1-101 | Glyphosate tolerance | GHB614 | *Gossypium hirsutum* | available, Bayer |
| T1-102 | Glyphosate tolerance | MON1445 | *Gossypium hirsutum L.* (cotton) | available, Monsanto Company |
| T1-103 | Glyphosate | MON14 | *Gossypium hirsutum* | available, Monsanto |
| T1-104 | Glyphosate | MON88 | *Gossypium hirsutum* | available, Monsanto |
| T1-105 | Glyphosate tolerance | MON-00101-8, MON-00163-7 (J101, J163) | *Medicago sativa* (alfalfa) | available, Monsanto and Forage Genetics International |
| T1-106 | Glyphosate tolerance | MON71 800 | *Triticum aestivum* (wheat) | available, Monsanto Company |
| T1-107 | Glyphosate | NK603 | *Zea mays L.* (corn, | available, Monsanto |
| T1-108 | Glyphosate | GA21 | *Zea mays L.* (corn, | available, Syngenta |
| T1-109 | Glyphosate | MON83 | *Zea mays L.* (corn, | Monsanto Company |
| T1-110 | Glufosinate tolerance | GS40/ 90pHoe 6/Ac | *Brassica napus* (Argentine canola) | available, Bayer CropScience |
| T1-111 | Glufosinate tolerance | Liberator pHoe6/ Ac | *Brassica napus* (Argentine canola) | available, Bayer CropScience |
| T1-112 | Glufosinate tolerance | TOPAS 19/2 | *Brassica napus* (Argentine canola) | available, Bayer CropScience |
| T1-113 | Glufosinate tolerance | T14, T25 (ACS-ZM002 | *Zea mays L.* (corn, maize) | Bayer CropScience (Aventis CropScience(AgrEvo) |
| T1-114 | Glufosinate ammonium tolerance | PHY14, PHY35 | *Brassica napus* (Argentine canola) | available, Aventis CropScience (formerly Plant Genetic Systems) |
| T1-115 | Glufosinate ammonium tolerance | PHY36 | *Brassica napus* (Argentine canola) | available, Aventis CropScience (formerly Plant Genetic Systems) |
| T1-116 | Glufosinate ammonium tolerance | HCR-1 | *Brassica raga* (Polish canola) | available, Bayer CropScience (Aventis CropScience(AgrEvo) |
| T1-117 | Glufosinate ammonium tolerance | RM3-3, RM3-4, RM3-6 | *Cichorium intybus* (Chicory) | available, Bejo Zaden BV |

TABLE 1-continued

| | | | | |
|---|---|---|---|---|
| T1-118 | Glufosinate ammonium tolerance | A2704-12, A2704-21, A5547-35 | *Glycine max L.* (soybean) | available, Bayer CropScience (Aventis CropScience(AgrEvo) |
| T1-119 | Glufosinate ammonium tolerance | A5547-127 | *Glycine max L.* (soybean) | available, Bayer CropScience (Aventis CropScience(AgrEvo) |
| T1-120 | Glufosinate ammonium tolerance | GU262 | *Glycine max L.* (soybean) | available, Bayer CropScience (Aventis CropScience(AgrEvo) |
| T1-121 | Glufosinate ammonium tolerance | W62, W98 | *Glycine max L.* (soybean) | available, Bayer CropScience (Aventis CropScience(AgrEvo) |
| T1-122 | Glufosinate ammonium | LLCotton25 | *Gossypium hirsutum L.* (cotton) | available, Bayer CropScience (Aventis |
| T1-123 | Glufosinate ammonium tolerance | LL RICE 62 | *Oryza sativa* (rice) | available, Bayer CropScience |
| T1-124 | Glufosinate ammonium tolerance | LLrice06 LLrice 62 | *Oryza sativa* (rice) | available, Bayer CropScience |
| T1-125 | Glufosinate ammonium tolerance | LLrice601 | *Oryza sativa* (rice) | available, Bayer CropScience |
| T1-126 | Glufosinate | 676, | *Zea mays L.* (corn, | available, Pioneer Hi- |
| T1-127 | Glufosinate | B16 | *Zea mays L.* (corn, | available, Dekalb |
| T1-128 | Imidazolinone tolerance | NS738, NS1471 | *Brassica napus* (Argentine canola) | available, Pioneer Hi-Bred International Inc. |
| T1-129 | Imidazolinone tolerance | X81359 | *Helianthus annuus* (sunflower) | available, BASF |
| T1-130 | Imidazolinone tolerance | RH44 | *Lens culinaris* (lentil) | available, BASF |
| T1-131 | Imidazolinone tolerance | CFX51 | *Oryza sativa* (rice) | available, BASF |
| T1-132 | Imidazolinone tolerance | IMINTA-1, IMINTA-4 | *Oryza sativa* (rice) | available, BASF |
| T1-133 | Imidazolinone tolerance | PWC16 | *Oryza sativa* (rice) | available, BASF |
| T1-134 | Imidazolinone tolerance | AP205CL | *Triticum aestivum* (wheat) | available, BASF Inc. |
| T1-135 | Imidazolinone | AP602C | *Triticum aestivum* | available, BASF Inc. |
| T1-136 | Imidazolinone | BW255- | *Triticum aestivum* | available, BASF Inc. |
| T1-137 | Imidazolinone | BW7 | *Triticum aestivum* | available, BASF Inc. |
| T1-138 | Imidazolinone | SWP96 | *Triticum aestivum* | available, Cyanamid |
| T1-139 | Imidazolinone | Teal | *Triticum aestivum* | available, BASF Inc. |
| T1-140 | Imidazolinone | 3751IR | *Zea mays L.* (corn, | available, Pioneer Hi- |
| T1-141 | Imidazolinone | EXP191 | *Zea mays L.* (corn, | available, Syngenta |
| T1-142 | Imidazolinone | IT | *Zea mays L.* (corn, | available, Pioneer Hi- |
| T1-143 | sulfonyl urea | 19-51A | *Gossypium hirsutum* | available, DuPont |
| T1-144 | sulfonyl urea tolerance | CDC-FL001-2 (FP967) | University of Saskatchewan, Crop Dev. Centre | available, *Linum usitatissirnum L.* (flax, linseed) |
| T1-145 | Bromoxynil and loxynil tolerance | OXY-235 | *Brassica napus* (Argentine canola) | available, Aventis CropScience (formerly Rhône Poulenc Inc.) |
| T1-146 | Bromoxynil and | BXN | *Gossypium hirsutum* | available, Calgene |
| T1-147 | Bromoxynil and loxynil tolerance | C/F/93/08-02 | *Nicotiana tabacum L.* (tobacco) | available, Societe National d'Exploitation des Tabacs et Allumettes |
| T1-148 | Cyclohexanone tolerance | DK404SR | *Zea mays L.* (corn, maize) | available, BASF Inc. |

A* refers to U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100.
B* refers to Tan et. al, Pest Manag. Sci 61, 246-257 (2005).
C* refers to imidazolinone-herbicide resistant rice plants with specific mutation of the acetohydroxyacid synthase gene: S653N (see e.g. US 2003/0217381), S654K (see e.g. US 2003/0217381), A122T (see e.g. WO 2004/106529) S653(At)N, S654(At)K, A122(At)T and other resistant rice plants as described in WO 2000/27182, WO 2005/20673 and WO 2001/85970 or US patents U.S. Pat. No. 5,545,822, U.S. Pat. No. 5,736,629, U.S. Pat. No. 5,773,703, U.S. Pat. No. 5,773,704, U.S. Pat. No. 5,952,553, U.S. Pat. No. 6274796, wherein plants with mutation S653A and A122T are most preferred.
D* refers to WO 2004/106529, WO 2004/16073, WO 2003/14357, WO 2003/13225 and WO 2003/14356.
E* refers to U.S. Pat. No. 5,188,642, U.S. Pat. No. 4,940,835, U.S. Pat. No. 5,633,435, U.S. Pat. No. 5,804,425 and U.S. Pat. No. 5,627,061.
F* refers to U.S. Pat. No. 5,646,024 and U.S. Pat. No. 5,561,236.
G* refers to U.S. Pat. No. 6,333,449, U.S. Pat. No. 6,933,111 and U.S. Pat. No. 6,468,747.

TABLE 1-continued

H* refers to U.S. Pat. No. 6,153,401, U.S. Pat. No. 6,100,446, WO 2005/107437, U.S. Pat. No. 5,670,454 and U.S. Pat. No. 5,608,147.
I* refers to WO 2004/055191, WO 199638567 and U.S. Pat. No. 6,791,014.
K* refers to HPPD inhibitor herbicides, such as isoxazoles (e.g. isoxaflutole), diketonitriles, trikeones (e.g. sulcotrione and mesotrione), pyrazolinates.
L* refers to protoporphyrinogen oxidase (PPO) inhibiting herbicides.
M* refers to US 2002/0073443, US 20080052798, Pest Management Science, 61, 2005, 277-285.
N* refers to the herbicide tolerant soybean plants presented under the name of Cultivance on the XVI Congresso Brasileiro de Sementes, 31st Augusta to $3^{rd}$ September 2009 at Estação Embratel Convention Center - Curitiba/PR, Brazil
U* "InVigor" (Bayer)
V* "Roundup Ready Canola" (Monsanto)
W* "Roundup Ready Corn", "Roundup Ready 2" (Monsanto), "Agrisure GT", "Agrisure GT/CB/LL", "Agrisure GT/RW", "Agrisure 3000GT" (Syngenta), "YieldGard VT Rootworm/RR2", "YieldGard VT Triple" (Monsanto)
X* "Roundup Ready Cotton", "Roundup Ready Flex" (Monsanto)
Y* "Roundup Ready Soybean" (Monsanto), "Optimum GAT" (DuPont, Pioneer)
Z* "Liberty Link" (Bayer), "Herculex I", "Herculex RW", "Herculex Xtra"(Dow, Pioneer), "Agrisure GT/CB/LL", "Agrisure CB/LL/RW" (Syngenta), A subset of especially preferred herbicide tolerant plants is given in table 2. In this subset, there are further preferred embodiments:

In a more preferred embodiment, the present invention relates to a method of controlling harmful insects and/or increasing the health of cultivated plants by treating plant propagation materials, preferably seeds with compounds I and their mixtures wherein the mixing partner is selected from endosulfan, ethiprole and fipronil, wherein the plant corresponds to row of table 2.

In another more preferred embodiment, the present invention relates to a method of controlling harmful insects and/or increasing the health of cultivated plants by treating cultivated plants, parts of such plants or at their locus of growth with compounds I and their mixtures, wherein the plant corresponds to row of table 2.

In a most preferred embodiment, the present invention relates to a method of controlling harmful insects and/or increasing the health of plants by treating cultivated plants, parts of such plants or at their locus of growth with compounds I and their mixtures, wherein the plant corresponds to a row of table 2.

In a most preferred embodiment, the present invention relates to a method of controlling harmful insects and/or increasing the health of plants by treating plant propagation materials, preferably seeds of cultivated plants of cultivated crops with compounds I and their mixtures, wherein the plant corresponds to a row of table 2.

In a utmost preferred embodiment, the present invention relates to a method of controlling harmful insects and/or increasing the health of plants by treating cultivated plants, parts of such plants or at their locus of growth with compounds I and their mixtures, wherein the plant is selected from T2-3, T2-8, T2-9, T2-10, T2-11, T2-13, T2-15, T2-16, T2-17, T2-18, T2-19 and T2-23.

In a utmost preferred embodiment, the present invention relates to a method of controlling harmful insects and/or increasing the health of plants by treating plant propagation materials, preferably seeds of cultivated plants of cultivated crops with compounds I and their mixtures, wherein the plant is selected from T2-3, T2-8, T2-9, T2-10, T2-11, T2-13, T2-15, T2-16, T2-17, T2-18, T2-19 and T2-23.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 2, wherein the compound I is compound I-C-36.

TABLE 2

| No | detailed description | plant | Literature/commercial plants |
|---|---|---|---|
| T2-1 | imidazolinone tolerance | canola | B* |
| T2-2 | imidazolinone tolerance | maize | A*, B* |
| T2-3 | imidazolinone tolerance | rice | C* |
| T2-4 | imidazolinone tolerance | sunflowers | B* |
| T2-5 | imidazolinone tolerance | wheat | D* |
| T2-6 | glyphosate tolerance | alfalfa | E*; "Roundup Ready Alfalfa" |
| T2-7 | glyphosate tolerance | canola | E*; U* |
| T2-8 | glyphosate tolerance | maize | E*; V* |
| T2-9 | glyphosate tolerance | cotton | E*; W* |
| T2-10 | glyphosate tolerance | rice | E*; "Roundup Ready Rice" (Monsanto) |
| T2-11 | glyphosate tolerance | soybean | E*; X* |
| T2-12 | glyphosate tolerance | sugar beet | E* |
| T2-13 | glufosinate tolerance | canola | F*; "InVigor" (Bayer) |

TABLE 2-continued

| No | detailed description | plant | Literature/commercial plants |
|---|---|---|---|
| T2-14 | glufosinate tolerance | maize | F*; Y* |
| T2-15 | glufosinate tolerance | cotton | F*; "FiberMax Liberty Link" (Bayer), |
| T2-16 | glufosinate tolerance | rice | F*, G*; "Liberty Link Rice" (Bayer), |
| T2-17 | glufosinate tolerance | soybean | I* |
| T2-18 | dicamba tolerance | cotton | U.S. Pat. No. 7,105,724 |
| T2-19 | dicamba tolerance | soybean | U.S. Pat. No. 7,105,724 |
| T2-20 | bromoxynil tolerance | canola | Z* |
| T2-21 | bromoxynil tolerance | cotton | "BXN" (Calgene) |
| T2-22 | 2,4-D tolerance | maize | H* |
| T2-23 | imidazolinone tolerance | soybean | N* |

A* refers to U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100.
B* refers to Tan et. al, Pest Manag. Sci 61, 246-257 (2005).
C* refers to imidazolinone-herbicide resistant rice plants with specific mutation of the acetohydroxyacid synthase gene: S653N (see e.g. US 2003/0217381), S654K (see e.g. US 2003/0217381), A122T (see e.g. WO 04/106529) S653(At)N, S654(At)K, A122(At)T and other resistant rice plants as described in WO 2000/27182, WO 2005/20673 and WO 2001/85970 or US patents U.S. Pat. No. 5,545,822, U.S. Pat. No. 5,736,629, U.S. Pat. No. 5,773,703, U.S. Pat. No. 5,773,704, U.S. Pat. No. 5,952,553, U.S. Pat. No. 6,274,796, wherein plants with mutation S653A and A122T are most preferred.
D* refers to WO 04/106529, WO 04/16073, WO 03/14357, WO 03/13225 and WO 03/14356.
E* refers to U.S. Pat. No. 5,188,642, U.S. Pat. No. 4,940,835, U.S. Pat. No. 5,633,435, U.S. Pat. No. 5,804,425 and U.S. Pat. No. 5,627,061.
F* refers to U.S. Pat. No. 5,646,024 and U.S. Pat. No. 5,561,236.
G* refers to U.S. Pat. No. 6,333,449, U.S. No. Pat. 6,933,111 and U.S. Pat. No. 6,468,747.
H* refers to U.S. Pat. No. 6,153,401, U.S. Pat. No. 6,100,446, WO 2005/107437 and U.S. Pat. No. 5,608,147.
I* refers to Federal Register (USA), Vol. 61, No. 160, 1996, page 42581. Federal Register (USA), Vol. 63, No. 204, 1998, page 56603.
N* refers to the herbicide tolerant soybean plants presented under the name of Cultivance on the XVI Congresso Brasileiro de Sementes, 31st Augusta to 3$^{rd}$ September 2009 at Estaç ão Embratel Convention Center - Curitiba/PR, Brazil
U* "Roundup Ready Canola" (Monsanto)
V* "Roundup Ready Corn", "Roundup Ready 2" (Monsanto), "Agrisure GT", "Agrisure GT/CB/LL", "Agrisure GT/RW", »Agrisure 3000GT" (Syngenta), "YieldGard VT Rootworm/RR2", "YieldGard VT Triple" (Monsanto)
W* "Roundup Ready Cotton", "Roundup Ready Flex" (Monsanto)
x* "Roundup Ready Soybean" (Monsanto), "Optimum GAT" (DuPont, Pioneer)
Y* "Liberty Link" (Bayer), "Herculex I", "Herculex RW", "Herculex Xtra"(Dow, Pioneer), "Agrisure GT/CB/LL", "Agrisure CB/LL/RW" (Syngenta)
Z* "Navigator", "Compass" (Rhone-Poulenc)

In a further preferred embodiment, the present invention relates to a method of controlling harmful insects and/or increasing the health of cultivated plants by treating cultivated plants, parts of such plants, plant propagation materials, or at their locus of growth with a compound I according to this invention or their mixtures, wherein the plant is a plant, which express at least one insecticidal toxin, preferably a toxin from *Bacillus* species, more preferably from *Bacillus thuringiensis*.

In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a more preferred embodiment, the present invention relates to a method of controlling harmful insects and/or increasing the health of cultivated plants by treating plant propagation materials, preferably seeds with compounds I or their as exemplified herein in Embodiment E2 or E3, preferably wherein the plant corresponds to a row of table A2 or table 3.

In another more preferred embodiment, the present invention relates to a method of controlling harmful insects and/or increasing the health of cultivated plants by treating cultivated plants, parts of such plants or at their locus of growth with compounds I or their mixtures wherein the plant corresponds to a row of table A2 or table 3.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table A2 or table 3.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table A2 or table 3.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table A2 or table 3, wherein the compound I is compound I-C-36.

In a utmost preferred embodiment, the present invention relates to a method of controlling harmful insects and/or increasing the health of plants by treating cultivated plants, parts of such plants or at their locus of growth with compounds I or their mixtures, wherein the plant is selected from T3-1, T3-2, T3-5, T3-6, T3-7, T3-8, T3-9, T3-10, T3-11, T3-12, T3-13, T3-14, T3-15, T3-16, T3-17, T3-18, T3-19, T3-20, T3-23 and T3-25.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T3-1, T3-2, T3-5, T3-6, T3-7, T3-8, T3-9, T3-10, T3-11, T3-12, T3-13, T3-14, T3-15, T3-16, T3-17, T3-18, T3-19, T3-20, T3-23 and T3-25.

TABLE A2

| No | description | transgenic event | plant | literature/ commercial plants |
|---|---|---|---|---|
| A2-1 | Lepidoptera resistance | 281-24-236 (DAS- | Gossypium hirsutum L. | available, DOW AgroSciences LLC |
| A2-2 | Lepidoptera resistance | 281-24-236 x 3006-210-23 | Gossypium hirsutum L. (cotton) | available, Dow AgroSciences |
| A2-3 | Lepidoptera resistance | 3006-210-23 (DAS- | Gossypium hirsutum L. | available, DOW AgroSciences LLC |
| A2-4 | Lepidoptera resistance | COT102 (SYN- | Gossypium hirsutum L. | available, Syngenta Seeds, Inc. |
| A2-5 | Lepidoptera resistance | DAS-21Ø23-5 x DAS-24236-5 | Gossypium hirsutum L. (cotton) | available, DOW AgroSciences LLC |
| A2-6 | Lepidoptera resistance | Event-1 | Gossypium hirsutum L. | available, JK Agri Genetics Ltd (India) |
| A2-7 | Lepidoptera resistance | MON531/757/1076 | Gossypium hirsutum L. | available, Monsanto Company |
| A2-8 | Lepidoptera resistance | 15985 (MON-15985-7) | Gossypium hirsutum L. (cotton) | available, Monsanto Company |
| A2-9 | Lepidoptera resistance | 5345 | Lycopersicon esculentum (tomato) | available, Monsanto Company |
| A2-10 | Lepidoptera resistance | MIR162 | Zea mays L. (corn, maize) | available, Syngenta Seeds, Inc. |
| A2-11 | Lepidoptera resistance | MON89034 | Zea mays L. (corn, maize) | available, Monsanto Company |
| A2-12 | Corn Rootworm resistance | MIR604 | Zea mays L. (corn, maize) | available, Syngenta Seeds, Inc. |
| A2-13 | Corn Rootworm resistance | MON863 | Zea mays L. (corn, maize) | available, Monsanto Company |
| A2-14 | European Corn Borer resistance | 176 | Zea mays L. (corn, maize) | available, Syngenta Seeds, Inc. |
| A2-15 | European Corn Borer resistance | MON80100 | Zea mays L. (corn, maize) | available, Monsanto Company |
| A2-16 | European Corn Borer resistance | MON810 | Zea mays L. (corn, maize) | available, Monsanto Company |
| A2-17 | Colorado potato beetle resistance | ATBT04-6, ATBT04-27, ATBT04-30, ATBT04-31, ATBT04-36, SPBT02-5, SPBT02-7 | Solanum tuberosum L. (potato) | available, Monsanto Company |
| A2-18 | Colorado potato beetle resistance | BT6, BT10, BT12, BT16, BT17, | Solanum tuberosum L. (potato) | available, Monsanto Company |
| A2-19 | Colorado potato beetle resistance | RBMT15-101, SEMT15-02, | Solanum tuberosum L. (potato) | available, Monsanto Company |
| A2-20 | Colorado potato beetle resistance | RBMT21-129, RBMT21-350, RBMT22- | Solanum tuberosum L. (potato) | available, Monsanto Company |

TABLE A2-continued

| No | description | transgenic event | plant | literature/ commercial plants |
|---|---|---|---|---|
| A2-21 | resistance to Lepidopteran pests | COT67B | Gossypium hirsutum L. (Cotton) | available, Syngenta Seeds |

TABLE 3

| No | detailed description | [Event] | plant | Literature/ commercial plants |
|---|---|---|---|---|
| T3-1 | corn rootworm resistance | | maize | B* |
| T3-2 | corn borer resistance | | maize | C* |
| T3-3 | western bean cutworm resistance | | maize | D* |
| T3-4 | black cutworm resistance | | maize | E* |
| T3-5 | fall armyworm resistance | | maize | „Herculex I" (Dow, Pioneer), „Herculex Xtra" (Dow, Pioneer) |
| T3-6 | tobacco budworm resistance | | cotton | "Bollgard I" (Monsanto), E* |
| T3-7 | cotton bollworm resistance | | cotton | E* |
| T3-8 | fall armyworm resistance | | cotton | E* |
| T3-9 | beet armyworm resistance | | cotton | E* |
| T3-10 | cabbage looper resistance | | cotton | E* |
| T3-11 | soybean lopper resistance | | cotton | E* |
| T3-12 | pink bollworm resistance | | cotton | E* |
| T3-13 | rice stemborer resistance | | rice | A* |
| T3-14 | striped rice borer resistance | | rice | A* |
| T3-15 | rice leaf roller resistance | | rice | A* |
| T3-16 | yellow stemborer resistance | | rice | A* |
| T3-17 | rice skipper resistance | | rice | A* |
| T3-18 | rice caseworm resistance | | rice | A* |
| T3-19 | rice cutworm resistance | | rice | A* |
| T3-20 | rice armyworm resistance | | rice | A* |
| T3-21 | brinjal fruit and shoot borer resistance | | eggplant | F* |
| T3-22 | cotton bollworm resistance | | eggplant | F*" |
| T3-23 | tobacco hornworm resistance | | potato | D* |
| T3-24 | lepidopteran resistance | | lettuce | U.S. Pat. No. 5,349,124 |
| T3-25 | lepidopteran resistance | | soybean | U.S. Pat. No. 7,432,421 |
| T3-26 | detailed description | Event | | |
| No | detailed description | [Event] | plant | Literature/ commercial plants |
| T3-27 | ILepidoptera resistance | 281-24-236 (DAS-24236-5) | Gossypium hirsutum L. | available, DOW AgroSciences LLC |
| T3-28 | ILepidoptera resistance | 281-24-236 x 3006-210-23 | Gossypium hirsutum L. (cotton) | available, Dow AgroSciences |
| T3-29 | ILepidoptera resistance | 3006-210-23 (DAS-21Ø23-5) | Gossypium hirsutum L. | available, DOW AgroSciences LLC |
| T3-30 | ILepidoptera resistance | COT102 (SYN-IR1Ø2-7) | Gossypium hirsutum L. | available, Syngenta Seeds, Inc. |
| T3-31 | ILepidoptera resistance | DAS-21Ø23-5 x DAS-24236-5 | Gossypium hirsutum L. (cotton) | available, DOW AgroSciences LLC |
| T3-32 | ILepidoptera resistance | Event-1 | Gossypium hirsutum L. | available, JK Agri Genetics Ltd (India) |
| T3-33 | ILepidoptera resistance | MON531/757/1076 | Gossypium hirsutum L. | available, Monsanto Company |

TABLE 3-continued

| | | | | |
|---|---|---|---|---|
| T3-34 | ILepidoptera resistance | 15985 (MON-15985-7) | Gossypium hirsutum L. (cotton) | available, Monsanto Company |
| T3-35 | ILepidoptera resistance | 5345 | Lycopersicon esculentum (tomato) | available, Monsanto Company |
| T3-36 | ILepidoptera resistance | MIR162 | Zea mays L. (corn, maize) | available, Syngenta Seeds, Inc. |
| T3-37 | ILepidoptera resistance | MON89034 | Zea mays L. (corn, maize) | available, Monsanto Company |
| T3-38 | Corn Rootworm resistance | MIR604 | Zea mays L. (corn, maize) | available, Syngenta Seeds, Inc. |
| T3-39 | Corn Rootworm resistance | MON863 | Zea mays L. (corn, maize) | available, Monsanto Company |
| T3-40 | European Corn Borer resistance | 176 | Zea mays L. (corn, maize) | available, Syngenta Seeds, Inc. |
| T3-41 | European Corn Borer resistance | MON80100 | Zea mays L. (corn, maize) | available, Monsanto Company |
| T3-42 | European Corn Borer resistance | MON810 | Zea mays L. (corn, maize) | available, Monsanto Company |
| T3-43 | Colorado potato beetle resistance | ATBT04-6, ATBT04-27, ATBT04-30, ATBT04-31, ATBT04-36, SPBT02-5, SPBT02-7 | Solanum tuberosum L. (potato) | available, Monsanto Company |
| T3-44 | Colorado potato beetle resistance | BT6, BT10, BT12, BT16, BT17, BT18, BT23 | Solanum tuberosum L. (potato) | available, Monsanto Company |
| T3-45 | Colorado potato beetle resistance | RBMT15-101, SEMT15-02, SEMT15-15 | Solanum tuberosum L. (potato) | available, Monsanto Company |
| T3-46 | Colorado potato beetle resistance | RBMT21-129, RBMT21-350, RBMT22-082 | Solanum tuberosum L. (potato) | available, Monsanto Company |
| T3-47 | resistance to lepidopteran pests | COT67B | Gossypium hirsutum L. (Cotton) | available, Syngenta Seeds |

A* refers to »Zhuxian B«, WO2001021821, Molecular Breeding, Volume 18, Number 1/August 2006.
B* "YieldGard corn rootworm" (Monsanto), "YieldGard Plus" (Monsanto), "YieldGard VT" (Monsanto), "Herculex RW" (Dow, Pioneer), "Herculex Rootworm" (Dow, Pioneer), "Agrisure 0CRW" (Syngenta)
C* "YieldGard corn borer" (Monsanto), »YieldGard Plus" (Monsanto), »YieldGard VT Pro" (Monsanto), "Agrisure CB/LL" (Syngenta), "Agrisure 3000GT" (Syngenta), "Hercules I", "Hercules II" (Dow, Pioneer), "KnockOut" (Novartis), »NatureGard" (Mycogen), »StarLink" (Aventis)
D* "NewLeaf" (Monsanto), "NewLeafY" (Monsanto), "NewLeaf Plus" (Monsanto), U.S. Pat. No. 6,100,456
E* "Bollgard II" (Monsanto), »WideStrike" (Dow), »VipCot" (Syngenta)
F* U.S. Pat. No. 5,128,130, "Bt brinjal", "Dumaguete Long Purple", "Mara"

In a further preferred embodiment, the present invention relates to a method of controlling harmful insects and/or increasing the health of cultivated plants by treating cultivated plants, parts of such plants, plant propagation materials, or at their locus of growth with compounds I or their mixtures, preferably selected from more preferably a compound of embodiment A, also preferably a compound of embodiment B, also preferably a compound of embodiment C; more preferably a compound as defined in Table ABC, more preferably selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35., wherein the plant is a plant, which shows increased resistance against fungal, viral and bacterial diseases, more preferably a plant, which expresses antipathogenic substances, such as antifungal proteins, or which has systemic acquired resistance properties.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to row of table 4.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to row of table 4.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 4 and in which the mixture partner compound II is is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 4 and the mixture with the compound of formula I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 4 and in which the mixture partner compound II is fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 4 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 4 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 4 and the mixing partner of the compound I is fipronil.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 4, wherein the compound I is compound I-C-36.

TABLE 4

| No | detailed description | plant | Literature |
|---|---|---|---|
| T4-1. | fungal resistance | apple | A*, B*, C* |
| T4-2. | fungal resistance | barley | A*, B*, C* |
| T4-3. | fungal resistance | banana | A*, B*, C* |
| T4-4. | fungal resistance | bean | B*, C* |
| T4-5. | fungal resistance | maize | A*, B*, C* |
| T4-6. | fungal resistance | cotton | A*, C* |
| T4-7. | fungal resistance | cucumber | B*, C* |
| T4-8. | fungal resistance | grape | C* |
| T4-9. | fungal resistance | oat | A*, C* |
| T4-10. | fungal resistance | pepper | B*, C* |
| T4-11. | fungal resistance | potato | A*, B*, C* |
| T4-12. | fungal resistance | rape | B*, C* |
| T4-13. | fungal resistance | rice | A*, B*, C* |
| T4-14. | fungal resistance | rye | A*, B*, C* |
| T4-15. | fungal resistance | sorghum | B*, C* |
| T4-16. | fungal resistance | soybean | A*, B*, C* |
| T4-17. | fungal resistance | sugarcane | B*, C* |
| T4-18. | fungal resistance | tobacco | A*, B*, C* |
| T4-19. | fungal resistance | tomato | A*, B*, C* |
| T4-20. | fungal resistance | wheat | A*, B*, C* |
| T4-21. | bacterial resistance | apple | D* |
| T4-22. | bacterial resistance | barley | D* |
| T4-23. | bacterial resistance | banana | D* |
| T4-24. | bacterial resistance | bean | D* |
| T4-25. | bacterial resistance | maize | |
| T4-26. | bacterial resistance | cotton | D* |
| T4-27. | bacterial resistance | cucumber | D* |
| T4-28. | bacterial resistance | grape | D*, U.S. Pat. No. 6,172,280 |
| T4-29. | bacterial resistance | oat | D* |
| T4-30. | bacterial resistance | pepper | D* |
| T4-31. | bacterial resistance | potato | D* |
| T4-32. | bacterial resistance | rape | D* |
| T4-33. | bacterial resistance | rice | D* |
| T4-34. | bacterial resistance | rye | D* |

TABLE 4-continued

| No | detailed description | plant | Literature |
|---|---|---|---|
| T4-35. | bacterial resistance | sorghum | D* |
| T4-36. | bacterial resistance | soybean | D* |
| T4-37. | bacterial resistance | sugarcane | D* |
| T4-38. | bacterial resistance | tobacco | D* |
| T4-39. | bacterial resistance | tomato | D* |
| T4-40. | bacterial resistance | wheat | D* |
| T4-41. | viral resistance | apple | C* |
| T4-42. | viral resistance | barley | C* |
| T4-43. | viral resistance | banana | C* |
| T4-44. | viral resistance | bean | C* |
| T4-45. | viral resistance | maize | C* |
| T4-46. | viral resistance | cotton | C* |
| T4-47. | viral resistance | cucumber | C* |
| T4-48. | viral resistance | oat | C* |
| T4-49. | viral resistance | pepper | C* |
| T4-50. | viral resistance | potato | C* |
| T4-51. | viral resistance | rape | C* |
| T4-52. | viral resistance | rice | C* |
| T4-53. | viral resistance | rye | C* |
| T4-54. | viral resistance | sorghum | C* |
| T4-55. | viral resistance | soybean | C* |
| T4-56. | viral resistance | sugarcane | C* |
| T4-57. | viral resistance | tobacco | C* |
| T4-58. | viral resistance | tomato | C* |
| T4-59. | viral resistance | wheat | C* |
| T4-60. | fungal resistance | potato | E* |
| T4-61. | viral resistance (PRSV) [55-1/63-1] | Carica papaya (papaya) | available, Cornell University |
| T4-62. | viral resistance (PRSV) [X17-2] | Carica papaya | available, University of Florida |
| T4-63. | viral resistance (CMV, ZYMV and WMV resistance), [CZW-3] | Cucurbita pepo (squash) | available, Asgrow (USA); Seminis Vegetable Inc. (Canada) |
| T4-64. | viral resistance (ZYMV and WMV resistance), [ZW20] | Cucurbita pepo | available, Upjohn (USA); Seminis Vegetable Inc. (Canada) |
| T4-65. | plum pox virus resistance [C5] | Prunus domestica (plum tree) | available, United States Department of Agriculture - Agricultural Research Service |

A* refers to U.S. Pat. No. 5,689,046 and U.S. Pat. No. 6,020,129.
B* refers to U.S. Pat. No. 6,706,952 and EP 1018553.
C* refers to U.S. Pat. No. 6,630,618.
D* refers to WO 1995/005731 and U.S. Pat. No. 5,648,599.
E* refers to the potato plant variety submitted for variety registration with the Community Plant Variety Office (CPVO), 3, boulevard Maréchal Foch, BP 10121, FR-49101 Angers Cedex 02, France and having the CPVO file number 20082800
Abbreviations used:
cucumber mosaiv virus = CMV,
zucchini yellow mosaic virus = ZYMV
watermelon mosaic virus =WMV) resistance,
papaya ringspot virus = PRSV In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 5. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 5, wherein the compound I is compound I-C-36.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which is listed in table 5.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to a row of table 5.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to a row of table 5.

In a most preferred embodiment, the present invention relates to a method of controlling harmful insects and/or increasing the health of plants by treating cultivated plants, parts of such plants or their locus of growth with compounds I or their mixtures, wherein the plant corresponds to a row of table 5 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 5 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 5 and the mixing partner of the compound I is fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 5 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 5 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 5 and the mixing partner of the compound I is fipronil.

In a utmost preferred embodiment, the present invention relates to a method of controlling harmful insects and/or increasing the health of plants by treating cultivated plants, parts of such plants or at their locus of growth with compounds I or their mixtures, wherein the plant is selected from T5-1, T5-3, T5-4, T5-6, T5-9, T5-10, T5-12 and T5-13 and the mixing partner of the compound I is endosulfan.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T5-1, T5-3, T5-4, T5-6, T5-9, T5-10, T5-12 and T5-13 and the mixing partner of the compound I is ethiprole.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T5-2, T5-5, T5-6, T5-9, T5-10, T5-11, T5-12 and T5-13 and the mixing partner of the compound I is fipronil.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T5-1, T5-3, T5-4, T5-6, T5-9, T5-10, T5-12 and T5-13 and the mixing partner of the compound I is endosulfan.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T5-1, T5-3, T5-4, T5-6, T5-9, T5-10, T5-12 and T5-13 and the mixing partner of the compound I is ethiprole.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T5-1, T5-3, T5-4, T5-6, T5-9, T5-10, T5-12 and T5-13 and the mixing partner of the compound I is fipronil.

TABLE 5

| No | detailed description | plant | Literature/ commercial plants |
|---|---|---|---|
| T5-1 | broad fungicide resistance | maize | A*, B*, C* |
| T5-2 | broad fungicide resistance | soybean | A*, B*, C* |
| T5-3 | asian soybean rust resistance | soybean | WO 2008017706 |
| T5-4 | resistance against anthracnose leaf bligh, anthracnose stalk rot (*colletotrichum graminicola*), diplodia ear rot, *fusarium verticilioides*, *gibberella zeae*, top dieback | maize | US2006/225152 |
| T5-5 | *fusarium* resistance | wheat | U.S. Pat. No. 6,646,184, EP 1477557 |
| T5-6 | apple scab resistance | apple | WO1999064600 |
| T5-7 | plum pox virus resistance | plum | US PP15154Ps |
| T5-8 | potato virus X resistance | potato | U.S. Pat. No. 5,968,828, EP0707069 |
| T5-9 | potato virus Y resistance | potato | EP0707069; "NewLeaf Y" (Monsanto) |
| T5-10 | potato leafroll virus resistance | potato | EP0707069, U.S. Pat. No. 5,576,202; "NewLeaf Plus" (Monsanto) |
| T5-11 | papaya ring spot virus resistance | papaya | U.S. Pat. No. 5,877,403, U.S. Pat. No. 6,046,384 |
| T5-12 | bacterial blight resistance | rice | D* |
| T5-13 | fungal resistance | potato | E* |

A* refers to U.S. Pat. No. 5,689,046 and U.S. Pat. No. 6,020,129.
B* refers to U.S. Pat. No. 6,706,952 and EP 1018553.
C* refers to U.S. Pat. No. 6,630,618.
D* refers to WO 2006/42145, U.S. Pat. No. 5,952,485, U.S. Pat. No. 5,977,434, WO 1999/09151 and WO 1996/22375.
E* refers to the potato plant variety submitted for variety registration with the Community Plant Variety Office (CPVO), 3, boulevard Maréchal Foch, BP 10121, FR-49101 Angers Cedex 02, France and having the CPVO file number 20082800.

In a further one preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which is tolerant to abiotic stress, preferably drought, high salinity, high light intensities, high UV irradiation, chemical pollution (such as high heavy metal concentration), low or high temperatures, limited supply of nutrients and population stress, most preferably drought, high salinity, low temperatures and limited supply of nitrogen.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to row of table 6.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to row of table 6.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 6. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 6, wherein the compound I is compound I-C-36.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 6 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 6 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 6 and mixture is a compound I with fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 6 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 6 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 6 and the mixing partner of the compound I is fipronil.

TABLE 6

| No | detailed description | plant | Literature |
|---|---|---|---|
| T6-1 | drought tolerance | alfalfa | A*, B*, F* |
| T6-2 | drought tolerance | barley | A*, B*, C* |
| T6-3 | drought tolerance | canola | A*, B*, F* |
| T6-4 | drought tolerance | maize (maize) | A*, B*, C*, F* |
| T6-5 | drought tolerance | cotton | A*, B*, C*, F* |
| T6-6 | drought tolerance | pomefruit | A*, B* |
| T6-7 | drought tolerance | potato | A*, B*, C* |
| T6-8 | drought tolerance | rapeseed | A*, B*, C* |
| T6-9 | drought tolerance | rice | A*, B*, C*, F* |
| T6-10 | drought tolerance | soybean | A*, B*, F* |
| T6-11 | drought tolerance | sugarbeet | A*, B* |
| T6-12 | drought tolerance | sugarcane | A*, B*, F* |
| T6-13 | drought tolerance | sunflower | A*, B* |
| T6-14 | drought tolerance | tomato | A*, B*, C* |
| T6-15 | drought tolerance | wheat | A*, B*, C*, F* |
| T6-16 | tolerance to high salinity | alfalfa | A*, B* |
| T6-17 | tolerance to high salinity | barley | A*, B* |
| T6-18 | tolerance to high salinity | canola | A*, B* |
| T6-19 | tolerance to high salinity | maize | A*, D* |
| T6-20 | tolerance to high salinity | cotton | A*, D* |
| T6-21 | tolerance to high salinity | pomefruit | A*, D* |
| T6-22 | tolerance to high salinity | potato | A*, D* |
| T6-23 | tolerance to high salinity | rapeseed | A*, D* |
| T6-24 | tolerance to high salinity | rice | A*, D*, U.S. Pat. No. 7,034,139, WO 2001/30990 |
| T6-25 | tolerance to high salinity | soybean | A*, D* |
| T6-26 | tolerance to high salinity | sugarbeet | A*, D* |
| T6-27 | tolerance to high salinity | sugarcane | A*, D* |
| T6-28 | tolerance to high salinity | sunflower | A*, D* |
| T6-29 | tolerance to high salinity | tomato | A*, D* |
| T6-30 | tolerance to high salinity | wheat | A*, D* |
| T6-31 | low temperature tolerance | alfalfa | A*, E* |
| T6-32 | low temperature tolerance | barley | A* |
| T6-33 | low temperature tolerance | canola | A* |
| T6-34 | low temperature tolerance | maize | A*, E* |
| T6-35 | low temperature tolerance | cotton | A*, E* |
| T6-36 | low temperature tolerance | pomefruit | A* |
| T6-37 | low temperature tolerance | potato | A* |
| T6-38 | low temperature tolerance | rapeseed | A*, E* |
| T6-39 | low temperature tolerance | rice | A*, E* |
| T6-40 | low temperature tolerance | soybean | A*, E* |
| T6-41 | low temperature tolerance | sugarbeet | A* |
| T6-42 | low temperature tolerance | sugarcane | A* |
| T6-43 | low temperature tolerance | sunflower | A* |
| T6-44 | low temperature tolerance | tomato | A* |
| T6-45 | low temperature tolerance | wheat | A*, E* |
| T6-46 | low nitrogen supply tolerance | alfalfa | A* |
| T6-47 | low nitrogen supply tolerance | barley | A* |
| T6-48 | low nitrogen supply tolerance | canola | A* |
| T6-49 | low nitrogen supply tolerance | maize | A* |
| T6-50 | low nitrogen supply tolerance | cotton | A* |
| T6-51 | low nitrogen supply tolerance | pomefruit | A* |
| T6-52 | low nitrogen supply tolerance | potato | A* |
| T6-53 | low nitrogen supply tolerance | rapeseed | A* |
| T6-54 | low nitrogen supply tolerance | rice | A* |
| T6-55 | low nitrogen supply tolerance | soybean | A* |
| T6-56 | low nitrogen supply tolerance | sugarbeet | A* |
| T6-57 | low nitrogen supply tolerance | sugarcane | A* |
| T6-58 | low nitrogen supply tolerance | sunflower | A* |
| T6-59 | low nitrogen supply tolerance | tomato | A* |
| T6-60 | low nitrogen supply tolerance | wheat | A* |

A* referes to WO 2000/04173, WO 2007/131699 and US 2008/0229448.
B* referes to WO 2005/48693.
C* referes to WO 2007/20001.
D* referes to U.S. Pat. No. 7,256,326.
E* referes to U.S. Pat. No. 4,731,499.
F* refers to WO 2008/002480.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which is listed in table 7.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 7. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 7, wherein the compound I is compound I-C-36.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to a row of table 7.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to a row of table 7.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 7 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 7 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 7 and the mixing partner of the compound I is fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 7 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 7 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 7 and the mixing partner of the compound I is fipronil.

In a utmost preferred embodiment, the present invention relates to a method of controlling harmful insects and/or increasing the health of plants by treating cultivated plants, parts of such plants or at their locus of growth with compounds I or their mixtures, wherein the plant is selected from T7-1, T7-3, T7-5, T7-6 and T7-8 and the mixing partner of the compound I is endosulfan.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T7-1, T7-3, T7-5, T7-6 and T7-8 and the mixing partner of the compound I is ethiprole.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T7-1, T7-3, T7-5, T7-6 and T7-8 and the mixing partner of the compound I is fipronil.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T7-1, T7-3, T7-5, T7-6 and T7-8 and the mixing partner of the compound I is endosulfan.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T7-1, T7-3, T7-5, T7-6 and T7-8 and the mixing partner of the compound I is ethiprole.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T7-1, T7-3, T7-5, T7-6 and T7-8 and the mixing partner of the compound I is fipronil.

TABLE 7

| No | detailed description | plant | Literature |
|---|---|---|---|
| T7-1 | drought tolerance | maize | A*, B*, C* |
| T7-2 | drought tolerance | canola | A*, B*, C* |
| T7-3 | drought tolerance | cotton | A*, B*, C* |
| T7-4 | drought tolerance | rapeseed | A*, B*, C* |
| T7-5 | drought tolerance | rice | A*, B*, C* |
| T7-6 | drought tolerance | soybean | A*, B* |
| T7-7 | drought tolerance | wheat | A*, B*, C* |
| T7-8 | tolerance to high salinity | rice | A*, D*, U.S. Pat. No. 7,034,139, WO 2001/30990 |
| T7-9 | tolerance to high salinity | tomato | A*, D* |
| T7-10 | low nitrogen supply tolerance | canola | A* |
| T7-11 | low nitrogen supply tolerance | maize | A* |

A* referes to WO 2000/04173, WO 2007/131699 and US 2008/0229448.
B* referes to WO 2005/48693.
C* referes to WO 2007/20001.
D* referes to U.S. Pat. No. 7,256,326.
E* referes to U.S. Pat. No. 4,731,499.

In a further one preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which shows improved maturation, preferably fruit ripening, early maturity and delayed softening.

In a more preferred embodiment, the present invention relates to a method of controlling harmful insects and/or increasing the health of cultivated plants by treating cultivated plants, parts of such plants, plant propagation materials, or at their locus of growth compounds I or their mixtures selected from, wherein the plant is a plant, which corresponds to a row of table 8.

In a more preferred embodiment, the present invention relates to a method of controlling harmful insects and/or increasing the health of cultivated plants by treating plant propagation materials, preferably seeds with compounds I or their mixtures selected from, wherein the plant corresponds to row of table 8.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 8. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 8, wherein the compound I is compound I-C-36.

In another more preferred embodiment, the present invention relates to a method of controlling harmful insects and/or increasing the health of cultivated plants by treating cultivated plants, parts of such plants or at their locus of growth with compounds I or their mixtures selected from ethiprole, fipronil, endosulfan, wherein the plant corresponds to row of table 8.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 8 and the mixing partner of the compound I is endosulfan.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 8 and the mixing partner of the compound I is endosulfan.

In a utmost preferred embodiment, the present invention relates to a method of controlling harmful insects and/or increasing the health of plants by treating cultivated plants, parts of such plants or at their locus of growth with compounds I or their mixtures, wherein the plant is T8-1 and the mixing partner of the compound I is endosulfan.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is T8-1 and the mixing partner of the compound I is endosulfan.

TABLE 8

| No | detailed description | plant/Event | Literature |
|---|---|---|---|
| T8-1 | fruit ripening | tomato | A* |
| T8-2 | fruit ripening | papaya | U.S. Pat. No. 5,767,376, U.S. Pat. No. 7,084,321 |
| T8-3 | fruit ripening | pepper | B* |
| T8-4 | fruit ripening | melon | WO1995035387 |
| T8-5 | fruit ripening | strawberry | WO1995035387 |
| T8-6 | fruit ripening | raspberry | WO1995035387 |
| T8-7 | fruit ripening | *Cucumis melo*/A, B | Agritope Inc. |
| T8-8 | fruit ripening | *Lycopersicon esculentum*/66 | Florigene Pty Ltd. |
| T8-9 | fruit ripening | *Lycopersicon esculentum*/1345-4 | DNA Plant Technology Corporation |
| T8-10 | fruit ripening | *Lycopersicon esculentum*/35 1 N | Agritope Inc. |
| T8-11 | fruit ripening | *Lycopersicon esculentum*/8338 | Monsanto Company |
| T8-12 | fruit ripening | *Lycopersicon esculentum*/B, Da, F | Zeneca Seeds |
| T8-13 | fruit ripening | *Lycopersicon esculentum*/FLAVR SAVR | Calgene Inc. |
| T8-14 | delayed ripening | *Cucumis melo*/A, B | available, Agritope Inc. |
| T8-15 | delayed sofenting | *Lycopersicon esculentum*/B, Da, F | available, Zeneca Seeds |
| T8-16 | delayed sofenting | *Lycopersicon esculentum*/FLAVR SAVR | available, Calgene Inc. |
| T8-17 | FRA | *Lycopersicon esculentum*/8338 | available, Monsanto Company |
| T8-18 | FRA | *Lycopersicon esculentum*/1345-4 | available, DNA plant technology corporation |
| T8-19 | FRA | *Lycopersicon esculentum*/35 1 N | available, Agritopoe Inc. |

*A U.S. Pat. No. 5,952,546, U.S. Pat. No. 5,512,466, WO1997/001952, WO1995035387 wo1992/008798, Plant Cell. 1989; 1(1): 53-63.
*B Plant Molecular Biology, Volume 50, 2002, Number 3
Abbreviations:
FRA = fruit ripening alteration
Lycopersicon *esculentum* = tomato;
*Cucumis melo* (melon)

In a further one preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a transgenic plant, which has modified content in comparison to wildtype plants, preferably increased vitamin content, altered oil content, nicotine reduction, increased or reduced amino acid content, protein alteration, modified starch content, enzyme alteration, altered flavonoid content and reduced allergens (hypoallergenic plants), most preferably increased vitamin content, altered oil content, nicotine reduction, increased lysine content, amylase alteration, amylopectin alteration.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 9. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 9, wherein the compound I is compound I-C-36.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which corresponds to a row of table 9.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to a row of table 9.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to a row of table 9.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 9 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 9 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 9 and the mixing partner of the compound I is fipronil.

In another most preferred embodiment, the present invention relates to a method of controlling harmful insects and/or increasing the health of plants by treating cultivated plants, parts of such plants or at their locus of growth with compounds I or their mixtures, wherein the plant corresponds to row T9-48 of table 9 and the mixture partner is selected from the group consisting of endosulfan, ethiprole and fipronil.

In a most preferred embodiment, the present invention relates to a method of controlling harmful insects and/or increasing the health of cultivated plants by treating plant propagation materials, preferably seeds of cultivated plants of cultivated crops with compounds I or their mixtures, wherein the plant corresponds to a row of table 9 and the mixing partner of the compound I is endosulfan.

In another most preferred embodiment, the present invention relates to a method of controlling harmful insects and/or increasing the health of cultivated plants by treating plant propagation materials, preferably seeds of cultivated plants of cultivated crops with compounds I or their mixtures, wherein the plant corresponds to a row of table 9 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 9 and the mixing partner of the compound I is fipronil.

TABLE 9

| No | detailed description | plant* | Literature/ commercial plants |
| --- | --- | --- | --- |
| T9-1 | increased Vitamin A content | tomato | U.S. Pat. No. 6,797,498 |
| T9-2 | increased Vitamin A content | rice | "Golden rice". Science 287, 303-305. |
| T9-3 | increased Vitamin E content | canola | U.S. Pat. No. 7,348,167, US 11/170711 (application) |
| T9-4 | increased Vitamin E content | barley | US 11/170,711 (application) |
| T9-5 | increased Vitamin E content | maize | US 11/170,711 (application) |
| T9-6 | increased Vitamin E content | rice | US 11/170,711 (application) |
| T9-7 | increased Vitamin E content | rye | US 11/170,711 (application) |
| T9-8 | increased Vitamin E content | potato | U.S. Pat. No. 7,348,167 |
| T9-9 | increased Vitamin E content | soybean | U.S. Pat. No. 7,348,167 |
| T9-10 | increased Vitamin E content | sunflower | U.S. Pat. No. 7,348,167 |
| T9-11 | increased Vitamin E content | wheat | US 11/170711 (application) |
| T9-12 | decreased nicotine content | tobacco | US 2006/0185684, WO 2005/000352, WO 2007/064636 |
| T9-13 | amylase alteration | maize | "AmylaseTM" |
| T9-14 | amylopectin alteration | potato | U.S. Pat. No. 6,784,338, WO 1997/044471 |
| T9-15 | amylopectin alteration | maize | US 20070261136 |
| T9-16 | modified oil content | balsam pear | A* |
| T9-17 | modified oil content | canola | U.S. Pat. No. 5,850,026, U.S. Pat. No. 6,441,278, U.S. Pat. No. 5,723,761 |
| T9-18 | modified oil content | catalpa | A* |
| T9-19 | modified oil content | cattail | A* |
| T9-20 | modified oil content | maize | A*, US 2006/0075515, U.S. Pat. No. 7,294,759 |
| T9-21 | modified oil content | cotton | U.S. Pat. No. 6,974,898, WO 2001/079499 |
| T9-22 | modified oil content | grape | A* |
| T9-23 | modified oil content | rapeseed | U.S. Pat. No. 5,723,761 |
| T9-24 | modified oil content | rice | A* |
| T9-25 | modified oil content | soybean | A*, U.S. Pat. No. 6,380,462, U.S. Pat. No. 6,365,802, "Vistive II", „Vistsive III" |
| T9-26 | modified oil content | safflower | U.S. Pat. No. 6,084,164 |
| T9-27 | modified oil content | sunflower | A*, U.S. Pat. No. 6,084,164 |
| T9-28 | modified oil content | wheat | A* |
| T9-29 | modified oil content | vernonia | A* |
| T9-30 | hypoallergenic modification | soybean | U.S. Pat. No. 6,864,362 |
| T9-31 | increased lysine content | canola | Bio/Technology 13, 577-582 (1995) |
| T9-32 | increased lysine content | maize | „Mavera high value corn" |

TABLE 9-continued

| No | detailed description | plant* | Literature/ commercial plants |
|---|---|---|---|
| T9-33 | increased lysine content | soybean | Bio/Technology 13, 577-582 (1995) |
| T9-34 | altered starch content | maize | U.S. Pat. No. 7,317,146, EP 1105511 |
| T9-35 | altered starch content | rice | U.S. Pat. No. 7,317,146, EP 1105511 |
| T9-36 | altered starch content | wheat | EP 1105511 |
| T9-37 | altered starch content | barley | EP 1105511 |
| T9-38 | altered starch content | rye | EP 1105511 |
| T9-39 | altered starch content | oat | EP 1105511 |
| T9-40 | altered fllavonoid content | alfalfa | WO 2000/04175 |
| T9-41 | altered fllavonoid content | apple | WO 2000/04175 |
| T9-42 | altered fllavonoid content | bean | WO 2000/04175 |
| T9-43 | altered fllavonoid content | maize | WO 2000/04175 |
| T9-44 | altered fllavonoid content | grape | WO 2000/04175 |
| T9-45 | altered fllavonoid content | pea | WO 2000/04175 |
| T9-46 | altered fllavonoid content | tomato | WO 2000/04175 |
| T9-47 | increased protein content | soybean | „Mavera high value soybeans" |
| T9-48 | amylopectin alteration | potato | B* |
| T9-49 | altered starch content | potato | C* |
| T9-50 | oil profile alteration/ 23-18-17, 23-198 | Brassica napus | av.**), Monsanto Company |
| T9-51 | oil profile alteration/ 46A12, 46A16 | Brassica napus | av., Pioneer Hi-Bred International Inc. |
| T9-52 | oleic acid and linolenic acid profile alteration/ 45A37, 46A40 | Brassica napus | av., Pioneer Hi-Bred International Inc. |
| T9-53 | increased shelf-life/ Carnation Moonshadow 2 | Dianthus caryophyllus | av., Florigene Ltd |
| T9-54 | linolenic acid profile alteration/OT96-15 | Glycine max L. | av., Agriculture & Agri-Food Canada |
| T9-55 | oil profile alteration/ G94-1, G94-19, G168 | Glycine max L. | av., DuPont Canada Agricultural Products |
| T9-56 | increased oleic acid content/DP-305423 | Glycine max L. | av., Pioneer Hi-Bred International Inc. |
| T9-57 | Nicotine reduction/ Vector 21-41 | Nicotiana tabacum L. | av., Vector Tobacco Inc. |
| T9-58 | starch with increased amylopectin content/ EH92-527-1 | Solanum tuberosum L. | av., BASF Plant Science |
| T9-59 | enhanced lysin level/ LY038 | Zea mays L. | av., Monsanto Company |
| T9-60 | modified amylase content/Event 3272 | Zea mays L. | av., Syngenta Seeds, Inc. |

A* refers to U.S. Pat. No. 7,294,759 and U.S. Pat. No. 7,157,621.
B* refers to the potato plant variety submitted for variety registration with the Community Plant Variety Office (CPVO), 3, boulevard Maréchal Foch, BP 10121, FR-49101 Angers Cedex 02, France and having the CPVO file number 20031520.
C* refers to the potato plant variety submitted for variety registration with the Community Plant Variety Office (CPVO), 3, boulevard Maréchal Foch, BP 10121, FR-49101 Angers Cedex 02, France and having the CPVO file number 20082534.
*) Brassica napus (Argentine canola), Glycine max L. (soybean), Nicotiana tabacum L. (tobacco), Dianthus caryophyllus (carnation), Solanum tuberosum L. (potato), Zea mays L. (corn, maize)
**) available In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which corresponds to a row of table 10.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 10. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 10, wherein the compound I is compound I-C-36.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to row of table 10.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to row of table 10.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 10 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 10 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 10 and the mixing partner of the compound I is fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 10 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 10 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 10 and the mixing partner of the compound I is fipronil.

In a utmost preferred embodiment, the present invention relates to a method of controlling harmful insects and/or increasing the health of plants by treating cultivated plants, parts of such plants or at their locus of growth with compounds I or their mixtures, wherein the plant is selected from T10-1, T10-2, T10-5, T10-6, T10-10, T10-11 and T10-12 and the mixing partner of the compound I is endosulfan.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T10-1, T10-2, T10-5, T10-6, T10-10, T10-11 and T10-12 and the mixing partner of the compound I is ethiprole.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T10-1, T10-2, T10-5, T10-6, T10-10, T10-11 and T10-12 and the mixing partner of the compound I is fipronil.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T10-1, T10-2, T10-5, T10-6, T10-10, T10-11 and T10-12 and the mixing partner of the compound I is endosulfan.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T10-1, T10-2, T10-5, T10-6, T10-10, T10-11 and T10-12 and the mixing partner of the compound I is ethiprole.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T10-1, T10-2, T10-5, T10-6, T10-10, T10-11 and T10-12 and the mixing partner of the compound I is fipronil.

TABLE 10

| No | detailed description | plant | Literature/commercial plants |
|---|---|---|---|
| T10-1 | increased Vitamin A content | tomato | U.S. Pat. No. 6,797,498 |
| T10-2 | increased Vitamin A content | rice | "Golden rice". Science 287, 303-305. |
| T10-3 | increased Vitamin E content | canola | U.S. Pat. No. 7,348,167, US 11/170711 (application) |
| T10-4 | decreased nicotine content | tobacco | US 20060185684, WO 2005/000352, WO 2007/064636 |
| T10-5 | amylase alteration | maize | "AmylaseTM" |
| T10-6 | amylopectin alteration | potato | U.S. Pat. No. 6,784,338, WO 1997/044471 |
| T10-7 | modified oil content | canola | U.S. Pat. No. 5,850,026, U.S. Pat. No. 6,441,278, U.S. Pat. No. 5,723,761 |
| T10-8 | modified oil content | rapeseed | U.S. Pat. No. 5,723,761 |
| T10-9 | modified oil content | safflower | U.S. Pat. No. 6,084,164 |
| T10-10 | modified oil content | soybean | A*, U.S. Pat. No. 6,380,462, U.S. Pat. No. 6,365,802; "Vistive II", „Vistsive III" |
| T10-11 | increased protein content | soybean | „Mavera high value soybeans" |
| T10-12 | increased lysine content | maize | „Mavera high value corn" |

A* refers to U.S. Pat. No. 7,294,759 and U.S. Pat. No. 7,157,621.

In a further preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which shows improved nutrient utilization, preferably the uptake, assimilation and metabolism of nitrogen and phosphorous.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which corresponds to a row of table 11.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to a row of table 11.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to a row of table 11.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 11. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 11, wherein the compound I is compound I-C-36.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 11 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 11 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 11 and the mixing partner of the compound I is fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 11 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 11 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 11 and the mixing partner of the compound I is fipronil.

In a utmost preferred embodiment, the present invention relates to a method of controlling harmful insects and/or increasing the health of plants by treating cultivated plants, parts of such plants or at their locus of growth with compounds I or their mixtures, wherein the plant is selected from T11-4, T11-5, T11-8 and T11-9 and the mixing partner of the compound I is endosulfan.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T11-4, T11-5, T11-8 and T11-9 and the mixing partner of the compound I is ethiprole.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T11-4, T11-5, T11-8 and T11-9 and the mixing partner of the compound I is fipronil.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T11-4, T11-5, T11-8 and T11-9 and the mixing partner of the compound I is endosulfan.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T11-4, T11-5, T11-8 and T11-9 and the mixing partner of the compound I is ethiprole.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T11-4, T11-5, T11-8 and T11-9 and the mixing partner of the compound I is fipronil.

TABLE 11

| No | detailed description | plant | Literature |
|---|---|---|---|
| T11-1 | nitrogen utilization (D*) | alfalfa | A*, B*, F* |
| T11-2 | nitrogen utilization (D*) | barley | A*, B* |
| T11-3 | nitrogen utilization (D*) | canola | A*, B*, F* |
| T11-4 | nitrogen utilization (D*) | maize | A*, B*, F* |
| T11-5 | nitrogen utilization (D*) | cotton | B*, F* |
| T11-6 | nitrogen utilization (D*) | potato | B*, E*, F* |
| T11-7 | nitrogen utilization (D*) | rapeseed | B* |
| T11-8 | nitrogen utilization (D*) | rice | A*, B*, F* |
| T11-9 | nitrogen utilization (D*) | soybean | A*, B*, F* |
| T11-10 | nitrogen utilization (D*) | sugarbeet | B*, E* |
| T11-11 | nitrogen utilization (D*) | sugarcane | B*, E* |
| T11-12 | nitrogen utilization (D*) | sunflower | B* |
| T11-13 | nitrogen utilization (D*) | tobacco | E*, F* |
| T11-14 | nitrogen utilization (D*) | tomato | B*, F* |
| T11-15 | nitrogen utilization (D*) | wheat | A*, B*, F* |
| T11-16 | phosphorous utilization (D*) | alfalfa | C* |
| T11-17 | phosphorous utilization (D*) | barley | C* |
| T11-18 | phosphorous utilization (D*) | canola | C* |
| T11-19 | phosphorous utilization (D*) | maize | C* |
| T11-20 | phosphorous utilization (D*) | cotton | C* |
| T11-21 | phosphorous utilization (D*) | potato | U.S. Pat. No. 7,417,181, C* |
| T11-22 | phosphorous utilization (D*) | rapeseed | C* |
| T11-23 | phosphorous utilization (D*) | rice | C* |
| T11-24 | phosphorous utilization (D*) | soybean | C* |
| T11-25 | phosphorous utilization (D*) | sugarbeet | C* |
| T11-26 | phosphorous utilization (D*) | sugarcane | C* |
| T11-27 | phosphorous utilization (D*) | sunflower | C* |
| T11-28 | phosphorous utilization (D*) | tomato | U.S. Pat. No. 7,417,181, C* |
| T11-29 | phosphorous utilization (D*) | wheat | C* |
| T11-30 | low nitrogen supply tolerance | canola | G* |
| T11-31 | low nitrogen supply tolerance | maize | G* |

A* refers to U.S. Pat. No. 6,084,153.
B* referes to U.S. Pat. No. 5,955,651 and U.S. Pat. No. 6,864,405.
C* refers to US 10/898,322 (application).
D* the term "utilization" refers to the improved nutrient uptake, assimilation or metabolism.
E* refers to WO 1995/009911.
F* refers to WO 1997/030163.
G* referes to WO 2000/04173, WO 2007/131699 and US 2008/0229448

In a further one preferred embodiment, the present invention relates to a method of controlling harmful insects and/or increasing the health of plants by treating cultivated plants parts of such plants, plant propagation materials, or at their locus of growth with a with a compound I according to this invention or their mixtures, wherein the plant is a plant selected from the group consisting of cotton, fiber plants (e.g. palms) and trees, preferably a cotton plant, which produces higher quality fiber, preferably improved micronaire of the fiber, increased strength, improved staple length, improved length unifomity and color of the fibers. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a more preferred embodiment, the present invention relates to a method of controlling harmful insects and/or increasing the health of cotton plants by treating cultivated plants parts of such plants, plant propagation materials, or at their locus of growth with compounds I or their mixtures as exemplified in embodiments E2 and E3, or in which the mixture partner compound II is selected from endosulfan, ethiprole and fipronil.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 12. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 12, wherein the compound I is compound I-C-36.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant, which is listed in table 12.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to row of table 12.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to row of table 12.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 12 and the mixing partner of the compound I is endosulfan.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 12 and the mixing partner of the compound I is endosulfan.

TABLE 12

| No | detailed description | plant | Literature |
|---|---|---|---|
| T12-1 | male sterility | canola | U.S. Pat. No. 6,720,481 |
| T12-2 | male sterility | maize | A*, B*, C* |
| T12-3 | male sterility | rice | B*, EP1135982 |
| T12-4 | male sterility | soybean | B*, C*, WO1996040949 |

TABLE 12-continued

| No | detailed description | plant | Literature |
|---|---|---|---|
| T12-5 | male sterility | sunflower | C* |
| T12-6 | male sterility | tomato | U.S. Pat. No. 7,345,222 |
| T12-7 | male sterility | wheat | B* |
| T12-8 | male sterility2)/MS1, RF1 =>PGS1 | B. napus 4) | AVC 1) |
| T12-9 | male sterility2)/MS1, RF2 =>PGS2 | B. napus 4) | AVC 1) |
| T12-10 | male sterility2)/MS8xRF3 | B. napus 4) | BCS 5) |
| T12-11 | male sterility3)/PH YL4, PHY35 | B. napus 4) | AVC 1) |
| T12-12 | male sterility3)/PHY36 | B. napus 4) | AVC 1) |

A* refers to U.S. Pat. No. 6,281,348, U.S. Pat. No. 6,399,856, U.S. Pat. No. 7,230,168, U.S. Pat. No. 6,072,102./
B* refers to WO2001062889.
C* refers to WO1996040949.
1) Aventis Crop Science (formerly Plant Genetic Systems)/5) Bayer CropScience (Aventis CropScience(AgrEvo)/
2) Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*.
3) Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*.
4) *Brassica napus* (Argentine Canola)

In a further one preferred embodiment, the present invention relates to a method of controlling harmful insects and/or increasing the health of cultivated plants by treating cultivated plants, parts of such plants, plant propagation materials, or at their locus of growth with with a compound I according to this invention or their mixtures as exemplified in embodiments E2 and E3, or in which the mixture partner compound II is selected from endosulfan, ethiprole and fipronil, wherein the plant is resistant to antibiotics, more referably resistant to kanamycin, neomycin and ampicillin, most preferably resistant to kanamycin. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a more preferred embodiment, the present invention relates to a method of controlling harmful insects and/or increasing the health of cultivated plants by treating cultivated plants, parts of such plants, plant propagation materials, or at their locus of growth with compounds I or their mixtures as exemplified in embodiments E2 and E3, or in which the mixture partner compound II is selected from endosulfan, ethiprole and fipronil, wherein the plant is a plant corresponding to a row of table 13.

In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to a row of table 13.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to a row of table 13.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 13. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 13, wherein the compound I is compound I-C-36.

In a most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 13 and the mixing partner of the compound I is endosulfan.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 13 and the mixing partner of the compound I is ethiprole.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 13 and the mixing partner of the compound I is fipronil.

In a most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 13 and the mixing partner of the compound I is endosulfan.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 13 and the mixing partner of the compound I is ethiprole.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 13 and the mixing partner of the compound I is fipronil.

In a utmost preferred embodiment, the present invention relates to a method of controlling harmful insects and/or increasing the health of plants by treating cultivated plants, parts of such plants or at their locus of growth with compounds I or their mixtures, wherein the plant is T13-2, T13-4 and the mixing partner of the compound I is endosulfan.

In another utmost preferred embodiment, the present invention relates to a method of controlling harmful insects and/or increasing the health of plants by treating cultivated plants, parts of such plants or at their locus of growth with compounds I or their mixtures, wherein the plant is T13-2, T13-4 and the mixing partner of the compound I is ethiprole.

In another utmost preferred embodiment, the present invention relates to a method of controlling harmful insects and/or increasing the health of plants by treating cultivated plants, parts of such plants or at their locus of growth with compounds I or their mixtures, wherein the plant is T13-2, T13-4 and the mixing partner of the compound I is fipronil.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is T13-2, T13-4 and the mixing partner of the compound I is endosulfan.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is T13-2, T13-4 and the mixing partner of the compound I is ethiprole.

In another utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is T13-2, T13-4 and the mixing partner of the compound I is fipronil.

TABLE 13

| No | detailed description | plant | Literature/commercial plants |
|---|---|---|---|
| T13-1 | kanamycin resistance | canola | A* |
| T13-2 | kanamycin resistance | cotton | A* |
| T13-3 | kanamycin resistance | flax | A* |
| T13-4 | kanamycin resistance | maize | A* |
| T13-5 | kanamycin resistance | oilseed rape | A* |
| T13-6 | kanamycin resistance | potato | A* |
| T13-7 | kanamycin resistance | rape seed | A* |
| T13-8 | kanamycin resistance | sugar beet | A* |
| T13-9 | kanamycin resistance | tomato | A*, B* |

A* refers to Plant Cell Reports, 20, 2001, 610-615. Trends in Plant Science, 11, 2006, 317-319. Plant Molecular Biology, 37, 1998, 287-296. Mol Gen Genet., 257, 1998, 606-13.
B* refers to Plant Cell Reports, 6, 1987, 333-336.

In a further preferred embodiment, the present invention relates to a method of controlling harmful insects and/or increasing the health of cultivated plants by treating cultivated plants, parts of such plants, plant propagation materials, or at their locus of growth with a with a compound I according to this invention or their mixtures, wherein the plant has the trait of improved fiber quality.

In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a more preferred embodiment, the present invention relates to a method of controlling harmful insects and/or increasing the health of cultivated plants by treating cultivated plants, parts of such plants, plant propagation materials, or at their locus of growth with a compound I or their mixtures as exemplified in embodiments E2 and E3, or in which the mixture partner compound II is selected from endosulfan, ethiprole and fipronil, wherein the plant is a cotton plant comprising the DP 104 B2RF event ("DP 104 B2RF—A new early maturing B2RF variety" presented at 2008 Beltwide Cotton Conferences by Tom R. Speed, Richard Sheetz, Doug Shoemaker, Monsanto/Delta and Pine Land, see www.monsanto.com/pdf/beltwide_08/dp104b2rf_doc.pdf.

In a further more preferred embodiment, the present invention relates to a method of controlling harmful insects and/or increasing the health of cultivated plants by treating cultivated plants, parts of such plants, plant propagation materials, or at their locus of growth with a compound I and a mixture partner selected from endosulfan, ethiprole and fipronil, wherein the plant is a transgenic plant, which has two traits stacked, more preferably two or more traits selected from the group consisting of herbicide tolerance, insect resistance, fungal resistance, viral resistance, bacterial resistance, stress tolerance, maturation alteration, content modification and modified nutrient uptake, most preferably the combination of herbicide tolerance and insect resistance, two herbicide tolerances, herbicide tolerance and stress tolerance, herbicide tolerance and modified content, two herbicide tolerances and insect resistance, herbicide tolerance, insect resistance and stress tolerance, herbicide tolerance, insect resistance and modified content. In a more preferred embodiment, the present invention relates to a method of controlling harmful insects and/or increasing the health of cultivated plants by treating plant propagation materials, preferably seeds with compounds I or their mixtures as exemplified in embodiments E2 and E3, or in which the mixture partner compound II is selected from endosulfan, ethiprole and fipronil, wherein the plant corresponds to a row of table 14.

In another more preferred embodiment, the present invention relates to a method of controlling harmful insects and/or increasing the health of cultivated plants by treating cultivated plants, parts of such plants or their locus of growth with a compound I according to this invention, wherein the plant corresponds to a row of table 14. In this embodiment the compound I is preferably selected from a compound of embodiment A, also preferably a compound of embodiment B, also preferably a compound of embodiment C; more preferably a compound as defined in Table ABC, more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-A-1.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-A-28.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-B-115.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-B-131.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-B-132.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-C-35.

In a most preferred embodiment, the present invention relates to a method of controlling harmful insects and/or increasing the health of plants by treating cultivated plants, parts of such plants or their locus of growth with compounds I, wherein the plant corresponds to a row of table 14, wherein the compound I is compound I-C-36.

In another more preferred embodiment, the present invention relates to a method of controlling harmful insects and/or increasing the health of cultivated plants by treating cultivated plants, parts of such plants or at their locus of growth with compounds I or their mixtures as exemplified in embodiments E2 and E3, or in which the mixture partner compound II is selected from endosulfan, ethiprole and fipronil, wherein the plant corresponds to a row of table 14.

In another most preferred embodiment, the present invention relates to a method of controlling harmful insects and/or increasing the health of plants by treating cultivated plants, parts of such plants or at their locus of growth with compounds I or their mixtures, wherein the plant corresponds to a row of table 14 and the mixing partner of the compound I is fipronil.

In another most preferred embodiment, the present invention relates to a method of controlling harmful insects and/or increasing the health of plants by treating plant propagation materials, preferably seeds of cultivated plants of cultivated crops with compounds I or their mixtures, wherein the plant corresponds to a row of table 14 and the mixing partner of the compound I is fipronil.

In another utmost preferred embodiment, the present invention relates to a method of controlling harmful insects and/or increasing the health of plants by treating cultivated plants, parts of such plants or at their locus of growth with compounds I or their mixtures, wherein the plant is selected from T14-1, T14-2, T14-3, T14-4, T14-5, T14-6, T14-7, T14-8, T14-9, T14-10, T14-11, T14-12, T14-13, T14-14, T14-15, T14-17, T14-23, T14-24, T14-25, T14-26, T14-31, T14-36 and T14-37 and the mixing partner of the compound I is fipronil.

In a utmost preferred embodiment, the present invention relates to a method of controlling harmful insects and/or increasing the health of plants by treating plant propagation materials, preferably seeds of cultivated plants of cultivated crops with compounds I or their mixtures, wherein the plant is selected from T14-1, T14-2, T14-3, T14-4, T14-5, T14-6, T14-7, T14-8, T14-9, T14-10, T14-11, T14-12, T14-13, T14-14, T14-15, T14-17, T14-23, T14-24, T14-25, T14-26, T14-31, T14-36 and T14-37 and the mixing partner of the compound I is endosulfan.

TABLE 14

| No | detailed description/Event | plant | Literature/commercial plants |
| --- | --- | --- | --- |
| T14-1 | corn borer resistance + glyphosate tolerance | maize | "YieldGard Roundup Ready", YieldGard Roundup Ready 2" (Monsanto) |
| T14-2 | corn borer resistance + glufosinate tolerance | maize | "Agrisure CB/LL" (Syntenta) |
| T14-3 | glyphosate tolerance + corn rootworm resistance | maize | "Yield Gard VT Rootworm/RR2" |
| T14-4 | glyphosate tolerance + corn rootworm/corn borer resistance | maize | "Yield Gard VT Triple" |
| T14-5 | glufosinate tolerance + LPn resistance (Cry1F; western bean cutworm, corn borer, black cutworm, fall armyworm resistance) | maize | "Herculex I" |
| T14-6 | glyphosate tolerance + corn rootworm resistance | maize | "YieldGard Corn Rootworm/Roundup Ready 2" (Monsanto) |
| T14-7 | glyphosate tolerance + gluphosinate tolerance + LPn resistance (Cry1F; western bean cutworm, corn borer, black cutworm, fall armyworm resistance) | maize | "Herculex I/Roundup Ready 2"; |
| T14-8 | glyphosate tolerance + corn rootworm resistance + corn borer resistance | maize | "YieldGard Plus/Roundup Ready 2" (Monsanto) |
| T14-9 | gluphosinate tolerance + LPn resistance (Cry3A; western corn rootworm, northern corn rootworm, Mexican corn rootworm resistance) | maize | "Agrisure GT/RW" (Syngenta) |
| T14-10 | glyphosate tolerance + gluphosinate tolerance + corn borer resistance | maize | "Agrisure GT/CB/LL" (Syngenta) |
| T14-11 | glufosinate tolerance + LPn resistance (Cry34/35Ab1; western corn rootworm, northern corn rootworm, Mexican corn rootworm resistance) | maize | "Herculex RW" (Dow, Pioneer) |
| T14-12 | glufosinate tolerance + LPn resistance (Cry1F + Cry34/35Ab1; western corn rootworm, northern corn rootworm, Mecxican corn rootworm, western bean cutworm, corn borer, black cutworm, fall armyworm resistance) | maize | "Herculex Xtra" (Dow, Pioneer) |
| T14-13 | glyphosate tolerance + glufosinate tolerance + corn borer resistance + corn rootworm resistance | maize | „Herculex Quad-Stack" |
| T14-14 | glyphosate tolerance + corn rootworm resistance | maize | "Yield Gard VT Rootworm/RR2" |
| T14-15 | glufosinate tolerance + corn borer resistance (Cry1Ab) + LPn resistance 3) | maize | "Agrisure CB/LL/RW" (Syngenta) |

TABLE 14-continued

| No | detailed description/Event | plant | Literature/commercial plants |
|---|---|---|---|
| T14-16 | glyphosate tolerance + corn borer resistance (Cry1Ab) + LPn resistance 3) | maize | "Agrisure 3000GT" (Syngenta) |
| T14-17 | glyphosate tolerance + resistance to corn borer and corn rootworm + high lysine content | maize | „Mavera high-value corn" (Monsanto) |
| T14-18 | glyphosate tolerance + ALS herbicide tolerance (F*) | soy-bean | "Optimum GAT" (DuPont, Pioneer) |
| T14-19 | glyphosate tolerance + LP resistance (Bt) | soy-bean | A*, U.S. Pat. No. 7,432,421 |
| T14-20 | glyphosate tolerance + Dicamba tolerance | soy-bean | A*, U.S. Pat. No. 7,105,724 |
| T14-21 | glyphosate tolerance + modified oil content | soy-bean | A*, G* |
| T14-22 | glufosinate tolerance + modified oil content | soy-bean | G*, I* |
| T14-23 | glyphosate tolerance + dicamba tolerance | cotton | A*, U.S. Pat. No. 7,105,724, WO2008051633 |
| T14-24 | glufosinate tolerance + LPn resistance | cotton | D*, U.S. Pat. No. 5,646,024, U.S. Pat. No. 5,561,236 |
| T14-25 | glyphosate tolerance + LPn resistance | cotton | A*, D* |
| T14-26 | glufosinate tolerance + dicamba tolerance | cotton | U.S. Pat. No. 5,646,024, U.S. Pat. No. 5,561,236, U.S. Pat. No. 7,105,724, WO2008051633 |
| T14-27 | glyphosate tolerance + improved fiber quality | cotton | A*, E* |
| T14-28 | glufosinate tolerance + improved fiber tolerance | cotton | E*, U.S. Pat. No. 5,646,024, U.S. Pat. No. 5,561,236 |
| T14-29 | glyphosate tolerance + drought tolerance | cotton | A*, C* |
| T14-30 | glyphosate tolerance + dicamba tolerance + drought tolerance | cotton | A*, C*, U.S. Pat. No. 7,105,724, WO 2008/051633 |
| T14-31 | glufosinate tolerance + insect resistance (tobacco budworm, cotton bollworm, fall armyworm, beet armyworm, cabbage looper, soybean lopper, pink bollworm resistance) | cotton | D*, U.S. Pat. No. 5,646,024, U.S. Pat. No. 5,561,236 |
| T14-32 | glyphosate tolerance + modified oil content | canola | A*, U.S. Pat. No. 5,850,026, U.S. Pat. No. 6,441,278, U.S. Pat. No. 5,723,761, WO 2005/033319 |
| T14-33 | glufosinate tolerance + modified oil content | canola | U.S. Pat. No. 5,646,024, U.S. Pat. No. 5,561,236, U.S. Pat. No. 5,850,026, U.S. Pat. No. 6,441,278, U.S. Pat. No. 5,723,761, WO 2005/033319 |
| T14-34 | glyphosate tolerance + insect resistance | canola | D*, A* |
| T14-35 | glufosinate tolerance + insect resistance | canola | D*, U.S. Pat. No. 5,646,024, U.S. Pat. No. 5,561,236 |
| T14-36 | IMI tolerance + Coleoptera resistance | rice | B*, WO 2001/021821 |
| T14-37 | IMI tolerance + LP resistance | rice | B*, WO 2001/021821 |
| T14-38 | IMI tolerance + modified oil content | sun-flower | Tan et. al, Pest Manag. Sci 61, 246-257 (2005). |
| T14-39 | Coleoptera resistance, + Kanamycin resistance | potato | H* |
| T14-40 | Coleoptera resistance, + Kanamycin resistance + potato leaf roll virus resistance | potato | H* |
| T14-41 | Coleoptera resistance, + Kanamycin resistance + potato leaf roll virus resistance | potato | H* |
| T14-42 | Glyphosate tolerance and ALH-inhibitor tolerance/DP356043 | Glycine max L. | available, Pioneer Hi-Bred International Inc. |
| T14-43 | Glyphosate tolerance and ALS-inhibitor/Event 98140 tolerance | Zea mays L. | available, Pioneer Hi-Bred International Inc. |
| T14-44 | LP resistance and enhanced lysine content/MON-00810-6 x LY038 | Zea mays L. | available, Monsanto Company |
| T14-45 | Corn root worm resistance and EPC/MON863 x MON810 (MON-00863-5, MON-00810-6)resistance | Zea mays L. | available, Monsanto Company |
| T14-46 | EPC resistance and enhanced lysine level/MON810 x LY038 | Zea mays L. | available, Monsanto Company |
| T14-47 | Glyphosate tolerance and LPn resistance/MON-00531-6 x MON-01445-2 | Gossypium hirsutum L. (cotton) | available, Monsanto Company |

TABLE 14-continued

| No | detailed description/Event | plant | Literature/commercial plants |
|---|---|---|---|
| T14-48 | Glufosinate ammonium tolerance and LPn resistance/LLCotton25 x MON15985 | Gossypium hirsutum L. (cotton) | available, Bayer CropScience (Aventis CropScience(AgrEvo)) |
| T14-49 | Glyphosate tolerance and LPn resistance/DAS-21023-5 x DAS-24236-5 x MON88913 (DAS-24236-5, DAS-21023-5, MON-88913-8) | Gossypium hirsutum L. (cotton) | available, DOW AgroSciences LLC and Pioneer Hi-Bred International Inc. |
| T14-50 | Glyphosate tolerance and LPn resistance/MON15985 x MON88913 (MON-15985-7, MON-88913-8) | Gossypium hirsutum L. (cotton) | available, Monsanto Company |
| T14-51 | Glyphosate tolerance and LPn resistance/MON-15985-7 x MON-01445-2 | Gossypium hirsutum L. (cotton) | available, Monsanto Company |
| T14-52 | Oxynil tolerance and LPn resistance/31807/31808 | Gossypium hirsutum L. (cotton) | available, Calgene Inc. |
| T14-53 | Glyphosate tolerance and LPn resistance/DAS-21023-5 x DAS-24236-5 x MON-01445-2 | Gossypium hirsutum L. (cotton) | available, DOW AgroSciences LLC |
| T14-54 | Glufosinate tolerance and Coleoptera and LP resistance/TC1507 x DAS-59122-7 (DAS-01507-1, DAS-59122-7) | Zea mays L. | available, DOW AgroSciences LLC and Pioneer Hi-Bred International Inc. |
| T14-55 | Glyphosate tolerance and Coleoptera and LP resistance/MON810 x MON88017 | Zea mays L. | available, Monsanto Company |
| T14-56 | Glyphosate tolerance and Coleoptera and LP resistance/MON89034 x MON88017 (MON-89034-3, MON-88017-3) | Zea mays L. | available, Monsanto Company |
| T14-57 | Glyphosate tolerance and Glufosinate ammonium tolerance and Coleoptera and LP resistance/DAS-59122-7 x TC1507 x NK603 | Zea mays L. | available, DOW AgroSciences LLC and Pioneer Hi-Bred International Inc. |
| T14-58 | Glufosinate ammonium tolerance and Coleoptera resistance/BT11 x MIR604 (SYN-BT011-1, SYN-IR604-5) | Zea mays L. | available, Syngenta Seeds, Inc. |
| T14-59 | Glyphosate tolerance and Coleoptera resistance/DAS-59122-7 x NK603 | Zea mays L. | available, DOW AgroSciences LLC and Pioneer Hi-Bred International Inc. |
| T14-60 | Glyphosate tolerance and Coleoptera resistance/MIR604 x GA21 | Zea mays L. | available, Syngenta Seeds, Inc. |
| T14-61 | Glyphosate tolerance and Coleoptera resistance/MON863 x NK603 (MON-00863-5, MON-00603-6 | Zea mays L. | available, Monsanto Company |
| T14-62 | Glyphosate tolerance and Coleoptera resistance and LP resistance/ MON863 x MON810 x NK603 | Zea mays L. | available, Monsanto Company |
| T14-63 | Glufosinate ammonium tolerance and Corn root worm resistance/DAS-59122-7 | Zea mays L. | available, DOW AgroSciences LLC and Pioneer Hi-Bred International Inc. |
| T14-64 | Glyphosate tolerance and Corn root worm resistance/MON88017 | Zea mays L. | available, Monsanto Company |
| T14-65 | Glufosinate ammonium tolerance and Corn root worm resistance/DAS-59122-7 | Zea mays L. | available, Dow AgroSciences |
| T14-66 | Glufosinate ammonium tolerance and EPC resistance/BT11 (X4334CBR, X4734CBR) | Zea mays L. | available, Syngenta Seeds, Inc. |
| T14-67 | Glufosinate ammonium tolerance and EPC resistance/CBH-351 | Zea mays L. | available, Aventis CropScience |
| T14-68 | Glufosinate ammonium tolerance and EPC resistance/DBT418 | Zea mays L. | available, Dekalb Genetics Corporation |
| T14-69 | Glufosinate ammonium tolerance and EPC resistance/TC1507 | Zea mays L. | available, Mycogen (c/o Dow AgroSciences); Pioneer (c/o Dupont) |
| T14-70 | Glyphosate tolerance and EPC resistance/MON802 | Zea mays L. | available, Monsanto Company |
| T14-71 | Glyphosate tolerance and EPC resistance/MON809 | Zea mays L. | available, Pioneer Hi-Bred International Inc. |
| T14-72 | Glufosinate ammonium tolerance and LPn resistance/BT11 x MIR162 (SYN-BT011-1, SYN-IR162-49 | Zea mays L. | available, Syngenta Seeds, Inc. |
| T14-73 | Glufosinate ammonium tolerance and LPn resistance/DAS-06275-8 | Zea mays L. | available, DOW AgroSciences LLC |

TABLE 14-continued

| No | detailed description/Event | plant | Literature/commercial plants |
|---|---|---|---|
| T14-74 | Glufosinate ammonium tolerance and Glyphosate tolerance and LP resistance/BT11 x GA21 (SYN-BT011-1, MON-00021-9 ) | Zea mays L. | available, Syngenta Seeds, Inc. |
| T14-75 | Glufosinate ammonium tolerance and Glyphosate tolerance and LP resistance/BT11 x MIR604 x GA21 (SYN-BT011-1, SYN-IR604-5, MON-00021-9) | Zea mays L. | available, Syngenta Seeds, Inc. |
| T14-76 | Glufosinate ammonium tolerance and Glyphosate tolerance and LP resistance/TC1507 x NK603 (DAS-01507-1 x 00603-6)MON- | Zea mays L. | available, DOW AgroSciences LLC |
| T14-77 | Glyphosate tolerance and LPn resistance/GA21 x MON810 | Zea mays L. | available, Monsanto Company |
| T14-78 | Glyphosate tolerance and LPn resistance/MON89034 x NK603 (MON-89034-3, MON-00603-6) | Zea mays L. | available, Monsanto Company |
| T14-79 | Glyphosate tolerance and LPn resistance/NK603 x MON810 (MON-00603-6, MON-00810-6) | Zea mays L. | available, Monsanto Company |
| T14-80 | Glufosinate ammonium tolerance and LPn resistance/T25 x MON810 (ACS-ZM003-2, MON-00810-6) | Zea mays L. | available, Bayer CropScience (Aventis CropScience(AgrEvo)) |
| T14-81 | Gluphosinate tolerance and male sterility/MS1, RF1 (PGS1) | Brassica napus | available, Bayer CropScience (Aventis CropScience(AgrEvo)) |
| T14-82 | Gluphosinate tolerance and male sterility/MS1, RF2 (PGS2) | Brassica napus | available, Aventis CropScience (formerly Plant Genetic Systems) |
| T14-83 | Gluphosinate tolerance and male sterility/MS8xRF3 | Brassica napus | available, Bayer CropScience (Aventis CropScience(AgrEvo)) |
| T14-84 | Gluphosinate tolerance and male sterility/MS3 (ACS-ZM001-9) | Zea mays L. | available, Bayer CropScience (Aventis CropScience(AgrEvo)) |
| T14-85 | Gluphosinate tolerance and male sterility/MS6 (ACS-ZM005-4) | Zea mays L. | available, Bayer CropScience (Aventis CropScience(AgrEvo)) |
| T14-86 | glyphosate tolerance and high oleic acid content/305423 x 40-3-2 | Glycine max L. | available, Pioneer Hi-Bred |
| T14-87 | coloration and sulfonylurea herbicide tolerance/4, 11, 15, 16 | D. caryophyllus | available, Florigene Pty Lt |
| T14-88 | coloration and sulfonylurea herbicide tolerance/959A, 988A, 1363A, 1400A 1226A, 1351A | D. caryophyllus | available, Florigene Pty Lt |
| T14-89 | Increased shelf-life and sulfonylurea herbicide tolerance/66 | D. caryophyllus | available, Florigene Pty Lt |

*) Glycine max L. (soybean), Zea mays L. (corn, maize), Brassica napus (Argentine canola), D. caryophyllus = Dianthus caryophyllus (carnation)
**) European corn borer = EPC, Lepidoptera LP, Lepidopteran LPn, Glyphosate tolerance = GLY-T
A* refers to U.S. Pat. No. 5,188,642, U.S. Pat. No. 4,940,835, U.S. Pat. No. 5,633,435, U.S. Pat. No. 5,804,425 and U.S. Pat. No. 5,627,061.
B* refers to imidazolinone-herbicide resistant rice plants with specific mutation of the acetohydroxyacid synthase gene: S653N (see e.g. US 2003/0217381), S654K (see e.g. US 2003/0217381), A122T (see e.g. WO 2004/106529) S653(At)N, S654(At)K, A122(At)T and other resistant rice plants as described in WO 2000/27182, WO 2005/20673 and WO 2001/85970 or US patents U.S. Pat. No. 5,545,822, U.S. Pat. No. 5,736,629, U.S. Pat. No. 5,773,703, U.S. Pat. No. 5,773,704, U.S. Pat. No. 5,952,553, U.S. Pat. No. 6,274,796, wherein plants with mutation S653A and A122T are most preferred.
C* referes to WO 2000/04173, WO 2007/131699, US 20080229448 and WO 2005/48693.
D* refers to WO 1993/07278 and WO 1995/34656.
E* refers to WO 1996/26639, U.S. Pat. No. 7,329,802, U.S. Pat. No. 6,472,588 and WO 2001/17333.
F* refers to sulfonylurea and imidazolinone herbicides, such as imazamox, imazethapyr, imazaquin, chlorimuron, flumetsulam, cloransulam, diclosulam and thifensulfuron.
G* refers to U.S. Pat. No. 6,380,462, U.S. Pat. No. 6,365,802, U.S. Pat. No. 7,294,759 and U.S. Pat. No. 7,157,621.
H* refers to Plant Cell Reports, 20, 2001, 610-615. Trends in Plant Science, 11, 2006, 317-319. Plant Molecular Biology, 37, 1998, 287-296. Mol Gen Genet., 257, 1998, 606-13. Federal Register (USA), Vol. 60, No. 113, 1995, page 31139. Federal Register (USA), Vol. 67, No. 226, 2002, page 70392. Federal Register (USA), Vol. 63, No. 88, 1998, page 25194. Federal Register (USA), Vol. 60, No. 141, 1995, page 37870. Canadian Food Inspection Agency, FD/OFB-095-264-A, October 1999, FD/OFB-099-127-A, October 1999.
I* refers to Federal Register (USA), Vol. 61, No. 160, 1996, page 42581. Federal Register (USA), Vol. 63, No. 204, 1998, page 56603.
3) (Cry3A; western corn rootworm, northern corn rootworm, Mexican corn rootworm resistance) Preferred embodiments of the invention are those methods of controlling harmful insects and/or increasing the health of plants by treating cultivated plants, parts of such plants or at their locus of growth with compounds I or their mixtures, wherein the plant , wherein the plant corresponds In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table A and the mixing partner of the compound Icompound is endosulfan.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table A and the mixing partner of the compound Icompound is ethiprole.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table A and the mixing partner of the compound Icompound is fipronil.

Another preferred embodiment of the invention are those methods of controlling harmful insects and/or increasing the health of plants by treating cultivated plants, parts of such plants or at their locus of growth with compounds I or their mixtures, wherein the plant is a transgenic plant which is selected from the plants listed in table B.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table B and the mixing partner of the compound Icompound is endosulfan.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table B and the mixing partner of the compound Icompound is ethiprole.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table B and the mixing partner of the compound Icompound is fipronil.

In another preferred embodiment, the present invention relates of methods of controlling harmful insects and/or increasing the health of plants by treating cultivated plants, parts of such plants or at their locus of growth with compounds I or their mixtures, wherein the plant is selected from B-3, B-4, B-5, B-7, B-8, B-11, B-23, B-28, B-29, B-30, B-39, B-42, B-44, B-46, B-47, B-55, B-59, B-61, B-63, B-64, B-69, B-70, B-71 of table B.

In a most preferred embodiment, the present invention relates of methods of controlling harmful insects and/or increasing the health of plants by treating cultivated plants, parts of such plants or at their locus of growth with compounds I or their mixtures, wherein the plant is selected from B-3, B-4, B-5, B-7, B-8, B-11, B-23, B-28, B-29, B-30, B-39, B-42, B-44, B-46, B-47, B-55, B-59, B-61, B-63, B-64, B-69, B-70, B-71 of table B and the mixing partner of the compound Icompound is endosulfan.

In a most preferred embodiment, the present invention relates of methods of controlling harmful insects and/or increasing the health of plants by treating cultivated plants, parts of such plants or at their locus of growth with compounds I or their mixtures, wherein the plant is selected from B-3, B-4, B-5, B-7, B-8, B-11, B-23, B-28, B-29, B-30, B-39, B-42, B-44, B-46, B-47, B-55, B-59, B-61, B-63, B-64, B-69, B-70, B-71 of table B and the mixing partner of the compound Icompound is ethiprole.

In a most preferred embodiment, the present invention relates of methods of controlling harmful insects and/or increasing the health of plants by treating cultivated plants, parts of such plants or at their locus of growth with compounds I or their mixtures, wherein the plant is selected from B-3, B-4, B-5, B-7, B-8, B-11, B-23, B-28, B-29, B-30, B-39, B-42, B-44, B-46, B-47, B-55, B-59, B-61, B-63, B-64, B-69, B-70, B-71 of table B and the mixing partner of the compound Icompound is fipronil.

Further preferred embodiments of the invention are those methods of controlling harmful insects and/or increasing the health of plants by treating cultivated plants, parts of such plants or at their locus of growth with compounds I or their mixtures, wherein the plant expresses one or more genes selected from CP4 epsps, pat, bar, Cry1Ab, Cry1Ac, Cry3Bb1, Cry2Ab, Cry1F, Cry34Ab1 and Cry35Ab1.

In a more preferred embodiment, the present invention relates of methods of controlling harmful insects and/or increasing the health of plants by treating cultivated plants, parts of such plants or at their locus of growth with compounds I or their mixtures, wherein the mixing partner of the compound Icompound is endosulfan and the plant expresses one or more genes selected from CP4 epsps, pat, bar, Cry1Ab, Cry1Ac, Cry3Bb1, Cry2Ab, Cry1F, Cry34Ab1 and Cry35Ab1.

In a more preferred embodiment, the present invention relates of methods of controlling harmful insects and/or increasing the health of plants by treating cultivated plants, parts of such plants or at their locus of growth with compounds I or their mixtures, wherein the mixing partner of the compound Icompound is ethiprole and the plant expresses one or more genes selected from CP4 epsps, pat, bar, Cry1Ab, Cry1Ac, Cry3Bb1, Cry2Ab, Cry1F, Cry34Ab1 and Cry35Ab1.

In a more preferred embodiment, the present invention relates of methods of controlling harmful insects and/or increasing the health of plants by treating cultivated plants, parts of such plants or at their locus of growth with compounds I or their mixtures, wherein the mixing partner of the compound Icompound is fipronil and the plant expresses one or more genes selected from CP4 epsps, pat, bar, Cry1Ab, Cry1Ac, Cry3Bb1, Cry2Ab, Cry1F, Cry34Ab1 and Cry35Ab1.

Further preferred embodiments of the invention are those methods of controlling harmful insects and/or increasing the health of plants by treating cultivated plants, parts of such plants or at their locus of growth with compounds I or their mixtures, wherein the plant corresponds to a row of table 14.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table ABC and the mixing partner of the compound Icompound is endosulfan.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table ABC and the mixing partner of the compound Icompound is ethiprole.

In a more preferred embodiment, the present invention relates of methods of controlling harmful insects and/or increasing the health of plants by treating cultivated plants, parts of such plants or at their locus of growth with compounds I or their mixtures, wherein the plant is selected from the plants listed in table ABC and the mixing partner of the compound Icompound is fipronil.

All embodiments of the mixing partner of the compound I as defined above are also referred to herein after as compounds I and their mixtures according to the present invention. They can also be converted into agrochemical compositions comprising a solvent or solid carrier and at least one compound I and their mixing partner according to the present invention.

An agrochemical composition comprises an insecticidal and/or plant health effective amount of compounds I or their mixtures according to the present invention. The term "effective amount" denotes an amount of the composition of the compound I and optionally a mixing partner according to the present invention, which is sufficient to achieve the synergistic effects related to fungal control and/or plant health and which does not result in a substantial damage to the treated plants. Such an amount can vary in a broad range and is dependent on various factors, such as the fungal species to be controlled, the treated cultivated plant or material, the climatic conditions.

Examples of agrochemical compositions are solutions, emulsions, suspensions, dusts, powders, pastes and granules. The composition type depends on the particular intended purpose; in each case, it should ensure a fine and uniform distribution of the compound according to the invention.

More precise examples for composition types are suspensions (SC, OD, FS), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF). Usually the composition types (e. g. SC, OD, FS, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 und ff. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e. g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e. g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borrespersе® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers therof.

Examples for thickeners (i. e. compounds that impart a modified flowability to compositions, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, U.S.A.).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned und the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds I and, if appropriate, further active substances, with at least one solid carrier.

Granules, e. g. coated granules, impregnated granules and homogenous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas and products of vegetable origin, such as cereal meal, tree bark meal, wood meal and nutshell meal, cellulose powders and other solid carriers.

Examples for composition types are the composition types i to xii as described in detail in embodiment E1:

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

In one embodiment, a suspoconcentration (SC) is preferred for the application in crop protection. In one sub-embodiment thereof, the SC agrochemical composition comprises between 50 to 500 g/L (grams per Litre), or between 100 and 250 g/L, or 100 g/L or 150 g/L or 200 g/L or 250 g/L.

In a further embodiment, the granules according to formulation type xii are especially preferred for the application in rice.

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art and include dressing, coating, pelleting, dusting, soaking and in-furrow application methods of the propagation material. In a preferred embodiment, the compounds or the compositions thereof, respectively, are applied on to the plant propagation material by a method such that germination is not induced, e. g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The compounds I or their mixtures according to the present invention can be used as such or in the form of their compositions, e. g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.001 to 1 kg per ha, more preferably from 0.005 to 0.9 kg per ha, in particular from 0.005 to 0.5 kg per ha.

In treatment of plant propagation materials such as seeds, e. g. by dusting, coating or drenching seed, amounts of active substance of from 0.1 to 1000 g, preferably from 0.1 to 300 g, more preferably from 0.1 to 100 g and most preferably from 0.25 to 100 g, per 100 kilogram of plant propagation material (preferably seed) are generally required.

Various types of oils, wetters, adjuvants, herbicides, fungicides, bactericides, other insecticides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®.

The compositions according to the invention can, in the use form as insecticides, also be present together with other active substances, e. g. with herbicides, fungicides, growth regulators or else with fertilizers, as pre-mix or, if appropriate, not until immediately prior to use (tank mix).

In a preferred embodiment of the invention, the inventive mixtures are used for the protection of the plant propagation material, e.g. the seeds and the seedlings' roots and shoots, preferably the seeds.

Seed treatment can be made into the seedbox before planting into the field.

For seed treatment purposes, the weight ration in the binary, ternary and quaternary mixtures of the present invention generally depends from the properties of the compounds I or their mixtures according to the present invention.

Compositions, which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

These compositions can be applied to plant propagation materials, particularly seeds, diluted or undiluted. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art and include dressing, coating, pelleting, dusting and soaking application methods of the propagation material (and also in furrow treatment). In a preferred embodiment, the compounds or the compositions thereof, respectively, are applied on to the plant propagation material by a method such that germination is not induced, e. g. by seed dressing, pelleting, coating and dusting.

In the treatment of plant propagation material (preferably seed), the application rates of the inventive mixture are generally for the formulated product (which usually comprises from 10 to 750 g/l of the active(s).

The invention also relates to the propagation products of cultivated plants and especially the seed comprising, that is, coated with and/or containing, compounds I and their mixtures as defined above or a composition containing the mixture of two or more active ingredients or a mixture of two or more compositions each providing one of the active ingredients. The plant propagation material (preferably seed) comprises the inventive mixtures in an amount of from 0.1 g to 10 kg per 100 kg of plant propagation material (preferably seed).

B. Biology

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, *Weeds*, 15, 20-22):

$$E = X + Y - \frac{XY}{100}$$

When the observed combined control effect is greater than the expected combined control effect (E), then the combined effect is synergistic.

The following tests demonstrate the control efficacy of compounds, mixtures or compositions of this invention on specific pests. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests.

The analysis of synergism or antagonism between the mixtures or compositions was determined using Colby's equation.

B1: Test on GMO Soybeans

Trial is carried out under greenhouse conditions on soybean (*Glycine max*, variety: BMX Potencia RR, growth stage 109). 12 treatments are compared in a complete randomize blocks (4 replications) with plot size of 1 m×3 meters.

Due to glyphosate timing for application on RR-soybeans, all treatments are applied in older plants (GS 109) otherwise a significant phytotoxicity is expected. Application is done, using 400 l/ha. All treatments are applied using a $CO_2$ backpack (nozzle type TXVK-10). Temperature at the time of applications is 31.8° C. and air humidity is of 55%. Soil condition is R4 (when <75% of surface is dried up) and the moisture is moist (normal).

Premio® (Chlorantraniliprole @200 g/L) is used as standard in the rate of 25 g a.i./ha.

Roundup Original® (Glyfosate-sal isopropilamina @360 g/L) is used in the rate of 867 g a.i./ha.

Artificial infestation is done one day after the application. The species used is e.g. *Anticarsia gemmatalis* (Hübner) [*Thermesia elegantula* (Herrich-Schaffer, 1869)], Noctuidae. 5 plants/plot are infested with 3 larvae (stage L2) using a entomological metallic tweezers, totaling 15 larvae per repetition. All larvae used in this trial are provided by BASF rearing laboratory, Campinas, Brazil.

A second infestation is held seven days after application in the same plants and using the same larval numbers. A third infestation might be done if necessary in order to observe residual activity.

The mortality (number) and eating damage (%) are evaluated with 01, 02, 05, 07, 14 and 21 DAA (days after application), comparing to untreated control plants.

In another test, a non-GM soybean variety is treated with 12.5 g a.i./ha.

Embodiment E6

The present invention relates to new uses and methods of N-thio-anthranilamide compounds.

The invention also relates to the use of the compounds I itself and their stereoisomers, salts, tautomers or N-oxides, and their mixtures, in non-agronomic applications, especially in nettings, e.g. mosquito nets, and the use against ants, flies, termites and other pests, especially household pests and stored product pests.

Pesticides, e.g. insecticides, are often used in crop applications. However, there is also a need for efficient pesticides, e.g. insecticides in non-crop applications, e.g. in the household, storage or the like.

In a first aspect, the invention relates to a method for controlling non-crop pests, comprising contacting the pests or their food supply, habitat, breeding grounds or their locus with at least one pesticidally active anthranilamide compound I as described above, or a stereoisomer, salt, tautomer or N-oxide, or a polymorphic crystalline form, a co-crystal or a solvate of a compound or a stereoisomer, salt, tautomer or N-oxide thereof.

Furthermore, the present invention also relates to a method for controlling a population of social insects, which method comprises applying a compound I as defined herein, or a stereoisomer, salt, tautomer or N-oxide thereof, or a composition comprising it. The social insects are preferably termites, ants, wasps and cockroaches. The invention also relates to the use of a compound I as defined herein, or a stereoisomer, salt, tautomer or N-oxide thereof, or a composition comprising it, for controlling a population of social insects.

The pests that can be controlled or combatted are as described above or herein, e.g. in embodiment E1.

The plants or crops to be protected are as described above or herein, e.g. in embodiment E1.

The formulations are as described herein, e.g. in embodiment E1.

The applications are as described herein, e.g. in embodiment E1.

The mixtures and preferred mixtures are as described herein.

Methods for Controlling or Combating Non-Crop Pests

The compounds I as defined herein, or a stereoisomer, salt, tautomer or N-oxide thereof, or the compositions comprising them, are used for combating or controlling non-crop pests.

The invention also relates to compositions containing compounds I in pesticidally effective amounts for controlling non-crop pests.

The invention further relates to the use of compounds I for the protection of non-living organic materials against non-crop pests.

Typical problems arising with the use of presently available non-crop pest control agents such as pyrethroids are e.g. resistance of pests or unfavorable environmental or toxicological properties. Another problem encountered concerns the need to have available non-crop pest control agents which are effective against a broad spectrum of non-crop pests. Accordingly, there is a need to provide new and improved non-crop pest control agents that overcome these problems.

It is therefore an object of the present invention to provide new non-crop pest control agents, preferably exhibiting an enhanced pesticidal spectrum of action.

We have found that these objects are achieved by use of compounds I and compositions comprising them.

In one embodiment, the compound I in the methods and uses according to the invention of E6 is selected from the compounds described in Embodiment A.

In one embodiment, the compound I in the methods and uses according to the invention of E6 is selected from the compounds described in Embodiment B.

In one embodiment, the compound I in the methods and uses according to the invention of E6 is selected from the compounds described in Embodiment C.

In one embodiment, the compound I in the methods and uses according to the invention of E6 is selected from the compounds listed in Table ABC.

In one embodiment, I-A-1 is the compound I in the methods and uses according to the invention of E6.

In one embodiment, I-A-28 is the compound I in the methods and uses according to the invention of E6.

In one embodiment, I-B-115 is the compound I in the methods and uses according to the invention of E6.

In one embodiment, I-B-131 is the compound I in the methods and uses according to the invention of E6.

In one embodiment, I-B-132 is the compound I in the methods and uses according to the invention of E6.

In one embodiment, I-C-19 is the compound I in the methods and uses according to the invention of E6.

In one embodiment, I-C-35 is the compound I in the methods and uses according to the invention of E6.

In one embodiment, I-C-36 is the compound I in the methods and uses according to the invention of E6.

In a further embodiment, the invention relates to the methods and uses of the compounds according to the invention (as defined in Embodiment A, B or C) in combination with other selected pesticidal compounds (II), as defined and specified in Embodiments 2 and 3.

Non-crop pests are pests of the classes Chilopoda and Diplopoda and of the orders Isoptera, Diptera, Blattaria (Blattodea), Dermaptera, Hemiptera, Hymenoptera, Orthoptera, Siphonaptera, Thysanura, Phthiraptera, Araneida, Parasitiformes and Acaridida.

The compounds of the formula (I) are especially suitable for efficiently combating the following pests:
centipedes (Chilopoda), e.g. *Scutigera coleoptrata*,
millipedes (Diplopoda), e.g. *Narceus* spp.,
spiders (Araneida), e.g. *Latrodectus mactans*, and *Loxosceles reclusa*,
scabies (Acaridida): e.g. *sarcoptes* sp,
ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Orni-thodorus hermsi, Ornithodorus turicata* and parasitic mites (Mesostigmata), e.g. *Orni-thonyssus bacoti* and *Dermanyssus gallinae*,
termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis*, and *Coptotermes formosanus*,
cockroaches (Blattaria—Blattodea), e.g. *Blattella germanica, Blattella asahinae, Peri-planeta americana, Periplaneta japonica, Periplaneta brunnea, Periplaneta fuligginosa, Periplaneta australasiae*, and *Blatta orientalis*,
flies, mosquitoes (Diptera), e.g. *Aedes aegypti, Aedes albopictus, Aedes vexans, Anas-trepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inor-nata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Lep-toconops torrens, Lucilia caprina, Lucilia cuprina, Lucilia se cata, Lycoria pectoralis, Mansonia* spp., *Musca domestica, Muscina stabulans, Oestrus ovis, Phlebotomus ar-gentipes, Psorophora columbiae, Psorophora discolor, Prosimulium mixtum, Sarco-phaga haemorrhoidalis, Sarcophaga* sp., *Simulium vittatum, Stomoxys calcitrans, Ta-banus bovinus, Tabanus atratus, Tabanus lineola*, and *Tabanus similis*,
Earwigs (Dermaptera), e.g. *forficula auricularia*,
true bugs (Hemiptera), e.g. *Cimex lectularius, Cimex hemipterus, Reduvius senilis, Triatoma* spp., *Rhodnius prolixus*, and *Arilus critatus*,
ants, bees, wasps, sawflies (Hymenoptera), e.g. *Cremato-gaster* spp., *Hoplocampa minuta, Hoplocampa testudinea, Monomo um pharaonis, Solenopsis gemi-* nata, Sole-nopsis invicta, Solenopsis richteri, Solenopsis xyloni, Pogonomyrmex barbatus, Pogo-nomyrmex californicus, Dasymutilla occidentalis, Bombus spp. Vespula squamosa, Paravespula vulgaris, Paravespula pennsylvanica, Paravespula germanica, Dolichovespula maculata, Vespa crabro, Polistes rubiginosa, Camponotus floridanus, and Li-nepithema humile, crickets, grasshoppers, locusts (Orthoptera), e.g. *Acheta domestica, Gryllotalpa gryllo-talpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Cho oicetes terminifera*, and *Locustana pardaliria*, fleas (Siphonaptera), e.g. *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharina* and *Thermobia domestica*, lice (Phthiraptera), e.g. *Pediculus humanus capitis, Pediculus humanus corporis, Pthi-rus pubis, Haematopinus eurystemus, Haematopinus suis, Linognathus vituli, Bovlcola bovis, Menopon gallinae, Menacanthus stramineus* and *Solenopotes capillatus*. The hydrazine derivatives I which can be used according to the invention are known from and can be prepared according to preparation methods described or referenced in EP-A 604 798. This document relates to plant protection in the agricultural field and discloses the insecticidal and acaricidal activity of compounds of formula I and other compounds against crop pests of the Coleoptera, Lepidoptera and Acarina orders.

Activity of a compound against pests for plant protection in the agricultural field, that is, against crop pests, does not generally suggest activity of that compound against non-crop pests. Crop pest control always is a part of plant protection. Non-crop pest control, on the contrary, e.g. relates to protection of non-living organic materials, or hygiene and disease prevention (public health).

The differences in requirements for crop/non-crop pest control generally and mainly—beside a possible difference in biochemical targets—emerge from the differences in the food and/or habitat of the pests.

Crop pests like that of the order Homoptera feed on the green parts of the plant by piercing them and sucking the plant liquids. Other crop pests of the Lepidoptera and Coleoptera order feed on the green parts of plants by biting off parts. On the contrary, non-crop pests do not live on plants and do not or only in rare occasions feed on the green parts of the plant. Non-crop pests e.g. feed on non-living organic materials such as the homes, clothing and the food etc of human beings and animals but also on electric wires etc thereby introducing pathogenic germs into the human being's environment and destroying their homes and food. An example is the termite (order Isoptera) that primarily feeds on cellulose which is the major component of wood and paper products. Another example is the mosquito (order Diptera) whose larvae feed on microorganisms and organic matter in the water and whose adults feed on blood.

The properties of pesticides need to be adapted to their specific use. Systemic pesticides for example that by virtue of their water-solubility are introduced into the plant parts are suitable for controlling piercing-sucking or biting (i.e. crop) pests. However, they cannot generally be expected to show equal activity against non-crop pests who do not feed on the green plant parts but are controlled by mostly water-insoluble pesticides in baiting systems or by direct treatment. In many cases crop pest control pesticides are not suitable for non-crop pest controlling and vice versa. The market insecticides pirimicarb, acephate, pyrimidiven, and pyridaben are examples. They are active against crop insects but show low activity against non-crop pests.

Surprisingly, it has now been found that a certain group of anthranilamides, namely the compounds I, exhibit a broad spectrum activity against non-crop pests.

In one embodiment, the invention relates to a method for controlling non-crop pests, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In an embodiment of the invention, in the methods and uses according to the invention, the non-crop pest is selected from flies, mosquitoes (Diptera).

In one embodiment, the invention relates to a method for controlling non-crop pest which is selected from flies, mosquitoes, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

More preferably, the non-crop pest is selected from: *Aedes aegypti, Aedes albopictus, Aedes vexans, Anas-trepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inor-nata, Culiseta melanura, Dermatobia hominis, Fannia canicularis, Gasterophilus intes-tinalis, Glossina morsitans, Glossina palpalis, Glossina fuscipes, Glossina tachinoides, Haematobia irritans, Haplodiplosis equestris, Hippelates* spp., *Hypoderma lineata, Lep-toconops torrens, Lucilia caprina, Lucilia cuprina, Lucilia se cata, Lycoria pectoralis, Mansonia* spp., *Musca domestica, Muscina stabulans, Oestrus ovis, Phlebotomus ar-gentipes, Psorophora columbiae, Psorophora discolor, Prosimulium mixtum, Sarco-phaga haemorrhoidalis, Sarcophaga* sp., *Simulium vittatum, Stomoxys calcitrans, Ta-banus bovinus, Tabanus atratus, Tabanus lineola*, and *Tabanus similis*, In an embodiment of the invention, in the methods and uses according to the invention, the non-crop pest is selected from termites (Isoptera). More preferably, the non-crop pest is selected from: *Calotermes flavicollis, Leucotermes flavipes, Heterotermes aureus, Reticulitermes flavipes, Reticuli-*

*termes virginicus, Reticulitermes lucifugus, Termes natalensis,* and *Coptotermes formosanus,*

In one embodiment, the invention relates to a method for controlling non-crop pest which is selected from termites, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In an embodiment of the invention, in the methods and uses according to the invention, the non-crop pest is selected from ants (Hymenoptera). More preferably, the non-crop pest is selected from: *Crematogaster* spp., *Hoplocampa minuta, Hoplocampa testudinea, Monomo um pharaonis, Solenopsis geminata, Sole-nopsis invicta, Solenopsis richteri, Solenopsis xyloni, Pogonomyrmex barbatus, Pogonomyrmex californicus, Dasymutilla occidentalis, Bombus* spp. *Vespula squamosa, Paravespula vulgaris, Paravespula pennsylvanica, Paravespula germanica, Dolicho-vespula maculata, Vespa crabro, Polistes rubiginosa, Camponotus floridanus,* and *Linepithema humile.*

In one embodiment, the invention relates to a method for controlling non-crop pest which is selected from ants, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In an embodiment of the invention, in the methods and uses according to the invention, the non-crop pest is selected from crickets, grasshoppers, locusts (Orthoptera). More preferably, the non-crop pest is selected from: *Acheta domestica, Gryllotalpa gryllo-talpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca ame-ricana, Schistocerca gregaria, Dociostaurus maroccanus, Tachycines asynamorus, Oedaleus senegalensis, Zonozerus variegatus, Hieroglyphus daganensis, Kraussaria angulifera, Callip-tamus italicus, Cho oicetes terminifera,* and *Locustana pardaliria.*

In one embodiment, the invention relates to a method for controlling non-crop pest which is selected from crickets, grasshoppers, locusts (Orthoptera), which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

Therefore, the invention relates to:
Method according to the invention, wherein the non-crop pest is selected from flies, mosquitoes (Diptera).
Netting or textile material, impregnated with a compound I as defined herein.
Method according to the invention, wherein stored products are protected from pests, especially a method according to the invention, wherein the stored product is selected from tobacco, nuts, cocoa, fruits, wood.
Method according to the invention, wherein the stored product is protected by a netting or textile material, impregnated with a compound I as defined herein.
Use of a compound I as defined herein, or a composition comprising said compound,
for controlling non-crop pests, and/or
for controlling flies, mosquitoes (Diptera), and/or
for protecting stored products, and/or
for protecting stored tobacco, nuts, cocoa, fruits, wood, and/or
for controlling resistant mosquitoes and/or bed bugs.

In a preferred embodiment of the present invention, compounds I, and their stereoisomers, salts, tautomers and N-oxides, and compositions comprising them, are used for the protection of non-living organic materials, including but are not limited to house-hold goods such as fats, oils, mono- oligo- or polyorganosaccharides, proteins, or fresh or decaying fruits; cellulose-containing materials e.g. wooden materials such as houses, trees, board fences, or sleepers and also paper; and also construction materials, furniture, leathers, animal, plant and synthetic fibers, vinyl articles, electric wires and cables as well as styrene foams.

More preferably, compounds I, and their stereoisomers, salts, tautomers and N-oxides, and compositions comprising them, are used for the protection of non-living organic materials against non-crop pests selected from the group consisting of the class Diplopoda and of the orders Isoptera, Diptera, Blattaria (Blattodea), Dermaptera, Hemiptera, Hymenoptera, Orthoptera, and Thysanura.

Most preferably, the invention relates to compounds according to the invention, for the protection of human beings and animals against mosquitos. In this respect, the invention especially relates to textile materials, foils or nettings which comprise or incorporate a compound according to the invention. In one aspect, "incorporated" means embedded. In another aspect, "incorporated" means comprised in impregnated form.

The invention also relates to abovementioned textile material for the protection of plants or crops, e.g. tobacco, nuts, fruits, trees, wood.

For example, the nettings or textile material can be impregnated in the manner of a composition as described in WO2005/064072 or WO20080/151984. The netting material, especially a material as described in WO2010/012671, can be used as a protection in the storage of tobacco as described in WO 2007/144401, and can also be used in a similar manner for the protection of other goods.

In the protection of wood, the use of the compounds according to the invention can be done as described in WO2008/142103. In the protection of living plants, the use of the compounds according to the invention can be done as described in WO2012/038460.

The foils or nettings can also be used as mulch foil in the protection of crops.

Furthermore, there is a broad use of the compounds according to the invention, e.g. for protecting stored goods in a container as described e.g. in WO2013/000907.

In one embodiment, the invention relates to a netting, which comprises a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In another embodiment, the invention relates to a method for protecting humans from insects, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In another embodiment, the invention relates to a method for protecting stored goods, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In another embodiment, the invention relates to a method for protecting stored goods which are selected from tobacco, nuts, cocoa, fruits, wood; which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

The present invention also relates to a method for the protection of non-living organic materials against non-crop pests, preferably against non-crop pests selected from the group consisting of the class Diplopoda and of the orders Isoptera, Diptera, Blattaria (Blattodea), Dermaptera, Hemiptera, Hymenoptera, Orthoptera, and Thysanura, comprising contacting the pests or their food supply, habitat, breeding grounds, their locus or the non-living organic materials themselves with a pesticidally effective amount of a compound I, or a stereoisomer, salt, tautomer or N-oxide thereof, or a composition comprising it.

Moreover, compounds I or a stereoisomer, salt, tautomer or N-oxide thereof, or a composition comprising it, are preferably used for protecting cellulose-containing non-living organic materials:

Preferably, compounds I or a stereoisomer, salt, tautomer or N-oxide thereof, or a composition comprising it, are used for protecting cellulose-containing non-living organic materials against non-crop pests from the Isoptera, Diptera, Blattaria (Blattodea), Hymenoptera, and Orthoptera orders, most preferably the Isoptera orders.

The present invention also provides a method for protecting cellulose-containing nonliving organic materials against non-crop pests, preferably from the Isoptera, Diptera, Blattaria (Blattodea), Hymenoptera, and Orthoptera orders, most preferably the Isoptera orders, comprising contacting the pests or their food supply, habitat, breeding grounds, their locus or the cellulose-containing non-living organic materials themselves with a pesticidally effective amount of a compound I or a stereoisomer, salt, tautomer or N-oxide thereof, or a composition comprising it.

In another preferred embodiment of the present invention, compounds I or a stereoisomer, salt, tautomer or N-oxide thereof, or a composition comprising it, are used for protecting mono-oligo- or polysaccharides and proteins.

Preferably, compounds I or a stereoisomer, salt, tautomer or N-oxide thereof, or a composition comprising it, are used for protecting mono- oligo- or polysaccharides and proteins against non-crop pests selected from the Dermaptera, Diplopoda, Isoptera, Diptera, Blattaria (Blattodea), Hymenoptera, Orthoptera and Tysanura orders, most preferably the Isoptera, Diptera, Blattaria (Blattodea), and Hymenoptra orders.

The present invention also provides a method for protecting mono- oligo- or polysac-charides and proteins against non-crop pests, preferably selected from the Dermaptera, Diplopoda, Isoptera, Diptera, Blattaria (Blattodea), Hymenoptera, Orthoptera and Tysanura orders, most preferably the Isoptera, Diptera, Blattaria (Blattodea), and Hymenoptra orders, comprising contacting the pests or their food supply, habitat, breeding grounds or their locus with a pesticidally effective amount of a compounds I or a stereoisomer, salt, tautomer or N-oxide thereof, or a composition comprising it.

Furthermore, compounds I or a stereoisomer, salt, tautomer or N-oxide thereof, or a composition comprising it, are preferably used for protection of animals against non-crop pest of the class Chilopoda, and of the orders Araneida, Hemiptera, Diptera, Phthiraptera, Siphonaptera, Parasitiformes and Acaridida by treatment of the pests in water bodies and/or in and around buildings, including but not limited to walls, ground,—manure piles, turf grass, pastures, sewers and materials used in the construction of buildings and also mattresses and bedding, with a pesticidally effective amount of a compound I or a composition comprising it. Most preferably, compounds I are used for protection of animals against non-crop pest of the Diptera, Phthiraptera, Siphonaptera, and Parasitiformes orders.

Animals include warm-blooded animals, including humans and fish. Compounds I are preferably used for protection of warm-blooded animals such as cattle, sheep, swine, camels, deer, horses, poultry, rabbits, goats, dogs and cats.

Methods for Vector Control of Insecticide-Resistant Pests

The invention is also in the technical field of vector control and in particular mosquito and bed bug control. The compounds, mixtures and compositions of this invention are used against animal pests such as arthropods which transmit disease pathogens or which annoy the well-being of humans and animals. The compounds, mixtures and compositions of this invention are in particular useful to overcome target-specific and/or metabolic-specific resistance of mosquitos and bed bugs.

Due to natural selection pests develop a resistance to chemicals and therefore there is a continuous need to improve the currently available active compounds or mixtures and compositions in order to allow an efficient resistance management.

With the present invention it has now been found that the compounds according to the invention, their mixtures and their compositions are suitable for controlling animal pests and in particular to control insecticide-resistant animal pests. This effect is in particular surprising in connection with the control of insecticide-resistant mosquitos and/or bed bugs.

The mixtures especially of interest in this context are mixtures of compounds I with ethiprole, fipronil, neonicotinoids (i.e. preferably a compound selected from the group of acetamiprid, clothianidin, dinotefuran, imidacloprid, nitenpyram, thiacloprid and thiamethoxam).

The compounds, mixtures and compositions of this invention are used to control animal pests, preferably arthropods and more preferably sucking, stinging and chewing insects and arachnids.

The arachnids include essentially mites (for example *Sarcoptes scabiei, Dermatophagoides pteronyssinus, Dermatophagoides farinae, Dermanyssus gallinae, Acarus siro*) and ticks (for example *Ixodes ricinus, Ixodes scapularis, Argas reflexus, Ornithodorus moubata, Rhipicephalus (Boophilus) microplus, Amblyomma hebraeum, Rhipicephalus sanguineus*). The sucking and stinging insects include essentially the mosquitoes (for example *Aedes aegypti, Aedes albopictus, Aedes vexans, Culex quinquefasciatus, Culex tarsalis, Anopheles albimanus, Anopheles stephensi, Anopheles gambiae, Anopheles funestus, Mansonia titillans*); the sandflies (for example *Phlebotomus papatasii*), gnats (for example *Culicoides furens*), black flies (for example *Simulium damnosum*); flies such as stinging flies (for example *Stomoxys calcitrans*), tsetse flies (for example *Glossina morsitans morsitans*), horse flies (for example *Tabanus nigrovittatus, Haematopota pluvialis, Chrysops caecutiens*), true flies (for example *Musca domestica, Musca autumnalis, Musca vetustissima, Fannia canicularis*), flesh flies (for example *Sarcophaga* carnaria), myiasis-causing flies (for example *Lucilia cuprina, Chrysomyia chloropyga, Hypoderma bovis, Hypoderma lineatum, Dermatobia hominis, Oestrus ovis, Gasterophilus intestinalis, Cochliomyia hominivorax*); bugs (for example *Cimex lectularius, Rhodnius prolixus, Triatoma infestans*); lice (for example *Pediculus humanis, Haematopinus suis, Damalina ovis*); fleas (for example *Pulex irritans, Xenopsylla cheopis, Ctenocephalides canis, Ctenocephalides felis*), sand fleas (*Tunga penetrans*), wasps (for example *Vespula germanica*). The chewing insects include essentially cockroaches (for example *Blattella germanica, Periplaneta americana, Blatta orientalis, Supella longipalpa*); beetles (for example *Sitiophilus granarius, Tenebrio molitor, Dermestes lardarius, Stegobium paniceum, Anobium punctatum, Hylotrupes bajulus*), termites (for example *Reticulitermes lucifugus*); ants (for example *Lasius niger, Monomorium pharaonis*); and larvae of moths (for example *Ephestia elutella, Ephestia cautella, Plodia interpunctella, Hofmannophila pseudospretella, Tineola bisselliella, Tinea pellionella, Trichophaga tapetzella*).

Even more preferred, the compounds, mixtures and compositions of the present invention are used to control insects and arachnids selected from the group of mosquitos, ticks, flies, bed bug (*Cimex lectularius*), ants, beetles, cockroaches and/or termites. Even more preferred, the compounds, mixtures and compositions of the present invention are used to control mosquitos and/or bed bugs.

A further embodiment of the invention relates to the use of the compounds, mixtures and compositions according to the invention to control insecticide-resistant mosquitos and/or insecticide-resistant bed bugs and more preferably mosquitos and/or bed bugs that are target-site- and/or metabolic-resistant. Target-site resistance refers to a form of biochemical resistance which occurs when the insecticide compound no longer binds to its target, and metabolic-resistance refers to a form of biochemical resistance which occurs when levels or modified activities of esterases, oxidases, or glutathione S-transferases (GST) prevent an insecticide compound from reaching its site of action.

In another preferred embodiment the compounds, mixtures and compositions of the present invention are preferably used to control insecticide-resistant mosquitos wherein the insecticide-resistant mosquitos are selected from the group of *Anopheles gambiae*, preferably the strain RSPH and *Anopheles funestus*, preferably the strain FUMOZ-R. In another preferred embodiment the compounds, mixtures and compositions of the present invention are used to control pyrethroid and/or carbamate-resistant mosquitos, preferably pyrethroid and/or carbamate-resistant *Anopheles gambiae* and/or *Anopheles funestus* mosquitos. More preferably, the compounds, mixtures and compositions of the present invention are used to control pyrethroid-resistant mosquitos, preferably pyrethroid-resistant *Anopheles gambiae* and/or *Anopheles funestus* mosquitos. Another preferred embodiment of the invention relates to the compounds, mixtures and compositions of the present invention used to control multi-resistant mosquitos.

The invention also relates to the use of an active compound composition according to the invention to control pyrethroid-resistant bed bugs. In a preferred embodiment, the active compound composition of the invention is used to control pyrethroid-resistant bed bugs, wherein the bed bugs have a Valine to Leucine mutation (V419L) and/or a Leucine to Isoleucine mutation (L925I) in the voltage-gated sodium channel alpha-subunit gene.

Another embodiment of the invention relates to a method to control animal pests, preferably arthropods, preferably insects and more preferably mosquitos and/or bed bugs in particular insecticide-resistant mosquitos and/or insecticide-resistant bed bugs and more preferably mosquitos and/or bed bugs that are target-site- and/or metabolic-resistant. Another preferred embodiment relates to a method to control insecticide-resistant mosquitos wherein the insecticide-resistant mosquitos are selected from the group of *Anopheles gambiae*, preferably the strain RSPH and *Anopheles funestus*, preferably the strain FUMOZ-R. In another preferred embodiment the current invention relates to a method to control pyrethroid and/or carbamate-resistant mosquitos, preferably pyrethroid and/or carbamate-resistant *Anopheles gambiae* and/'or *Anopheles funestus* mosquitos with the active compound composition of the invention. More preferably, the current invention relates to a method to control pyrethroid-resistant mosquitos, preferably pyrethroid-resistant *Anopheles gambiae* and/or *Anopheles funestus* mosquitos with the active compound composition of the invention. Another preferred embodiment of the invention relates to a method to control multi-resistant mosquitos with the active compound composition of the invention.

The invention also relates to a method to control of pyrethroid-resistant bed bugs with the active compound composition of the invention. More preferably, the current invention relates to a method to control pyrethroid-resistant bed bugs that have a Valine to Leucine mutation (V419L) and or a Leucine to Isoleucine mutation (L925I) in the voltage-gated sodium channel alpha-subunit gene.

Another embodiment of the invention relates to a method to overcome insecticide resistance, preferably a target-site and/or metabolic-resistance, in mosquitos and/or bed bugs by applying an active compound composition according to invention to mosquitos and/or bed bugs that have insecticide-resistance respectively a target-site and/or metabolic-resistance. In a preferred embodiment, the invention relates to a method to overcome insecticide resistance in insecticide-resistant mosquitos selected from the group of *Anopheles gambiae*, preferably the strain RSPH and *Anopheles funestus*, preferably the strain FUMOZ-R by applying an active compound composition of the invention to such mosquitos. In another preferred embodiment the current invention relates to a method to overcome pyrethroid and/or carbamate resistance in mosquitos, preferably in *Anopheles gambiae* and/or *Anopheles funestus* mosquitos, by applying an active compound composition of the invention to such mosquitos. More preferably, the compounds, mixtures and compositions of the present invention are used to overcome insecticide resistance in pyrethroid-resistant mosquitos, preferably pyrethroid-resistant *Anopheles gambiae* and/or *Anopheles funestus* mosquitos. Another preferred embodiment of the invention relates to a method to overcome multi-resistance in mosquitos by applying an active compound composition of the invention to such multi-resistant mosquitos.

The invention also relates to a method to overcome pyrethroid resistance by applying an active compound composition according to invention to bed bugs that have pyrethroid resistance.

More preferably, the compounds, mixtures and compositions of the present invention are used to overcome insecticide resistance in pyrethroid-resistant bed bugs that have a Valine to Leucine mutation (V419L) and/or a Leucine to Isoleucine mutation (L925I) in the voltage-gated sodium channel alpha-subunit gene.

The phrase "to overcome insecticide-resistance" refers to the observation that the compounds, mixtures and compositions of the invention are more efficient in killing a certain insecticide-resistant mosquito than a similarly concentrated active compound from an insecticidal class towards which such an insecticide-resistant mosquito has developed a resistance.

*Anopheles gambiae*, the strain RSPH is a multi-resistant mosquito (target-site and metabolic-resistance) that is described in the reagent catalog of the Malaria Research and Reference Reagent Resource Center (www.MR4.org; MR4-number: MRA-334). *Anopheles funestus*, strain FUMOZ-R is a metabolic-resistant strain and is described in Hunt et al., Med Vet Entomol. 2005 September; 19(3):271-5). In this article it has been reported that *Anopheles funestus*—as one of the major malaria vector mosquitos in Africa—showed resistance to pyrethroids and carbmate insecticides in South Africa.

Certain Bed bugs are known to be resistant to pyrethroids, wherein the pyrethorids resistance can be ascribed to metabolic resistance such as increased metabolic detoxification by P450s, glutathione transferases, and esterases as well as target-site resistance due to decreased target-site sensitivity of voltage-gated sodium channels. It has been also reported that a Valine to Leucine mutation (V419L) and/or the Leucine to Isoleucine mutation (L925I) in voltage-gated sodium channel alpha-subunit gene is responsible for target-site resistance to deltamethrin in bed bugs (Fan Zhu et al., Archives of Insect Biochemistry and Physiology, 2010, Vol. 00, No 0, 1-13).

Pyrethroid and/or carbamate-resistant mosquitos are mosquitos that are resistant to the treatment of pyrethroid insecticides and/or carbamate insecticides. Pyrethroid insecticides are e.g. allethrin, bifenthrin, cyfluthrin, cypermethrin, cyphenothrin, deltamethrin, esfenvalerate, etofenprox, fenpropathrin, fenvalerate, flucythrinate, imiprothrin, lambda-cyhalothrin, metofluthrin, permethrin, prallethrin resmethrin, silafluofen, sumithrin, tau-fluvalinate, tefluthrin, tetramethrin, tralomethrin, transfluthrin. Carbamate insecticides are e.g. aldicarb, benfuracarb, carbaryl, carbofuran, carbosulfan, fenobucarb, methiocarb, methomyl, oxamyl, thiodicarb, triazamate.

Insecticide-resistant mosquitos refers to mosquitos that are resistant to at least one insecticide chemical class. Multi-resistant mosquitos refers to a mosquitos where several different resistance mechanisms are present simultaneously such as target-site resistance and metabolic resistance. The different resistance mechanisms may combine to provide resistance to multiple classes of products (IRAC publication: "Preventation and Management of Insecticide Resistance in Vectors of Public Health Importance"; second edition; 2011). The compounds, mixtures and compositions according to the invention may comprise further components, for example additional active compounds of a different type (e.g. other insecticides, antibacterial compounds, fungicides, herbicides etc.) and/or additives customary in crop protection and/or formulation auxiliaries, or may be used together with these compounds. In a preferred embodiment, the compounds, mixtures and compositions according to the invention have synergistic actions preferably in regard to the above outlined uses. The synergistic effects permit a reduction of the application rates, a higher efficacy at the same application rate and/or a reduction in the number of individual applications required and/or to overcome an existing insecticide resistance and—as a result for the user—an economically and ecologically improved control of animal pests and in particular an improved resistant management of mosquitos.

In one embodiment, the invention relates to a method for controlling mosquitoes and/or bed bugs, which method comprises applying a a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the invention relates to a method for controlling mosquitoes and/or bed bugs, wherein the mosquitoes and/or bed bugs are target-site and/or metabolic-resistant, which method comprises applying a a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In the case of mixtures, the ratio of the compounds I and the mixture partner, and the total amount of the mixture to be employed, depend on the species and the occurrence of the arthropods. The optimal ratios and overall rates used can be determined for each application by test series. For the use of mosquitos, it may e.g. be from 1:1 to 1:200, preferably from, 1:1 to 1:125, more preferably from 1:5 to 1:125, even more preferably from 1:25 to 1:125.

The application rate of the compounds, mixtures and compositions according to the invention varies preferably within ranges of between 0.001 and 1000 mg/m2, more preferably, 2 and 500 mg/m2 and even more preferred between 5 and 250 mg/m2.

The compounds, mixtures and compositions of the invention can be converted to the customary compositions as described in this application.

The compounds, mixtures and compositions of the invention can be used for liquid applications such as e.g a spray solution to control animal pests on a variety of surfaces. The treatment of surfaces for example within or outside from buildings is necessary to control spreading of diseases that are transmitted by arthropods such as insects or arachnids (such as for example mosquitos or bed bugs) that transmit diseases or that annoys animals and humans. There is a great need for protecting the inhabitants effectively and with a long-lasting residuality. Moreover, reasons of hygiene and structural engineering require that animal pests be prevented from entering into buildings, spreading and dwelling in buildings and infesting wood or other materials.

Other uses include the intergration or coating of the active compound composition according to the invention into/of materials such as pellets, granules, dusts, yarns, foils, sleeping mats, mosquito nets, textiles, wovens, braids, knits, felts, nonwovens, curtains, draperies, tarpaulins, fabrics, wood, papers, furnitures, fences in particular animal fences, paints etc. (integration of active ingredients into foils and mosquito nets is e.g. described in WO-A-2009/121580; PCT/EP2011/0055822, WO2011/128380).

The present invention also relates to a material which comprises the active compound composition of the invention. The material is preferably selected from the group of foil, sleeping net, sleeping mat, mosquito net, textile, woven, braid, knit, felt, nonwoven, curtain, drapery, tarpaulin, fabric, wood, paper, furniture, fence preferably animal fence, paint. Another preferred embodiment of the invention relates to a bed bug bait which comprises the active compound composition of the invention and means to attract bed bugs. Means to attract bed bugs are know to a skilled person in the art (see e.g WO 2011/149899).

Alternatively, in another embodiment of the invention, the compounds, mixtures and compositions is used to control bed bugs via an ovicidial activity. For this purpose, the compounds, mixtures and compositions of the invention are applied to (e.g. sprayed on) bed bugs and eggs directly (such as e.g. on bedsprings, box springs, and the interior of bed frames or headboards, including all cracks and joints).

A further embodiment of this invention relates to the use of the above described material to control animal pests, preferably arthropods, preferably insects and more preferably mosquitos and/or bed bugs in particular insecticide-resistant mosquitos and/or insecticide-resistant bed bugs and more preferably mosquitos and/or bed bugs that are target-site- and/or metabolic-resistant. Another preferred embodiment relates to the use of such a material to control insecticide-resistant mosquitos wherein the insecticide-resistant mosquitos are selected from the group of *Anopheles gambiae*, preferably the strain RSPH and *Anopheles funestus*, preferably the strain FUMOZ-R. In another preferred embodiment the current invention relates to the use of such a material to control pyrethroid and/or carbamate-resistant mosquitos, preferably pyrethroid and/or carbamate-resistant *Anopheles gambiae* and/or *Anopheles funestus* mosquitos. More preferably, the material of the present invention is used to control pyrethroid-resistant mosquitos, preferably pyrethroid-resistant *Anopheles gambiae* and/or *Anopheles funestus* mosquitos. Another preferred embodiment of the invention relates to the use of such a material to control multi-resistant mosquitos.

The invention also relates to the use of the above described material to control pyrethroid-resistant bed bugs. In a preferred embodiment, the material is used to control pyrethroid-resistant bed bugs, wherein the bed bugs have a Valine to Leucine mutation (V419L) and/or a Leucine to Isoleucine mutation (L925I) in the voltage-gated sodium channel alpha-subunit gene. The good insecticidal activity of the compounds, mixtures and compositions is illustrated by the examples below. Whereas the individual active compounds show weaknesses in their activity, the combinations show an activity which exceeds a simple addition of activities.

In the case of mixtures, a synergistic effect of the active compound combination is always present when the activity of the active compound combination exceeds the total of the activities of the active compounds when applied individually.

The expected activity for a given combination of two active compounds can be calculated according to S. R. Colby, Weeds 15 (1967), 20-22.

If, in the context of this description, the short form of the "common name" of an active compound is used, this comprises in each case all customary derivatives, such as the esters and salts, and isomers, in particular optical isomers, especially the commercially available form or forms. If the "common name" refers to an ester or a salt, this in each case also comprises all other customary derivatives, such as other esters and salts, the free acids and neutral compounds, and isomers, in particular optical isomers, especially the commercially available form or forms.

Methods for Controlling a Population of Social Insects

The subject of the present invention is a method for controlling a population of social insects, especially ants, termites, wasps and cockroaches.

It is often very desirable to combat the drawbacks caused by populations of social insects such as ants or termites or wasps or cockroaches, especially in the case of ant populations. Social insects are insects which live in a large society, or in a colony comprising a large number of such insects or congeners.

In the case of ants, for example, these drawbacks generally stem from the inconvenience caused to individuals by the presence or passage of columns of ants in living areas or in the immediate vicinity thereof, such as in the garden or on the patio. The passage of such columns of ants on the lawn next to a private house may especially be particularly unpleasant for the resident wishing to relax by stretching out on the said lawn, on account of the bites inflicted by certain species.

The control of ants is also desirable as regards the cultivation of fruit trees and/or ornamental trees. The reason for this is that certain species of ant provide a role of defending aphids against their predators and thus contribute towards maintaining high populations of aphids, which are harmful to the good health of the trees concerned and/or to fruit yields.

Certain species of ant sometimes cause even greater inconvenience. Thus, the pharaoh ant (*Monomorium pharaonis*) may create anthills even inside living areas, which, in the case of blocks of flats and especially of hospitals, poses hygiene problems.

Now, the inconvenience and/or damage caused by social insects such as ants or termites or wasps or cockroaches, and preferably ants or cockroaches, are in direct proportion with the sometimes very large number which a population of such insects may reach, for example, in the case of ants, the very large number of individuals in the population of an anthill.

Methods for controlling ants or termites or wasps or cockroaches using insecticidal compounds are known. However, these methods are not always satisfactory.

The reason for this is that they often destroy only a small portion of the population concerned, for example, in the case of ants, a fraction of the workers whose function is to collect food outside the anthill. The destruction of this population category is not, however, sufficient to overcome the drawbacks caused by the ants. Indeed, the large capacity of ants to proliferate and their specialization based on the needs of the anthill are capable of rapidly compensating for this destruction, bringing about a new increase in the population.

The known methods moreover have the drawback that it is very difficult to treat all the individuals of the population, especially on account of the fact that, as regards ants, the anthills are fairly inaccessible, since they are generally located at a depth of several tens of centimetres below the surface of the ground.

One aim of the present invention is to overcome these drawbacks.

Another aim of the present invention is to ensure the destruction of the larvae present in the anthill, or more generally in the nest or dwelling place of the said social insects.

Another aim of the present invention is to ensure the destruction of the laying females present in the anthill, or more generally in the nest or dwelling place of the said social insects.

Another aim of the present invention is to propose a method which allows the definitive destruction of all or almost all of a population of social insects such as ants or termites or wasps or cockroaches, preferably such as ants or cockroaches, or in another embodiment such as termites.

It has now been found that these aims could be totally or partly achieved by means of the control method according to the invention which is described in detail below.

In one embodiment, the invention relates to a method for controlling a population of social insects, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

The subject of the present invention is thus a method for controlling a population of social insects such as ants or termites or wasps or cockroaches, characterized in that there is applied to a minor fraction of this population an effective amount of a composition comprising a bait and a compound I as defined herein.

Populations of ants are more especially preferred among the populations of social insects which may be controlled using the method according to the invention.

Populations of termites are also more especially preferred among the populations of social insects which may be controlled using the method according to the invention.

In the sense of the present invention, control of a population of social insects such as ants, termites, wasps or cockroaches is understood to mean the control of the said insects, and more particularly the total or almost total destruction of the said population, in other words the destruction of more than 60%, preferably more than 70% and even more preferably of 95 to 100%, of the said population.

An effective amount of the composition used in the method according to the invention is understood to mean an amount which is capable of controlling the whole population of social insects such as a population of ants or termites or wasps or cockroaches.

More particularly, the invention relates to a method for treating social insects such as ants, termites, cockroaches or wasps with an effective amount of active material I, this effective amount of composition being an amount used equal to the dose required to destroy at least 90 percent of the minor fraction of the population of social insects to which the said composition is applied, within a period of between 2 and 30 days, preferably between 2 and 7 days. The minor fraction often corresponds in practice to the population living or circulating outside the common dwelling place or nest.

According to a more preferred variant of the invention, when the population of social insects is a population of ants, the effective amount of composition used for the method according to the invention is generally such that the dose of compound I is between 0.05 and 50 mg per anthill treated, preferably from 0.1 to 20 mg. This effective amount may be determined more precisely within this range by systematic tests, depending on the species of ant whose population it is desired to control, and also depending on the size and extent of the anthills which may vary according to the nature of these species.

The invention thus also relates to a method for controlling social insects such as ants, termites, wasps or cockroaches (but preferably cockroaches) which have a common dwelling place or nest in which they live with a substantial population of their congeners, the said method comprising a treatment with an effective dose, preferably a dose of between 0.0001 and 20 grams per 100 m2, of one or more areas frequented by, or assumed to be frequented by, the said social insects (preferably cockroaches), the said area being outside the place of the said common dwelling but being a place in which the cockroaches circulate or are assumed to circulate.

The ants which may be controlled using the method according to the invention are especially:

ants of the genus *Lasius*, for example the black ant (*Lasius niger*);
the pavement ant (*Tetramorium caespitum*);
the pharaoh ant (*Monomorium pharaonis*);
the Argentine ant (*Iridomyrmex humilis*);
fire ants belonging to the genus *Solenopsis*;
fungal ants, such as the ants of the genus *Acromyrmex* (for example the *cassaya* ant) and the
ants of the genus *Atta*.

The cockroaches which may be treated by the method of the invention are mainly *Blatella germanica, Blatella orientalis, Periplaneta americana, Periplaneta fuliginosa*.

The bait employed in the composition used in the method according to the invention is a product which is sufficiently appetizing to incite social insects such as ants or wasps or cockroaches to eat it. In the case of ants, this bait is chosen, for example, but not exclusively, from animal and/or plant proteins, or alternatively from fats, also of animal and/or plant origin, or even from mono-, oligo- or polyorganosaccharides, especially from sucrose, lactose, fructose, dextrose, glucose or even molasses or honey.

The minor fraction of the population to which the composition employed in the method according to the invention is applied is generally between 1 and 50 percent of the total population, preferably between 2 and 20 percent.

According to a preferred variant of the invention, the population of ants which may be controlled using the method according to the invention is a population of ants living in the same anthill. In this case, the minor fraction of the population to which the composition is applied generally consists of workers whose function is to collect food from outside the anthill, these being known as the harvester workers of the anthill.

According to another preferred variant of the invention, the ant or cockroach population which can be controlled by means of the method according to the invention is a population of cockroaches living in the same common dwelling place for cockroaches.

The dose of compound I in the composition used is between 0.0005 and 0.5 percent, preferably between 0.001 and 0.2 percent. In the present text, the percentages corresponding to doses are, except where otherwise mentioned, weight/weight percentages.

The dose of bait in the composition used is generally between 1 and 99 percent, preferably between 30 and 99%. The composition used may also comprise other additives such as a solvent for the active material, a flavoring, a preserving agent, a dye or a bitter agent.

According to a particularly advantageous variant of the method according to the invention, it is preferred to apply the composition by placing it in a closed bait-carrier box containing openings which are reserved, on account of their size, for the exclusive use of ants or cockroaches, or insects of similar size, in an area where these insects are likely to be found. The area may especially be in a public or private place, such as a living area, or alternatively on a balcony, a patio, in a garden or in a field. This variant is of improved safety, since it concerns an active material which is liable to present a risk in the case of accidental contact or ingestion by pets or children.

The details of applications for termites are in principle the same as described herein for ants. In addition, the methods and uses according to the invention may also be applied in buildings and construction, e.g. houses. According to climatic conditions and occurrence of termites, it may be a relevant goal to protect houses and other buildings from termites.

Especially, the invention relates to:
Method according to the invention, wherein the non-crop pest is selected from termites (Isoptera).
Method according to the invention, wherein the non-crop pest is selected from ants (Hymenoptera).
Method according to the invention, wherein the non-crop pest is selected from crickets, grasshoppers, locusts (Orthoptera).
Bait comprising a compound I as defined herein.
A method for controlling a population of social insects, comprising contacting the pests or their food supply, habitat, breeding grounds or their locus with at least one pesticidally active anthranilamide compound I as defined herein.
Use of a compound I as defined herein, or a composition comprising said compound,
for controlling a population of social insects, and/or
for controlling termites (Isoptera), and/or
for controlling ants (Hymenoptera), and/or
for controlling crickets, grasshoppers, locusts (Orthoptera).

B. Biological Examples

1. Activity against Argentine ant, harvester ant, acrobat ant, carpenter ant, fire ant, house fly, stable fly, flesh fly, yellowfever mosquito, house mosquito, malaria mosquito, German cockroach, cat flea, and brown dog tick via glass contact Glass vials (20 ml scintillation vials) are treated with 0.5 ml of a solution of active ingredient in acetone. Each vial is rolled uncapped for ca. 10 minutes to allow the a.i. to completely coat the vial and to allow for full drying of the acetone. Insects or ticks are placed into each vial. The vials are kept at 22 degrees centigrade and are observed for treatment effects at various time intervals.

2. Activity against Argentine ant, acrobat ant, carpenter ant, fire ant, and eastern subterranean termite via soil contact For ants, tests are conducted in Petri dishes. A thin layer of 1 percent agar in water is dispensed into the dishes and Florida sandy soil is spread over the agar (5 g for the small dishes and 11 g for the larger dishes). The active ingredient is dissolved in acetone and dispensed over the sand. Dishes are vented to evaporate the acetone, infested with ants, and covered. A 20% honey water solution is placed in each dish. The dishes are maintained at 22° C. and observed for mortality at various time intervals.

For termites, a thin layer of 1% agar is dispensed into Petri dishes. A thin layer of pre-treated soil is spread over the agar. For soil treatment, the active ingredient is diluted in acetone on a weight-to-weight basis and incorporated into 100 g of soil. The soil is placed in a jar and vented for 48 hours. The moisture level of the soil is brought to field capacity by adding 7 ml of water.

Termite workers are introduced into each dish. A small piece of filter paper is placed into each dish after 1 day as a food source, and additional water is added as needed to maintain soil moisture. Test dishes are held at a dark incubator at 25° C. and appr. 80% relative humidity.

Termites are observed daily for mortality (dead or unable to stand upright and showing only weak movement).

3. Activity against Argentine ant, acrobat ant, carpenter ant, fire ant, house fly, eastern subterranean termite, formosan subterranean termite, and German cockroach via bait For Argentine ant, acrobat ant, and carpenter ant, tests are conducted in Petri dishes. Ants are given a water source, and then are starved of a food source for 24 hours. Baits are prepared with either 20% honey/water solutions or ground cat chow. Active ingredient in acetone is added to the bait. 0.2 ml of treated honey water solution or 150 mg of treated cat chow, placed in a cap, is added to each dish. The dishes are covered and maintained at a temperature of 22° C. The ants are observed for mortality daily.

For the fire ants, corn grit is used as a bait matrix. Corn grit bait is prepared using a mixture of defatted corn grit (80%), soybean oil (19.9%), acetone, and the active ingredient (0.1%). Petri dishes are supplied with a water source. Fire ant adults are placed into each dish. The next day, 250 mg of bait in bait containers is placed into the dishes. The ants are observed for mortality daily.

For house flies. Bait tests are conducted with adults aged 2-5 days post-emergence. Active ingredient in acetone is applied to a bait matrix consisting of a 1:1 mixture of powdered milk and sugar which was then allowed to dry. Assays are conducted in jars with 250 mg of bait in a pan placed in the bottom of each jar. House flies are placed into the bait jars which are covered. The test jars are held at 22° C. Test jars are observed at 4 hours after treatment for knockdown (death plus morbidity (unable to stay upright).

For termites, active ingredient in acetone is applied to filter papers. % a.i. are calculated on basis of the weight of the filter paper. Acetone only is applied for untreated controls. Treated papers are vented to evaporate the acetone, moistened with ml water, and placed Petri dishes with sand. Water is added during the test as needed. Bioassays are conducted with one treated filter and ca. 30 termite workers per test dish. Test dishes are maintained at 25° C. and appr. 85% relative humidity and observed daily for mortality (dead or moribund insects) or intoxication. Dead or moribund insects are removed daily.

For cockroaches, plastic roach boxes with ventilated lids are used as test arenas. The top 3-4 cm of the arenas are treated with Vaseline and mineral oil to prevent roaches from escaping.

Water is provided as needed. The bait is prepared using ground cat chow, and the active ingredient in acetone is incorporated on a weight-to-weight ratio. The treated chow is allowed to dry. The cockroaches are placed in the boxes and starved for 24 hours prior to bait introduction. 0.03 grams of bait per box are placed in a weigh boat. The boxes are maintained at 22° C. and observed daily for mortality of the cockroaches.

4. Activity against yellowfever mosquito, southern house mosquito, and malaria mosquito larvae via water treatment Well plates are used as test arenas. The active ingredient is dissolved in acetone and diluted with water to obtain the concentrations needed. The final solutions contain ing appr. 1% acetone are placed into each well. Approximately 10 mosquito larvae (4th-instars) in 1 ml water are added to each well. Larvae are fed one drop of liver powder each day. The dishes are covered and maintained at 22° C. Mortality is recorded daily and dead larvae and live or dead pupae are removed daily. At the end of the test remaining live larvae are recorded and percent mortality is calculated.

Each test is replicated at least 3 times.

For evaluating control of yellow fever mosquito (*Aedes aegypti*) the test unit consists of 96-well-microtiter plates containing 200 µl of tap water per well and 5-15 freshly hatched *A. aegypti* larvae.

The compounds or mixtures are formulated using a solution containing 75% water and 25% DMSO. Different concentrations of formulated compounds or mixtures are sprayed onto the insect diet at 2.5 µl, using a custom built micro atomizer, at two replications.

For experimental mixtures in these tests identical volumes of both mixing partners at the desired concentrations respectively, are mixed together.

After application, microtiter plates are incubated at 28±1° C., 80±5% RH for 2 days. Larval mortality is then visually assessed.

Embodiment E7

The present invention relates to a composition comprising an anthranilamide compound I, the use of this composition for improving plant health and a method for improving plant health by treating a plant, its propagules or the locus where the plant is growing or is to grow with the above composition.

The invention relates to to the use of the compounds I itself and their stereoisomers, salts, tautomers or N-oxides, especially their salts, and their mixtures, for increasing the health of plants, for increasing the yield, the resistance against fungi or animal pests or external factors like heat, cold or drought, and for increasing the quality of the crops and other parameters. This also includes the use or method of reducing nitrous oxide emission from soils.

In crop protection, there is a continuous need for compositions that improve the health of plants. Healthier plants are desirable since they result in better crop yields and/or a better quality of the plants or crops. Healthier plants also better resist to biotic and/or abiotic stress. A high resistance against biotic stresses in turn allows the person skilled in the art to reduce the quantity of pesticides applied and consequently to slow down the development of resistances against the respective pesticides.

It was therefore an object of the present invention to provide a pesticidal composition which solves the problems outlined above. In particular, the composition should improve plant health.

The present invention is based on the surprising finding that a compound selected from the compounds I as defined herein can be successfully used to improve plant health.

Thus in the first aspect of the invention there is provided a method of improving plant health, which method comprises applying at least one pesticidally active anthranilamide compound I as defined herein, or a stereoisomer, salt, tautomer or N-oxide, or a polymorphic crystalline form, a co-crystal or a solvate of a compound or a stereoisomer, salt, tautomer or N-oxide thereof.

Accordingly, the present invention relates to the use of a compound I as defined herein, or a stereoisomer, salt, tautomer or N-oxide thereof, or a composition comprising it, for improving the plant health of at least one plant variety.

In one embodiment, the compound I in the methods and uses according to the invention of E7 is selected from the compounds described in Embodiment A.

In one embodiment, the compound I in the methods and uses according to the invention of E7 is selected from the compounds described in Embodiment B.

In one embodiment, the compound I in the methods and uses according to the invention of E7 is selected from the compounds described in Embodiment C.

In one embodiment, the compound I in the methods and uses according to the invention of E7 is selected from the compounds listed in Table ABC.

In some embodiments, the invention relates to methods and uses, wherein the compound I is applied in an application type which corresponds in each case to one row of Table AP-T.

In one embodiment, I-A-1 is the compound I in the methods and uses according to the invention of E7.

In one embodiment, I-A-28 is the compound I in the methods and uses according to the invention of E7.

In one embodiment, I-B-115 is the compound I in the methods and uses according to the invention of E7.

In one embodiment, I-B-131 is the compound I in the methods and uses according to the invention of E7.

In one embodiment, I-B-132 is the compound I in the methods and uses according to the invention of E7.

In one embodiment, I-C-19 is the compound I in the methods and uses according to the invention of E7.

In one embodiment, I-C-35 is the compound I in the methods and uses according to the invention of E7.

In one embodiment, I-C-36 is the compound I in the methods and uses according to the invention of E7.

In a further embodiment of E7, the invention relates to the methods and uses of the compounds according to the invention (as defined in Embodiment A, B or C) in combination with other selected pesticidal compounds (II), as defined and specified in Embodiments 2 and 3.

The plants or crops to be protected are as described above or herein, e.g. in embodiment E1.

The formulations are as described herein, e.g. in embodiment E1.

The applications are as described herein, e.g. in embodiment E1.

The mixtures and preferred mixtures are as described herein, e.g. in E2 and E3.

Methods of Improving Plant Health

The compounds I as defined herein, or a stereoisomer, salt, tautomer or N-oxide thereof, or the compositions comprising them, are used for improving the health of plants when applied to plants, parts of plants, propagules of the plants or to their actual or intended locus of growth.

Thus, the invention also relates to a method for improving the health of plants, which comprises treating the plant, a part of the plant, the locus where the plant is growing or is expected to grow, and/or the propagules from which the plant grows with the compound or composition used according to the invention.

As a matter of course, the compound I is used in an effective and non-phytotoxic amount. This means that they are used in a quantity which allows to obtain the desired effect but which does not give rise to any phytotoxic symptom on the treated plant or on the plant grown from the treated propagule or treated soil.

The plants to be treated are generally plants of economic importance and/or men-grown plants. Thus, they are preferably selected from agricultural, silvicultural and ornamental plants.

The term "plant health" (health of a plant) is defined as a condition of the plant and/or its products which is determined by several aspects alone or in combination with each other such as yield (for example increased biomass and/or increased content of valuable ingredients), plant vigor (for example improved plant growth and/or greener leaves ("greening effect")), quality (for example improved content or composition of certain ingredients) and tolerance to abiotic and/or biotic stress.

The above identified indicators for the health condition of a plant may be interdependent or they may result from each other. Each listed plant health indicator listed below, and which is selected from the groups consisting of yield, plant vigor, quality and tolerance to abiotic and/or biotic stress, is to be understood as a preferred embodiment of the present invention either each on its own or preferably in combination with each other.

One indicator for the condition of the plant is the crop yield. "Crop yield" is to be understood as any plant product of economic value that is produced by the plant such as grains, fruits in the proper sense, vegetables, nuts, grains, seeds, wood (e.g. in the case of silviculture plants) or even flowers (e.g. in the case of gardening plants, ornamentals). The plant products may in addition be further utilized and/or processed after harvesting.

Thus, the invention relates to a method for increasing the yield of a plant or its product.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the compound or composition of the invention.

Increased crop yield can be characterized, among others, by following improved properties of the plant:
  increased plant weight,
  increased plant height,
  increased biomass such as higher overall fresh weight
  higher grain yield
  more tillers
  larger leaves
  increased shoot growth
  increased protein content
  increased oil content
  increased starch content
  increased pigment content According to one embodiment of the present invention, the yield is increased by at least 1%.

According to one embodiment of the present invention, the yield is increased by at least 2%.

According to one embodiment of the present invention, the yield is increased by at least 4%.

According to one embodiment of the present invention, the yield is increased by at least 5%.

According to another embodiment of the present invention, the yield is increased by least 10%.

According to another embodiment of the present invention, the yield is increased by least 15%.

According to another embodiment of the present invention, the yield is increased by least 30%.

Another indicator for the condition of the plant is the plant vigor. The plant vigor becomes manifest in several aspects such as the general visual appearance.

Thus, the invention relates to a method for increasing the vigor of a plant or its product. Improved plant vigor can be characterized, among others, by following improved properties of the plant:
  improved vitality of the plant,
  improved plant growth,
  improved plant development,
  improved visual appearance,
  improved plant stand (less plant verse/lodging),
  improved emergence,
  enhanced root growth and/or more developed root system,
  enhanced nodulation, in particular rhizobial nodulation,
  bigger leaf blade,
  bigger size,
  increased plant weight,
  increased plant height,
  increased tiller number,
  increased shoot growth,
  increased root growth (extensive root system),
  increased yield when grown on poor soils or unfavorable climate,
  enhanced photosynthetic activity
  enhanced pigment content (e.g. Chlorophyll content)
  earlier flowering,
  earlier fruiting,
  earlier and improved germination,
  earlier grain maturity,
  improved self-defence mechanisms
  improved stress tolerance and resistance of the plants against biotic and abiotic stress factors such as fungi, bacteria, viruses, insects, heat stress, cold stress, drought stress, UV stress and/or salt stress
  less non-productive tillers,
  less dead basal leaves,
  less input needed (such as fertilizers or water)
  greener leaves
  complete maturation under shortened vegetation periods
  less fertilizers needed,
  less seeds needed,
  easier harvesting
  faster and more uniform ripening
  longer shelf-life longer panicles,
delay of senescence,
stronger and/or more productive tillers,
better extractability of ingredients
improved quality of seeds (for being seeded in the following seasons for seed production)
reduced production of ethylene and/or the inhibition of its reception by the plant The improvement of the plant vigor according to the present invention particularly means that the improvement of any one or several or all of the above mentioned plant characteristics are improved independently of the pesticidal action of the composition or active ingredients.

Another indicator for the condition of the plant is the "quality" of a plant and/or the products of the respective plant. According to the present invention, enhanced quality means that certain crop characteristics such as the content or composition of certain ingredients are increased or improved by a measurable or noticeable amount over the same factor of the plant produced under the same conditions, but without the application of the composition of the present invention. The quality of a product of the respective plant becomes manifest in several aspects. Thus, the invention relates to a method for increasing the quality of a plant or its product.

Enhanced quality can be characterized, among others, by following improved properties of the plant or its product:
increased nutrient content
increased protein content
increased content of fatty acids
increased metabolite content
increased carotenoid content
increased sugar content
increased amount of essential amino acids
improved nutrient composition
improved protein composition
improved composition of fatty acids
improved metabolite composition
improved carotenoid composition
improved sugar composition
improved amino acids composition
improved or optimal fruit color
improved leaf color
higher storage capacity
higher processability of the harvested products Another indicator for the condition of the plant is the plant's tolerance or resistance to biotic and/or abiotic stress factors. Biotic and abiotic stress, especially over longer terms, can have harmful effects on plants.

Thus, the invention relates to a method for increasing the tolerance and/or resistance of a plant or its product against biotic and/or abiotic stress.

Biotic stress is caused by living organisms while abiotic stress is caused for example by environmental extremes. According to the present invention, "enhanced tolerance or resistance to biotic and/or abiotic stress factors" means (1.) that certain negative factors caused by biotic and/or abiotic stress are diminished in a measurable or noticeable amount as compared to plants exposed to the same conditions, but without being treated with the compound or composition of the invention and (2.) that the negative effects are not diminished by a direct action of the composition on the stress factors, e.g. by its fungicidal or insecticidal action which directly destroys the microorganisms or pests, but rather by a stimulation of the plants' own defensive reactions against said stress factors.

Increased tolerance or resistance can be characterized, among others, by following improved properties of the plant or its product: when grown under the impact of biotic and/or abiotic stress factors.

Negative factors caused by biotic stress such as pathogens and pests are widely known and range from dotted leaves to total destruction of the plant. Biotic stress can be caused by living organisms, such as:
pests (for example insects, arachnides, nematodes),
competing plants (for example weeds),
microorganisms such as phythopathogenic fungi bacteria, viruses Negative factors caused by abiotic stress are also well-known and can often be observed as reduced plant vigor (see above), for example dotted leaves, "burned leaves", reduced growth, less flowers, less biomass, less crop yields, reduced nutritional value of the crops, later crop maturity, to give just a few examples. Abiotic stress can be caused for example by:
extremes in temperature such as heat or cold (heat stress/cold stress),
strong variations in temperature,
temperatures unusual for the specific season,
drought (drought stress),
extreme wetness,
high salinity (salt stress),
radiation (for example by increased UV radiation due to the decreasing ozone layer),
increased ozone levels (ozone stress)
organic pollution (for example by phythotoxic amounts of pesticides)
inorganic pollution (for example by heavy metal contaminants).

Thus, in one embodiment, the invention relates to a method for increasing the resistance to heat, cold or strong variations in temperature.

As a result of biotic and/or abiotic stress factors, the quantity and the quality of the stressed plants, their crops and fruits decrease. As far as quality is concerned, reproductive development is usually severely affected with consequences on the crops which are important for fruits or seeds. Synthesis, accumulation and storage of proteins are mostly affected by temperature; growth is slowed by almost all types of stress; polysaccharide synthesis, both structural and storage is reduced or modified: these effects bring to a decrease in biomass (yield) and to changes in the nutritional value of the product.

Advantageous properties, obtained especially from treated seeds, are e.g. improved germination and field establishment, better vigor, more homogen field establishment.

The above identified indicators for the health condition of a plant may be interdependent and may result from each other. For example, an increased resistance to biotic and/or abiotic stress may lead to a better plant vigor, e.g. to better and bigger crops, and thus to an increased yield.

Inversely, a more developed root system may result in an increased resistance to biotic and/or abiotic stress. However, these interdependencies and interactions are neither all known nor fully understood and therefore the different indicators will be described separately.

In one embodiment, the invention relates to a methods and uses according to the invention wherein the plant is an agricultural, silvicultural and/or ornamental plant.

In one embodiment of the invention, the present invention provides the use of the compound of the invention for increasing the yield of a plant or its product, preferably of an agricultural, silvicultural and/or ornamental plant.

In one embodiment of the invention, the present invention provides the use of the compound of the invention for increasing the vigor of a plant or its product, preferably of an agricultural, silvicultural and/or ornamental plant.

In one embodiment of the invention, the present invention provides the use of the compound of the invention for increasing the quality of a plant or its product, preferably of an agricultural, silvicultural and/or ornamental plant.

In one embodiment of the invention, the present invention provides the use of the compound of the invention for increasing the tolerance and/or resistance of a plant or its product against biotic and/or abiotic stress, preferably of an agricultural, silvicultural and/or ornamental plant.

In one embodiment of the invention, the present invention provides the use of the compound of the invention for increasing the yield and/or improving the vigor of a plant, e.g. of an agricultural, silvicultural and/or ornamental plant.

In one embodiment of the invention, the tolerance of and/or resistance against biotic stress factors is enhanced. Thus, according to a preferred embodiment of the present invention, the inventive compounds or compositions are used for stimulating the natural defensive reactions of a plant against a pathogen and/or a pest. Thereby, the plant can be protected against unwanted microorganisms such as phytopathogenic fungi and/or bacteria or even viruses and/or against pests such as insects, arachnids and nematodes, and it has been found that the inventive compositions result in plant strengthening effects. Therefore, they are useful for mobilizing the plant's defense mechanisms against the attack of unwanted microorganisms and/or pests. Consequently, the plant becomes tolerant or even resistant towards these microorganisms and/or pests.

In one embodiment of the invention, the tolerance of and/or resistance against abiotic stress factors is enhanced. Thus, according to a further embodiment of the present invention, the inventive compounds or compositions are used for stimulating a plant's own defensive reactions against abiotic stress such as extremes in temperature, e.g. heat or cold or strong variations in temperature or temperatures unusual for the specific season, drought, extreme wetness, high salinity, radiation (e.g. increased UV radiation due to the decreasing ozone protective layer), increased ozone levels, organic pollution (e.g. by phytotoxic amounts of pesticides) and/or inorganic pollution (e.g. by heavy metal contaminants).

In one embodiment of the invention, the inventive compositions are used for stimulating a plant's own defensive reactions against abiotic stress, where the abiotic stress factors are preferably selected from extremes in temperature, drought, salt and extreme wetness.

Therefore, the invention relates to the use of a compound I as defined herein, or a composition comprising said compound, for
improving the health of a plant, and/or
for increasing the yield of a plant or its product, and/or
for increasing the vigor of a plant or its product, and/or
for increasing the quality of a plant or its product, and/or
for increasing the tolerance and/or resistance of a plant or its product against biotic and/or abiotic stress, and/or
for increasing the resistance to heat, cold or strong variations in temperature.

In one embodiment, the invention relates to a method for improving the health of a plant, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the invention relates to a method for increasing the yield of a plant or its product, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the invention relates to a method for increasing the vigor of a plant or its product, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the invention relates to a method for increasing the quality of a plant or its product, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the invention relates to a method for increasing the tolerance and/or resistance of a plant or its product against biotic and/or abiotic stress, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the invention relates to a method for increasing the resistance to heat, cold or strong variations in temperature, which method comprises applying a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment of the invention, the plant of which the health is to be improved by the treatment with the compound or composition of the invention is an agricultural plant. Agricultural plants are plants of which a part or all is harvested or cultivated on a commercial scale or which serve as an important source of feed, food, fibers (e.g. cotton, linen), combustibles (e.g. wood, bioethanol, biodiesel, biomass) or other chemical compounds. Agricultural plants also horticultural plants, i.e. plants grown in gardens (and not on fields), such as certain fruits and vegetables.

It has to be emphasized that the above mentioned effects of the compound or composition according to the invention, i.e. enhanced health of the plant, are also present when the plant is not under biotic stress and in particular when the plant is not under fungal- or pest pressure. It is evident that a plant suffering from fungal or insecticidal attack produces a smaller biomass and a smaller crop yield as compared to a plant which has been subjected to curative or preventive treatment against the pathogenic fungus or pest and which can grow without the damage caused by the biotic stress factor. However, the method according to the invention leads to an enhanced plant health even in the absence of any biotic stress and in particular of any phytopathogenic fungi or pest. This means that the positive effects of the compound or composition of the invention cannot be explained just by the fungicidal or insecticidal activities of the compounds of components (A) and (B), but are based on further activity profiles. But of course, plants under biotic stress can be treated, too, according to the methods of the present invention.

Method and Uses for Reducing Nitrous Oxide Emission

As mentioned above, the uses and methods according to the invention also include methods for reducing nitrous oxide emission from soils. These methods may also be considered as methods improving plant health, due to the beneficial effect on the plant itself.

Thus, the present invention relates to a method for reducing nitrous oxide emission from soils comprising treating a plant growing on the respective soil and/or the locus where the plant is growing or is intended to grow and/or the seeds from which the plant grows with at least one compound I according to the invention, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In one embodiment, the compound I in the methods and uses for reducing nitrous oxide emission according to the invention of E7 is selected from the compounds described in Embodiment A.

In one embodiment, the compound I in the methods and uses for reducing nitrous oxide emission according to the invention of E7 is selected from the compounds described in Embodiment B.

In one embodiment, the compound I in the methods and uses for reducing nitrous oxide emission according to the invention of E7 is selected from the compounds described in Embodiment C.

In one embodiment, the compound I in the methods and uses for reducing nitrous oxide emission according to the invention of E7 is selected from the compounds listed in Table ABC.

In one embodiment, I-A-1 is the compound I in the methods and uses for reducing nitrous oxide emission according to the invention of E7.

In one embodiment, I-A-28 is the compound I in the methods and uses for reducing nitrous oxide emission according to the invention of E7.

In one embodiment, I-B-115 is the compound I in the methods and uses for reducing nitrous oxide emission according to the invention of E7.

In one embodiment, I-B-131 is the compound I in the methods and uses for reducing nitrous oxide emission according to the invention of E7.

In one embodiment, I-B-132 is the compound I in the methods and uses for reducing nitrous oxide emission according to the invention of E7.

In one embodiment, I-C-19 is the compound I in the methods and uses for reducing nitrous oxide emission according to the invention of E7.

In one embodiment, I-C-35 is the compound I in the methods and uses for reducing nitrous oxide emission according to the invention of E7.

In one embodiment, I-C-36 is the compound I in the methods and uses for reducing nitrous oxide emission according to the invention of E7.

In a further embodiment of E7, the invention relates to the methods and uses for reducing nitrous oxide emission of the compounds according to the invention (as defined in Embodiment A, B or C) in combination with other selected pesticidal compounds (II), as defined and specified in Embodiments 2 and 3.

The present invention relates to a method for reducing nitrous oxide emission from soils comprising treating a plant growing on the respective soil and/or the locus where the plant is growing or is intended to grow and/or the seeds from which the plant grows with A) at least one compound I according to the invention, more preferably a compound I, which is selected from the compounds as defined in Table ABC. More specifically, the compound I is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

B) and at least one ammonium- or urea-containing fertilizer (compound B) selected from the group consisting of:

(B1) inorganic fertilizer:

NPK fertilizer, ammonium nitrate, calcium ammonium nitrate, ammonium sulfate; nitrate, ammonium sulfate and ammonium phosphate;

(B2) organic fertilizer:

liquid manure, semi-liquid manure, stable manure and straw manure, worm castings, compost, seaweed and guano;

The invention relates to such a method as described above, wherein the application of at least one compound I (A) and at least one compound (B) is carried out with a time lag of at least 1 day.

In addition, the present invention relates to a method for reducing nitrous oxide emission from soils as described above, wherein the ammonium- or urea-containing fertilizer (compound B) is applied together with at least one nitrification inhibitor (compound C) selected from the group consisting of 2-(3,4-dimethyl-pyrazol-1-yl)-succinic acid, 3,4-dimethylpyrazolephosphate (DMPP), dicyandiamide (DCD), 1H-1,2,4-triazole, 3-methylpyrazole (3-MP), 2-chloro-6-(trichloromethyl)-pyridine, 5-ethoxy-3-trichloromethyl-1,2,4-thiadiazol, 2-amino-4-chloro-6-methyl-pyrimidine, 2-mercapto-benzothiazole, 2-sulfanilamidothiazole, thiourea, sodium azide, potassium azide, 1-hydroxypyrazole, 2-methylpyrazole-1-carboxamide, 4-amino-1,2,4-triazole, 3-mercapto-1,2,4-triazole, 2,4-diamino-6-trichloromethyl-5-triazine, carbon bisulfide, ammonium thiosulfate, sodium trithiocarbonate, 2,3-dihydro-2,2-dimethyl-7-benzofuranol methyl carbamate and N-(2,6-dimethylphenyl)-N-(methoxyacetyl)-alanine methyl ester.

Nitrogen is an essential element for plant growth and reproduction. About 25% of the plant-available nitrogen in soils (ammonium and nitrate) originate from decomposition processes (mineralization) of organic nitrogen compounds such as humus, plant and animal residues and organic fertilizers. Approximately 5% derive from rainfall. On a global basis, the biggest part (70%), however, are supplied to the plant by inorganic nitrogen fertilizers. Without the use of nitrogenous fertilizers, the earth would not be able to support its current population.

Soil microorganisms convert organic nitrogen to ammonium ($NH_4^+$) which is subsequently oxidized to nitrate ($NO_3^-$) in a process known as nitrification. Nitrate is very important in agriculture, because it is one form of nitrogen which is preferably taken up by the plants due to its high plant-availability. However, nitrate is also highly mobile in the soil. As a consequence, it may be readily lost from soils leaching to groundwater. In addition, nitrogen is lost by denitrification which is the microbiological conversion of nitrate and nitrite ($NO_2^-$) to gaseous forms of nitrogen such as nitrous oxide ($N_2O$) and molecular nitrogen ($N_2$). As a result of the various losses, approximately 50% of the applied nitrogen is lost during the year following fertilizer addition (cf. Nelson and Huber; Nitrification inhibitors for corn production (2001). National Corn Handbook, Iowa State University).

Consequently, there is great concern that the intensive use of fertilizer and the application of livestock wastes may lead to increased nitrogen levels in the groundwater and surface waters which in turn could lead to increased eutrophication of lakes and streams.

In addition, nitrogen fertilization and livestock wastes may increase the production of nitrous oxide, significantly contributing to the stratospheric ozone destruction and global warming. Besides nitrous oxide, carbon dioxide ($CO_2$) and methane ($CH_4$) are important gases produced by native and agricultural soils. Depending on various parameters such as weather and soil type, increased fertilization and tillage can additionally increase nitrous oxide emissions.

As a consequence, one of the biggest challenge to the world community in the coming years will be the reduction of gases responsible for the greenhouse effect in the atmosphere or at least the stabilization of greenhouse gas concentrations in the atmosphere at a level that would prevent dangerous anthropogenic interference with the climate system. This concern is expressed in the Kyoto Protocol in which the ratifying countries commit to reduce their emissions of greenhouse gases or engage in emissions trading if they maintain or increase emissions of these gases.

One of the best known greenhouse gases is carbon dioxide. However, nitrous oxide is another cause of great concern. Throughout the 20th century and continuing into the 21st century, nitrous oxide has increased by 50 parts per billion in the atmosphere and is rising further by 0.25% each year. Although nitrous oxide only accounts for around 9% of the total greenhouse gas emissions, one has to keep in mind that it has a 300-fold greater global warming potential than carbon dioxide over the next 100 years and an atmospheric lifetime of approximately 150 years.

The above listed trends may result in increased levels of nitrogen in natural waters, crop residue, and municipal and agricultural wastes, creating national and international concerns about the environment and the public health.

Dharnaraj P. S. in Lal and Lal (Editors) (Effects of pesticides on nitrification and denitrification (1988). Pesticides and Nitrogen Cycle) describes the effect of various pesticides on nitrification and denitrification. The studies described therein show that most fungicides do not have any effect on nitrification and denitrification. In addition, the method steps according to the invention as well as the surprising effect are not disclosed.

Mosier et al. (Nitrous oxide emission from agricultural fields; Assessment, measurement and mitigation (1996). Plant and Soil 131: 95.108) summarized the effects of nitrification inhibitors on $N_2O$ emissions from fertilized soils. A number of studies indicated that nitrification inhibitors did limit $N_2O$ emission from soils fertilized with ammonium-based fertilizers.

Furthermore, Kinney et al. (Effects of fungicides on trace gas fluxes (2004). Journal of Geophysical Research 109: 1-15) have hypothesized that the variations in gases flux from agricultural soils may also be affected by the quantity and type of agricultural chemicals (pesticides) used. They carried out field experiments and determined the effect to two commonly used multi-site fungicides, mancozeb and chlorothalonil, on trace gas exchange. Kinney et al. (Laboratory investigations into the effects of the pesticides mancozeb, chlorothalonil, and prosulfuron on nitrous oxide and nitric oxide production in fertilized soil (2005). Soil Biology & Biochemistry 37: 837-850) additionally investigated the effects of mancozeb, chlorthalonil and the herbicide prosulfuron on $N_2O$ production by nitrifying and denitrifying bacteria in fertilized soil.

Somda et al. (1991). Influence of biocides on tomato nitrogen uptake and soil nitrification and denitirification. Journal of Plant Nutrition 14 (11): 1187-99) investigated the impact of benlate, captan, and lime-sulfur fungicides compared to nitrification inhibitors on nitrification.

WO 98/05607 is directed to the use of inorganic or organic polyacids for the treatment of inorganic fertilizers, in particular the use of the polyacids as a mixture with at least one nitrification inhibitor for the treatment of inorganic fertilizers.

WO 08/059053 relates to a method for increasing the carbon dioxide sequestration from the atmosphere by treating a plant, a part of the plant, the locus where the plant is growing or is intended to grow and/or the plant propagules with certain active ingredients. The invention also relates to the use of the compounds for increasing the dry biomass of a plant.

Nitrification and denitrification are the two main processes by which nitrous oxide is produced in soil environments. It is expected that the yearly application of nitrogen fertilizers and pesticides will more than double over the next 50 years. In addition, the agricultural cropland is expected to increase by $5.5 \times 10^8$ ha hectares by the year 2050 (cf. Tilman et al. (2001): Forecasting agriculturally driven global environmental change. Science. Vol. 292: 281-284). As a consequence, agricultural soils will likely have an ever-increasing influence on the global atmospheric budgets of carbon dioxide, nitrous oxide and methane. With respect to agricultural production systems, it could be shown that fertilization and tillage more than double $N_2O$ emissions from soils.

There is also concern that the intensive use of fertilizer and the application of livestock wastes could lead to increased nitrogen levels in groundwater and surface waters, and that this in turn could lead to increased eutrophication of lakes and streams.

Besides the potential impact on global warming, the production of $N_2O$ reduces the amount of nitrogen available to the plants.

It was therefore an object of the present invention to provide a reliable method which solves the problems outlined above, and which should, in particular, reduce nitrous oxide emission from soils. In particular, from soils which are fertilized.

Surprisingly, we have found that this object is achieved when treating a plant and/or the locus such as the soil where the plant is growing or is intended to grow and/or the seeds from which the plant grows with at least one compound I according to the invention (compound A) and at least one ammonium- or urea-containing fertilizer (compound B) wherein the application of compound (A) and compound (B) is carried out with a time lag of at least 1 day.

The object of the present invention can also be achieved when treating a plant and/or the locus such as the soil where the plant is growing or is intended to grow and/or the seeds from which the plant grows with an agrochemical mixture, comprising at least one compound I according to the invention, in combination with at least one compound II as defined herein (compound group A), and at least one ammonium- or urea-containing fertilizer (compound B) wherein the application of the mixture comprising at least two compounds (A) and compound (B) must be carried out with a time lag of at least 1 day.

The time gap between the application of a compound I according to the invention (or a respective mixture thereof) (compound A) from the application of a fertilizer (compound B) is the crucial method step because it could be shown that the joint application may have no impact or even results in an increased $N_2O$ emission while only a timely separated application of a fungicide and a fertilizer according to the method of the present invention, results in a strong decrease of $N_2O$ emission. Consequently, the time gap between the application of a fungicide (compound A) and a fertilizer (compound B) is a special technical feature which results in a surprising effect being a new and inventive technical teaching to any person skilled in the art.

The application of active ingredients according to the method of the invention provides significant ecological and economical advantages. From an ecological stand point, the cutback of $N_2O$ emissions significantly reduces the impact of modern agriculture on the environment and its atmosphere as well as on global warming. In addition, losses of nitrogen to the groundwater, risk of eutrophication of lakes and streams are also minimized due to an optimized use of soil nitrogen.

The compounds I may be combined with further pesticides in the methods and uses.

In one embodiment of the method according to the invention, the nitrous oxide emission from soils is reduced by applying a compound I together with a compound II selected from the group consisting of azoxystrobin, coumethoxystrobin, coumoxystrobin, dimoxystrobin, enestroburin, fenaminstrobin, fenoxystrobin (flufenoxystrobin), fluoxastrobin, kresoxim-methyl, mandestrobin, metominostrobin, orysastrobin, picoxystrobin, pyraclostrobin, pyrametostrobin, pyraoxystrobin, pyribencarb, triclopyricarb (chlorodincarb), trifloxystrobin, 2-[2-(2,5-dimethyl-phenoxymethyl)-phenyl]-3-methoxy-acrylic acid methyl ester and 2-(2-(3-(2,6-di-chlorophenyl)-1-methyl-allylidene-aminooxy-methyl)-phenyl)-2-methoxyimino-N-methyl-acetamide.

In a preferred embodiment of the method according to the invention, compound II is a strobilurin selected from the group consisting of azoxystrobin, dimoxystrobin, fluoxastrobin, kresoxim-methyl, metominostrobin, orysastrobin, picoxystrobin, pyraclostrobin and trifloxystrobin.

In a preferred embodiment of the method according to the invention, compound II is a strobilurin selected from the group consisting of pyraclostrobin, orysastrobin, azoxystrobin, dimoxystrobin, enestroburin, fluoxastrobin, kresoxim-methyl, metominostrobin, picoxystrobin, pyribencarb and trifloxystrobin.

In a preferred embodiment of the method according to the invention, compound II is a strobilurin selected from the group consisting of azoxystrobin, pyraclostrobin and trifloxystrobin.

In an especially preferred embodiment of the method according to the invention, compound II is pyraclostrobin.

In one embodiment of the method according to the invention, compound (B) is an ammonium- or urea-containing fertilizer (compound B) selected from the group of inorganic fertilizer (B1) consisting of NPK fertilizer, ammonium nitrate, calcium ammonium nitrate, ammonium sulfate nitrate, ammonium sulfate and ammonium phosphate.

In a preferred embodiment of the method according to the invention, compound (B) is selected from the group consisting of ammonium sulfate nitrate and ammonium sulfate.

In another embodiment of the method according to the invention, compound (B) is an ammonium- or urea-containing fertilizer (compound B) selected from the group of organic fertilizer (B2) consisting of liquid manure, semi-liquid manure, stable manure and straw manure, worm castings, compost, seaweed and guano.

In a preferred embodiment of the method according to the invention, compound (B) is liquid manure.

In one embodiment of the method according to the invention, the application of at least one compound (A) and at least one compound (B) is carried out with a time lag of at least 1 day.

In a preferred embodiment of the method according to the invention, the application of at least one compound (A) and at least one compound (B) is carried out with a time lag of at least 4 days.

In another preferred embodiment of the method according to the invention, the application of at least one compound (A) and at least one compound (B) is carried out with a time lag of at least 8 days.

In another preferred embodiment of the method according to the invention, the application of at least one compound (A) and at least one compound (B) is carried out with a time lag of at least days.

In yet another preferred embodiment of the method according to the invention, the application of at least one compound (A) and at least one compound (B) is carried out with a time lag of at least 16 days.

In one embodiment of the method according to the invention, the nitrous oxide emission from soils is reduced by applying the compound I according to the invention (compound A) and the ammonium- or urea-containing fertilizer (compound B) together with at least one nitrification inhibitor (compound C) selected from the group consisting of 2-(3,4-dimethyl-pyrazol-1-yl)-succinic acid, 3,4-dimethylpyrazolephosphate (DMPP), dicyandiamide (DCD), 1H-1,2,4-triazole, 3-methylpyrazole (3-MP), 2-chloro-6-(trichloromethyl)-pyridine, 5-ethoxy-3-trichloromethyl-1,2,4-thiadiazol, 2-amino-4-chloro-6-methyl-pyrimidine, 2-mercapto-benzothiazole, 2-sulfanilamidothiazole, thiourea, sodium azide, potassium azide, 1-hydroxypyrazole, 2-methylpyrazole-1-carboxamide, 4-amino-1,2,4-triazole, 3-mercapto-1,2,4-triazole, 2,4-diamino-6-trichloromethyl-5-triazine, carbon bisulfide, ammonium thiosulfate, sodium trithiocarbonate, 2,3-dihydro-2,2-dimethyl-7-benzofuranol methyl carbamate and N-(2,6-dimethylphenyl)-N-(methoxyacetyl)-alanine methyl ester.

In a preferred embodiment of the method according to the invention, the nitrous oxide emission from soils is reduced by applying the compound I according to the invention (compound A) and the ammonium- or urea-containing fertilizer (compound B) together with at least one nitrification inhibitor (compound C) selected from the group consisting of 2-(3,4-dimethyl-pyrazol-1-yl)-succinic acid, 3,4-dimethylpyrazole-phosphate (DMPP), dicyandiamide (DCD), 1H-1,2,4-triazole, 3-methylpyrazole (3-MP), 2-chloro-6-(trichloromethyl)-pyridine and 5-ethoxy-3-trichloromethyl-1,2,4-thiadiazol.

In another embodiment of the method according to the invention, the nitrous oxide emission from soils is reduced by applying an agrochemical mixture comprising at lease one the compound I according to the invention (compound A) and at least one compound (B) and at least one nitrification inhibitor (compound C).

In another embodiment of the method according to the invention, the nitrous oxide emission from soils is reduced by applying an agrochemical mixture comprising one compound I according to the invention (compound A) and one compound (B) and one nitrification inhibitor (compound C).

The secondary mixtures listed in table BC, comprising one compound (B) and one compound (C) are a preferred embodiment of the method of the current invention.

TABLE BC

| Mixture | Compound (B) | Compound (C) |
|---|---|---|
| BC-1 | ammonium sulfate nitrate | 3,4-dimethylpyrazolephosphate |
| BC-2 | ammonium sulfate | 3,4-dimethylpyrazolephosphate |
| BC-3 | ammonium sulfate nitrate | dicyandiamide |
| BC-4 | ammonium sulfate | dicyandiamide |
| BC-5 | ammonium sulfate nitrate | 2-chloro-6-(trichloromethyl)-pyridine |
| BC-6 | ammonium sulfate | 2-chloro-6-(trichloromethyl)-pyridine |
| BC-7 | ammonium sulfate nitrate | 2-(3,4-dimethyl-pyrazol-1-yl)-succinic acid |
| BC-8 | ammonium sulfate | 2-(3,4-dimethyl-pyrazol-1-yl)-succinic acid |

In the terms of the present invention "agrochemical mixture" is not restricted to a physical mixture comprising at least two compounds, but refers to any preparation form of at least one compound I according to the invention and at least one further compound, the use of which is time- and locus-related.

In one embodiment of the invention "agrochemical mixture" refers to a physical mixture comprising compounds A and B.

In one embodiment of the invention "agrochemical mixture" refers to a physical mixture of at lease one compound A and at least one compound (B) and at least one compound (C).

The agrochemical mixtures may be formulated separately but applied in a temporal relationship, i.e. simultaneously or subsequently, the subsequent application having a time interval which allows a combined action of the compounds.

Furthermore, the individual compounds of the agrochemical mixtures according to the invention such as parts of a kit or parts of the binary mixture may be mixed by the user himself in a spray tank and further auxiliaries may be added, if appropriate (tank mix). This applies also in case ternary mixtures are used according to the invention.

In one embodiment of the invention, the method according to the invention comprises the steps a) application of at least one compound (A) as defined in any of the embodiments above; and b) application of at least one compound (B) as defined in any of the embodiments above; to a plant and/or the locus where the plant is growing or is intended to grow and/or the seeds from which the plant grows, wherein the application of at least one compound (A) in step a) and at least one compound (B) in step b) is carried out with a time lag of at least 1 day.

In another embodiment of the invention, the method according to the invention comprises the steps a) application of at least one compound (A) as defined in any of the embodiments above; and b) application of at least one compound (B) as defined in any of the embodiments above together with at least one compound (C) as defined in any of the embodiments above; to a plant and/or the locus where the plant is growing or is intended to grow and/or the seeds from which the plant grows wherein the application of at least one compound (A) in step a) and at least one compound (B) together with at least one compound (C) in step b) is carried out with a time lag of at least 1 day.

In yet another embodiment of the invention, the method according to the invention comprises the steps a) application of at least one compound (B) as defined in any of the embodiments above; and b) application of at least one compound (A) as defined in any of the embodiments above; to a plant and/or the locus where the plant is growing or is intended to grow and/or the seeds from which the plant grows, wherein the application of at least one compound (B) in step a) and at least one compound (a) in step b) is carried out with a time lag of at least 1 day.

In yet another embodiment of the invention, the method according to the invention comprises the steps a) application of at least one compound (B) as defined in any of the embodiments above together with at least one compound (C) as defined in any of the embodiments above; and b) application of at least one compound (A) as defined in any of the embodiments above to a plant and/or the locus where the plant is growing or is intended to grow and/or the seeds from which the plant grows; wherein the application of at least one compound (B) together with at least one compound (C) in step a) and the application of at least one compound (A) in step b) is carried out with a time lag of at least 1 day.

The plants to be treated according to the invention are selected from the group consisting of agricultural, silvicultural, ornamental and horticultural plants, each in its natural or genetically modified form, more preferably from agricultural plants.

More preferred agricultural plants are field crops, such as potatoes, sugar beets, wheat, barley, rye, oat, *sorghum*, rice, corn, cotton, rape, oilseed rape, canola, soybeans, peas, field beans, sunflowers, sugar cane; cucumbers, tomatoes, onions, leeks, lettuce, squashes; even more preferably the plant is selected from the group consisting of wheat, barley, oat, rye, soybean, corn, oilseed rape, cotton, sugar cane, rice and *sorghum*.

In an especially preferred embodiment of the current invention, the plants to be treated are selected from the group consisting of wheat, barley, oat, rye, soybean, corn, oilseed rape, canola, sunflower, cotton, sugar cane, sugar beet, rice and *sorghum*.

In one embodiment, the aforementioned method for reducing nitrous oxide emission from soils comprises treating the plant propagules, preferably the seeds of an agricultural, horticultural, ornamental or silivcultural plant selected from the group consisting of transgenic or non-transgenic plants.

The term "plants" is to be understood as plants of economic importance and/or men-grown plants. They are preferably selected from agricultural, silvicultural and horticultural (including ornamental) plants. The term "plant" as used herein includes all parts of a plant such as germinating seeds, emerging seedlings, herbaceous vegetation as well as established woody plants including all belowground portions (such as the roots) and aboveground portions.

The term "nitrification inhibitors" is to be understood as any chemical substance which slows down or stops the nitrification process. Nitrification inhibitors retard the natural transformation of ammonium into nitrate, by inhibiting the activity of bacteria such as *Nitrosomonas* spp.

The term "nitrification" is to be understood as the biological oxidation of ammonia ($NH_3$) or ammonium ($NH_4^+$) with oxygen into nitrite ($NO_2^-$) followed by the oxidation of these nitrites into nitrates ($NO_3^-$) by microorganisms. Besides nitrate ($NO_3^-$) nitrous oxide is also produced though nitrification. Nitrification is an important step in the nitrogen cycle in soil.

The term "denitrification" is to be understood as the microbiological conversion of nitrate ($NO_3^-$) and nitrite ($NO_2$) to gaseous forms of nitrogen, generally $N_2$ or $N_2O$. This respiratory process reduces oxidized forms of nitrogen in response to the oxidation of an electron donor such as organic matter. The preferred nitrogen electron acceptors in order of most to least thermodynamically favorable include: nitrate ($NO^{3-}$), nitrite ($NO^{2-}$), nitric oxide (NO), and nitrous oxide ($N_2O$). Within the general nitrogen cycle, denitrification completes the cycle by returning $N_2$ to the atmosphere. The process is performed primarily by heterotrophic bacteria (such as *Paracoccus denitrificans* and various pseudomonads), although autotrophic denitrifiers have also been identified (e.g. *Thiobacillus denitrificans*). Denitrifiers are represented in all main phylogenetic groups. When faced with a shortage of oxygen many bacterial species, are able switch from using oxygen to using nitrates to support respiration in a process known as denitrification, during which the water-soluble nitrates are converted to gaseous products, including nitrous oxide, that are emitted into the atmosphere.

"Nitrous oxide", commonly known as happy gas or laughing gas, is a chemical compound with the chemical formula $N_2O$. At room temperature, it is a colorless non-flammable gas. Nitrous oxide is produced naturally in soils through the microbial processes of nitrification and denitrification. These natural emissions of nitrous oxide can be increased by a variety of agricultural practices and activities including for example a) direct addition of nitrogen to soils by using mineral and organic fertilizers b) growing of nitrogen-fixing crops c) cultivation of high organic content soils d) application of livestock manure to croplands and pasture.

The term "fertilizers" is to be understood as chemical compounds applied to promote plant and fruit growth. Fertilizers are typically applied either through the soil (for uptake by plant roots) or by foliar feeding (for uptake through leaves). The term "fertilizers" can be subdivided into two major categories: a) organic fertilizers (composed of decayed plant/animal matter) and b) inorganic fertilizers (composed of chemicals and minerals). Organic fertilizers include manure, slurry, worm castings, peat, seaweed, sewage, and guano. Green manure crops are also regularly grown to add nutrients (especially nitrogen) to the soil. Manufactured organic fertilizers include compost, blood meal, bone meal and seaweed extracts. Further examples are enzyme digested proteins, fish meal, and feather meal. The decomposing crop residue from prior years is another source of fertility. In addition, naturally occurring minerals such as mine rock phosphate, sulfate of potash and limestone are also considered inorganic fertilizers. Inorganic fertilizers are usually manufactured through chemical processes (such as the Haber process), also using naturally occurring deposits, while chemically altering them (e.g. concentrated triple superphosphate). Naturally occurring inorganic fertilizers include Chilean sodium nitrate, mine rock phosphate, and limestone.

"NPK fertilizer" are inorganic fertilizers formulated in appropriate concentrations and combinations comprising the three main nutrients nitrogen (N), phosphorus (P) and potassium (K).

In one embodiment, the plant to be treated according to the method of the invention is an agricultural plant. "Agricultural plants" are plants of which a part (e.g. seeds) or all is harvested or cultivated on a commercial scale or which serve as an important source of feed, food, fibres (e.g. cotton, linen), combustibles (e.g. wood, bioethanol, biodiesel, biomass) or other chemical compounds. Preferred agricultural plants are for example cereals, e.g. wheat, rye, barley, triticale, oats, *sorghum* or rice, beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, oil-seed rape, canola, linseed, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, *asparagus*, cabbages, carrots, onions, tomatoes, potatoes, cucurbits or paprika; lauraceous plants, such as avocados, cinnamon or camphor; energy and raw material plants, such as corn, soybean, rape, canola, sugar cane or oil palm; tobacco; nuts; coffee; tea; bananas; vines (table grapes and grape juice grape vines); hop; turf; natural rubber plants.

In one embodiment, the plant to be treated according to the method of the invention is a horticultural plant. The term "horticultural plants" are to be understood as plants which are commonly used in horticulture—e.g. the cultivation of ornamentals, vegetables and/or fruits. Examples for ornamentals are turf, geranium, pelargonia, petunia, begonia and fuchsia. Examples for vegetables are potatoes, tomatoes, peppers, cucurbits, cucumbers, melons, watermelons, garlic, onions, carrots, cabbage, beans, peas and lettuce and more preferably from tomatoes, onions, peas and lettuce. Examples for fruits are apples, pears, cherries, strawberry, citrus, peaches, apricots and blueberries.

In one embodiment, the plant to be treated according to the method of the invention is an ornamental plants. "Ornamental plants" are plants which are commonly used in gardening, e.g. in parks, gardens and on balconies. Examples are turf, geranium, pelargonia, petunia, begonia and fuchsia.

In one embodiment, the plant to be treated according to the method of the invention is a silvicultural plants. The term "silvicultural plant" is to be understood as trees, more specifically trees used in reforestation or industrial plantations. Industrial plantations generally serve for the commercial production of forest products, such as wood, pulp, paper, rubber tree, Christmas trees, or young trees for gardening purposes. Examples for silvicultural plants are conifers, like pines, in particular *Pinus* spec., fir and spruce, *eucalyptus*, tropical trees like teak, rubber tree, oil palm, willow (*Salix*), in particular *Salix* spec., poplar (cottonwood), in particular *Populus* spec., beech, in particular *Fagus* spec., birch, oil palm, and oak.

The term "locus" is to be understood as any type of environment, soil, area or material where the plant is growing or intended to grow. Especially preferred according to the invention is soil.

The term "at least one" is to be understood as 1, 2, 3 or more of the respective compound selected from the group consisting of compound I (compound A), fertilizer (compound B) and nitrification inhibitors (compound C).

The reduction of nitrous oxide emission is independent of the presence of pests. Accordingly, in a preferred embodiment of the method, the application of the active ingredients (compound A) and/or mixtures comprising at least one compound (A) is carried out in the absence of pest pressure.

The term "BBCH principal growth stage" refers to the extended BBCH-scale which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry.

In one embodiment of the invention, at least one compound (A) is applied at a growth stage (GS) between GS 00 and GS 65 BBCH of the plant.

In preferred embodiment of the invention, at least one compound (A) is applied at a growth stage between GS 14 and GS 55 BBCH of the plant.

In a more preferred embodiment of the invention, at least one compound (A) is applied at the growth stage between GS 14 and GS 47 BBCH of the plant.

In one embodiment of the invention, at least one fertilizer (compound B) is applied before and at sowing, before emergence, and until harvest (GS 00 to GS 89 BBCH).

In another embodiment of the invention, at least one fertilizer (compound B) is applied together with at least one nitrification inhibitor (compound C) before and at sowing, before emergence, and until harvest (GS 00 to GS 89 BBCH).

In another embodiment of the invention, at least one compound (A) is applied during leaf development to flowering (GS 14 to GS 65 BBCH) of the treated plant, provided that the application of at least one compound (A) and at least one compound (B) is carried out with a time lag of at least 1 day.

In a preferred embodiment of the invention, an agrochemical mixture comprising an ammonium- or urea-containing fertilizer (compound B) and at least one nitrification inhibitor (compound C) is applied at least once during the growth stages GS 00 to GS 89 BBCH (before sowing until harvest) while at least one compound (A) is applied at least once during the growth stages GS 14 to GS 65 BBCH (leaf development to flowering) of the treated plant, provided that the application of at least one compound (A) and at least one compound (B) is carried out with a time lag of at least 1 day.

In another embodiment of the invention, the agrochemical mixture comprising an ammonium- or urea-containing fertilizer (compound B) and at least one nitrification inhibitor (compound C) is applied before and at sowing, before emergence, and until shooting/shoot development (GS 00 to GS 33 BBCH) of the plant while at least one compound (A) is applied during leaf development to inflorescence emergence (GS 14 to GS 55 BBCH) provided that the application of at least one compound (A) and at least one compound (B) is carried out with a time lag of at least 1 day.

If an agricultural mixture comprising at least two compounds (A) according to the present invention (compound I and a compound II) is used in this inventive method, the plant propagules are preferably treated simultaneously (together or separately) or subsequently.

The subsequent application is carried out with a time interval which allows a combined action of the applied compounds. Preferably, the time interval for a subsequent application of a first compound (A) and a second compound (A) ranges from a few seconds up to 3 months, preferably, from a few seconds up to 1 month, more preferably from a few seconds up to 2 weeks, even more preferably from a few seconds up to 3 days and in particular from 1 second up to 24 hours.

In a preferred embodiment of the invention, the application according to the method of the current invention is repeatedly carried out. In one embodiment, the application is repeated two to ten times, preferably, two to five times; most preferably two times.

In one embodiment, the application of at least one compound (A) is repeatedly carried out. In another embodiment, the application of at least one compound (B) is repeatedly carried out. In yet another embodiment, the application of one compound (B) together with one compound (C) is repeatedly applied. In each case, there must be a time lag of at least 1 day between the last application of at least one compound (A) and the last application of at least one compound (B) (optionally together with at least one compound C).

As a matter of course, compounds (A), (B) and (C) and in case mixtures are employed, compounds selected from the group consisting of compounds (A), (B) and (C) are used in an effective and non-phytotoxic amount. This means that they are used in a quantity which allows to obtain the desired effect but which does not give rise to any phytotoxic symptoms on the treated plant or on the plant raised from the treated propagule or treated soil.

Application rates for compounds I, also in seed treatment, are as defined in this application. For the use according to the invention, the application rates of compounds (B) are between 10 kg and 300 kg of N per hectare, preferably between 50 kg and 250 kg of N per hectare.

In all embodiments, the agrochemical mixtures are applied in nitrous oxide emission from soils reducing amounts. In one embodiment, the agrochemical mixtures are applied in synergistically the nitrous oxide emission from soils reducing amounts.

In an especially preferred embodiment of the method for reducing nitrous oxide emission, compound (A) is applied as seed treatment.

In another especially preferred embodiment of the method for reducing nitrous oxide emission, compound (A) is applied as foliar and/or in-furrow application.

Embodiment E8

The present invention relates to new uses and methods of reducing insect-vectored viral infection and transmission in plants, methods of reducing damage to plants caused by viral infection, methods of crop enhancement including methods for improving plant growth, vigour and yield, by application of N-thio-anthranilamide compounds, and their mixtures with selected other pesticides.

The agrochemical industry is continually seeking methods of controlling plant pests and improving the growth of plants. Chemicals are typically used (i) to control undesirable species (for example, pests, such as insects, or vegetation, e.g., weeds, or fungi), and (ii) to promote plant growth (e.g., by providing nutrients), and thereby improve the growth of plants. Insect-vectored viral infections are a widespread cause of plant damage, for which there are few effective measures of control.

There exists a need for alternative methods for controlling insect-vectored viral infection and transmission in plants, and for reducing the damage to plants caused by such viral infections, especially useful plants such as crops.

It is therefore an object of the present invention to provide compounds suitable and effective in said methods.

Surprisingly, it has now been found that anthranilamide compounds I and their mixtures are suitable for reducing insect-vectored viral infection in a plant, reducing insect-vectored-viral transmission amongst plants, and reducing damage to a plant caused by one or more insect-vectored viral infections.

Therefore, in a first aspect, the present invention relates to the use of at least one pesticidally active anthranilamide compound I as defined herein,
or a stereoisomer, salt, tautomer or N-oxide, or a polymorphic crystalline form, a co-crystal or a solvate of a compound or a stereoisomer, salt, tautomer or N-oxide thereof;
for reducing insect-vectored viral infection in a plant.

Furthermore, the invention relates to a method of reducing insect-vectored viral infection in a plant by application of at least one pesticidally active compound I as defined above.

In one embodiment, the compound I in the methods and uses according to the invention of E8 is selected from the compounds described in Embodiment A.

In one embodiment, the compound I in the methods and uses according to the invention of E8 is selected from the compounds described in Embodiment B.

In one embodiment, the compound I in the methods and uses according to the invention of E8 is selected from the compounds described in Embodiment C.

In one embodiment, the compound I in the methods and uses according to the invention of E8 is selected from the compounds listed in Table ABC.

In one embodiment, I-A-1 is the compound I in the methods and uses according to the invention of E8.

In one embodiment, I-A-28 is the compound I in the methods and uses according to the invention of E8.

In one embodiment, I-B-115 is the compound I in the methods and uses according to the invention of E8.

In one embodiment, I-B-131 is the compound I in the methods and uses according to the invention of E8.

In one embodiment, I-B-132 is the compound I in the methods and uses according to the invention of E8.

In one embodiment, I-C-19 is the compound I in the methods and uses according to the invention of E8.

In one embodiment, I-C-35 is the compound I in the methods and uses according to the invention of E8.

In one embodiment, I-C-36 is the compound I in the methods and uses according to the invention of E8.

In a further embodiment, the invention relates to the methods and uses of the compounds according to the invention (as defined in Embodiment A, B or C) in combination with other selected pesticidal compounds (II), as defined and specified in Embodiments 2 and 3.

Furthermore, in this context, it has also been found that the compounds I and their mixtures with other pesticides, are especially suitable for the purpose of the invention.

Thus, also the mixtures of compounds I, or a stereoisomer, salt, tautomer or N-oxide thereof, with other selected pesticides, are highly suitable in the use for reducing insect-vectored viral infection in a plant, or reducing insect-vectored-viral transmission amongst plants, or reducing damage to a plant caused by one or more insect-vectored viral infections, and the respective methods by application of at least one pesticidally active compound I.

The pests that can be controlled or combatted are as described above or herein, e.g. in embodiment E1.

The plants or crops to be protected are as described above or herein, e.g. in embodiment E1.

The formulations are as described herein, e.g. in embodiment E1.

The applications are as described herein, e.g. in embodiment E1.

The mixtures and preferred mixtures are as described herein, e.g. in embodiment E2 and E3.

Methods of E8

In one embodiment of the invention, the method is connected with controlling hemiptera, preferably aphids or whitefly. Plants exhibiting aphid damage can have a variety of symptoms, such as decreased growth rates, mottled leaves, yellowing, stunted growth, curled leaves, browning, wilting, low yields and death. The removal of sap creates a lack of vigour in the plant, and aphid saliva is toxic to plants. Hemiptera, in particular aphids, frequently transmit disease-causing organisms like plant viruses to their hosts. The green peach aphid (*Myzus persicae*) is a vector for more than 110 plant viruses. Cotton aphids (*Aphis gossypii*) often infect sugarcane, *papaya* and groundnuts with viruses. Aphids contributed to the spread of late blight (*Phytophthora infestans*) among potatoes in the Great Irish Potato Famine of the 1840s.

The cherry aphid or black cherry aphid, *Myzus cerasi*, is responsible for some leaf curl of cherry trees. This can easily be distinguished from 'leaf curl' caused by *Taphrina* fungus species due to the presence of aphids beneath the leaves.

The coating of plants with honeydew can contribute to the spread of fungi which can damage plants. Honeydew produced by aphids has been observed to reduce the effectiveness of fungicides as well. The damage of plants, and in particular commercial crops, has resulted in large amounts of resources and efforts being spent attempting to control the activities of Hemiptera. The neonicotinoids represent the fastest-growing class of insecticides introduced to the market since the commercialization of pyrethroids (Nauen and Denholm, 2005: Archives of Insect Biochemistry and Physiology 58:200-215) and are extremely valuable insect control agents not least because they had exhibited little or no cross-resistance to the older insecticide classes, which suffer markedly from resistance problems By virtue of the surprising ability of a compound I to control aphids, and even aphids resistant to other insecticides, especially neonicotinoids, the invention also provides a method of protecting a crop of useful plants, from virus infection. Such a method involves applying to said crop, treating a plant propagation material of said crop with, and/or applying to said insects, a compound I.

In one embodiment of the invention, the method of reducing insect-vectored viral infection in a plant is not connected to the ability of a compound I to control insects, in particular aphids. The method of reducing insect-vectored viral infection in a plant is especially surprisingly effective if the compound I in question is not effective, or not very effective, or not sufficiently effective in the control of insects (e.g. aphids).

Since the compound I does not exhibit cross-resistance to neonicotinoid resistant Hemiptera, it may be used in a resistance management strategy with a view to controlling resistance to the neonicotinoid class of insecticides. Such a strategy may involve alternating applications of a compound I and a neonicotinoid insecticide, either on an application by application alternation (including different types of application, such as treatment of plant propagation material and foliar spray), or seasonal/crop alternation basis (e.g. use a compound I on a first crop/for control in a first growing season, and use a neonicotinoid insecticide for a subsequent crop/growing season, or vice versa), and this forms yet a further aspect of the invention.

As mentioned herein, not only are insects from the Hemiptera order pests of a number of commercially important crops, the viruses that these insects carry also pose a threat. With the emergence of resistance to neonicotinoid insecticides, the severity of this threat has increased.

Thus, a further aspect of the invention provides a method of controlling a plant virus in a crop of useful plants susceptible to and/or under attack by neonicotinoid resistant insects which carry said plant virus, which method comprises applying to said crop, treating a plant propagation material of said crop with, and/or applying to said insects, a compound I.

Examples of plant viruses that may be controlled according to this aspect of the invention include Sobemovirus, Caulimovirus (Caulimoviridae), Closterovirus (Closteroviridae), Sequivirus (Sequiviridae), Enamovirus (Luteoviridae), Luteovirus (Luteoviridae), Polerovirus (Luteoviridae), Umbravirus, Nanovirus (Nanoviridae), Cytorhabdovirus (Rhabdoviridae), Nucleorhabdovirus (Rhabdoviridae).

In one embodiment, the invention relates to the a use or method for reducing insect-vectored viral infection in a plant, which method comprises applying a compound I, wherein the virus is Sobemovirus.

In one embodiment, the invention relates to the a use or method for reducing insect-vectored viral infection in a plant, which method comprises applying a compound I, wherein the virus is Caulimovirus.

In one embodiment, the invention relates to the a use or method for reducing insect-vectored viral infection in a plant, which method comprises applying a compound I, wherein the virus is Closterovirus.

In one embodiment, the invention relates to the a use or method for reducing insect-vectored viral infection in a plant, which method comprises applying a compound I, wherein the virus is Sequivirus.

In one embodiment, the invention relates to the a use or method for reducing insect-vectored viral infection in a plant, which method comprises applying a compound I, wherein the virus is Enamovirus.

In one embodiment, the invention relates to the a use or method for reducing insect-vectored viral infection in a plant, which method comprises applying a compound I, wherein the virus is Luteovirus.

In one embodiment, the invention relates to the a use or method for reducing insect-vectored viral infection in a plant, which method comprises applying a compound I, wherein the virus is Polerovirus.

In one embodiment, the invention relates to the a use or method for reducing insect-vectored viral infection in a plant, which method comprises applying a compound I, wherein the virus is Umbravirus.

In one embodiment, the invention relates to the a use or method for reducing insect-vectored viral infection in a plant, which method comprises applying a compound I, wherein the virus is Nanovirus.

In one embodiment, the invention relates to the a use or method for reducing insect-vectored viral infection in a plant, which method comprises applying a compound I, wherein the virus is Cytorhabdovirus.

In one embodiment, the invention relates to the a use or method for reducing insect-vectored viral infection in a plant, which method comprises applying a compound I, wherein the virus is Nucleorhabdovirus.

In one embodiment, the invention relates to the a use or method for reducing insect-vectored viral infection in a plant or crop, which method comprises applying a compound I, wherein the plant or crop is soybean.

In one embodiment, the invention relates to the a use or method for reducing insect-vectored viral infection in a plant or crop, which method comprises applying a compound I, wherein the plant or crop is rice.

In one embodiment, the invention relates to the a use or method for reducing insect-vectored viral infection in a plant or crop, which method comprises applying a compound I, wherein the plant or crop is cotton.

In one embodiment, the invention relates to the a use or method for reducing insect-vectored viral infection in a plant or crop, which method comprises applying a compound I, wherein the plant or crop is oilseed rape.

In one embodiment, the invention relates to the a use or method for reducing insect-vectored viral infection in a plant or crop, which method comprises applying a compound I, wherein the plant or crop is peanut.

In one embodiment, the invention relates to the a use or method for reducing insect-vectored viral infection in a plant or crop, which method comprises applying a compound I, wherein the plant or crop is cereal.

In one embodiment, the invention relates to the a use or method for reducing insect-vectored viral infection in a plant or crop, which method comprises applying a compound I, wherein the plant or crop is wheat.

In one embodiment, the invention relates to the a use or method for reducing insect-vectored viral infection in a plant or crop, which method comprises applying a compound I, wherein the plant or crop is barley.

In one embodiment, the invention relates to the a use or method for reducing insect-vectored viral infection in a plant or crop, which method comprises applying a compound I, wherein the plant or crop is corn.

In one embodiment, the invention relates to the a use or method for reducing insect-vectored viral infection in a plant or crop, which method comprises applying a compound I, wherein the plant or crop is a specialty crop.

In one embodiment, the invention relates to the a use or method for reducing insect-vectored viral infection in a plant or crop, which method comprises applying a compound I, wherein the plant or crop is fruiting vegetable.

In one embodiment, the invention relates to the a use or method for reducing insect-vectored viral infection in a plant or crop, which method comprises applying a compound I, wherein the plant or crop is leafy vegetable.

In one embodiment, the invention relates to the a use or method for reducing insect-vectored viral infection in a plant or crop, which method comprises applying a compound I, wherein the plant or crop is tomato.

In one embodiment, the invention relates to the a use or method for reducing insect-vectored viral infection in a plant or crop, which method comprises applying a compound I, wherein the plant or crop is pepper.

In one embodiment, the invention relates to the a use or method for reducing insect-vectored viral infection in a plant or crop, which method comprises applying a compound I, wherein the plant or crop is eggplant.

In one embodiment, the invention relates to the a use or method for reducing insect-vectored viral infection in a plant or crop, which method comprises applying a compound I, wherein the plant or crop is cabbage.

In one embodiment, the invention relates to the a use or method for reducing insect-vectored viral infection in a plant or crop, which method comprises applying a compound I, wherein the plant or crop is lettuce.

In one embodiment, the invention relates to the a use or method for reducing insect-vectored viral infection in a plant or crop, which method comprises applying a compound I, wherein the plant or crop is potatoes.

In one embodiment, the invention relates to the a use or method for reducing insect-vectored viral infection in a plant or crop, which method comprises applying a compound I, wherein the plant or crop is onions.

In one embodiment, the invention relates to the a use or method for reducing insect-vectored viral infection in a plant or crop, which method comprises applying a compound I, wherein the plant or crop is tobacco.

In one embodiment, the invention relates to a use or method for reducing insect-vectored viral infection in a plant, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35. More specifically, the invention relates to a use or method for reducing insect-vectored viral infection in a plant, which method comprises applying a compound I-A-1. Analogously, the invention relates to a use or method as explained, applying specifically compound I-B-131. Analogously, the invention relates to a use or method as explained, applying specifically compound I-C-35.

In embodiments E-8-1 to E-8-224, the invention relates to a use or method for reducing insect-vectored viral infection in a plant/crop, wherein the virus and the plant/crop is as defined in entries VC-1 to VC-224 of Table VC, which method comprises applying a compound I, which is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35. More specifically, the invention relates to a use or method for reducing insect-vectored viral infection in a plant, which method comprises applying a compound I-A-1.

Analogously, the invention relates to a use or method as explained, applying specifically compound I-B-131. Analogously, the invention relates to a use or method as explained, applying specifically compound I-C-35.

TABLE VC

| | Virus | Crop |
|---|---|---|
| VC-1 | Sobemovirus | soybean |
| VC-2 | Sobemovirus | rice |
| VC-3 | Sobemovirus | cotton |
| VC-4 | Sobemovirus | oilseed rape |
| VC-5 | Sobemovirus | peanut |
| VC-6 | Sobemovirus | cereal |
| VC-7 | Sobemovirus | wheat |
| VC-8 | Sobemovirus | barley |
| VC-9 | Sobemovirus | corn |
| VC-10 | Sobemovirus | specialty crops |
| VC-11 | Sobemovirus | fruiting vegetable |
| VC-12 | Sobemovirus | leafy vegetable |
| VC-13 | Sobemovirus | tomato |
| VC-14 | Sobemovirus | pepper |
| VC-15 | Sobemovirus | eggplant |
| VC-16 | Sobemovirus | cabbage |
| VC-17 | Sobemovirus | lettuce |
| VC-18 | Sobemovirus | potatoes |
| VC-19 | Sobemovirus | onions |
| VC-20 | Sobemovirus | tobacco |
| VC-21 | Caulimovirus | soybean |
| VC-22 | Caulimovirus | rice |
| VC-23 | Caulimovirus | cotton |
| VC-24 | Caulimovirus | oilseed rape |
| VC-25 | Caulimovirus | peanut |
| VC-26 | Caulimovirus | cereal |
| VC-27 | Caulimovirus | wheat |
| VC-28 | Caulimovirus | barley |
| VC-29 | Caulimovirus | corn |
| VC-30 | Caulimovirus | specialty crops |
| VC-31 | Caulimovirus | fruiting vegetable |
| VC-32 | Caulimovirus | leafy vegetable |
| VC-33 | Caulimovirus | tomato |
| VC-34 | Caulimovirus | pepper |
| VC-35 | Caulimovirus | eggplant |
| VC-36 | Caulimovirus | cabbage |
| VC-37 | Caulimovirus | lettuce |
| VC-38 | Caulimovirus | potatoes |
| VC-39 | Caulimovirus | onions |
| VC-40 | Caulimovirus | tobacco |
| VC-41 | Closterovirus | soybean |
| VC-42 | Closterovirus | rice |
| VC-43 | Closterovirus | cotton |
| VC-44 | Closterovirus | oilseed rape |
| VC-45 | Closterovirus | peanut |
| VC-46 | Closterovirus | cereal |
| VC-47 | Closterovirus | wheat |
| VC-48 | Closterovirus | barley |
| VC-49 | Closterovirus | corn |
| VC-50 | Closterovirus | specialty crops |
| VC-51 | Closterovirus | fruiting vegetable |
| VC-52 | Closterovirus | leafy vegetable |
| VC-53 | Closterovirus | tomato |
| VC-54 | Closterovirus | pepper |
| VC-55 | Closterovirus | eggplant |
| VC-56 | Closterovirus | cabbage |
| VC-57 | Closterovirus | lettuce |
| VC-58 | Closterovirus | potatoes |
| VC-59 | Closterovirus | onions |
| VC-60 | Closterovirus | tobacco |
| VC-61 | Sequivirus | soybean |
| VC-62 | Sequivirus | rice |
| VC-63 | Sequivirus | cotton |
| VC-64 | Sequivirus | oilseed rape |
| VC-65 | Sequivirus | peanut |
| VC-66 | Sequivirus | cereal |
| VC-67 | Sequivirus | wheat |
| VC-68 | Sequivirus | barley |
| VC-69 | Sequivirus | corn |
| VC-70 | Sequivirus | specialty crops |
| VC-71 | Sequivirus | fruiting vegetable |
| VC-72 | Sequivirus | leafy vegetable |

TABLE VC-continued

| Virus | Crop | |
|---|---|---|
| VC-73 | *Sequivirus* | tomato |
| VC-74 | *Sequivirus* | pepper |
| VC-75 | *Sequivirus* | eggplant |
| VC-76 | *Sequivirus* | cabbage |
| VC-77 | *Sequivirus* | lettuce |
| VC-78 | *Sequivirus* | potatoes |
| VC-79 | *Sequivirus* | onions |
| VC-80 | *Sequivirus* | tobacco |
| VC-81 | *Enamovirus* | soybean |
| VC-82 | *Enamovirus* | rice |
| VC-83 | *Enamovirus* | cotton |
| VC-84 | *Enamovirus* | oilseed rape |
| VC-85 | *Enamovirus* | peanut |
| VC-86 | *Enamovirus* | cereal |
| VC-87 | *Enamovirus* | wheat |
| VC-88 | *Enamovirus* | barley |
| VC-89 | *Enamovirus* | corn |
| VC-90 | *Enamovirus* | specialty crops |
| VC-91 | *Enamovirus* | fruiting vegetable |
| VC-92 | *Enamovirus* | leafy vegetable |
| VC-93 | *Enamovirus* | tomato |
| VC-94 | *Enamovirus* | pepper |
| VC-95 | *Enamovirus* | eggplant |
| VC-96 | *Enamovirus* | cabbage |
| VC-97 | *Enamovirus* | lettuce |
| VC-98 | *Enamovirus* | potatoes |
| VC-99 | *Enamovirus* | onions |
| VC-100 | *Enamovirus* | tobacco |
| VC-101 | *Luteovirus* | soybean |
| VC-102 | *Luteovirus* | rice |
| VC-103 | *Luteovirus* | cotton |
| VC-104 | *Luteovirus* | oilseed rape |
| VC-105 | *Luteovirus* | peanut |
| VC-106 | *Luteovirus* | cereal |
| VC-107 | *Luteovirus* | wheat |
| VC-108 | *Luteovirus* | barley |
| VC-109 | *Luteovirus* | corn |
| VC-110 | *Luteovirus* | specialty crops |
| VC-111 | *Luteovirus* | fruiting vegetable |
| VC-112 | *Luteovirus* | leafy vegetable |
| VC-113 | *Luteovirus* | tomato |
| VC-114 | *Luteovirus* | pepper |
| VC-115 | *Luteovirus* | eggplant |
| VC-116 | *Luteovirus* | cabbage |
| VC-117 | *Luteovirus* | lettuce |
| VC-118 | *Luteovirus* | potatoes |
| VC-119 | *Luteovirus* | onions |
| VC-120 | *Luteovirus* | tobacco |
| VC-121 | *Polerovirus* | soybean |
| VC-122 | *Polerovirus* | rice |
| VC-123 | *Polerovirus* | cotton |
| VC-124 | *Polerovirus* | oilseed rape |
| VC-125 | *Polerovirus* | peanut |
| VC-126 | *Polerovirus* | cereal |
| VC-127 | *Polerovirus* | wheat |
| VC-128 | *Polerovirus* | barley |
| VC-129 | *Polerovirus* | corn |
| VC-130 | *Polerovirus* | specialty crops |
| VC-131 | *Polerovirus* | fruiting vegetable |
| VC-132 | *Polerovirus* | leafy vegetable |
| VC-133 | *Polerovirus* | tomato |
| VC-134 | *Polerovirus* | pepper |
| VC-135 | *Polerovirus* | eggplant |
| VC-136 | *Polerovirus* | cabbage |
| VC-137 | *Polerovirus* | lettuce |
| VC-138 | *Polerovirus* | potatoes |
| VC-139 | *Polerovirus* | onions |
| VC-140 | *Polerovirus* | tobacco |
| VC-141 | *Umbravirus* | soybean |
| VC-142 | *Umbravirus* | rice |
| VC-143 | *Umbravirus* | cotton |
| VC-144 | *Umbravirus* | oilseed rape |
| VC-145 | *Umbravirus* | peanut |
| VC-146 | *Umbravirus* | cereal |
| VC-147 | *Umbravirus* | wheat |
| VC-148 | *Umbravirus* | barley |
| VC-149 | *Umbravirus* | corn |
| VC-150 | *Umbravirus* | specialty crops |

TABLE VC-continued

| Virus | Crop | |
|---|---|---|
| VC-151 | *Umbravirus* | fruiting vegetable |
| VC-152 | *Umbravirus* | leafy vegetable |
| VC-153 | *Umbravirus* | tomato |
| VC-154 | *Umbravirus* | pepper |
| VC-155 | *Umbravirus* | eggplant |
| VC-156 | *Umbravirus* | cabbage |
| VC-157 | *Umbravirus* | lettuce |
| VC-158 | *Umbravirus* | potatoes |
| VC-159 | *Umbravirus* | onions |
| VC-160 | *Umbravirus* | tobacco |
| VC-161 | *Nanovirus* | soybean |
| VC-162 | *Nanovirus* | rice |
| VC-163 | *Nanovirus* | cotton |
| VC-164 | *Nanovirus* | oilseed rape |
| VC-165 | *Nanovirus* | peanut |
| VC-166 | *Nanovirus* | cereal |
| VC-167 | *Nanovirus* | wheat |
| VC-168 | *Nanovirus* | barley |
| VC-169 | *Nanovirus* | corn |
| VC-170 | *Nanovirus* | specialty crops |
| VC-171 | *Nanovirus* | fruiting vegetable |
| VC-172 | *Nanovirus* | leafy vegetable |
| VC-173 | *Nanovirus* | tomato |
| VC-174 | *Nanovirus* | pepper |
| VC-175 | *Nanovirus* | eggplant |
| VC-176 | *Nanovirus* | cabbage |
| VC-177 | *Nanovirus* | lettuce |
| VC-178 | *Nanovirus* | potatoes |
| VC-179 | *Nanovirus* | onions |
| VC-180 | *Nanovirus* | tobacco |
| VC-181 | *Cytorhabdovirus* | soybean |
| VC-182 | *Cytorhabdovirus* | rice |
| VC-183 | *Cytorhabdovirus* | cotton |
| VC-184 | *Cytorhabdovirus* | oilseed rape |
| VC-185 | *Cytorhabdovirus* | peanut |
| VC-186 | *Cytorhabdovirus* | cereal |
| VC-187 | *Cytorhabdovirus* | wheat |
| VC-188 | *Cytorhabdovirus* | barley |
| VC-189 | *Cytorhabdovirus* | corn |
| VC-190 | *Cytorhabdovirus* | specialty crops |
| VC-191 | *Cytorhabdovirus* | fruiting vegetable |
| VC-192 | *Cytorhabdovirus* | leafy vegetable |
| VC-193 | *Cytorhabdovirus* | tomato |
| VC-194 | *Cytorhabdovirus* | pepper |
| VC-195 | *Cytorhabdovirus* | eggplant |
| VC-196 | *Cytorhabdovirus* | cabbage |
| VC-197 | *Cytorhabdovirus* | lettuce |
| VC-198 | *Cytorhabdovirus* | potatoes |
| VC-199 | *Cytorhabdovirus* | onions |
| VC-200 | *Cytorhabdovirus* | tobacco |
| VC-201 | *Nucleorhabdovirus* | soybean |
| VC-202 | *Nucleorhabdovirus* | rice |
| VC-203 | *Nucleorhabdovirus* | cotton |
| VC-204 | *Nucleorhabdovirus* | oilseed rape |
| VC-205 | *Nucleorhabdovirus* | peanut |
| VC-206 | *Nucleorhabdovirus* | cereal |
| VC-207 | *Nucleorhabdovirus* | wheat |
| VC-208 | *Nucleorhabdovirus* | barley |
| VC-209 | *Nucleorhabdovirus* | corn |
| VC-210 | *Nucleorhabdovirus* | specialty crops |
| VC-211 | *Nucleorhabdovirus* | fruiting vegetable |
| VC-212 | *Nucleorhabdovirus* | leafy vegetable |
| VC-213 | *Nucleorhabdovirus* | tomato |
| VC-214 | *Nucleorhabdovirus* | pepper |
| VC-215 | *Nucleorhabdovirus* | eggplant |
| VC-216 | *Nucleorhabdovirus* | cabbage |
| VC-217 | *Nucleorhabdovirus* | lettuce |
| VC-218 | *Nucleorhabdovirus* | potatoes |
| VC-219 | *Nucleorhabdovirus* | onions |
| VC-220 | *Nucleorhabdovirus* | tobacco |
| VC-221 | barley yellow dwarf virus | Barley |
| VC-222 | tomato yellow leaf curl virus | Tomato |
| VC-223 | tomato yellow leaf curl virus | Tomato-foliar use |
| VC-224 | tomato yellow leaf curl virus | Tomato-seed treatment |

These viruses are spread preferably by insects which are one or more of as an example *Acyrthosiphum pisum, Aphis citricola, Aphis craccivora, Aphis fabae, Aphis frangulae,*

*Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L, *Schizaphis graminum* Rond., *Sitobion avenae, Toxoptera aurantii, Toxoptera citricola, Phylloxera vitifoliae, Bemisia tabaci, Myzus persicae, Nilaparvata lugens, Aphis gossypii, Trialeurodes vaporariorum, Bactericera cockerelli.*

Methods of the invention as described herein may also involve a step of assessing whether insects are resistant to neonicotinoid insecticides and/or whether said insects carry a plant virus. This step will in general involve collecting a sample of insects from the area (e.g. crop, field, habitat) to be treated, before actually applying a compound I, and testing (for example using any suitable phenotypic, biochemical or molecular biological technique applicable) for resistance/sensitivity and/or the presence or absence of a virus.

The active agents of the invention may be applied as sole ingredients, or alternatively, each agent may be in the form of an agrochemical composition comprising an agrochemically acceptable diluent or carrier. References herein to the active agents of the invention or components comprising said agents shall be deemed to include the agents as sole ingredients or agrochemical compositions thereof.

The active agents of the invention may be applied simultaneously, separately or sequentially. Each active agent may be applied directly as separate components or as a mixture of the two.

In a particularly preferred embodiment of the invention, the compound (II) pesticides, together with which the compounds I may be used according to the purpose of the present invention, and with which potential synergistic effects with regard to the method of uses might be produced, are plant activators.

Plant activators are substances that protect plants by activating their defence mechanisms against pests or diseases. Plant activators suitable for use in the methods of the present invention include, for example, acibenzolar, acibenzolar-S-methyl and probenazole. Mixtures of plant activators can also be used in the present invention. In preferred embodiments of the invention, the plant activator is acibenzolar-S-methyl.

Accordingly, in a first preferred aspect, the present invention provides a method of reducing insect-vectored viral infection in a plant by application of a combination of a compound I, and acibenzolar-S-methyl. In a preferred embodiment, the present invention provides a method of reducing insect-vectored viral infection in a plant by application of a combination of a compound I as exemplified herein, especially Table ABC, and acibenzolar-S-methyl.

Therefore, in one embodiment, the invention relates to the uses according to the invention, especially the use for reducing insect-vectored viral infection in a plant, wherein the compound I as defined herein is combined with one or more other pesticidally active compound(s) II selected from insecticides, fungicides and plant activators.

The compound I, or a combination comprising it, may be applied to the plant, plant propagation material or locus thereof, or any combination thereof. Accordingly, the present invention provides methods as described herein comprising the application of a compound I, or a combination comprising it to a plant, plant propagation material or locus thereof, or any combination thereof.

In an additional aspect, the present invention provides the use of pesticidally active compounds I as defined herein for reducing insect-vectored-viral transmission amongst plants. The invention also provides the method of reducing insect-vectored-viral transmission amongst plants, by application of at least one pesticidally active compound I as defined herein, which is preferably selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

In a further aspect, the present invention provides the use of the compounds I as defined herein for reducing damage to a plant caused by one or more insect-vectored viral infections, by application of a combination of a pesticidally active compound I and a plant activator. The invention also provides the method of reducing damage to a plant caused by one or more insect-vectored viral infections, by application of at least one pesticidally active anthranilamide compound I as defined herein, which is preferably selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

The invention also comprises pesticidally active compounds I as defined herein, for use in the methods of the present invention, e.g. the method of reducing insect-vectored viral infection in a plant, or method of reducing insect-vectored-viral transmission amongst plants, or method of reducing damage to a plant caused by one or more insect-vectored viral infections.

The invention also comprises the use of at least one pesticidally active compound I as defined herein, in the methods of the invention as described herein.

In the uses and methods of the invention, the application may be the simultaneous, separate or sequential application to a plant, plant propagation material or locus thereof.

The methods and uses according to the invention improve the growth of the plants, increase the yield and improve the tolerance of the plants to abiotic stress.

The term "Locus" means the fields on which the plants to be treated are growing, or where the seeds of cultivated plants are sown, or the place where the seed will be placed into the soil.

The term "increasing the yield" of a plant means that the yield of a product of the plant is increased by a measurable amount over the yield of the same product of the plant produced under the same conditions, but without the application of the combinations according to the present invention. It is preferred that the yield is increased by at least about 0.5%, preferably 1%, more preferably 2%, yet more preferably 4% or more. Even more preferred is an increase in yield of at least about 5%, 10%, 15% or 20% or more.

According to the present invention, 'crop enhancement' means an improvement in plant vigour, an improvement in plant quality and/or improved tolerance to stress factors.

According to the present invention, an 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

According to the present invention, an 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

According to the present invention, an 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life.

Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least. 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

The plant, plant propagation material or locus thereof may be treated with a compound of formula I, or a combination comprising it, before the material is sown or planted. Alternatively, the plant, plant propagation material or locus thereof may be treated with a compound I, or a combination comprising it, after the material is sown or planted. Additionally, the compound I, or a combination comprising it, may be applied to the previously treated propagation material, either before its planting, and/or at its planting and/or during its growth. Therefore, the invention also comprises a method according to the invention, wherein the plant, plant propagation material, or the locus thereof, is treated before its planting, and/or at its planting and/or during its growth.

In one embodiment, the invention relates to a use or method for reducing insect-vectored viral infection in a plant, which method comprises applying a compound I, by treating the plant, plant propagation material, or the locus thereof, before its planting, and/or at its planting and/or during its growth, wherein the compound I is selected from the compounds of Table ABC. In one embodiment, the compound is a compound of embodiment A, also preferably a compound of embodiment B, also preferably a compound of embodiment C; more preferably a compound as defined in Table ABC selected from the compounds I-A-1 and I-A-28, or from I-B-115, I-B-131 and I-B-132; more preferably selected from I-B-115 and I-B-131, most preferably I-B-131; or selected from I-C-19, I-C-35 and I-C-36, most preferably I-C-35.

More specifically, the invention relates to a use or method for reducing insect-vectored viral infection in a plant, which method comprises applying a compound I-A-1 by treating the plant, plant propagation material, or the locus thereof, before its planting, and/or at its planting and/or during its growth. Analogously, the invention relates to a use or method as explained, applying specifically compound I-B-131. Analogously, the invention relates to a use or method as explained, applying specifically compound I-C-35.

Typically, the treatment of the soil with a compound I, or a combination comprising it, whether as a single composition or as individual components, can occur on several occasions during the growth of a plant up to the harvest (i.e. before its planting, and/or at its planting and/or during its growth). The treatment of a single composition and then the individual components in succession is also envisaged during the growth of a plant.

The compound I, or a combination comprising it, may be applied to the locus of the plant on one or more occasions during the growth of the plant. It can be applied to the planting site before the seed is sown, during the sowing of the seed, pre-emergence and/or post-emergence. The combination can also be used while the plant is being grown in a green house and the use can be continued after transplantation. The soil may, for example, be treated directly, prior to transplanting, at transplanting or after transplanting.

The use of the compound I, or a combination comprising it, can be via any suitable method, which ensures that the agents penetrate the soil, for example, nursery tray application, in furrow application, soil drenching, soil injection, drip irrigation, application through sprinklers or central pivot, incorporation into soil (broad cast or in band) are such methods.

The rate and frequency of use of the compound I, or a combination comprising it, on the plant may vary within wide limits and depends on the type of use, the specific active agents, the nature of the soil, the method of application (pre- or post-emergence, etc.), the plant to be controlled, the prevailing climatic conditions, and other factors governed by the method of application, the time of application and the target plant.

When employed in plant protection, the amounts of active substances applied are, depending on the kind of effect desired, from 0.001 to 2 kg per ha, preferably from 0.001 to 1 kg per ha., more preferably from 0.005 to 0.9 kg per ha, in particular from 0.005 to 0.5 kg per ha.

In general, "virucidally effective amount" means the amount of active ingredients or mixture according to the invention needed to achieve an observable effect on growth, including the effects of necrosis, death, retardation, prevention, and removal, destruction, or otherwise diminishing the occurrence and activity of the target virus. The virucidally effective amount can vary for the various mixtures/compositions used in the invention. A virucidally effective amount of the compositions will also vary according to the prevailing conditions such as desired virucidally effect and duration, weather, target species, locus, mode of application, and the like. In the case of foliar treatment, the quantity of active ingredient ranges from 0.0001 to 500 g per 100 $m^2$, preferably from 0.001 to 20 g per 100 $m^2$, or from 1 to 100 g per hectare, preferably from 10 to 50 g per hectare, or from 12 to 50 g per hectare, or from 10 to 30 g per hectare, or from 20 to 40 g per hectare, or from 10 to 20 g per hectare, or from 20 to 30 g per hectare, or from 30 to 40 g per hectare, or from 40 to 50 g per hectare.

In treatment of plant propagation materials such as seeds, e. g. by dusting, coating or drenching seed, amounts of active substance of from 0.1 to 1000 g, preferably from 0.1 to 300 g, more preferably from 0.1 to 100 g and most preferably from 0.25 to 100 g, per 100 kilogram of plant propagation material (preferably seed) are generally required.

In the case of soil treatment, the quantity of active ingredient ranges from 0.0001 to 500 g per 100 $m^2$, preferably from 0.001 to 20 g per 100 $m^2$ In the event the compound I, is used in a combination comprising it, and the components of the invention are applied individually, the time elapse between applications of the components to the locus of the plant should be such that on application of the second component the improved plant growth characteristics are demonstrated. The order of the application of the components is not critical. The second component is applied within preferably 14, such as 10, for example, 5, more preferably 4, especially 3, advantageously 1, days of the first component. Most preferably, the components are applied simultaneously or sequentially.

If the compound I is used in combination with e.g. a plant activator, the rate of application of the compound I is as described above and is most preferably, 50 g to 200 g/ha, and the rate of application of plant activator is from 5 g to 50 g/ha.

When used as seed drenching agent, convenient rates of application are from 10 mg to 1 g of active substance per kg of seeds.

The term "plant propagation material" is understood to denote all the generative parts of the plant, such as seeds, which can be used for the multiplication of the latter and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Further, the present invention is also applicable for use with a plant propagation material, e.g. plant seed that has already undergone a treatment with a pesticide. Even distribution of the combination of the invention and adherence thereof to the seeds is desired during treatment of the propagation material, for example, a seed. The treatment could vary from a thin film of the formulation containing the combination of the invention on a plant propagation material, such as a seed, where the original size and/or shape are recognizable to a thick film (such as a coating or pelleting with many layers of different materials (such as carriers, for example, clays; different formulations, such as of active ingredients; polymers; and colourants) where the original shape and/or size of the seed is no longer recognisable.

Accordingly, in one embodiment the compound I, or a combination comprising it, is adhered to the propagation material, such as a seed. In an alternative embodiment, the compound I, or a combination comprising it, is present on the seed in a pellet form.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed treatment occurs to an unsown seed, and the term "unsown seed" is meant to include seed at any period between the harvest of the seed and the sowing of the seed in the ground for the purpose of germination and growth of the plant. Treatment to an unsown seed is not meant to include those practices in which the pesticide is applied to the soil but would include any application practice that would target the seed during the sowing/planting process.

The treated plant propagation material of the present invention can be treated in the same manner as conventional plant propagation material. The treated propagation material can be stored, handled, sowed and tilled in the same manner as any other pesticide treated material, such as seeds. Preferably, the treatment occurs before sowing of the seed so that the seed being sown or planted has been pre-treated.

The compounds, combinations, compositions, uses and methods of the present invention may be used for the treatment of any plant including, for example, cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurse-ries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, for example, cool-season turf grasses (for example, bluegrasses (*Poa* L), such as Kentucky bluegrass (*Poa pratensis* L), rough bluegrass (*Poa trivialis* L), Canada bluegrass (*Poa compressa* L.) and annual bluegrass (*Poa annua* L); bentgrasses (*Agrostis* L), such as creeping bentgrass (*Agrostis palustris* Huds.), colonial bentgrass (*Agrostis tenius* Sibth.), velvet bentgrass (*Agrostis canina* L.) and redtop (*Agrostis alba* L); fescues (*Festuca* L), such as tall fescue (*Festuca arundinacea* Schreb.), meadow fescue (*Festuca elatior* L.) and fine fescues such as creeping red fescue (*Festuca rubra* L), chewings fescue (*Festuca rubra* var. *commutata* Gaud.), sheep fescue (*Festuca ovina* L.) and hard fescue (*Festuca longifolia*); and ryegrasses (*Lolium* L), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)).

The compounds, combinations, compositions, uses and methods of the present invention are particularly suitable for the treatment of crops, such as field crops, fruits, vegetables, nuts (particularly peanuts), berries, tropical plantations, ornamentals and others, such as wheat, barley, rye, oats, rice, maize, sorghum, beans, lentils, peas, soybeans, rape, mustard, poppy, sugar- and fodder-beet, cotton, flax, hemp, jute, sunflowers, castor oil, groundnuts, potatoes, tobacco, sugar cane, apples, pears, plums, peaches, nectarines, apricots, cherries, oranges, lemons, grapefruit, mandarins, olives vines, hops, almonds, walnuts, hazelnuts, avocado, bananas, tea, coffee, coconut, cocoa, natural rubber plants, oil plants, strawberries, raspberries, blackberries, spin-ach, lettuce, *asparagus*, cabbages, Chinese kale, carrots, onions, tomatoes, cucumbers, pepper, eggplants, melons, paprika, chilli, roses, chrysanthemums and carnations. The compounds, combinations, compositions, uses and methods of the present invention are particularly suitable for the treatment of tomato, tobacco, peanut or barley.

In a further preferred embodiment, the present invention provides a method of reducing damage to a tomato, tobacco, peanut or barley plant caused by one or more insect-vectored viral infections, by application of a compound I.

The plants may also be genetically modified. The present invention may preferably be used in high pH (such as 7 to 8.5) soil types.

Suitable plants also include plants that have been rendered tolerant to herbicides like bromoxynil or classes of herbicides (such as HPPD inhibitors, ALS inhibitors; for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones (e.g. imazamox) by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®. Suitable plants also include plants which have been so transformed by the use of recombinant DNA techniques that they are capable of synthesising one or more selectively acting toxins, such as are known from toxin-producing bacteria, especially those of the genus *Bacillus*.

Suitable plants also include plants which have been so transformed by the use of recombinant DNA techniques that they are capable of synthesising antipathogenic substances having a selective action, such as the so-called "pathogenesis-related proteins" (PRPs, see e.g. European patent application EP 0,392,225). Examples of such antipathogenic substances and transgenic plants capable of synthesising such antipathogenic substances are known, for example, from European patent applications EP 0,392,225 and EP 0,353,191 and International patent application WO 95/33818. The methods of producing such transgenic plants are generally known to the person skilled in the art and are described, for example, in the publications mentioned above.

The compounds, combinations, compositions, uses and methods of the present invention are particularly suitable for the treatment of plants which are susceptible to damage by insect-vectored viral infections transmitted by whitefly, aphid, leafhopper or *thrips*, such as leaf curl virus, which may be transmitted by whitefly.

Accordingly, in a preferred embodiment, the present invention provides a method or use for reducing insect-vectored viral infection in a plant by application of a compound I, optionally in a combination, preferably in combination with a plant activator, and most preferably in combination with acibenzolar-S-methyl, wherein the plant is susceptible to damage by viral infections transmitted by whitefly, aphid, leafhopper or *thrips*.

In an additional preferred embodiment, the present invention provides a method or use for reducing insect-vectored viral transmission amongst plants by application of a compound of formula I, optionally in a combination, preferably in combination with a plant activator, wherein the plant is susceptible to damage by viral infections transmitted by whitefly, aphid, leafhopper or *thrips*.

In a further preferred embodiment, the present invention provides a method or use for reducing damage to a plant caused by one or more viral infections transmitted by whitefly, aphid, leaf-hopper or *thrips*, by application of a compound I, optionally in a combination, preferably in combination with a plant activator, and most preferably in combination with acibenzolar-S-methyl.

In further additional preferred aspects, the present invention provides for the use of a compound I, optionally in a combination, preferably in combination with a plant activator, and most preferably in combination with acibenzolar-S-methyl, in the methods of the present invention, wherein the plant is susceptible to damage by viral infections transmitted by whitefly, aphid, leafhopper or *thrips*.

In each and every aspect of the present invention, the compounds, combinations, compositions, uses and methods of the present invention, as defined herein, are particularly suitable for the treatment of tomato, tobacco, peanut and barley, in order to protect them from damage by insect-vectored viral infections transmitted by whitefly, aphid, leafhopper or *thrips*.

In the treatments or applications of the invention the compounds of the invention (compound I, more preferably a compound of embodiment A, also preferably a compound of embodiment B, also preferably a compound of embodiment C, as described herein) are generally in the form of a formulation containing other customary formulation adjuvants because it allows, for example, less burden-some handling and application.

A variety of formulation types exist: dry flowables (DF), liquid flowables (LF), true liquids (TL), emulsifiable concentrates (EC), suspension concentrates (SC), dusts (D), wettable powders (WP), suspoemulsions (SE), water-dispersible granules (WG) and others, such as encapsulations in polymeric substances. Some are registered for use only by commercial applicators using closed application systems; others are readily available for on-farm use as dusts, slurries, water-soluble bags, or liquid ready-to-apply formulations. Normally however, commercial products are usually formulated as concentrates, where the end user will normally employ dilute formulations. How the components of the invention are to be used will also determine the formulation type, for example, if they are to be used as a seed treatment, then an aqueous composition is preferred.

If used in a combination, the compound I and the combination partner, e.g. a plant activator, can be part of a single composition and used simultaneously (i.e. they are mixed together—often referred to as "a pre-mix"), or can be separate products and used separately or sequentially. In the event they are separate products, they can be mixed together shortly before use by the user.

It is often more practical, where possible, for commercially available formulations of the compound I, more preferably a compound of embodiment A, also preferably a compound of embodiment B, also preferably a compound of embodiment C, and the combination partner, e.g. a plant activator, to be brought together in the desired mixing ratio in a container (often referred to as a "tank mixture") in water shortly before application.

In an embodiment, the compound I, more preferably a compound of embodiment A, also preferably a compound of embodiment B, also preferably a compound of embodiment C, and the combination partner, e.g. a plant activator, are used in single composition that has been specifically formulated, the composition comprising at least one of the adjuvants customary in formulation technology, such as extenders, e.g., solvents or solid carriers, or surface-active compounds (surfactants).

Suitable formulation adjuvants are, for example, solid carriers, solvents, stabilisers, slow-release adjuvants, dyes and optionally surface-active substances (surfactants). Suitable carriers and adjuvants in this case include all substances customarily used in crop protection products, especially in products for controlling snails and slugs. Suitable adjuvants, such as solvents, solid carriers, surface-active compounds, non-ionic surfactants, cationic surfactants, anionic surfactants and further adjuvants in the compositions used in accordance with the invention are, for example, the same as those described in EP 0,736,252.

The compositions may comprise from 0.1 to 99%, in particular 0.1 to 95%, of the combination and from 1 to 99.9%, in particular 5 to 99.9%, of at least one solid or liquid auxiliary. The composition may additionally comprise from 0 to 25%, in particular 0.1 to 20%, of surfactants (percent is in each case per cent by weight). While concentrated compositions are more preferred as commercial goods, the end user generally uses dilute compositions that comprise considerably lower concentrations of the combination.

Further Aspects of Formulations

The invention also relates to agrochemical compositions suitable for applying in the methods and uses according to the invention, comprising an auxiliary and at least one compound I according to the invention.

An agrochemical composition comprises a pesticidally effective amount of a compound I. The term "effective amount" denotes an amount of the compound I, optionally in combination with compound II, which is sufficient for observing an effect on cultivated plants, especially for controlling harmful pests on cultivated plants and which does not result in a substantial damage to the treated plants. Such an amount can vary in a broad range and is dependent on various factors, such as the animal pests species to be controlled, the treated cultivated plant or material, the climatic conditions and the specific compound I used.

The compounds I, their stereoisomers, salts, tautomers and N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are e.g. solvents, liquid carriers, solid carriers or fillers, surfactants, dispersants, emulsifiers, wetters, adjuvants, solubilizers, penetration enhancers, protective colloids, adhe-sion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclo-hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl-naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkyl-polyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or poly-ethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

The compounds and mixtures according to the invention are suitable for use in seed treatment. Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

Usually, the agrochemical composition is made up with water, buffer, and/or further auxiliaries to the desired application concentration and the ready-to-use spray liquor or the agrochemical composition according to the invention is thus obtained.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds I and/or optionally active compound II, may be mixed by the user in a spray tank and further auxiliaries and additives may be added, if appropriate.

In a further embodiment, either individual components of the composition according to the invention or partially premixed components, can be applied jointly (e.g. after tank mix) or consecutively.

B. Biology

Trial results: Applications of compounds of the invention, or combinations comprising it, to control tomato yellow leaf curl virus (TYLC) in tomatoes.

1. Foliar Use

Studies are carried out on tomato plants of the variety Fayrouz with the main goal to measure efficacy on the whitefly *Bemisia tabaci*. The plot size is e.g. 4.8 m$^2$ and 6 replicates are used in the trial. Products are applied 3 times on young tomato plants at BBCH stages 14, 17 and 51 at spray intervals between 12 and 19 days. The spray volume is at the first application 350 l/ha and later 500 l/ha. The evaluation of this study is done counting the adult whiteflies (*Bemisia tabaci*) as well as the nymphs and the eggs in each plot. In addition to the direct whitefly effect, visual symptoms of the virus, mainly TYLCV (tomato yellow leaf curl virus) are evaluated also.

2. Soil Use 2.1. Soil studies are carried out on tomato plants with the main goal to measure efficacy on the whitefly *Bemisia tabaci*. The plot size is e.g. 4.8 m$^2$ and 6 replicates are used in the trial. Products are applied once on young tomato plants at BBCH stage 14 as a drench. The spray volume is at the first application 350 l/ha. The evaluation of this study is done counting the adult whiteflies (*Bemisia tabaci*) as well as the nymphs and the eggs in each plot. In addition to the direct whitefly effect, visual symptoms of the virus, mainly TYLCV (tomato yellow leaf curl virus) are evaluated also.

2.2. Barley seeds are treated with ten different concentrations of technical active ingredient, dissolved in acetone. Treated barley seeds are sown into small plastic flowerpots (4 pots per concentration) containing standard soil. The pots are carefully irrigated and kept in a greenhouse (23C, 50% RH). When the plants are approximately 5 cm high (BBCH12), the young barley plants are infested with BYDV-viruliferous *Rhopalosiphum padi* (BYDV: barley yellow dwarf virus). Two weeks after planting single leaves are removed from each pot, and leaf disks are punched out of the tip of five different leaves. They are transferred into 96 well microtiter plates. Each treatment-dose combination is represented 20 times. Fresh aphids from the aphid colony are added to each well. The plates w are covered with an air permeable plastic foil and incubated for three days. Compound efficacy is then assessed. ED50 values are obtained fitting the data with a non-linear two parameter logistic model. Plant height is recorded shortly before harvesting the treated plants, by measuring the length of the longest leaf growing in the respective pot. On day 14 after the first infestation, aphid population densities are scored on the barley plants and ranked (4=very high aphid density; 3=many aphids; 2=average aphid density; 1=few aphids; 0=no aphids). Fourteen days after the first infestation, leafs are cut from the potted plants. The leaf samples are later used for the ELISA test. For the ELISA test, leaves from each pot are treated separately, resulting in four replicates per treatment and dilution. For the test, three identical plates are prepared. In addition to plant material from the differently treated plants, a BYDV positive control and a BYDV negative control (one well) provided with the ELISA test kit, is added to the plates. At the end of each ELISA test preparation the 96-well microtiter plates containing the sample extracts are assessed measuring optical absorbances (405 nm) using a plate reader.

Embodiment E9

The present invention relates to a method of controlling insects, that are resistant to an insecticide. In particular, the present invention relates to a method of controlling insects from the order Lepidoptera, Coleoptera or Diptera, which are resistant to an insecticide. The present invention also relates to a method of controlling insects from the order Thysanoptera or Homoptera, which are resistant to an insecticide.

The invention relates to a method, in which the compounds I itself and their stereoisomers, salts, tautomers or N-oxides, especially their salts, and their mixtures, are used for controlling Lepidoptera or Coleoptera that are resistant to other insecticides and are surprisingly useful in this context.

The present invention is based on the surprising finding that a compound I can be successfully used to control insecticide resistant populations of arthropods, in particular insects, and more particular insects from the order Lepidoptera, Coleoptera or Diptera, and also insects from the order Thysanoptera or Homoptera.

Thus in the first aspect of the invention there is provided a method of controlling insects which are resistant to an insecticide, which method comprises applying to said insecticide resistant insects at least one pesticidally active compound I as defined herein, or a stereoisomer, salt, tautomer or N-oxide, or a polymorphic crystalline form, a co-crystal or a solvate of a compound or a stereoisomer, salt, tautomer or N-oxide thereof.

The pests that can be controlled or combatted are as described above or herein, e.g. in embodiment E1, but are resistant.

The plants or crops to be protected are as described above or herein, e.g. in embodiment E1.

The formulations are as described herein, e.g. in embodiment E1.

The applications are as described herein, e.g. in embodiment E1.

The mixtures and preferred mixtures are as described herein.

In one embodiment, the compound I in the methods and uses according to the invention of E9 is selected from the compounds described in Embodiment A.

In one embodiment, the compound I in the methods and uses according to the invention of E9 is selected from the compounds described in Embodiment B.

In one embodiment, the compound I in the methods and uses according to the invention of E9 is selected from the compounds described in Embodiment C.

In one embodiment, the compound I in the methods and uses according to the invention of E9 is selected from the compounds listed in Table ABC.

In some embodiments, the invention relates to methods and uses, wherein the compound I is applied in an application type which corresponds in each case to one row of Table AP-T.

In one embodiment, I-A-1 is the compound I in the methods and uses according to the invention of E9.

In one embodiment, I-A-28 is the compound I in the methods and uses according to the invention of E9.

In one embodiment, I-B-115 is the compound I in the methods and uses according to the invention of E9.

In one embodiment, I-B-131 is the compound I in the methods and uses according to the invention of E9.

In one embodiment, I-B-132 is the compound I in the methods and uses according to the invention of E9.

In one embodiment, I-C-19 is the compound I in the methods and uses according to the invention of E9.

In one embodiment, I-C-35 is the compound I in the methods and uses according to the invention of E9.

In one embodiment, I-C-36 is the compound I in the methods and uses according to the invention of E9.

In a further embodiment, the invention relates to the methods and uses of the compounds according to the invention (as defined in Embodiment A, B or C) in combination with other selected pesticidal compounds (II), as defined and specified in Embodiments 2 and 3.

Insecticide Resistant Insects and Methods for Controlling them

Resistance may be defined as 'a heritable change in the sensitivity of a pest population that is reflected in the repeated failure of a product to achieve the expected level of control when used according to the label recommendation for that pest species'. (IRAC) Cross-resistance occurs when resistance to one insecticide confers resistance to another insecticide via the same biochemical mechanism. This can happen within insecticide chemical groups or between insecticide chemical groups. Cross-resistance may occur even if the resistant insect has never been exposed to one of the chemical classes of insecticide.

Resistance therefore means that the original activity of a pesticide against the target organisms (arthropods, insects) decreases or is even lost, due to genetic adaptation of the target organism.

"Resistant" to an insecticide is understood to mean resistant to at least one insecticide, i.e. the insect may be resistant to only one, but also to several insecticides.

The resistance may be also against an insecticidal effect which is due to a genetic modification of a plant (modified or transgenic plant), which caused a resistance of the plant or crop to certain pests, especially insect pests, in susceptible insects.

This is to be understood to include plants that are by the use of recombinant DNA techniques capable to synthesize one or more insecticidal proteins, especially those mentioned herein, especially those known from the bacterial genus *Bacillus*, particularly from *Bacillus thuringiensis*, such as endotoxins, e. g. CryIA(b), CryIA(c), CryIF, CryIF (a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp., and so on.

Methods and uses of the invention as described herein may also involve a step of assessing whether insects are resistant to certain insecticides. This step will in general involve collecting a sample of insects from the area (e.g. crop, field, habitat) to be treated, before actually applying a compound I, and testing (for example using any suitable phenotypic, biochemical or molecular biological technique applicable) for resistance/sensitivity.

Insecticides to which the arthropods or insects may be resistant, in the sense of the methods and uses according to the invention, are listed in the following categorized list M of pesticides, which are, whenever possible, classified according to the Insecticide Resistance Action Committee (IRAC), M.1 Acetylcholine esterase (AChE) inhibitors from the class of M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cyclopro-thrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a] azepine; or M.4A.2: 1-[(6-chloro-3-pyridyl)methyl]-2-nitro-1-[(E)-pentylideneamino]guanidine; or M.4A.3: 1-[(6-chloro-3-pyridyl)methyl]-7-methyl-8-nitro-5-propoxy-3,5,6,7-tetrahydro-2H-imidazo[1,2-a]pyridine; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb, or M.7C pyriproxyfen;

M.8 miscellaneous non-specific (multi-site) inhibitors, for example

M.8A alkyl halides as methyl bromide and other alkyl halides, or

M.8B chloropicrin, or

M.8C sulfuryl fluoride, or

M.8D borax, or

M.8E tartar emetic;

M.9 Selective homopteran feeding blockers, for example

M.9B pymetrozine, or

M.9C flonicamid;

M.10 Mite growth inhibitors, for example

M.10A clofentezine, hexythiazox and diflovidazin, or

M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis*, *bacillus sphaericus*, *bacillus thuringiensis* subsp. *aizawai*, *bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or

M.20B acequinocyl, or

M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or

M.22B metaflumizone; or

M.22C 1-[(E)-[2-(4-cyanophenyl)-1-[3-(trifluoromethyl)phenyl]ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds M.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound M.X.2: cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester, or the compound M.X.3: 11-(4-chloro-2,6-dimethylphenyl)-12-hydroxy-1,4-dioxa-9-azadispiro[4.2.4.2]-tetradec-11-en-10-one, or the compound M.X.4: 3-(4'-fluoro-2,4-dimethylbiphenyl-3-yl)-4-hydroxy-8-oxa-1-azaspiro[4.5]dec-3-en-2-one, or the compound M.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, 1-1582), or M.X.6: a compound selected from the group of M.X.6a: (E/Z)—N-[1-[(6-chloro-3-pyridyl)methyl]-2-pyridylidene]-2,2,2-trifluoro-acetamide;

M.X.6b: (E/Z)—N-[1-[(6-chloro-5-fluoro-3-pyridyl)methyl]-2-pyridylidene]-2,2,2-trifluoro-acetamide;

M.X.6c: (E/Z)-2,2,2-trifluoro-N-[1-[(6-fluoro-3-pyridyl)methyl]-2-pyridylidene]acetamide;

M.X.6d: (E/Z)—N-[1-[(6-bromo-3-pyridyl)methyl]-2-pyridylidene]-2,2,2-trifluoro-acetamide;

M.X.6e: (E/Z)—N-[1-[1-(6-chloro-3-pyridyl)ethyl]-2-pyridylidene]-2,2,2-trifluoro-acetamide;

M.X.6f: (E/Z)—N-[1-[(6-chloro-3-pyridyl)methyl]-2-pyridylidene]-2,2-difluoro-acetamide;

M.X.6g: (E/Z)-2-chloro-N-[1-[(6-chloro-3-pyridyl)methyl]-2-pyridylidene]-2,2-difluoro-acetamide;

M.X.6h: (E/Z)—N-[1-[(2-chloropyrimidin-5-yl)methyl]-2-pyridylidene]-2,2,2-trifluoro-acetamide and M.X.6i: (E/Z)—N-[1-[(6-chloro-3-pyridyl)methyl]-2-pyridylidene]-2,2,3,3,3-pentafluoro-propanamide); or M.X.7: triflumezopyrim; or M.X.8: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or M.X.9: 3-[3-chloro-5-(trifluoromethyl)phenyl]-4-oxo-1-(pyrimidin-5-ylmethyl)pyrido[1,2-a]pyrimidin-1-ium-2-olate; or M.X.10: 8-chloro-N-[2-chloro-5-methoxyphenyl)sulfonyl]-6-trifluoromethyl)-imidazo[1,2-a]pyridine-2-carboxamide; or M.X.11: 4-[5-(3,5-dichlorophenyl)-5-(trifluoromethyl)-4H-isoxazol-3-yl]-2-methyl-N-(1-oxothietan-3-yl)benzamide; or M.X.12: 5-[3-[2,6-dichloro-4-(3,3-dichloroallyloxyl)phenoxy]propoxy]-1H-pyrazole; or M.Y Biopesticides, e.g.

M.Y-1: Microbial pesticides with insecticidal, acaricidal, molluscidal and/or nematicidal activity: *Bacillus firmus, B. thuringiensis* ssp. *israelensis*, B. t. ssp. *galleriae*, B. t. ssp. *kurstaki, Beauveria bassiana, Burkholderia* sp., *Chromobacterium subtsugae, Cydia pomonella granulosis virus, Isaria fumosorosea, Lecanicillium longisporum, L. muscarium* (formerly *Verticillium lecanii*), *Metarhizium anisopliae, M. anisopliae* var. *acridum, Paecilomyces fumosoroseus, P. lilacinus, Paenibacillus poppiliae, Pasteuria* spp., *P. nishizawae*, P. reneformis, P. usagae, Pseudomonas fluorescens, Steinernema feltiae, Streptomces galbus;

M.Y-2) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodae*, Catnip oil, neem oil, Quillay extract, *Tagetes* oil.

The commercially available compounds of the group M listed above may be found in The Pesticide Manual, 15th Edition, C. D. S. Tomlin, British Crop Protection Council (2011) or as described in embodiment E2.

In a preferred embodiment, the method according to the invention is a method of controlling insects, which are resistant to an insecticide, which method comprises applying to said insecticide resistant insects at least one pesticidally active anthranilamide compound I, wherein the insecticide to which the insect is resistant is selected from a) neonicotinoids comprising acetamiprid, chlothianidin, dinotefuran, imidacloprid, nitenpyram, thiacloprid and thiamethoxam, as well as any compound having the same mode of action, b) pyrethroids comprising acrinathrin, allethrin, d-cis-trans allethrin, d-trans allethrin, bifenthrin, bioallethrin, bioallethrin S-cylclopentenyl, bioresmethrin, cyclopro-thrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin c) chitin biosynthesis Inhibitors of type 0, comprising benzoylureas including bistrifluron, chlorfluazuron, diflubenzuron, flucycloxuron, flufenoxuron, hexaflumuron, lufenuron, novaluron, noviflumuron, teflubenzuron and triflumuron; and chitin biosynthesis inhibitors of type 1, comprising buprofezin.

In an especially preferred embodiment of the invention, the method according to the invention is a method of controlling insects, which are resistant to an insecticide, which method comprises applying to said insecticide resistant insects at least one pesticidally active anthranilamide compound I, wherein the insecticide to which the insect is resistant is a neonicotinoid compound.

The term neonicotinoid insecticide as used herein refers to any insecticidal compound that acts at the insect nicotinic acetylcholine receptor, and in particular refers to those compounds classified as neonicotinoid insectides according to Yamamoto (1996, Agrochem Jpn 68:14-15). Examples of neonicotinoid insecticides include those in Group 4A of the IRAC (insecticide resistance action committee, Crop Life) mode of action classification scheme, e.g. acetamiprid, clothianidin, dinotefuran, imidacloprid, nitenpyram, thiacloprid, and thiamethoxam, as well as any compound having the same mode of action.

In a further preferred embodiment of the invention, the insecticide to which the insect is resistant is imidacloprid.

By the terms "control" or "controlling" as applied to insects, it is meant that the targeted insects are repelled from or less attracted to the crops to be protected. Additionally, as applied to insects, the terms "control" or "controlling" may also refer to the inability, or reduced ability, of the insects to feed or lay eggs. These terms may further include that the targeted insects are killed.

Thus the method of the invention may involve the use of an amount of the active ingredient that is sufficient to repel insects (i.e a repellently effective amount of active ingredient), an amount of the active ingredient that is sufficient to stop insects feeding, or it may involve the use of an insecticidally effective amount of active ingredient (i.e. an amount sufficient to kill insects), or any combination of the above effects.

The terms "applying" and "application" are understood to mean direct application to the insect to be controlled, as well as indirect application to said insect, for example through application to the crop or plant on which the insect acts as pest, or to the locus of said crop or insect, or indeed through treatment of the plant propagation material of said crop of plant.

Thus a compound I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the plant propagation material, such as seed, before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

In a further preferred embodiment of the invention, the invention relates to a method of protecting a crop of useful plants susceptible to and/or under attack by insects, which are resistant to an insecticide, which method comprises applying to said crop, treating a plant propagation material of said crop with, and/or applying to said insecticide resistant insects, a compound I as defined herein.

In a further preferred embodiment of the invention, the invention relates to a method of controlling resistance to one or more insecticides in insects, which comprises alternately applying a compound I as defined herein, and the insecticide, towards which the insects are resistant, to said insects or to a crop of useful plants susceptible to and/or under attack from said insects.

In these methods of the invention, the methods are also preferred wherein the insecticide resistant insect is from the order Lepidoptera, Coleoptera or Diptera or is selected from *thrips*, hoppers and whitefly.

In these methods of the invention, preferred are also the methods of protecting a crop of useful plants susceptible to and/or under attack by insects, which insects are resistant to an insecticide, and enhancing the crop, which method comprises applying to the propagation material of said crop an insecticide followed by the foliar application of a compound of the formula (I), as defined herein, beginning with the 3- to 5-leaf crop stage.

B. BIOLOGICAL EXAMPLES

The effect according to the invention can be determined as described e.g. in WO2011/151249:

B1: *Myzus persicae* (Green peach aphid): mixed population, feeding/residual contact activity, preventive Sunflower leaf discs are placed on agar in a 24-well microtiter plate and sprayed with test solutions. After drying, the leaf discs are infested with an aphid population of mixed ages. After an incubation period of 6 DAT, samples are checked for mortality.

A group A (neonicotinoid insecticides susceptible *Myzus persicae*, mixed age population) is compared to a group B (neonicotinoid insecticides resistant *Myzus persica*, mixed age population).

B2: Determination of the cross-resistance status of compounds I when applied against agronomically important pest species resistant to one or more commercially available class of insecticide.

As mentioned above, resistance may be defined as 'a heritable change in the sensitivity of a pest population that is reflected in the repeated failure of a product to achieve the expected level of control when used according to the label recommendation for that pest species'. (IRAC) Cross-resistance occurs when resistance to one insecticide confers resistance to another insecticide via the same biochemical mechanism. This can happen within insecticide chemical groups or between insecticide chemical groups. Cross-resistance may occur even if the resistant insect has never been exposed to one of the chemical classes of insecticide.

The level of resistance and therefore the impact on the performance of the insecticide can be measured by the use of a 'Resistance Factor'. The resistance factor can be calculated by dividing the concentration of an insecticide that provides a set level of mortality (i.e. 80 percent) for the 'resistant' strain with the concentration of the same insecticide that provides the same level of mortality for the 'susceptible' insect of the same species and life-stage. Although there are no set rules, a low value (1-10) indicates no cross-resistance and only natural levels of variation and a high value (50+) provides strong evidence of cross-resistance.

a) Neonicotinoid and Pyrethroid Resistant Strain of the Green Peach Aphid (*Myzus persicae*)

*Myzus persicae* strains utilised:
  Standard screening strain of *Myzus persicae* (Neonicotinoid susceptible)
  FRC-P strain of *Myzus persicae* (Neonicotinoid resistant)

Bioassay Method

*Myzus persicae*: mixed population, contact activity, curative on pea seedlings

Pea seedlings, infested with an aphid population of mixed ages, are treated with the test solutions in a spray chamber. 6 days after treatment, samples are checked for mortality.

The Resistance Factor ($RF_{80}$) of different compounds is tested.

Resistance fac or ($RF_{80}$)=Lowest concentration tested that provides greater than 80% mortality of resistant aphids/Lowest concentration tested that provides greater than 80% mortality of susceptible aphids.

The Resistance Factor ($RF_{80}$) of the neonicotinoid thiamethoxam is >250.

b) Neonicotinoid Resistant Strain of the Brown Planthopper (*Nilaparvata lugens*)

*Nilaparvata lugens* strains utilised:
  Standard screening strain of *Nilaparvata lugens* (Neonicotinoid susceptible)
  IND3 strain of *Nilaparvata lugens* (Neonicotinoid resistant)

Bioassay Method:

*Nilaparvata lugens*: Larvicide, Feeding/Contact Activity, Preventive

Rice seedlings are treated with the diluted test solutions in a turn table spray chamber. After drying, they are infested with 20 N3 nymphs. 6 and 12 days after the treatment samples are checked for mortality, growth regulation, and effects on the Fi generation.

The Resistance Factor ($RF_{80}$) of different compounds is tested.

Resistance factor ($RF_{80}$)=Lowest concentration tested that provides greater than 80% mortality of resistant hoppers/Lowest concentration tested that provides great-er than 80% mortality of susceptible hoppers.

The Resistance Factor ($RF_{80}$) of the neonicotinoid thiamethoxam in this test is >64.

c) Neonicotinoid and Pyrethroid Resistant Strain of the Tobacco Whitefly (*Bemisia tabaci*) *Bemisia tabaci* Strains Utilised:
  Standard screening strain of *Bemisia tabaci*(Neonicotinoid susceptible)
  ALM07 strain of *Nilaparvata lugens* (Neonicotinoid and pyrethroid resistant) (>250 RF in residual mortality bioassay of adult whitefly with thiamethoxam).

Bioassay Method

*Bemisia tabaci* Residual Activity, Preventive Egg Lay

Cotton seedlings, with all but a single leaf removed are treated with the diluted test solutions in a turn table spray chamber. 24 hours after drying, they are infested with 20 adult whitefly. 3 days after exposure, the total number of adult whitefly and the total number of whitefly eggs laid on the leaf are counted. Percentage control of egg lay is calculated and corrected for control mortality.

The Resistance Factor ($RF_{50}$) of different compounds is tested.

Resistance factor ($RF_{50}$)=Concentration tested that provides 50% control of resistant whitefly egg lay/concentration that provides 50% control of susceptible whitefly egg lay.

B3. Testing for cross-resistance to neonic-resistant Colorado potato beetles (CPBs) To test for cross-resistance of compounds according to the invention to neonic-resistant Colorado potato beetles (CPBs), three colonies are used: an Imidacloprid resistant colony (New York), a Thiamethoxam resistant colony (Hadley) and a susceptible reference colony (New Jersey). All three colonies were obtained from Michigan State University.

Serial dilutions of compound are made in 50:50 acetone: deionized water & 0.01% kinetic. Eggplants, first pair of true leaves, are dipped in treatment solutions for three seconds and allowed to air dry for 30 minutes in the fume hood. Treated leaves are excised from plants and two leaves per petri-dish are infested with three 3rd instar CPBs. The test is held in a holding room at 26° C. with no exposure to UV light. Each treatment is replicated five times.

Treatments are evaluated for mortality and feeding damage at four days after infestation.

Embodiment E10

The present invention relates to a method of controlling insects, that are resistant to a ryanodine-modulator insecticide. In particular, the present invention relates to a method of controlling insects from the order Lepidoptera, Coleoptera or Diptera, which are resistant to a ryanodine-modulator insecticide. The present invention also relates to a method of controlling insects from the order Thysanoptera or Homoptera, which are resistant to a ryanodine-modulator insecticide.

The invention relates to a method, in which the compounds I itself and their stereoisomers, salts, tautomers or N-oxides, especially their salts, and their mixtures, are used for controlling Lepidoptera or Coleoptera that are resistant to other ryanodine-modulator insecticides and are surprisingly useful in this context.

The present invention is based on the surprising finding that a compound I can be successfully used to control ryanodine-modulator insecticide resistant populations of arthropods, in particular insects, and more particular insects from the order Lepidoptera, Coleoptera or Diptera, and also insects from the order Thysanoptera or Homoptera.

Thus in the first aspect of the invention there is provided a method of controlling insects which are resistant to a ryanodine-modulator insecticide, which method comprises applying to said ryanodine-modulator insecticide resistant insects at least one pesticidally active anthranilamide compound I as defined herein.

The pests that can be controlled or combatted are as described above or herein, e.g. in embodiment E1.

The plants or crops to be protected are as described above or herein, e.g. in embodiment E1.

The formulations are as described herein, e.g. in embodiment E1.

The applications are as described herein, e.g. in embodiment E1.

The mixtures and preferred mixtures are as described herein.

The invention of Embodiment 10 is analogous to the invention of Embodiment 11, with the exception that the insecticide to which the insect is resistant, is a ryanodin modulator insecticide.

In one embodiment, the compound I in the methods and uses according to the invention of E10 is selected from the compounds described in Embodiment A.

In one embodiment, the compound I in the methods and uses according to the invention of E10 is selected from the compounds described in Embodiment B.

In one embodiment, the compound I in the methods and uses according to the invention of E10 is selected from the compounds described in Embodiment C.

In one embodiment, the compound I in the methods and uses according to the invention of E10 is selected from the compounds listed in Table ABC.

In some embodiments, the invention relates to methods and uses, wherein the compound I is applied in an application type which corresponds in each case to one row of Table AP-T.

In one embodiment, I-A-1 is the compound I in the methods and uses according to the invention of E10.

In one embodiment, I-A-28 is the compound I in the methods and uses according to the invention of E10.

In one embodiment, I-B-115 is the compound I in the methods and uses according to the invention of E10.

In one embodiment, I-B-131 is the compound I in the methods and uses according to the invention of E10.

In one embodiment, I-B-132 is the compound I in the methods and uses according to the invention of E10.

In one embodiment, I-C-19 is the compound I in the methods and uses according to the invention of E10.

In one embodiment, I-C-35 is the compound I in the methods and uses according to the invention of E10.

In one embodiment, I-C-36 is the compound I in the methods and uses according to the invention of E10.

In a further embodiment, the invention relates to the methods and uses of the compounds according to the invention (as defined in Embodiment A, B or C) in combination with other selected pesticidal compounds (II), as defined and specified in Embodiments 2 and 3.

Ryanodine-Modulator Insecticide Resistant Insects and Methods for Controlling them Resistance may be defined as 'a heritable change in the sensitivity of a pest population that is reflected in the repeated failure of a product to achieve the expected level of control when used according to the label recommendation for that pest species'. (IRAC) Cross-resistance occurs when resistance to one insecticide confers resistance to another insecticide via the same biochemical mechanism. This can happen within insecticide chemical groups or between insecticide chemical groups. Cross-resistance may occur even if the resistant insect has never been exposed to one of the chemical classes of insecticide.

Resistance therefore means that the original activity of a pesticide against the target organisms (arthropods, insects) decreases or is even lost, due to genetic adaptation of the target organism.

"Resistant" to a ryanodine-modulator insecticide is understood to mean resistant to at least one ryanodine-modulator insecticide, i.e. the insect may be resistant to only one, but also to several ryanodine-modulator insecticides.

The resistance may be also against an insecticidal effect which is due to a genetic modification of a plant (modified or transgenic plant), which caused a resistance of the plant or crop to certain pests, especially insect pests, in susceptible insects.

This is to be understood to include plants that are by the use of recombinant DNA techniques capable to synthesize one or more insecticidal proteins, especially those mentioned herein, especially those known from the bacterial genus Bacillus, particularly from Bacillus thuringiensis, such as endotoxins, e. g. CryIA(b), CryIA(c), CryIF, CryIF (a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example Photorhabdus spp. or Xenorhabdus spp., and so on.

Methods and uses of the invention as described herein may also involve a step of assessing whether insects are resistant to certain ryanodine-modulator insecticides. This step will in general involve collecting a sample of insects from the area (e.g. crop, field, habitat) to be treated, before actually applying a compound I, and testing (for example using any suitable phenotypic, biochemical or molecular biological technique applicable) for resistance/sensitivity.

Ryanodine-modulator Insecticides to which the arthropods or insects may be resistant, in the sense of the methods and uses according to the invention, are M.26 Ryanodine receptor-modulators from the class of diamides, as for example flubendiamide, chlorantraniliprole (Rynaxypyr®), cyantraniliprole (Cyazypyr®), or the phthalamide compounds M.26.1: (R)-3-Chlor-N1-{2-methyl-4-[1,2,2,2-tetrafluor-1-(trifluormethyl)ethyl]phenyl}-N2-(1-methyl-2-methyl-sulfonylethyl)phthalamid and M.26.2: (S)-3-Chlor-N1-{2-methyl-4-[1,2,2,2-tetrafluor-1-(trifluormethyl)ethyl]phenyl}-N2-(1-methyl-2-methyl-sulfonylethyl)phthalamid, or the anthranilamide compounds M.26.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.26.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.26.5a) to M.26.5d):

M.26.5a: N-[2-(5-amino-1,3,4-thiadiazol-2-yl)-4-chloro-6-methyl-phenyl]-5-bromo-2-(3-chloro-2-pyridyl)pyrazole-3-carboxamide;

M.26.5b: 5-chloro-2-(3-chloro-2-pyridyl)-N-[2,4-dichloro-6-[(1-cyano-1-methyl-ethyl)carbamoyl]phenyl]pyrazole-3-carboxamide;

M.26.5c: 5-bromo-N-[2,4-dichloro-6-(methylcarbamoyl)phenyl]-2-(3,5-dichloro-2-pyridyl)pyrazole-3-carboxamide;

M.26.5d: N-[2-(tert-butylcarbamoyl)-4-chloro-6-methyl-phenyl]-2-(3-chloro-2-pyridyl)-5-(fluoromethoxy)pyrazole-3-carboxamide; or M.26.6: N2-(1-cyano-1-methyl-ethyl)-N1-(2,4-dimethyl-phenyl)-3-iodo-phthalamide; or M.26.7: 3-chloro-N2-(1-cyano-1-methyl-ethyl)-N1-(2,4-dimethylphenyl)phthalamide.

The commercially available compounds listed above may be found in The Pesticide Manual, 15th Edition, C. D. S. Tomlin, British Crop Protection Council (2011) among other publications. Cyantraniliprole (Cyazypyr) is known from e.g. WO 2004/067528. The phthalamides M.26.1 and M.26.2 are both known from WO 2007/101540. The anthranilamide M.26.3 has been described in WO 2005/077934. The hydrazide compound M.26.4 has been described in WO 2007/043677. The anthranilamide M.26.5a) is described in WO2011/085575, the M.26.5b) in WO2008/134969, the M.26.5c) in US2011/046186 and the M.26.5d in WO2012/034403. The diamide compounds M.26.6 and M.26.7 can be found in CN102613183.

In one embodiment, the Ryanodine-modulator Insecticide is Chlorantraniliprole.

In one embodiment, the Ryanodine-modulator Insecticide is Cyantraniliprole.

In one embodiment, the Ryanodine-modulator Insecticide is Cyclaniliprole.

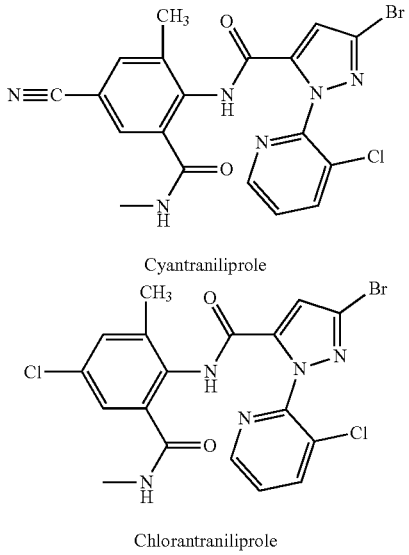

Cyantraniliprole

Chlorantraniliprole

In a preferred embodiment, the method according to the invention is a method of controlling insects, which are resistant to a ryanodine-modulator insecticide, which method comprises applying to said ryanodine-modulator insecticide resistant insects at least one pesticidally active anthranilamide compound I, wherein the ryanodine-modulator insecticide to which the insect is resistant is selected from chlorantraniliprole or cyantraniliprole.

The compounds I, and their stereoisomers, salts, tautomers and N-oxides, may be applied with other insecticides as compound II, which are either listed as Ryanodine-modulator Insecticides above (which may be useful apart from the mentioned resistant insects), or are listed in the following categorized list M of pesticides, which are, whenever possible, classified according to the Insecticide Resistance Action Committee (IRAC):

B. BIOLOGICAL EXAMPLES

B.1 Testing for Cross-Resistance to Diamide-Resistant Diamond Back Moth (Plutella xylostella)

Compounds I, chlorantraniliprole, cyantraniliprole and flubendiamide are dissolved using pure analytical acetone and then diluted with 50:50 distilled water: pure analytical acetone. Kinetic HV is added as surfactant at 0.01% v/v.

Cabbage leaves are cut into discs and dipped into serially prepared test solutions (6-8 test concentrations). Treated leaves are air-dried in petri dishes (150×20 mm) lined with moistened filter paper. Each treatment concentration is replicated 3× and after air drying of about an hour, each replicate is inoculated with 10 third instar larvae of (Plutella xylostella). After inoculation, each dish is covered with soft tissue paper with the plate cover on its top and then transferred in a room maintained at 24° C. and 64% relative humidity. Assessment of larvae mortality is recorded 3 days after inoculation (3 DAI).

Diamond back moth pupae from Cebu region in the Philippines were collected in May 2010 and in the last week of March 2012 with F1 and F2 generations used in the assay. The Diamond back moths collected from the Cebu region (Philippines) are reported to show diamide cross resistance, as for example reported by the Insecticide Resistance Action Committee (www.irac-online.org/).

Commercial diamide chemistries like flubendiamide show only weak efficacies against the field collected Cebu strain of *Plutella xylostella*. Compounds I show higher efficacies compared to flubendiamide, chlorantraniliprole and cyantraniliprole, respectively, when comparing $LC_{50}$s and $LC_{90}$s.

$LC_{50}$ defines the lethal concentration where 50% of a respective population is killed. $LC_{90}$ defines the lethal concentration where 90% of a respective population is killed.

The invention claimed is:
1. A mixture comprising a compound of formula (I-A-1):

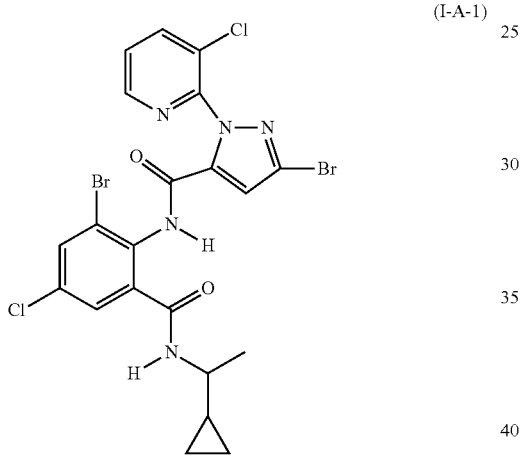

(I-A-1)

and an insecticide or a fungicide selected from the group of sulfoxaflor, flupyradifurone, 1-[(6-chloro-3-pyridinyl)methyl]-2,3,5,6,7,8-hexahydro-9-nitro-(5S,8R)-5,8-expoxy-1H-imidazo[1,2-a]azepine(cycloxaprid), triticonazole, 2-[2-chloro-4-(4-chorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-2[2-chloro-4-(4-chlorophenoxy)phenyl]-1-(1,2,4-triazol-1-yl)butan-2-ol, 2-[4-(4-chlorophhenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy )phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pental-2-ol, and 2-[4-(4-fluorophenoxy)-2-(trifluoromethyl)phenyl]-1-(1,2,4-triazol-1-yl)propan-2-ol;
in synergistically effective amounts.

2. A method for controlling and/or combating animal pests in soil application methods and seed treatment methods, comprising applying synergistically effective amounts of a compound of formula (I-A-1):

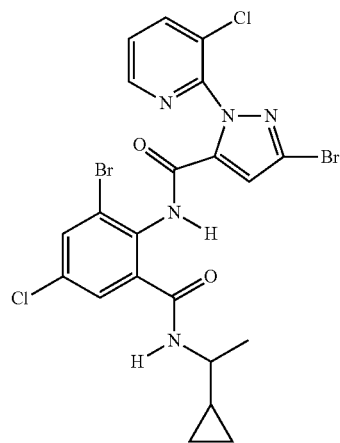

(I-A-1)

and an insecticide or a fungicide selected from the group consisting of sulfoxaflor, flupyradifurone, 1-[(6-chloro-3-pyridinyl)methyl]-2,3,5,6,7,8-hexahydro-9-nitro-(5S,8R)-5,8-epoxy-1H-imidazo[1,2-a]azepine (cycloxaprid), triticonazole, 2-[2-chloro-4-(4-chlorophenoxy)phenyl]-1-(1,2,4-triazol- 1 -yl)pentan-2-ol, 1-[4-(4-chlorophenoxy)-2- (trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2- (trifluoromethyl)phenyl]-1-(1,2,4-triazol- 1 -yl)pentan-2-ol, and 2-[4-(4-fluorophenoxy)-2- (trifluoromethyl)phenyl]-1-(1,2,4-triazol- 1 -yl)propan-2-ol;
directly and/or indirectly to the plant and/or to plant propagation material by drenching the soil, by drip application onto the soil, by soil injection, by dipping or by treatment of seeds.

3. A method for controlling pests and/or increasing the plant health of a cultivated plant with at least one modification as compared to the respective non-modified control plant, comprising the application of the mixture of claim 1 to a plant with at least one modification, parts of such plant, plant propagation material, or at its locus of growth.

4. A method for controlling non-crop pests, comprising contacting the pests or their food supply, habitat, breeding grounds or their locus with the mixture of claim 1.

5. A netting or textile material, impregnated with the mixture of claim 1.

6. A method for controlling a population of social insects, comprising contacting the pests or their food supply, habitat, breeding grounds or their locus with the mixture of claim 1.

7. A method of improving plant health, said method comprising applying synergistically effective amounts of a compound of formula (I-A-1):

(I-A-1)

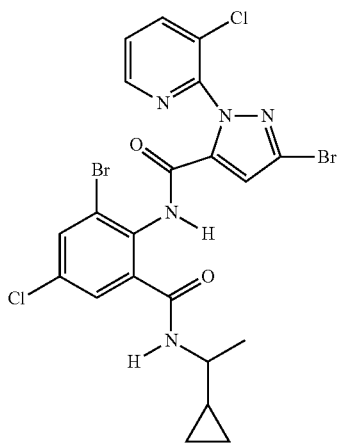

and an insecticide or a fungicide selected from the group consisting of sulfoxaflor, flupyradifurone, 1-[(6-chloro-3-pyridinyl)methyl]-2,3,5,6,7,8-hexahydro-9-nitro-(5S,8R)-5,8-epoxy-1H-imidazo[1,2-a]azepine (cycloxaprid), triticonazole, 2-[2-chloro-4-(4-chlorophenoxy) phenyl]-1-(1,2,4-triazol- 1 -yl)pentan-2-ol, 1-[4-(4-chlorophenoxy)-2- (trifluoromethyl)phenyl]-1-cyclopropyl-2-(1,2,4-triazol-1-yl)pethanol, 2-[4-(4-chlorophenoxy)-2- (trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2- (trifluoromethyl)phenyl]-3-methyl-1-(1,2,4-triazol-1-yl)butan-2-ol, 2-[4-(4-chlorophenoxy)-2- (trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl) butan-2-ol, 2-[4-(4-chlorophenoxy)-2- (trifluoromethyl)phenyl]-1-(1,2,4-triazol- 1 -yl)pentan-2-ol, and 2-[4-(4-fluorophenoxy)-2- (trifluoromethyl)phenyl]-1-(1,2,4-triazol- 1 -yl)propan-2-ol.

8. The mixture of claim 1, wherein the weight ratio is from 1000:1 to 1:000.

9. The mixture of claim 1, comprising the compound of formula (I-A-1) and triticonazole.

10. The mixture of claim 1, comprising the compound of formula (I-A-1) and sulfoxaflor.

11. The mixture of claim 1, comprising the compound of formula (I-A-1) and 2-[4-(4-chlorophenoxy)-2-(trifluoromethyl)phenyl]-1-(1,2,4-triazol-1-yl)propan-2-ol.

12. A pesticidal composition comprising a liquid or solid carrier and the mixture of claim 1.

13. A method for controlling insects, acarids or nematodes comprising contacting an insect, acarid or nematode or theirs food supply, habitat, breeding grounds or their locus with the mixture of claim 1 in pesticidally effective amounts, excluding a method of treatment of the human or animal body.

14. A method of protecting plants from attack or infestation by insects, acarids or nematodes comprising contacting the plant, or the soil or water in which the plant is growing, with a pesticidally effective amount of the mixture of claim 1.

15. The method of claim 2, wherein the weight ratio of the compound of formula (I-A-1) and the insecticide or the fungicide is from 1000:1 to 1:1000.

16. The method of claim 15, wherein the mixture comprises the compound of formula (I-A-1) and triticonazole.

17. The method of claim 15, wherein the mixture comprises the compound of formula (I-A-1) and sulfoxaflor.

18. The method of claim 7, wherein the weight ratio of the compound of formula (I-A-1) and the insecticide or the fungicide is from 1000:1 to 1:1000.

* * * * *